US011542262B2

(12) United States Patent
Hao

(10) Patent No.: US 11,542,262 B2
(45) Date of Patent: Jan. 3, 2023

(54) PHOSPHATIDYLINOSITOL 3-KINASE INHIBITORS

(71) Applicant: NANJING ZHENGXIANG PHARMACEUTICALS CO., LTD., Nanjing (CN)

(72) Inventor: Xiaolin Hao, Foster City, CA (US)

(73) Assignee: NANJING ZHENGXIANG PHARMACEUTICALS CO., LTD., Nanjing (CN)

(*) Notice: Subject to any disclaimer, the term of this patent is extended or adjusted under 35 U.S.C. 154(b) by 0 days.

(21) Appl. No.: 17/702,703

(22) Filed: Mar. 23, 2022

(65) Prior Publication Data

US 2022/0220113 A1 Jul. 14, 2022

Related U.S. Application Data

(63) Continuation of application No. 17/602,206, filed as application No. PCT/US2020/027303 on Apr. 8, 2020.

(60) Provisional application No. 62/836,659, filed on Apr. 20, 2019, provisional application No. 62/832,133, filed on Apr. 10, 2019.

(51) Int. Cl.

| C07D 471/04 | (2006.01) |
|---|---|
| C07D 491/107 | (2006.01) |
| C07D 417/10 | (2006.01) |
| C07D 498/08 | (2006.01) |
| C07D 519/00 | (2006.01) |
| A61P 37/06 | (2006.01) |
| A61P 35/00 | (2006.01) |
| A61P 25/28 | (2006.01) |
| A61K 31/437 | (2006.01) |
| A61K 31/5377 | (2006.01) |
| A61K 31/5386 | (2006.01) |
| C07F 9/6558 | (2006.01) |

(52) U.S. Cl.
CPC ............ *C07D 471/04* (2013.01); *A61P 35/00* (2018.01); *A61P 37/06* (2018.01); *C07D 417/10* (2013.01); *C07D 491/107* (2013.01); *C07D 498/08* (2013.01); *C07D 519/00* (2013.01); *C07F 9/65583* (2013.01); *C07F 9/65586* (2013.01)

(58) Field of Classification Search
CPC .. C07D 471/04; C07D 417/10; C07D 519/00; C07D 491/107; C07D 498/08; A61P 35/00; A61P 37/06; A61P 25/28; A61P 37/00; C07F 9/65583; C07F 9/65586; A61K 31/437; A61K 31/5377; A61K 31/5386

See application file for complete search history.

(56) References Cited

U.S. PATENT DOCUMENTS

| 2016/0214980 A1 | 7/2016 | Boyd et al. |
| 2017/0119786 A1 | 5/2017 | Buckley et al. |
| 2018/0243297 A1 | 8/2018 | Bellenie et al. |
| 2022/0213096 A1 | 7/2022 | Hao |

FOREIGN PATENT DOCUMENTS

| WO | 2011087776 A1 | 7/2011 |
| WO | 2014037480 A1 | 3/2014 |
| WO | 2015048318 A1 | 4/2015 |
| WO | 2017120194 A1 | 7/2017 |
| WO | 2017153527 A1 | 9/2017 |

OTHER PUBLICATIONS

Berge, S.M. et al. (Jan. 1977). "Pharmaceuticals Salts," J. Pharmaceutical Sciences 66(1):1-19.
Camps, M. et al. (Sep. 2005, e-pub. Aug. 28, 2005). "Blockade of PI3Kγ Suppresses Joint Inflammation and damage in mouse Models of Rheumatoid Arthritis," Nat. Med. 11(9):936-943.
Cantly, C. (May 31, 2002). "The Phosphoinositide 3-Kinase Pathway," Science, 296(5573):1655-1657.
Come, J.H. et al. (Jun. 28, 2018, e-pub. May 30, 2018). "Design and Synthesis of a Novel Series of Orally Bioavailable, CNS-Penetrant, Isoform Selective Phosphoinositide 3-Kinase # Inhibitors (PI3K#) with Potential for the Treatment of Multiple Sclerosis (MS)," Journal of Medicinal Chemistry, 61:5245-5256.
Cushing, T.D. et al. (Aug. 27, 2012). "PI3Kδand PI3Kγ as Targets For Autoimmune and Inflammatory Diseases," J. Med. Chem. 55:8559-8581.
De Henau, O. et al., (Nov. 17, 2016). "Overcoming Resistance To Checkpoint Blockade Therapy By Targeting PI3K-γ In Myeloid Cells," Nature 539:443-447, 26 pages.
Di Paolo, G. et al. (Oct. 2006). "Phosphoinositides in Cell Regulation and Membrane Dynamics," Nature 443:651-657.
Evans, C.A. et al. (Jul. 22, 2016). "Discovery of a Selective Phosphoinositide-3-Kinase (PI3K)-γ Inhibitor (IPI-549) as an Immuno-Oncology Clinical Candidate," ACS Med. Chem. Lett. 7:862-867.
Hawkins, P.T. et al. (Nov. 2006). "Signalling Through Class I PI3Ks In Mammalian Cells," Biochem. Soc. Trans. 34(5):647-662.
International Preliminary Report on Patentability, dated Sep. 28, 2021, for PCT Application No. PCT/US2020/027303 filed Apr. 8, 2020, 6 pages.
International Search Report and Written Opinion, dated Aug. 31, 2020, for PCT Application No. PCT/US2020/027303, filed Apr. 8, 2020, 10 pages.

(Continued)

*Primary Examiner* — John M Mauro
(74) *Attorney, Agent, or Firm* — Morrison & Foerster LLP

(57) ABSTRACT

The present disclosure provides selective phosphoinositide 3-kinase gamma inhibitors of Formula (I) including (I-a), (I-b), (I-c), and (I-d), or pharmaceutically acceptable salts thereof. These compounds are useful for the treatment of conditions mediated by one or more PI3K isoforms, such as PI3K gamma (PI3Kγ). The present disclosure further provides methods of inhibiting phosphoinositide 3-kinase gamma using these compounds for treatment of disorders related to phosphatidylinositol 3-kinase gamma activity.

26 Claims, 2 Drawing Sheets

(56) References Cited

OTHER PUBLICATIONS

Kaneda, M.M. et al. (Nov. 17, 2016). "PI3Kγ is a Molecular Switch That Controls Immune Suppression," Nature 539(7629):437-442, 33 pages.

Knight, Z.A. et al. (May 19, 2006). "A Pharmacological Map of the PI3-K Family Defines a Role for p110a in Insulin Signaling," Cell 125:733-747.

Parker, P.J. (2004). "The Ubiquitous Phosphoinositides," Biochem. Soc. Trans. 32(6):893-898.

Pemberton, N. et al. (May 31, 2018). "Discovery of Highly Isoform Selective Orally Bioavailable Phosphoinositide 3-Kinase (PI3K)-γ Inhibitors," Journal of Medicinal Chemistry 61:5435-5441.

PubChem (Oct. 7, 2017). CID: 130421534 "N-[5-[2-[(1S)-1-Cyclopropylethyl]-7-methylsulfinyl-1-oxo-3H-isoindol-5-yl]-4-methyl-1,3-thiazol-2-yl]acetamide," 9 pages.

Rückle, T. et al. (Nov. 2006, e-pub. Oct. 13, 2006). "PI3Kγ Inhibition: Towards An 'Aspirin of The 21st Century'?," Nat. Rev. Drug Discovery 5:903-918.

Schaeffer, E.M. et al. (Jun. 2000). "Tec Family Kinases In Lymphocyte Signaling and Function," Curr. Opin. Immnunol. 12:282-288.

Schmid, M.C. et al. (2013). "PI3-kinase γ Promotes Rap1a-Mediated Activation of Myeloid Cell Integrin α4β1, Leading To Tumor Inflammation and Growth," PLoS One 8:e60226, 12 pages.

Schmid, M.C. et al. (Jun. 14, 2011). "Receptor Tyrosine Kinases and TLR/IL1Rs Unexpectedly Activate Myeloid Cell PI3kγ, A Single Convergent Point Promoting Tumor Inflammation and Progression," Cancer Cell 19:715-727.

Stark, A.-K et al. (2015). "PI3K Inhibitors In Inflammation, Autoimmunity and Cancer," Curr. Opin. Pharmacol. 23:82-91.

PHOSPHATIDYLINOSITOL 3-KINASE INHIBITORS

CROSS-REFERENCE TO RELATED APPLICATIONS

This application is a continuation of U.S. application Ser. No. 17/602,206, which is a national stage application under 35 U.S.C. § 371 of International Application No. PCT/US2020/027303, filed Apr. 8, 2020, which claims prior benefit of U.S. Provisional Patent Application No. 62/832,133, filed Apr. 10, 2019, and of U.S. Provisional Patent Application No. 62/836,659, filed Apr. 20, 2019, the disclosures of each of which are hereby incorporated herein by reference in their entirety.

FIELD OF THE INVENTION

The present disclosure relates generally to novel inhibitors of phosphatidylinositol 3-kinase (PI3K). More specifically, the invention further relates to the preparation of the disclosed PI3K gamma inhibitor analogs and their use in pharmaceutical compositions for the treatment of various diseases, conditions and disorders related to PI3K gamma activity.

BACKGROUND OF THE INVENTION

The class I phosphoinositide 3-kinases (PI3Ks) regulate phosphatidylinositol 4,5-bisphosphate (PIP2) phosphorylation. PI3K Converts PIP2 to the scaffolding binding element phosphatidylinositol (3,4,5)-trisphosphate (PIP3). PIP3 plays a key regulatory role in cell survival, signal transduction, control of membrane trafficking and other functions. (Di Paolo, G. et al. Nature 2006, 443, 651; Parker, P. J. et al. Biochem. Soc. Trans. 2004, 32, 893; Hawkins, P. T. et al. Biochem. Soc. Trans. 2006, 34, 647; Schaeffer, E. M. et al. Curr. Opin. Immnunol. 2000, 12, 282). Its dysregulation leads to various disease states such as cancer, inflammatory and auto-immune disorders.

The Class I PI3Ks consist of four kinases further delineated into 2 subclasses. Class 1A PI3Ks consist of three closely related kinases, PI3Kα, β, and δ existing as heterodimers composed of a catalytic subunit (p110α, β or δ) and one of several regulatory subunits. They generally respond to signaling through receptor tyrosine kinases (RTKs). PI3Kγ single class 1B isoform, responds mainly to G-protein coupled receptors (GPCRs), and is composed of a p110γ catalytic subunit and one of two distinct regulatory subunits. PI3Kα and PI3Kβ are ubiquitously expressed throughout a wide variety of tissue and organ types. The expression pattern of PI3Kδ is restricted, to spleen, thymus, and peripheral blood leukocytes (Knight, Z. et al. Cell 2006, 125, 733). PI3Kγ is found mainly in leukocytes, but also in skeletal muscle, liver, pancreas, and heart (Cantly, C. Science 2002, 1655).

Recently, Schmid showed that p110γ can be activated by receptor tyrosine kinases and TLR/IL1Rs in myeloid cells. PI3kγ serves as a single convergent point promoting tumor inflammation and progression. In an animal model, treatment of mice with selective PI3Kγ inhibiter inhibited myeloid cell p110γ catalytic activity and adhesion to VCAM-1, due to effect on the tumor microenvironment instead of direct inhibition of tumor cells. (Schmid, M. C. et al. *Cancer Cell* 19, 715-727, 2011, *PLoS ONE* 8, e60226, 2013). Furthermore, inhibition of PI3Kγ enhanced pro-inflammatory cytokines and decreased the expression of immune-suppressive factors in tumors and TAMs. Kaneda and De Henau concluded that PI3Kγ controls the TAM switch between immune suppression and immune stimulation. (Kaneda, M. M. et al. *Nature* 539, 437-442, 2016; De Henau, O. et al. *Nature* 539, 443-447, 2016).

Camps et al. described that treatment with selective PI3Kγ inhibitor AS-60485023 suppresses the progression of joint inflammation and damage in two distinct mouse models of rheumatoid arthritis (Camps M, et al., Nat. Med. 2005, 11, 936-943).

Based on the studies in cellular levels and efficacies observed in various disease models, PI3Kγ inhibitors could potentially be used to treat a variety of diseases such as inflammation, metabolic and cancer (Cushing, T. D., et al, J. Med. Chem. 2012, 55, 8559-8581; Ruckle, T. et al, Nat. Rev. Drug Discovery 2006, 5, 903-918; Stark, A. K. et al, Curr. Opin. Pharmacol. 2015, 23, 82-91).

PI3K gamma selective inhibitors have been disclosed in recent years. IPI-549 has been in the clinical trials as single agent and combination immuno-oncology therapies with check point agent PD-1 inhibitor Nivolumab (Evans, C. A. et al, ACS Med. Chem. Lett. 2016, 7, 862-867). Pemberton N et al reported that selective PI3K gamma inhibition resulted in a dose dependent inhibition of LPS-induced airway neutrophilia in rats (Pemberton, N. et al, Journal of Medicinal Chemistry 2018, 61, 5435-5441). Modification of a series of azaisoindolinones by Come, J. H. et al provided CNS-penetrant and orally bioavailable PI3K gamma inhibitors that were efficacious in murine EAE model, which demonstrated PI3K gamma inhibition have the potential for the treatment of multiple sclerosis (Come, J. H. et al, Journal of Medicinal Chemistry 2018, 61, 5245-5256).

PI3K gamma inhibitors with related structure but different binding mode have been disclosed in recent years. For example, WO2015048318 disclosed (R)-6-(1-(2,2-difluoro-ethyl)-1H-pyrazol-4-yl)-4,7,7-trimethyl-2-(5-(2,2,2-trifluoro-1-hydroxyethyl)pyhdin3-yl)-6,7-dihydro-5H-pyrrolo[3,4-b]pyridin-5-one as a selective inhibitor of PI3K gamma. WO2011087776 disclosed Isoindolinone inhibitors of phosphatidylinositol 3-kinase. WO2017153527 disclosed novel inhibitors of phosphatidylinositol 3-kinase gamma. Discovery of highly isoform selective orally bioavailable phosphoinositide 3-kinase (PI3K) γ inhibitors, and design and synthesis of a novel series of 3-kinase γ (PI3Kγ) inhibitors were reported (Journal of Medicinal Chemistry 2018, 61, 5435-5441 and Journal of Medicinal Chemistry 2018, 61, 5245-5256).

However, these reported PI3K gamma inhibitors have less optimal potency, selectivity and pharmacokinetic properties. Therefore, there are needs in the art to develop novel PI3K gamma inhibitors that have improved potency, selectivity and pharmacokinetic properties.

SUMMARY

Compounds and pharmaceutically acceptable salts, stereoisomers, prodrugs, or solvates thereof useful for inhibiting PI3K isoforms, such as PI3K gamma, are described herein. Compositions, including pharmaceutical compositions that include the compounds are also provided, as are methods of using and making the compounds. The compounds provided herein may find use in treating diseases, disorders, or conditions that are mediated by PI3K isoforms, such as PI3K gamma.

In one aspect, provided herein is a compound of Formula (I):

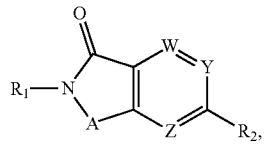
(I)

or a pharmaceutically acceptable salt, stereoisomer, prodrug, or solvate thereof, wherein:
A is $CH_2$, $CH(C_{1-6}alkyl)$, O, or S;
Y is CH or N;
Z is CH or N;
W is N, CH, or CX;
wherein X is selected from the group consisting of

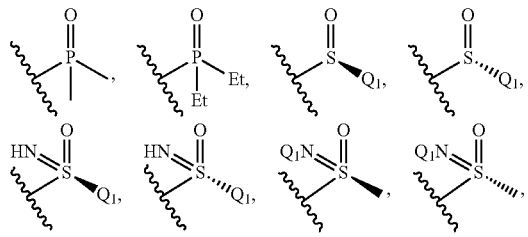

NHG, $CHG_2$, COOH, OG, $SO_2G$, $SO_2NHG$, $NGSO_2G$, $C_{1-6}alkyl$-$NGSO_2G$, NHC(O)G, NHC(O)$NG_2$, C(O)NHG, C(O)$NG_2$, $C_{3-10}cycloalkyl$, and 3-10 membered heterocyclyl, wherein each 3-10 membered heterocyclyl independently contains 1 or 2 heteroatoms, wherein the 1 or 2 heteroatoms are selected from the group consisting of O, N, and S, and wherein each $C_{3-10}cycloalkyl$ or 3-10 membered heterocyclyl is independently optionally substituted with one or more G, wherein:

$Q_1$ is $C_{1-6}alkyl$, wherein the $C_{1-6}alkyl$ is optionally substituted with one or more OH or halo, and each G is independently selected from the group consisting of H, D, OH, $C_{1-6}alkoxy$, oxo, $NH_2$, $SO_2(C_{1-6}alkyl)$, C(O)—$C_{1-6}alkyl$, $C_{3-10}cycloalkyl$, 3-10 membered heterocyclyl, and $C_{1-6}alkyl$, wherein the $C_{3-10}cycloalkyl$ or $C_{1-6}alkyl$ is independently optionally substituted with one or more D, OH, $C_{1-6}alkoxy$, CN, $N(C_{1-6}alkyl)_2$, $SO_2(C_{1-6}alkyl)$, or halo, or two G groups, together with the atoms to which they are attached, form a $C_{3-10}cycloalkyl$ or 3-10 membered heterocyclyl, provided that, when Y and Z are each CH, and W is CX, then X is selected from the group consisting of

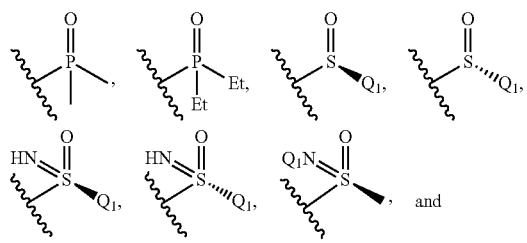
and

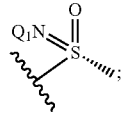

$R_1$ is $C_{1-6}alkyl$, $C_{3-10}cycloalkyl$, or $C_{1-6}alkyl$-$C_{3-10}cycloalkyl$, wherein the $C_{1-6}alkyl$, $C_{3-10}cycloalkyl$, or $C_{1-6}alkyl$-$C_{3-10}cycloalkyl$ is independently optionally substituted with one or more halo; and $R_2$ is selected from the group consisting of

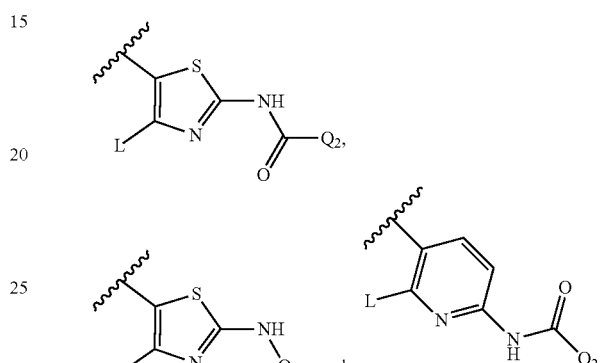

wherein:
L is H, halo, or $C_{1-6}alkyl$, wherein the $C_{1-6}alkyl$ is optionally substituted with one or more halo, $C_{1-6}alkoxy$, or OH, and each $Q_2$ and $Q_3$ is independently $C_{1-6}alkyl$, $C_{3-10}cycloalkyl$, or 3-10 membered heterocyclyl, wherein the $C_{1-6}alkyl$, $C_{3-10}cycloalkyl$, or 3-10 membered heterocyclyl is independently optionally substituted with one or more halo.

In some embodiments, provided is a compound of Formula (I-a):

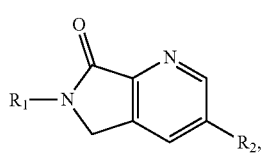
(I-a)

or a pharmaceutically acceptable salt, stereoisomer, solvate, or prodrug thereof.

In some embodiments, provided is a compound of Formula (I-b):

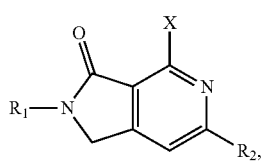
(I-b)

or a pharmaceutically acceptable salt, stereoisomer, solvate, or prodrug thereof.

In some embodiments, provided is a compound of Formula (I-c):

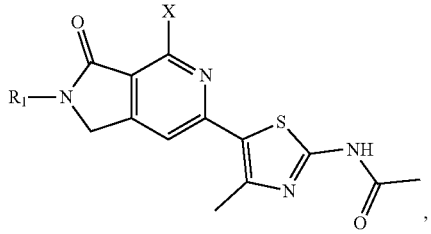

(I-c)

or a pharmaceutically acceptable salt, stereoisomer, solvate, or prodrug thereof.

In some embodiments, provided is a compound of Formula (I-d):

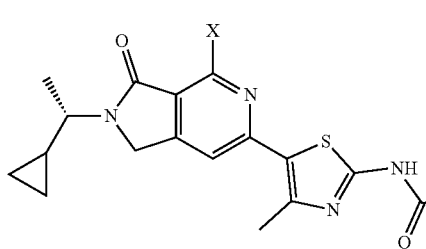

(I-d)

or a pharmaceutically acceptable salt, stereoisomer, solvate, or prodrug thereof.

In some embodiments, the compound described herein has improved selectivity against the PI3Kδ isoform, improved solubility, or improved oral bioavailability in comparison to a known PI3K gamma inhibitor (e.g., IPI-549 (Evans, C. et al, ACS Med. Chem. Lett. 2016, 7, 862-867) or AZ-17 (Pemberton, N, et al, Journal of Medicinal Chemistry 2018, 61, 5435-5441)), or any combination of the foregoing.

In one aspect, provided herein is a method of selectively inhibiting a growth or a proliferation phosphoinositide 3-kinase gamma (PI3Kγ) comprising contacting the PI3Kγ with a compound of Formula (I), (I-a), (I-b), (I-c), or (I-d), or a pharmaceutically acceptable salt, stereoisomer, solvate, or prodrug thereof, and one or more pharmaceutically acceptable carriers.

In some embodiments, provided herein is a method of selectively inhibiting a growth or a proliferation phosphoinositide 3-kinase gamma (PI3Kγ) of Formula (I), (I-a), (I-b), (I-c), or (I-d), or a pharmaceutically acceptable salt, stereoisomer, solvate, or prodrug thereof, wherein the compound has improved selectivity against the PI3Kδ isoform, improved solubility, or improved oral bioavailability in comparison to a known PI3K gamma inhibitor (e.g., IPI-549 or AZ-17), or any combination of the foregoing.

In yet another aspect, provided herein is a method of treating a disorder of uncontrolled cellular proliferation related to related to one or more PI3K isoforms, such as PI3K gamma (PI3Kγ), comprising administering to a subject in need thereof a therapeutically effective amount of a compound of Formula (I), (I-a), (I-b), (I-c), or (I-d), or a pharmaceutically acceptable salt, stereoisomer, solvate, or prodrug thereof.

In some embodiments, provided herein is a method of treating an autoimmune diseases, comprising administering to a subject in need thereof a therapeutically effective amount of a compound of Formula (I), (I-a), (I-b), (I-c), or (I-d), or a pharmaceutically acceptable salt, stereoisomer, solvate, or prodrug thereof.

In some embodiments, provided herein is a method of treating a cancer, comprising administering to a subject in need thereof a therapeutically effective amount of a compound of Formula (I), (I-a), (I-b), (I-c), or (I-d), or a pharmaceutically acceptable salt, stereoisomer, solvate, or prodrug thereof.

DETAILED DESCRIPTION

PI3K Gamma Inhibitor Compounds

Figure 1:
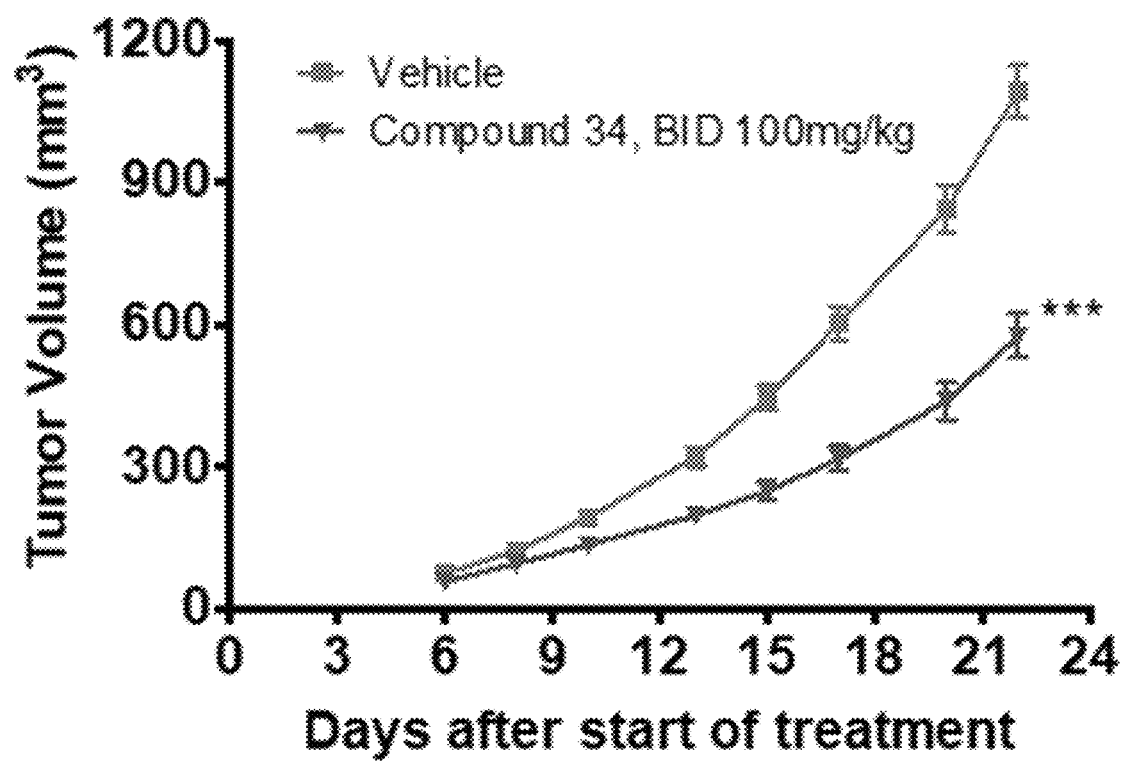
FIG. 1 shows the antitumor efficacy of an exemplary compound (compound 34) in 4T1 syngeneic mouse tumor model.

Provided herein are compounds that function as PI3K gamma inhibitors. In some embodiments, provided herein is a compound of Formula (I):

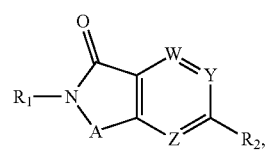

(I)

or a pharmaceutically acceptable salt, stereoisomer, prodrug, or solvate thereof.
wherein:
A is $CH_2$, $CH(C_{1-6}alkyl)$, O, or S;
Y is CH or N;
Z is CH or N;
W is N, CH, or CX; wherein X is selected from the group consisting of

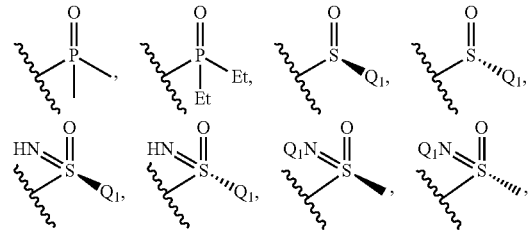

$NHG$, $CHG_2$, $COOH$, $OG$, $SO_2G$, $SO_2NHG$, $NGSO_2G$, $C_{1-6}alkyl$-$NGSO_2G$, $NHC(O)G$, $NHC(O)NG_2$, $C(O)NHG$, $C(O)NG_2$, $C_{3-10}cycloalkyl$, and 3-10 membered heterocyclyl, wherein each 3-10 membered heterocyclyl independently contains 1 or 2 heteroatoms, wherein the 1 or 2 heteroatoms are selected from the group consisting of O, N, and S, and wherein each $C_{3-10}cycloalkyl$ or 3-10 membered heterocyclyl is independently optionally substituted with one or more G, wherein:

$Q_1$ is $C_{1-6}alkyl$, wherein the $C_{1-6}alkyl$ is optionally substituted with one or more OH or halo, and each G is independently selected from the group consisting of H, D, OH, $C_{1-6}$alkoxy, oxo, $NH_2$, $SO_2(C_{1-6}$alkyl), C(O)—$C_{1-6}$alkyl, $C_{3-10}$cycloalkyl, 3-10 membered heterocyclyl, and $C_{1-6}$alkyl, wherein the $C_{3-10}$cycloalkyl or $C_{1-6}$alkyl is independently optionally substituted with one or more D, OH, $C_{1-6}$alkoxy, CN, N($C_{1-6}$alkyl)$_2$, $SO_2(C_{1-6}$alkyl), or halo, or two G groups, together with the atoms to which they are attached, form a $C_{3-10}$cycloalkyl or 3-10 membered heterocyclyl, provided that, when Y and Z are each CH, and W is CX, then X is selected from the group consisting of

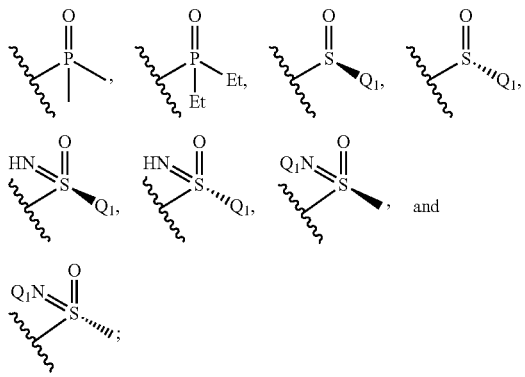

$R_1$ is $C_{1-6}$alkyl, $C_{3-10}$cycloalkyl, or $C_{1-6}$alkyl-$C_{3-10}$cycloalkyl, wherein the $C_{1-6}$alkyl, $C_{3-10}$cycloalkyl, or $C_{1-6}$alkyl-$C_{3-10}$cycloalkyl is independently optionally substituted with one or more halo; and $R_2$ is selected from the group consisting of

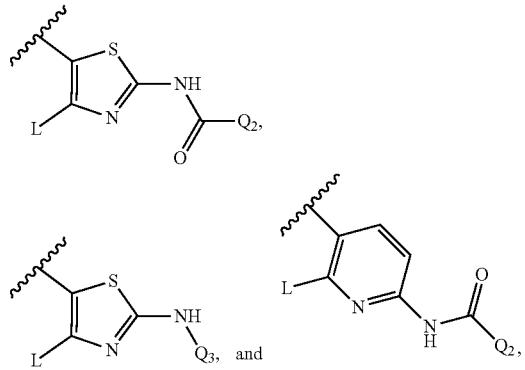

wherein:

L is H, halo, or $C_{1-6}$alkyl, wherein the $C_{1-6}$alkyl is optionally substituted with one or more halo, $C_{1-6}$alkoxy, or OH, and each $Q_2$ and $Q_3$ is independently $C_{1-6}$alkyl, $C_{3-10}$cycloalkyl, or 3-10 membered heterocyclyl, wherein the $C_{1-6}$alkyl, $C_{3-10}$cycloalkyl, or 3-10 membered heterocyclyl is independently optionally substituted with one or more halo.

In some embodiments, at least one of Y, Z and W is N. In some embodiments, Y is N and Z is CH. In some embodiments, Z is N and Y is CH.

In some embodiments, X is selected from the group consisting of

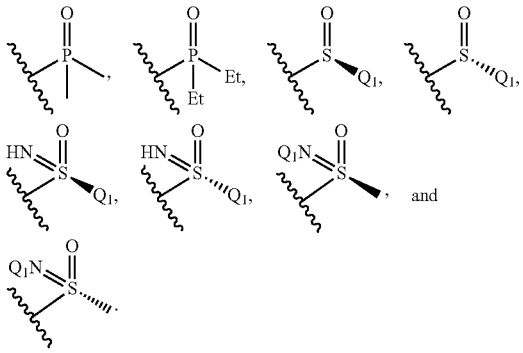

In some embodiments, X is selected from the group consisting of NHG, CHG$_2$, COOH, OG, SO$_2$G, SO$_2$NHG, NGSO$_2$G, $C_{1-6}$alkyl-NGSO$_2$G, NHC(O)G, NHC(O)NG$_2$, C(O)NHG, C(O)NG$_2$, $C_{3-10}$cycloalkyl, and 3-10 membered heterocyclyl, wherein each 3-10 membered heterocyclyl independently contains 1 or 2 heteroatoms, wherein the 1 or 2 heteroatoms are selected from the group consisting of O, N, and S, and wherein each $C_{3-10}$cycloalkyl or 3-10 membered heterocyclyl is independently optionally substituted with one or more G.

In some embodiments, Y and Z are each CH, W is CX, and X is selected from the group consisting of

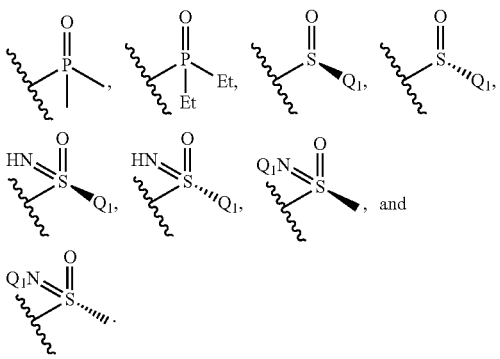

In some embodiments, Y is N, Z is CH, W is CX, and X is selected from the group consisting of NHG, CHG$_2$, COOH, OG, SO$_2$G, SO$_2$NHG, NGSO$_2$G, $C_{1-6}$alkyl-NGSO$_2$G, NHC(O)G, NHC(O)NG$_2$, C(O)NHG, C(O)NG$_2$, $C_{3-10}$cycloalkyl, and 3-10 membered heterocyclyl, wherein each 3-10 membered heterocyclyl independently contains 1 or 2 heteroatoms, wherein the 1 or 2 heteroatoms are selected from the group consisting of O, N, and S, and wherein each $C_{3-10}$cycloalkyl or 3-10 membered heterocyclyl is independently optionally substituted with one or more G.

It is intended and understood that each and every variation of $R_1$, $R_2$, and A described herein may be combined with each and every variation of W, Y and Z as described, as if each and every combination is individually described.

In some embodiments, provided herein is a compound of Formula (I), wherein W is N, A is CH$_2$, Y is CH, and Z is CH, such that the compound has the structure of Formula (I-a):

(I-a)

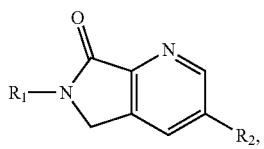

or a pharmaceutically acceptable salt, stereoisomer, solvate, or prodrug thereof.

In some embodiments, provided herein is a compound of Formula (I), wherein W is CX, A is CH$_2$, Y is N, and Z is CH, such that the compound of Formula (I) has the structure of Formula (I-b):

(I-b)

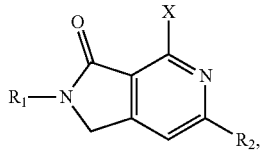

or a pharmaceutically acceptable salt, stereoisomer, solvate, or prodrug thereof.

In some embodiments, R$_2$ is selected from the group consisting of

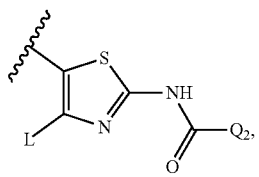

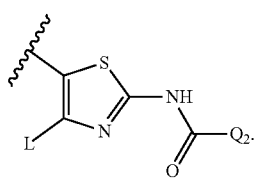

In some embodiments, R$_2$ is

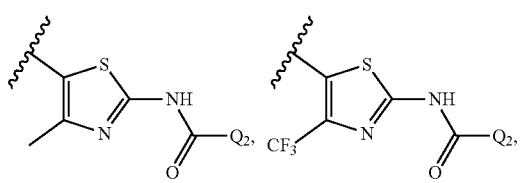

In certain embodiments, R$_2$ is selected from the group consisting of

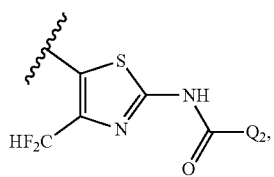

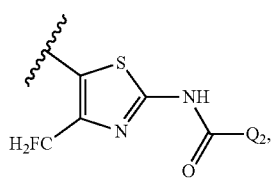

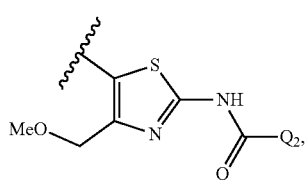

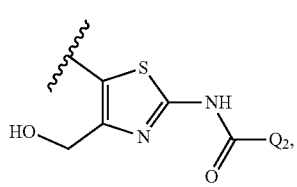

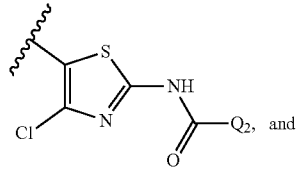

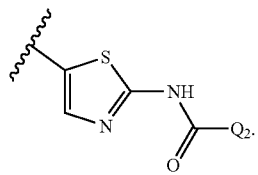

In some embodiments, Q$_2$ is methyl, ethyl, isopropyl, cyclopropyl, or difluoromethyl.

In some embodiments, R$_2$ is

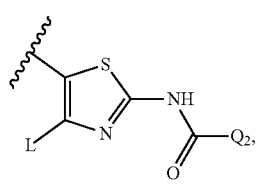

wherein L is methyl and Q$_2$ is methyl, such that the compound of Formula (I) has the structure of Formula (I-c):

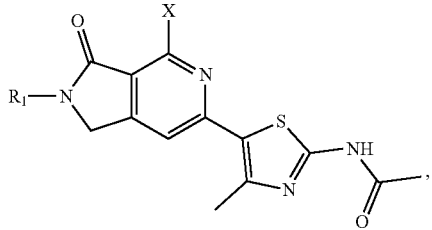
(I-c)

or a pharmaceutically acceptable salt, stereoisomer, prodrug, or solvate thereof.

In some embodiments, $R_1$ is selected from the group consisting of

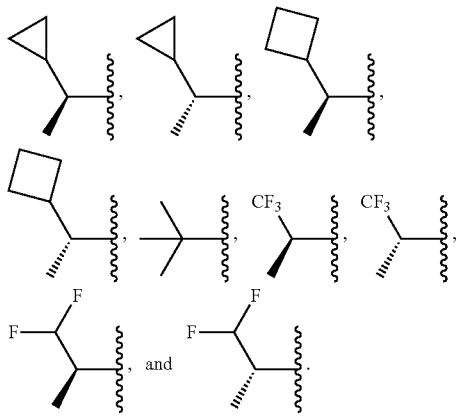

In some embodiments, $R_1$ is selected from the group consisting of

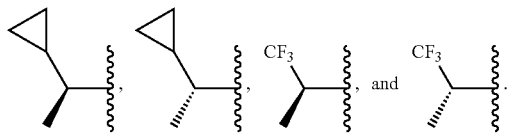

In some embodiments, $R_1$ is

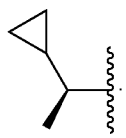

In certain embodiments, $R_1$ is

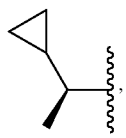 [SMILES: *[C@@H](C)C1CC1]

and the compound of Formula (I) has the structure of Formula (I-d):

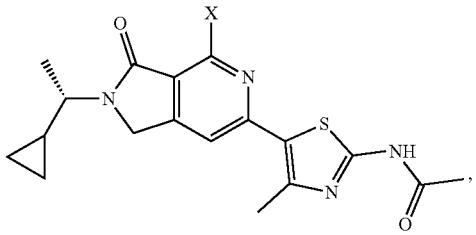
(I-d)

or a pharmaceutically acceptable salt, stereoisomer, prodrug, or solvate thereof.

In some embodiments, X is selected from the group consisting of

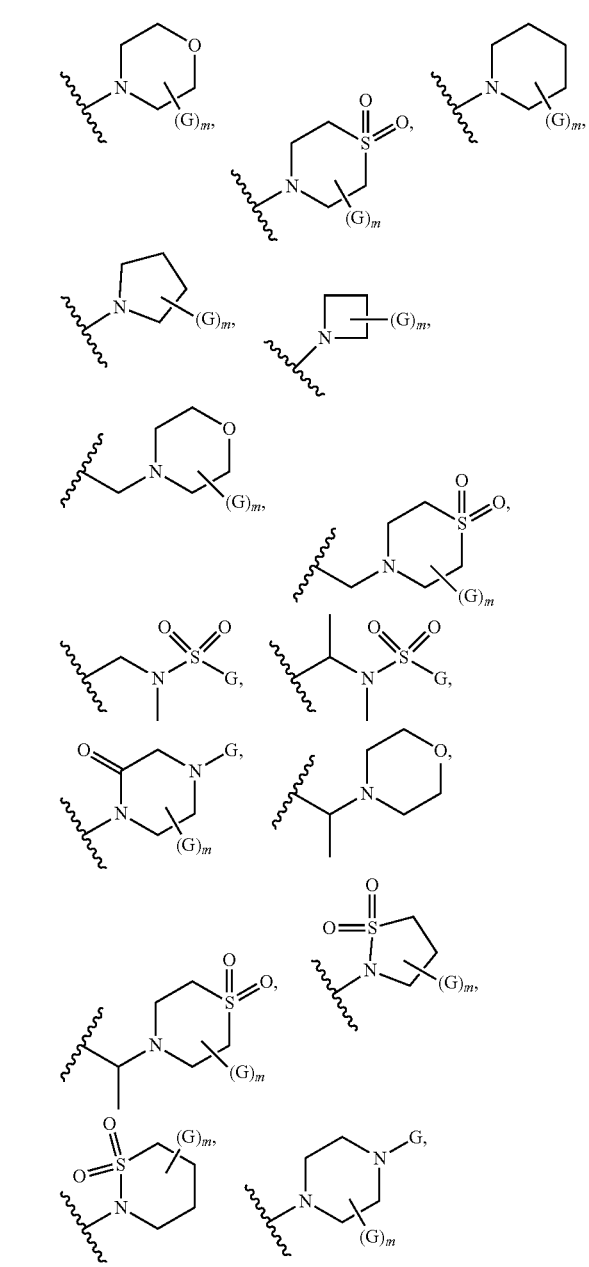

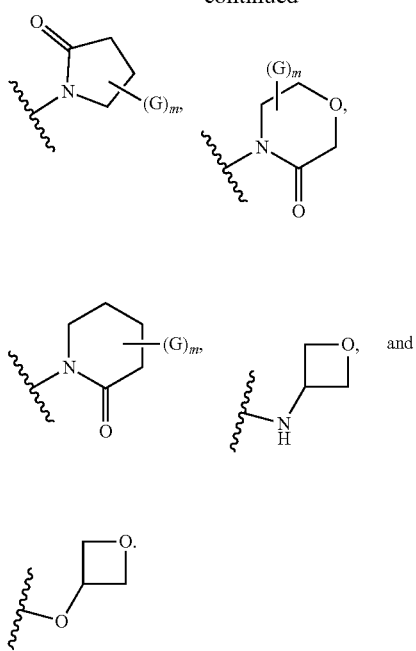

In other embodiments, X is selected from the group consisting of

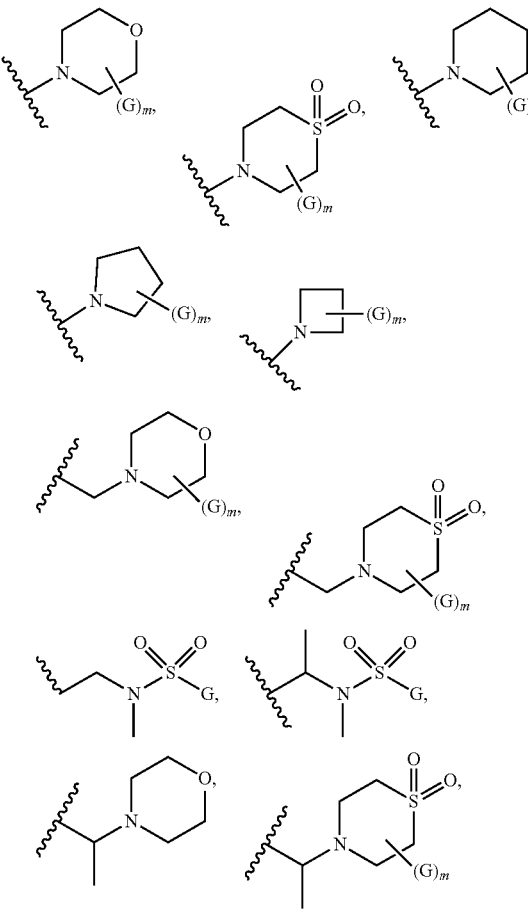

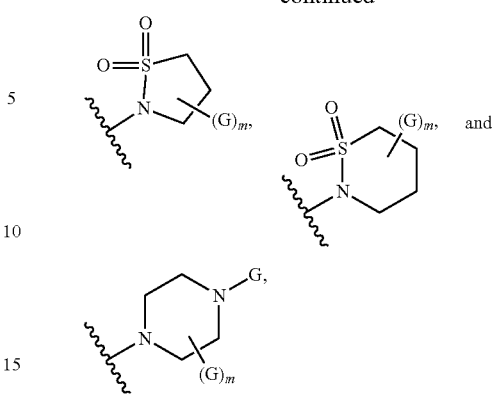

In still other embodiments, X is selected from the group consisting of NHG, OG, NHSO$_2$G, and C(O)NG$_2$. In still other embodiments, X is selected from the group consisting of OMe, OCD$_3$, NHSO$_2$Me, NHSO$_2$Et, C(O)NH$_2$, C(O)NHMe, and C(O)NMe$_2$.

In some embodiments, provided herein is a compound of Formula (I), (I-a), (I-b), (I-c), or (I-d), as the case may be, wherein: wherein the compound is selected from the group consisting of:

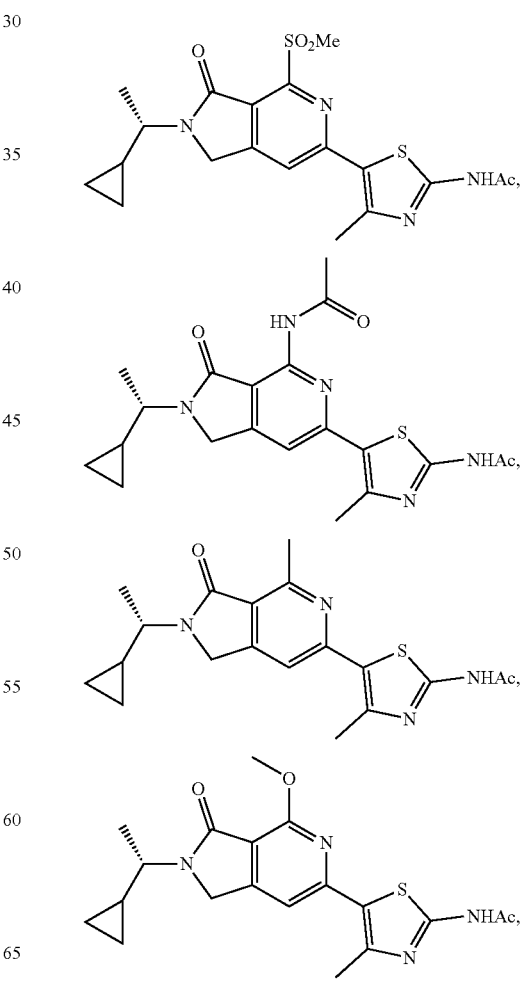

-continued
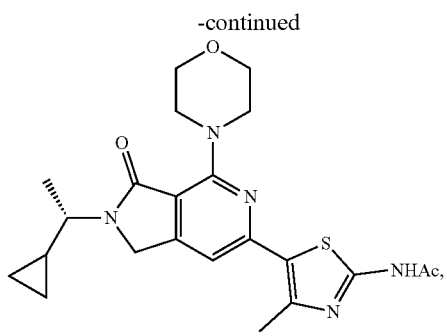
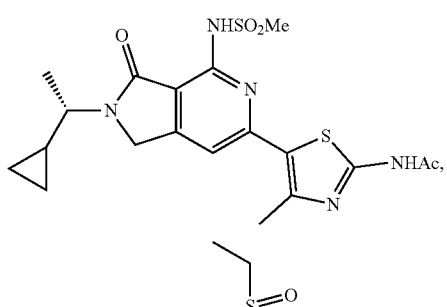
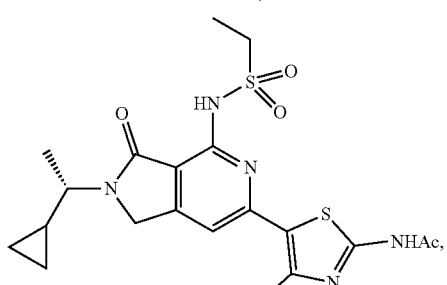
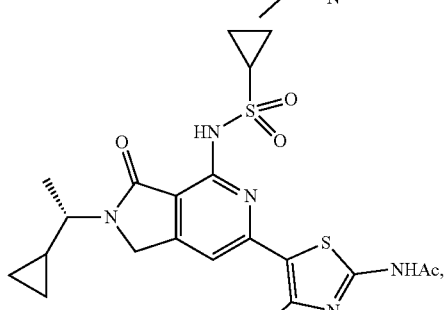
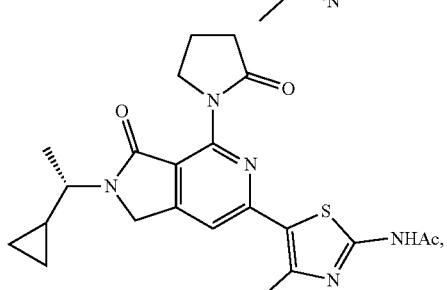
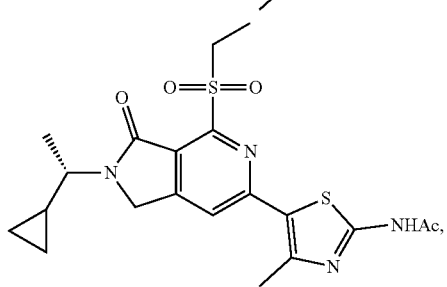
-continued
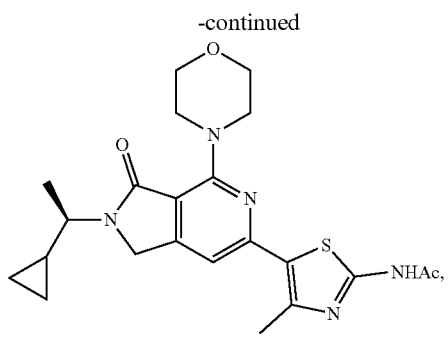
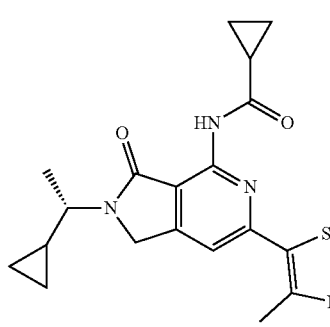
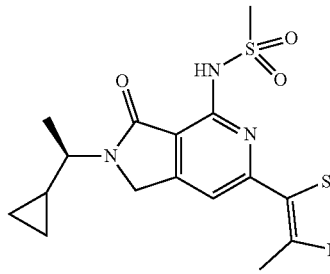
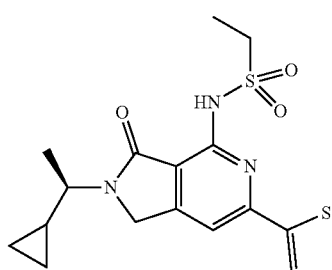
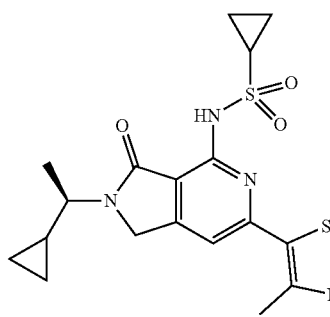

17
-continued
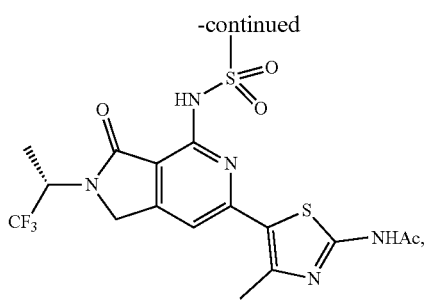
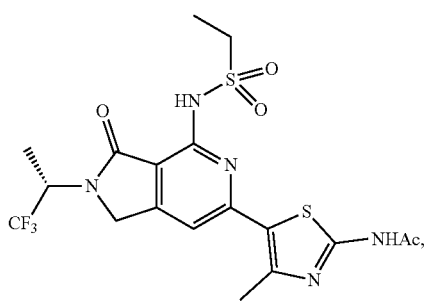
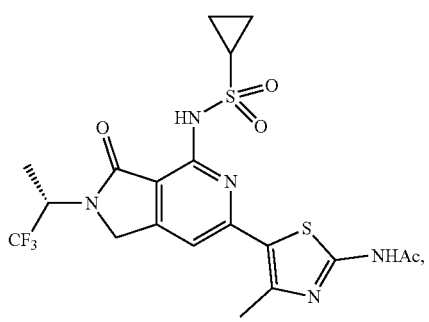
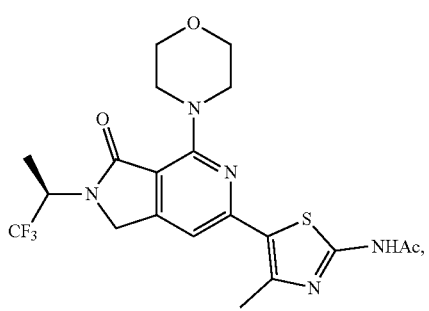
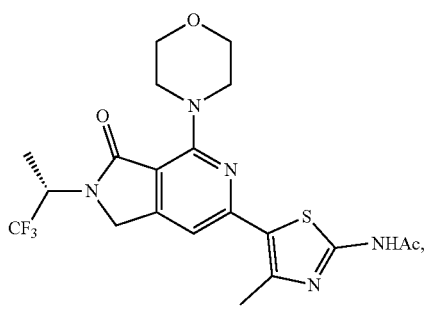
18
-continued
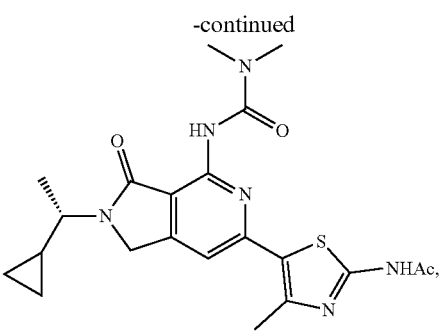
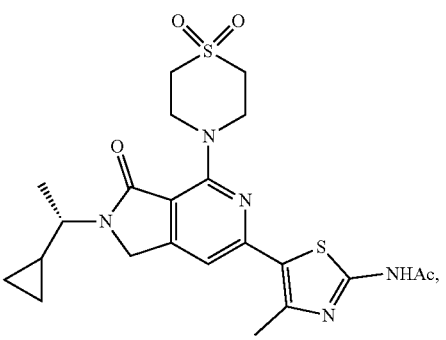
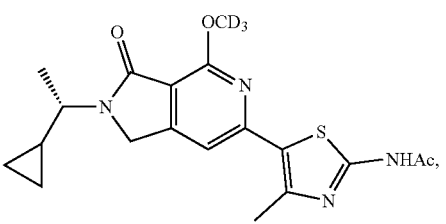
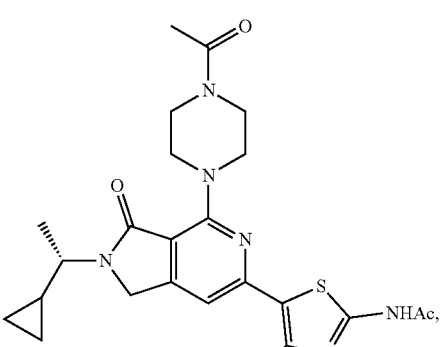
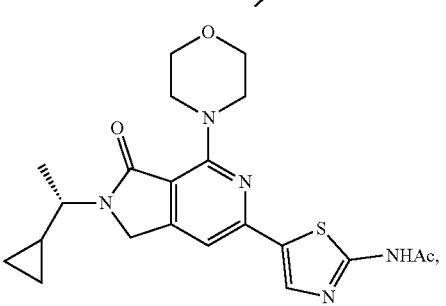

-continued
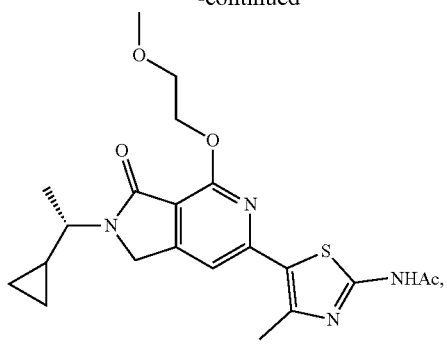
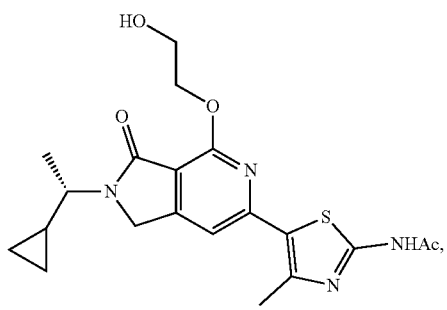
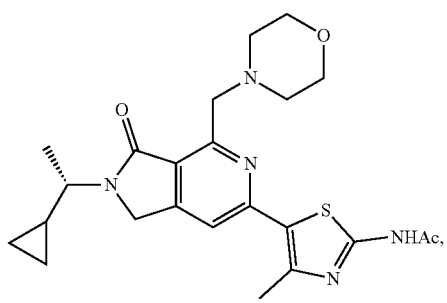
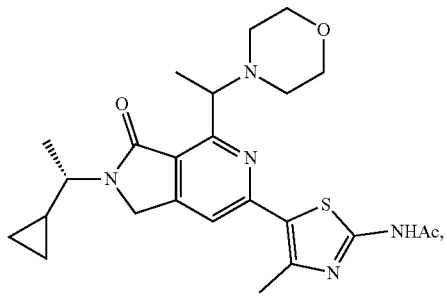
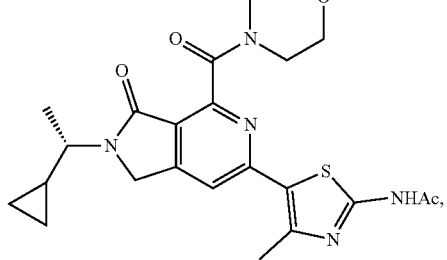
-continued
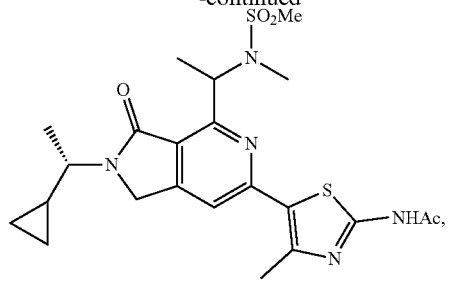
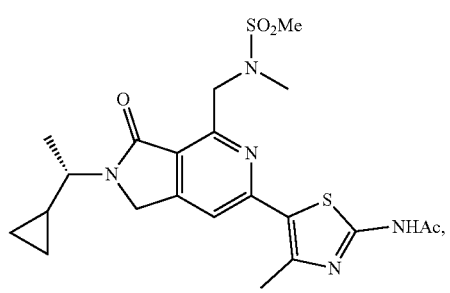
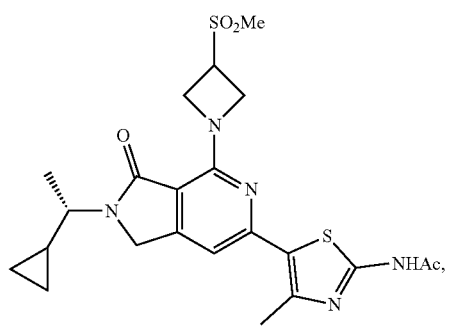
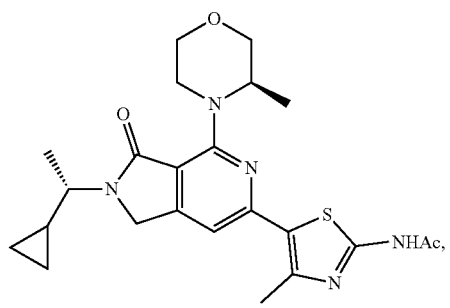
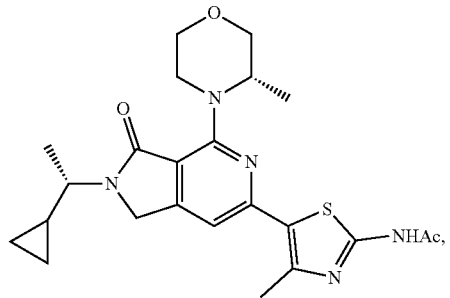

-continued
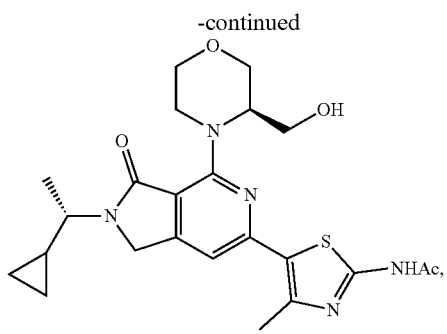
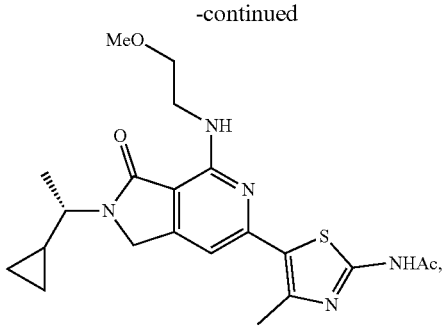
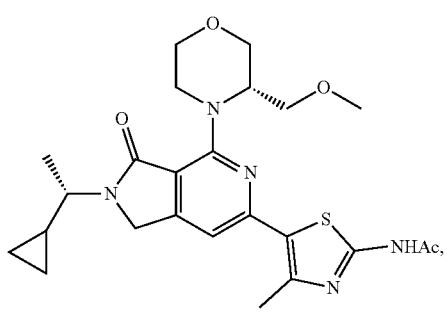
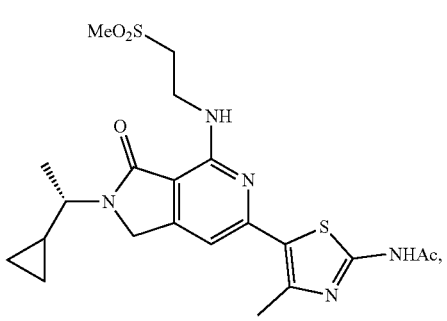
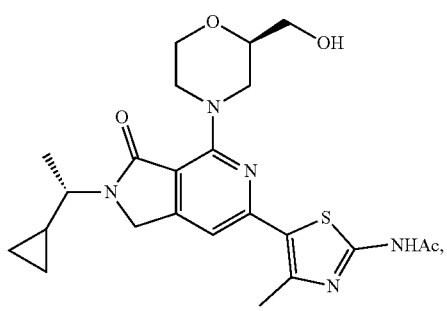
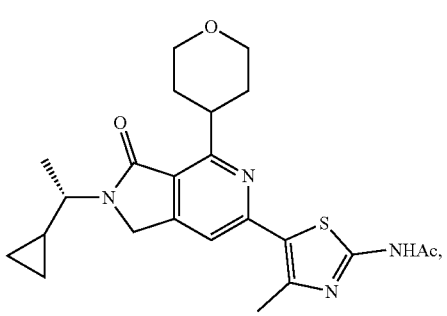
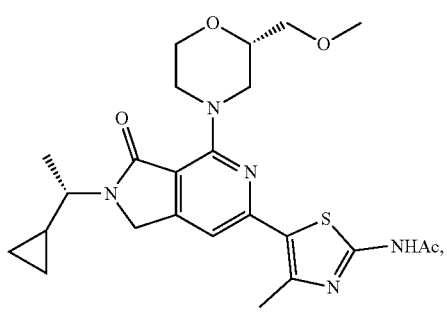
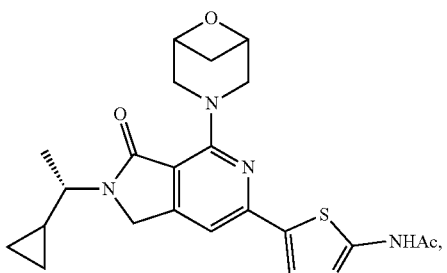
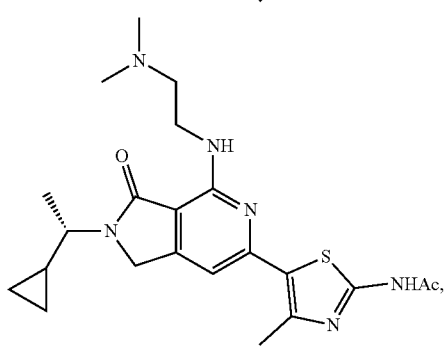
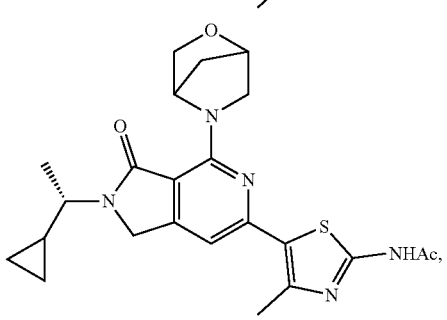

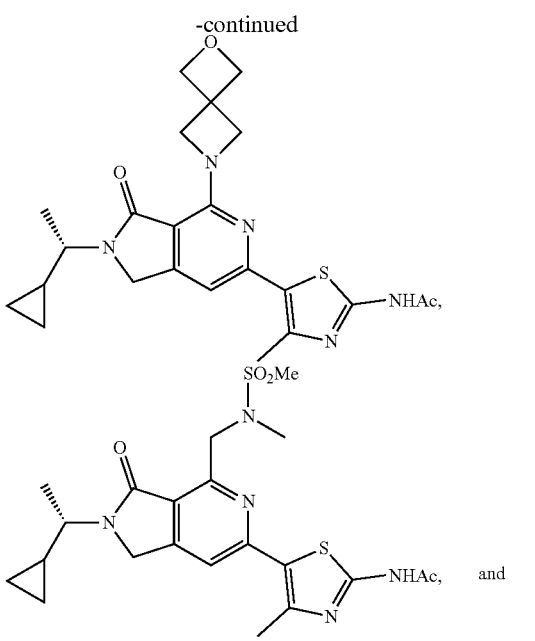
and

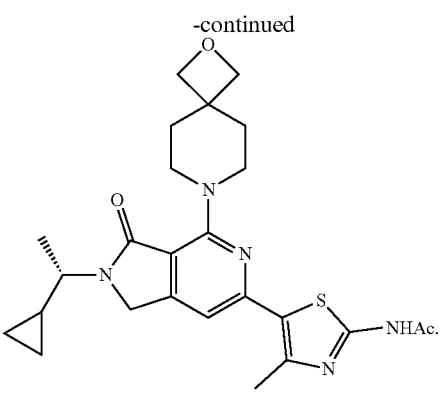

In one embodiment, provided herein is a compound of Formula (I), wherein Z is N, A is $CH_2$, Y is CH, and W is CH, or a pharmaceutically acceptable salt, stereoisomer, prodrug, or solvate thereof.

In one embodiment, provided is a compound of the following structures (Table 1), or a pharmaceutically acceptable salt, prodrug, or solvate wherein:

TABLE 1

Representative Compounds and their flat names.

| # | Structure | Flat Name |
|---|---|---|
| 1 | 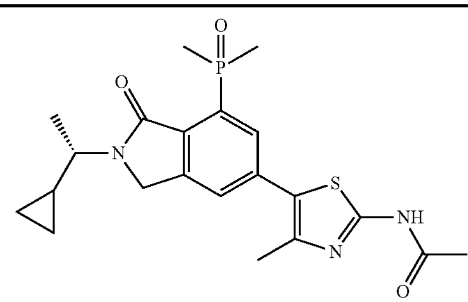 | N-(5-(2-(1-cyclopropylethyl)-7-(dimethylphosphoryl)-1-oxoisoindolin-5-yl)-4-methylthiazol-2-yl)acetamide |
| 2 | 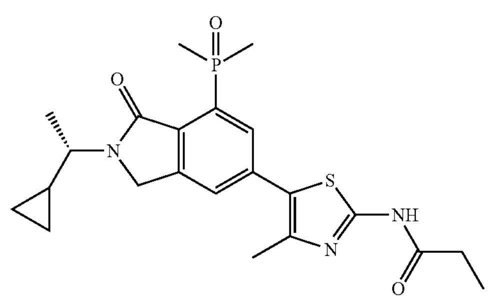 [SMILES: CCC(=O)Nc1nc(C)c(-c2cc3c(c(P(C)(C)=O)c2)C(=O)N([C@@H](C)C2CC2)C3)s1] | N-(5-(2-(1-cyclopropylethyl)-7-(dimethylphosphoryl)-1-oxoisoindolin-5-yl)-4-methylthiazol-2-yl)propionamide |
| 3 | 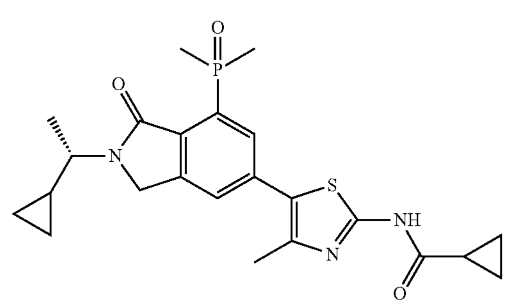 [SMILES: Cc1nc(NC(=O)C2CC2)sc1-c1cc2c(c(P(C)(C)=O)c1)C(=O)N([C@@H](C)C1CC1)C2] | N-(5-(2-(1-cyclopropylethyl)-7-(dimethylphosphoryl)-1-oxoisoindolin-5-yl)-4-methylthiazol-2-yl)cyclopropanecarboxamide |

TABLE 1-continued

Representative Compounds and their flat names.

| # | Structure | Flat Name |
|---|---|---|
| 4 | 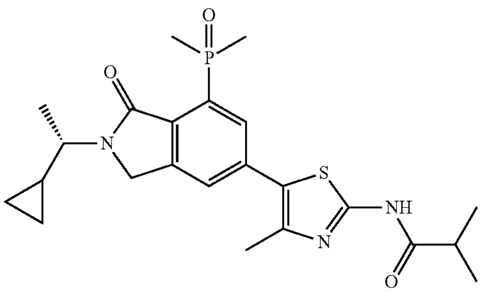 [SMILES: Cc1nc(NC(=O)C(C)C)sc1-c1cc2c(c(P(C)(C)=O)c1)C(=O)N([C@@H](C)C1CC1)C2] | N-(5-(2-(1-cyclopropylethyl)-7-(dimethylphosphoryl)-1-oxoisoindolin-5-yl)-4-methylthiazol-2-yl)isobutyramide |
| 5 | 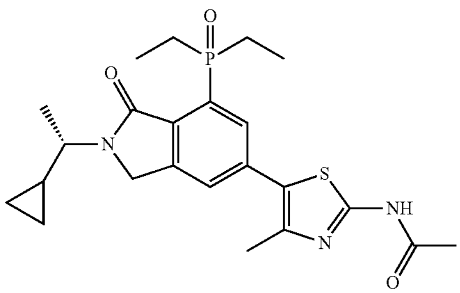 [SMILES: CCP(=O)(CC)c1cc(-c2sc(NC(C)=O)nc2C)cc2c1C(=O)N([C@@H](C)C1CC1)C2] | N-(5-(2-(1-cyclopropylethyl)-7-(diethylphosphoryl)-1-oxoisoindolin-5-yl)-4-methylthiazol-2-yl)acetamide |
| 6 | 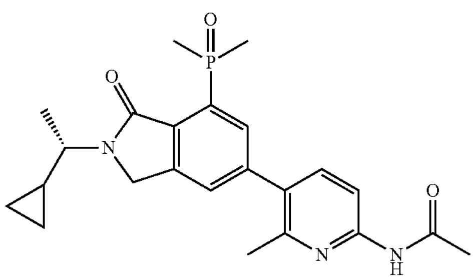 [SMILES: CC(=O)Nc1ccc(-c2cc3c(c(P(C)(C)=O)c2)C(=O)N([C@@H](C)C2CC2)C3)c(C)n1] | N-(5-(2-(1-cyclopropylethyl)-7-(dimethylphosphoryl)-1-oxoisoindolin-5-yl)pyridin-2-yl)acetamide |
| 7 | 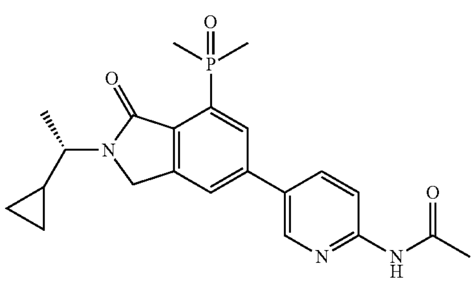 [SMILES: CC(=O)Nc1ccc(-c2cc3c(c(P(C)(C)=O)c2)C(=O)N([C@@H](C)C2CC2)C3)cn1] | N-(5-(2-(1-cyclopropylethyl)-7-(dimethylphosphoryl)-1-oxoisoindolin-5-yl)pyridin-2-yl)acetamide |
| 8 | 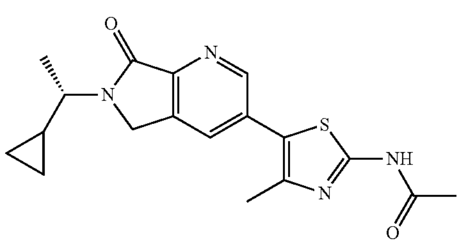 [SMILES: CC(=O)Nc1nc(C)c(-c2cnc3c(c2)CN([C@@H](C)C2CC2)C3=O)s1] | N-(5-(6-(1-cyclopropylethyl)-7-oxo-6,7-dihydro-5H-pyrrolo[3,4-b]pyridin-3-yl)-4-methylthiazol-2-yl)acetamide |

TABLE 1-continued

Representative Compounds and their flat names.

| # | Structure | Flat Name |
|---|---|---|
| 9 | 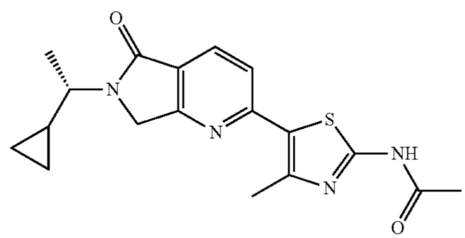 [SMILES: CC(=O)Nc1nc(C)c(-c2ccc3c(n2)CN([C@@H](C)C2CC2)C3=O)s1] | N-(5-(6-(1-cyclopropylethyl)-5-oxo-6,7-dihydro-5H-pyrrolo[3,4-b]pyridin-2-yl)-4-methylthiazol-2-yl)acetamide |
| 10 | 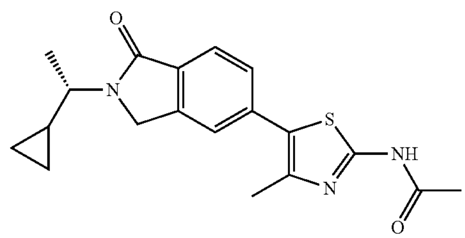 [SMILES: CC(=O)Nc1nc(C)c(-c2ccc3c(c2)CN([C@@H](C)C2CC2)C3=O)s1] | N-(5-(2-(1-cyclopropylethyl)-1-oxoisoindolin-5-yl)-4-methylthiazol-2-yl)acetamide |
| 11 | 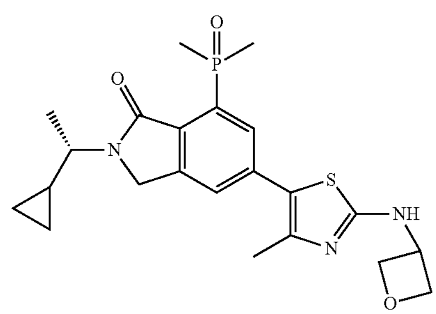 [SMILES: Cc1nc(NC2COC2)sc1-c1cc2c(c(P(C)(C)=O)c1)C(=O)N([C@@H](C)C1CC1)C2] | 2-(1-cyclopropylethyl)-7-(dimethylphosphoryl)-5-(4-methyl-2-(oxetan-3-ylamino)thiazol-5-yl)isoindolin-1-one |
| 12 | 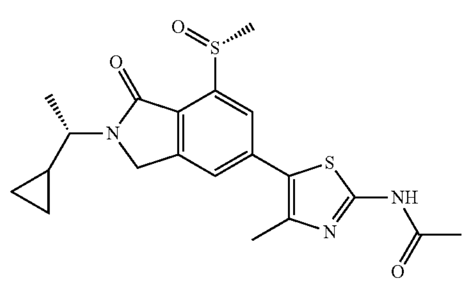 [SMILES: CC(=O)Nc1nc(C)c(-c2cc3c(c([S@@](C)=O)c2)C(=O)N([C@@H](C)C2CC2)C3)s1] | N-(5-(2-(1-cyclopropylethyl)-7-(methylsulfinyl)-1-oxoisoindolin-5-yl)-4-methylthiazol-2-yl)acetamide |

TABLE 1-continued

Representative Compounds and their flat names.

| # | Structure | Flat Name |
|---|---|---|
| 13 | | N-(5-(2-(1-cyclopropylethyl)-7-(ethylsulfinyl)-1-oxoisoindolin-5-yl)-4-methylthiazol-2-yl)acetamide |
| | | |
| 14 | | N-(5-(2-(1-cyclopropylethyl)-7-(isopropylsulfinyl)-1-oxoisoindolin-5-yl)-4-methylthiazol-2-yl)acetamide |
| | | |
| 15 | 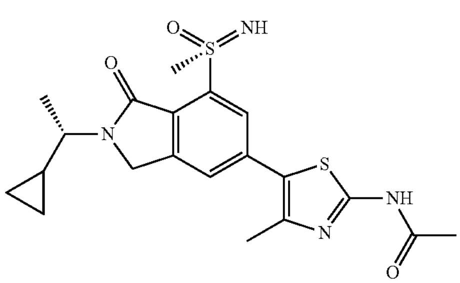 [SMILES: CC(=O)Nc1nc(C)c(-c2cc3c(c([S@](C)(=N)=O)c2)C(=O)N([C@@H](C)C2CC2)C3)s1] | N-(5-(2-(1-cyclopropylethyl)-7-(S-methylsulfonimidoyl)-1-oxoisoindolin-5-yl)-4-methylthiazol-2-yl)acetamide |

TABLE 1-continued

Representative Compounds and their flat names.

| # | Structure | Flat Name |
|---|---|---|
| 16 | 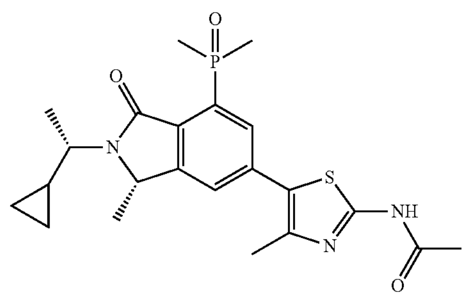 [SMILES: CC(=O)Nc1nc(C)c(-c2cc3c(c(P(C)(C)=O)c2)C(=O)N([C@@H](C)C2CC2)[C@H]3C)s1] | N-(5-(2-(1-cyclopropylethyl)-7-(dimethylphosphoryl)-3-methyl-1-oxoisoindolin-5-yl)-4-methylthiazol-2-yl)acetamide |
| 17 | 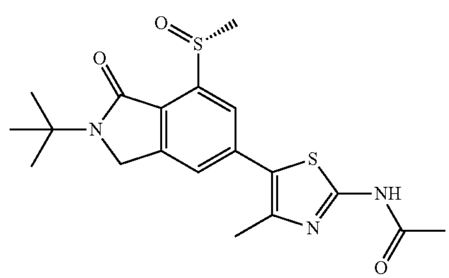 [SMILES: CC(=O)Nc1nc(C)c(-c2cc3c(c([S@@](C)=O)c2)C(=O)N(C(C)(C)C)C3)s1] | N-(5-(2-(tert-butyl)-7-(methylsulfinyl)-1-oxoisoindolin-5-yl)-4-methylthiazol-2-yl)acetamide |

TABLE 1-continued

Representative Compounds and their flat names.

| # | Structure | Flat Name |
|---|---|---|
| 18 | | N-(5-(2-(1-cyclopropylethyl)-7-(methylsulfinyl)-1-oxoisoindolin-5-yl)-4-(difluoromethyl)thiazol-2-yl)acetamide |
| 19 | 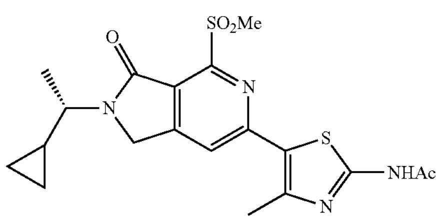 [SMILES: CC(=O)Nc1nc(C)c(-c2cc3c(c(S(C)(=O)=O)n2)C(=O)N([C@@H](C)C2CC2)C3)s1] | N-(5-(2-(1-cyclopropylethyl)-4-(methylsulfonyl)-3-oxo-2,3-dihydro-1H-pyrrolo[3,4-c]pyridin-6-yl)-4-methylthiazol-2-yl)acetamide |
| 20 | 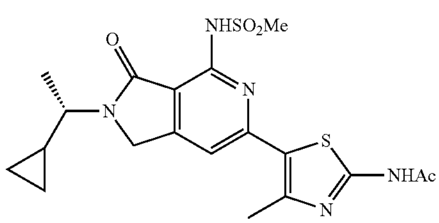 | N-(5-(2-(1-cyclopropylethyl)-4-(methylsulfonamido)-3-oxo-2,3-dihydro-1H-pyrrolo[3,4-c]pyridin-6-yl)-4-methylthiazol-2-yl)acetamide |
| 21 | 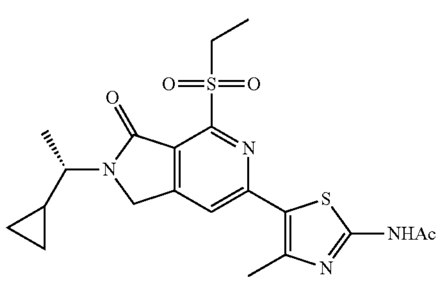 [SMILES: CCS(=O)(=O)c1nc(-c2sc(NC(C)=O)nc2C)cc2c1C(=O)N([C@@H](C)C1CC1)C2] | N-(5-(2-(1-cyclopropylethyl)-4-(ethylsulfonyl)-3-oxo-2,3-dihydro-1H-pyrrolo[3,4-c]pyridin-6-yl)-4-methylthiazol-2-yl)acetamide |
| 22 | 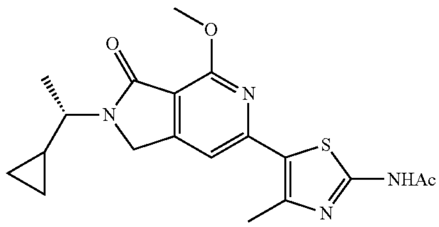 [SMILES: COc1nc(-c2sc(NC(C)=O)nc2C)cc2c1C(=O)N([C@@H](C)C1CC1)C2] | N-(5-(2-(1-cyclopropylethyl)-4-methoxy-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|-----------|-----------|
| 23 | 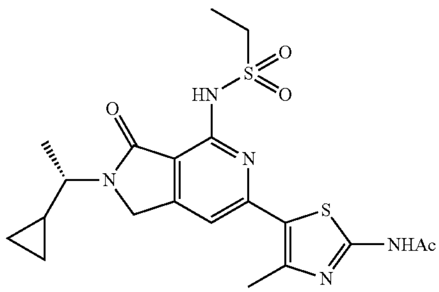 [SMILES: CCS(=O)(=O)Nc1nc(-c2sc(NC(C)=O)nc2C)cc2c1C(=O)N([C@@H](C)C1CC1)C2] | N-(5-(2-(1-cyclopropylethyl)-4-(ethylsulfonamido)-3-oxo-2,3-dihydro-1H-pyrrolo[3,4-c]pyridin-6-yl)-4-methylthiazol-2-yl)acetamide |
| 24 | 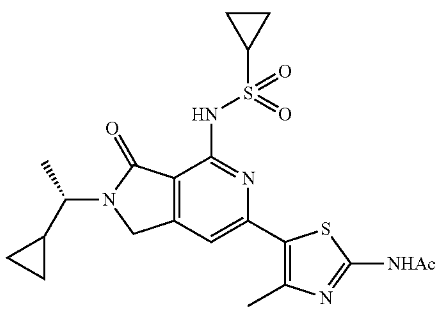 [SMILES: CC(=O)Nc1nc(C)c(-c2cc3c(c(NS(=O)(=O)C4CC4)n2)C(=O)N([C@@H](C)C2CC2)C3)s1] | N-(5-(4-(cyclopropanesulfonamido)-2-(1-cyclopropylethyl)-3-oxo-2,3-dihydro-1H-pyrrolo[3,4-c]pyridin-6-yl)-4-methylthiazol-2-yl)acetamide |
| 25 | 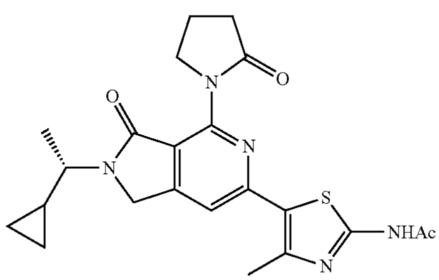 [SMILES: CC(=O)Nc1nc(C)c(-c2cc3c(c(N4CCCC4=O)n2)C(=O)N([C@@H](C)C2CC2)C3)s1] | N-(5-(2-(1-cyclopropylethyl)-3-oxo-4-(2-oxopyrrolidin-1-yl)-2,3-dihydro-1H-pyrrolo[3,4-c]pyridin-6-yl)-4-methylthiazol-2-yl)acetamide |
| 26 | 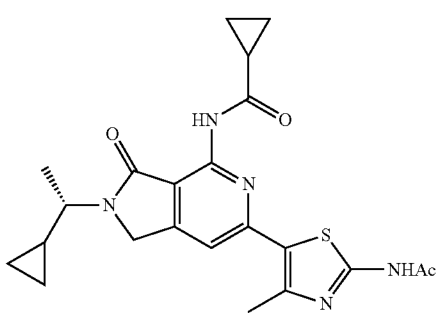 [SMILES: CC(=O)Nc1nc(C)c(-c2cc3c(c(NC(=O)C4CC4)n2)C(=O)N([C@@H](C)C2CC2)C3)s1] | N-(6-(2-acetamido-4-methylthiazol-5-yl)-2-(1-cyclopropylethyl)-3-oxo-2,3-dihydro-1H-pyrrolo[3,4-c]pyridin-4-yl)cyclopropanecarboxamide |
| 27 | 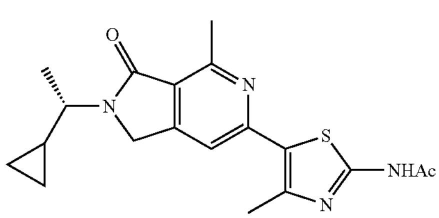 [SMILES: CC(=O)Nc1nc(C)c(-c2cc3c(c(C)n2)C(=O)N([C@@H](C)C2CC2)C3)s1] | N-(5-(2-(1-cyclopropylethyl)-4-methyl-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| 28 | 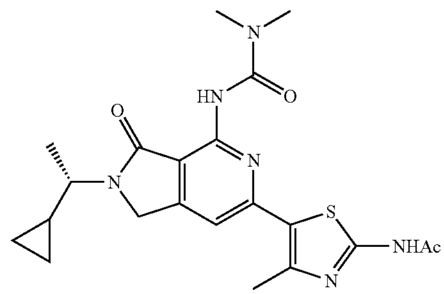 [SMILES: CC(=O)Nc1nc(C)c(-c2cc3c(c(NC(=O)N(C)C)n2)C(=O)N([C@@H](C)C2CC2)C3)s1] | N-(5-(2-(1-cyclopropylethyl)-4-(3,3-dimethylureido)-3-oxo-2,3-dihydro-1H-pyrrolo[3,4-c]pyridin-6-yl)-4-methylthiazol-2-yl)acetamide |
| 29 | 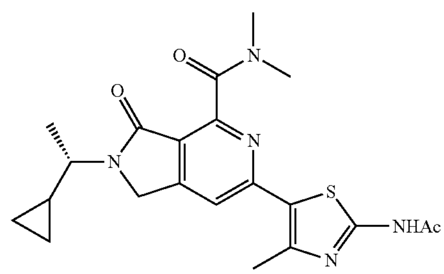 [SMILES: CC(=O)Nc1nc(C)c(-c2cc3c(c(C(=O)N(C)C)n2)C(=O)N([C@@H](C)C2CC2)C3)s1] | 6-(2-acetamido-4-methylthiazol-5-yl)-2-(1-cyclopropylethyl)-N,N-dimethyl-3-oxo-2,3-dihydro-1H-pyrrolo[3,4-c]pyridine-4-carboxamide |
| 30 | 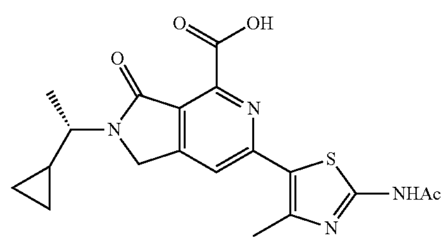 [SMILES: CC(=O)Nc1nc(C)c(-c2cc3c(c(C(=O)O)n2)C(=O)N([C@@H](C)C2CC2)C3)s1] | 6-(2-acetamido-4-methylthiazol-5-yl)-2-(1-cyclopropylethyl)-3-oxo-2,3-dihydro-1H-pyrrolo[3,4-c]pyridine-4-carboxylic acid |
| 31 | 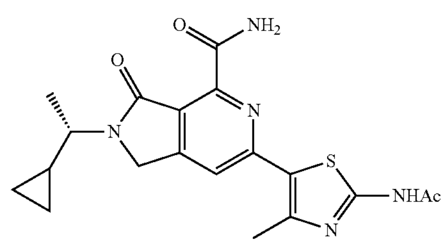 [SMILES: CC(=O)Nc1nc(C)c(-c2cc3c(c(C(N)=O)n2)C(=O)N([C@@H](C)C2CC2)C3)s1] | 6-(2-acetamido-4-methylthiazol-5-yl)-2-(1-cyclopropylethyl)-3-oxo-2,3-dihydro-1H-pyrrolo[3,4-c]pyridine-4-carboxamide |
| 32 | 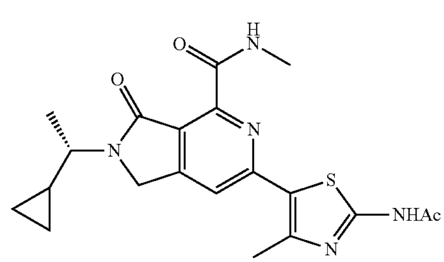 [SMILES: CNC(=O)c1nc(-c2sc(NC(C)=O)nc2C)cc2c1C(=O)N([C@@H](C)C1CC1)C2] | 6-(2-acetamido-4-methylthiazol-5-yl)-2-(1-cyclopropylethyl)-N-methyl-3-oxo-2,3-dihydro-1H-pyrrolo[3,4-c]pyridine-4-carboxamide |

TABLE 1-continued

Representative Compounds and their flat names.

| # | Structure | Flat Name |
|---|---|---|
| 33 | 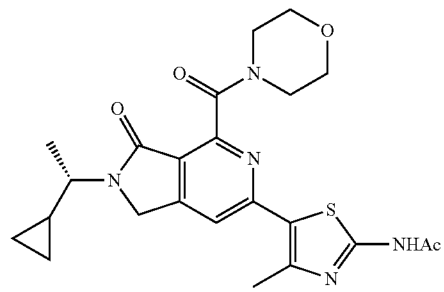 [SMILES: CC(=O)Nc1nc(C)c(-c2cc3c(c(C(=O)N4CCOCC4)n2)C(=O)N([C@@H](C)C2CC2)C3)s1] | N-(5-(2-(1-cyclopropylethyl)-4-(morpholine-4-carbonyl)-3-oxo-2,3-dihydro-1H-pyrrolo[3,4-c]pyridin-6-yl)-4-methylthiazol-2-yl)acetamide |
| 34 | 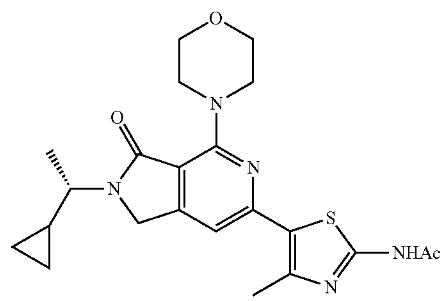 | N-(5-(2-(1-cyclopropylethyl)-4-morpholino-3-oxo-2,3-dihydro-1H-pyrrolo[3,4-c]pyridin-6-yl)-4-methylthiazol-2-yl)acetamide |
| 35 | 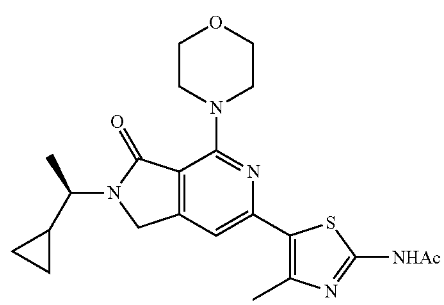 [SMILES: CC(=O)Nc1nc(C)c(-c2cc3c(c(N4CCOCC4)n2)C(=O)N([C@H](C)C2CC2)C3)s1] | N-(5-(2-(1-cyclopropylethyl)-4-morpholino-3-oxo-2,3-dihydro-1H-pyrrolo[3,4-c]pyridin-6-yl)-4-methylthiazol-2-yl)acetamide |
| 36 | 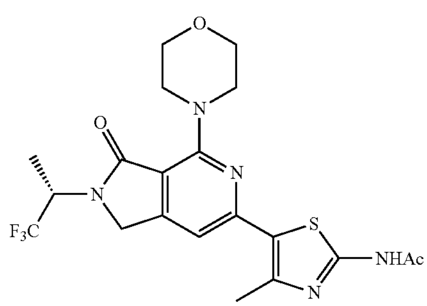 [SMILES: CC(=O)Nc1nc(C)c(-c2cc3c(c(N4CCOCC4)n2)C(=O)N([C@@H](C)C(F)(F)F)C3)s1] | N-(4-methyl-5-(4-morpholino-3-oxo-2-(1,1,1-trifluoropropan-2-yl)-2,3-dihydro-1H-pyrrolo[3,4-c]pyridin-6-yl)thiazol-2-yl)acetamide |
| 37 | 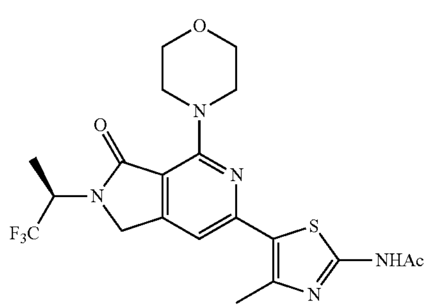 [SMILES: CC(=O)Nc1nc(C)c(-c2cc3c(c(N4CCOCC4)n2)C(=O)N([C@H](C)C(F)(F)F)C3)s1] | N-(4-methyl-5-(4-morpholino-3-oxo-2-(1,1,1-trifluoropropan-2-yl)-2,3-dihydro-1H-pyrrolo[3,4-c]pyridin-6-yl)thiazol-2-yl)acetamide |

TABLE 1-continued

Representative Compounds and their flat names.

| # | Structure | Flat Name |
|---|---|---|
| 38 | 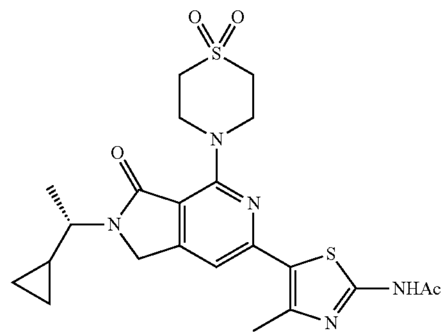 [SMILES: CC(=O)Nc1nc(C)c(-c2cc3c(c(N4CCS(=O)(=O)CC4)n2)C(=O)N([C@@H](C)C2CC2)C3)s1] | N-(5-(2-(1-cyclopropylethyl)-4-(1,1-dioxidothiomorpholino)-3-oxo-2,3-dihydro-1H-pyrrolo[3,4-c]pyridin-6-yl)-4-methylthiazol-2-yl)acetamide |
| 39 | 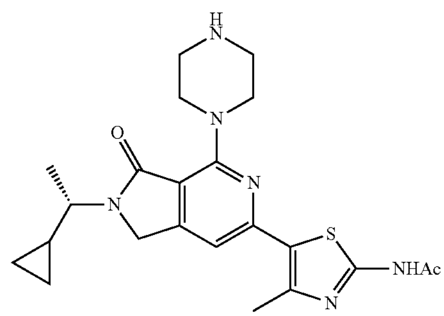 [SMILES: CC(=O)Nc1nc(C)c(-c2cc3c(c(N4CCNCC4)n2)C(=O)N([C@@H](C)C2CC2)C3)s1] | N-(5-(2-(1-cyclopropylethyl)-3-oxo-4-(piperazin-1-yl)-2,3-dihydro-1H-pyrrolo[3,4-c]pyridin-6-yl)-4-methylthiazol-2-yl)acetamide |
| 40 | 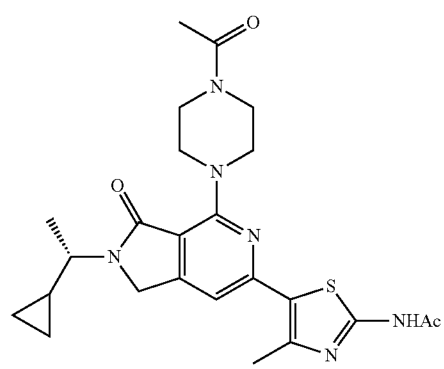 [SMILES: CC(=O)Nc1nc(C)c(-c2cc3c(c(N4CCN(C(C)=O)CC4)n2)C(=O)N([C@@H](C)C2CC2)C3)s1] | N-(5-(4-(4-acetylpiperazin-1-yl)-2-(1-cyclopropylethyl)-3-oxo-2,3-dihydro-1H-pyrrolo[3,4-c]pyridin-6-yl)-4-methylthiazol-2-yl)acetamide |
| 41 | 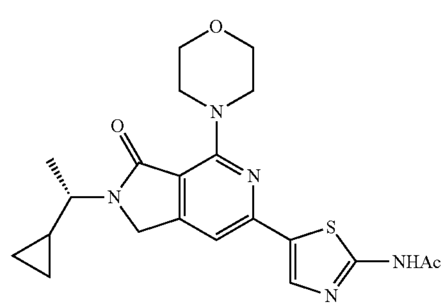 [SMILES: CC(=O)Nc1ncc(-c2cc3c(c(N4CCOCC4)n2)C(=O)N([C@@H](C)C2CC2)C3)s1] | N-(5-(2-(1-cyclopropylethyl)-4-morpholino-3-oxo-2,3-dihydro-1H-pyrrolo[3,4-c]pyridin-6-yl)thiazol-2-yl)acetamide |

TABLE 1-continued

Representative Compounds and their flat names.

| # | Structure | Flat Name |
|---|-----------|-----------|
| 42 | 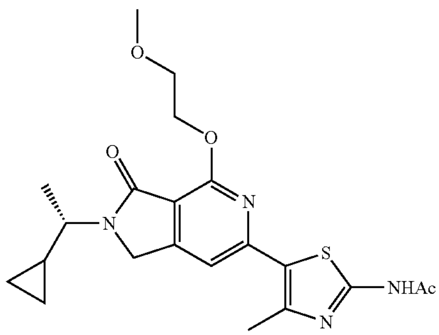 [SMILES: COCCOc1nc(-c2sc(NC(C)=O)nc2C)cc2c1C(=O)N([C@@H](C)C1CC1)C2] | N-(5-(2-(1-cyclopropylethyl)-4-(2-methoxyethoxy)-3-oxo-2,3-dihydro-1H-pyrrolo[3,4-c]pyridin-6-yl)-4-methylthiazol-2-yl)acetamide |
| 43 | 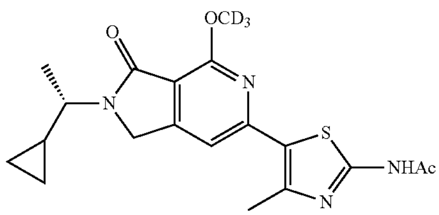 | N-(5-(2-(1-cyclopropylethyl)-4-(methoxy-d3)-3-oxo-2,3-dihydro-1H-pyrrolo[3,4-c]pyridin-6-yl)-4-methylthiazol-2-yl)acetamide |
| 44 | 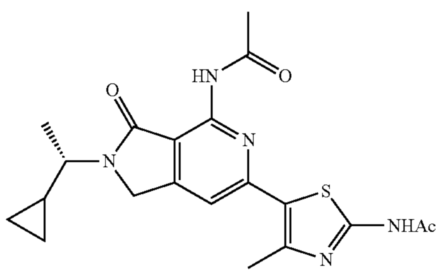 [SMILES: CC(=O)Nc1nc(C)c(-c2cc3c(c(NC(C)=O)n2)C(=O)N([C@@H](C)C2CC2)C3)s1] | N-(5-(4-acetamido-2-(1-cyclopropylethyl)-3-oxo-2,3-dihydro-1H-pyrrolo[3,4-c]pyridin-6-yl)-4-methylthiazol-2-yl)acetamide |
| 45 | 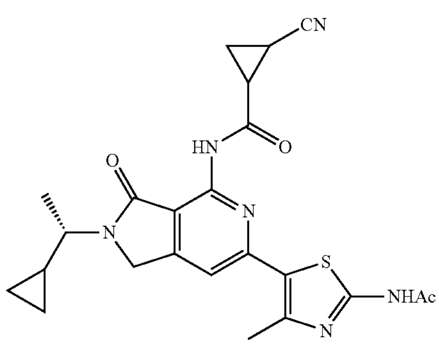 [SMILES: CC(=O)Nc1nc(C)c(-c2cc3c(c(NC(=O)C4CC4C#N)n2)C(=O)N([C@@H](C)C2CC2)C3)s1] | N-(6-(2-acetamido-4-methylthiazol-5-yl)-2-(1-cyclopropylethyl)-3-oxo-2,3-dihydro-1H-pyrrolo[3,4-c]pyridin-4-yl)-2-cyanocyclopropane-1-carboxamide |
| 46 | 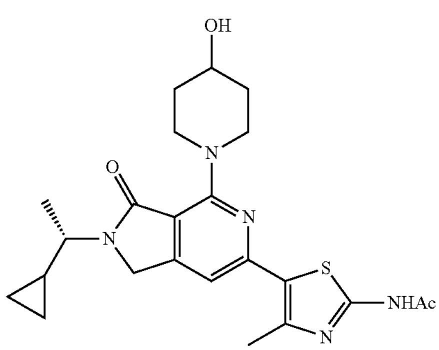 [SMILES: CC(=O)Nc1nc(C)c(-c2cc3c(c(N4CCC(O)CC4)n2)C(=O)N([C@@H](C)C2CC2)C3)s1] | N-(5-(2-(1-cyclopropylethyl)-4-(4-hydroxypiperidin-1-yl)-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| 47 | 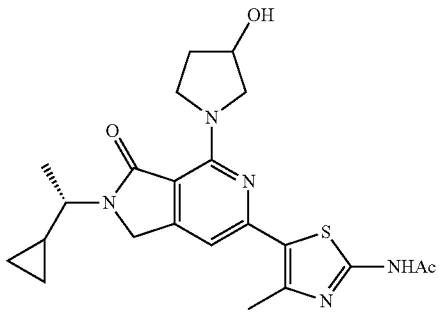 [SMILES: CC(=O)Nc1nc(C)c(-c2cc3c(c(N4CCC(O)C4)n2)C(=O)N([C@@H](C)C2CC2)C3)s1] | N-(5-(2-(1-cyclopropylethyl)-4-(3-hydroxypyrrolidin-1-yl)-3-oxo-2,3-dihydro-1H-pyrrolo[3,4-c]pyridin-6-yl)-4-methylthiazol-2-yl)acetamide |
| 48 | 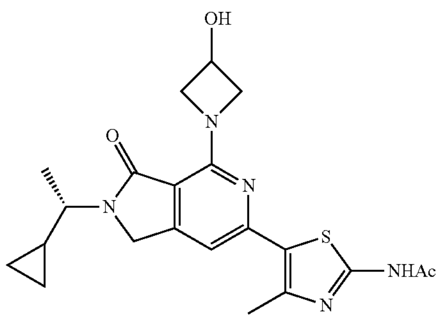 [SMILES: CC(=O)Nc1nc(C)c(-c2cc3c(c(N4CC(O)C4)n2)C(=O)N([C@@H](C)C2CC2)C3)s1] | N-(5-(2-(1-cyclopropylethyl)-4-(3-hydroxyazetidin-1-yl)-3-oxo-2,3-dihydro-1H-pyrrolo[3,4-c]pyridin-6-yl)-4-methylthiazol-2-yl)acetamide |
| 49 | 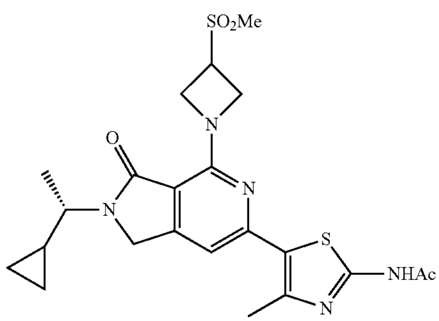 [SMILES: CC(=O)Nc1nc(C)c(-c2cc3c(c(N4CC(S(C)(=O)=O)C4)n2)C(=O)N([C@@H](C)C2CC2)C3)s1] | N-(5-(2-(1-cyclopropylethyl)-4-(3-(methylsulfonyl)azetidin-1-yl)-3-oxo-2,3-dihydro-1H-pyrrolo[3,4-c]pyridin-6-yl)-4-methylthiazol-2-yl)acetamide |
| 50 | 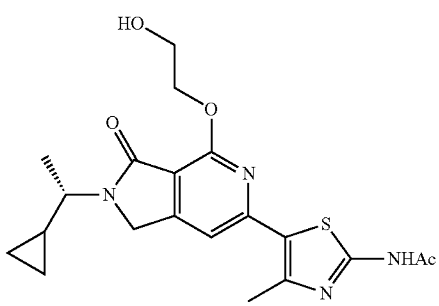 [SMILES: CC(=O)Nc1nc(C)c(-c2cc3c(c(OCCO)n2)C(=O)N([C@@H](C)C2CC2)C3)s1] | N-(5-(2-(1-cyclopropylethyl)-4-(2-hydroxyethoxy)-3-oxo-2,3-dihydro-1H-pyrrolo[3,4-c]pyridin-6-yl)-4-methylthiazol-2-yl)acetamide |
| 51 | 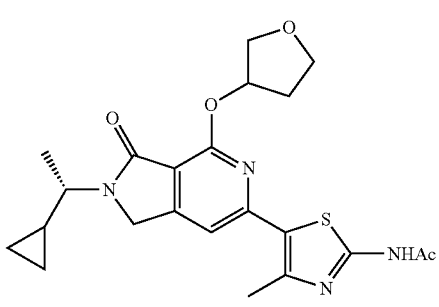 [SMILES: CC(=O)Nc1nc(C)c(-c2cc3c(c(OC4CCOC4)n2)C(=O)N([C@@H](C)C2CC2)C3)s1] | N-(5-(2-(1-cyclopropylethyl)-3-oxo-4-((tetrahydrofuran-3-yl)oxy)-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| 52 | 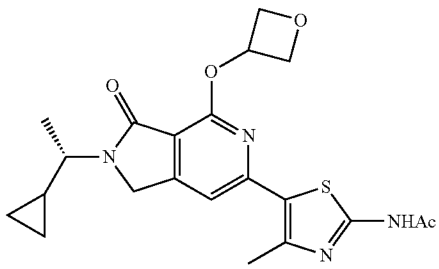 [SMILES: CC(=O)Nc1nc(C)c(-c2cc3c(c(OC4COC4)n2)C(=O)N([C@@H](C)C2CC2)C3)s1] | N-(5-(2-(1-cyclopropylethyl)-4-(oxetan-3-yloxy)-3-oxo-2,3-dihydro-1H-pyrrolo[3,4-c]pyridin-6-yl)-4-methylthiazol-2-yl)acetamide |
| 53 | 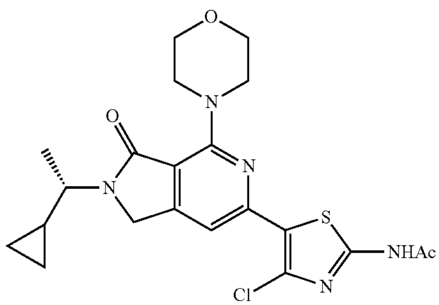 [SMILES: CC(=O)Nc1nc(Cl)c(-c2cc3c(c(N4CCOCC4)n2)C(=O)N([C@@H](C)C2CC2)C3)s1] | N-(4-chloro-5-(2-(1-cyclopropylethyl)-4-morpholino-3-oxo-2,3-dihydro-1H-pyrrolo[3,4-c]pyridin-6-yl)thiazol-2-yl)acetamide |
| 54 | 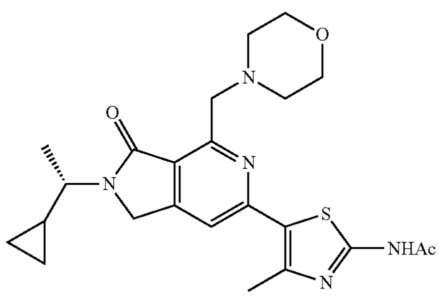 [SMILES: CC(=O)Nc1nc(C)c(-c2cc3c(c(CN4CCOCC4)n2)C(=O)N([C@@H](C)C2CC2)C3)s1] | N-(5-(2-(1-cyclopropylethyl)-4-(morpholinomethyl)-3-oxo-2,3-dihydro-1H-pyrrolo[3,4-c]pyridin-6-yl)-4-methylthiazol-2-yl)acetamide |
| 55 | 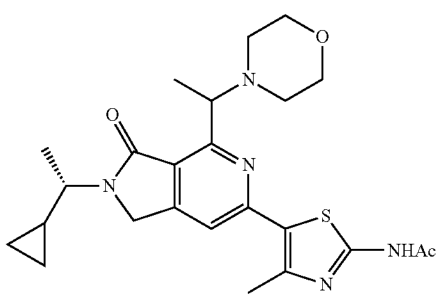 [SMILES: CC(=O)Nc1nc(C)c(-c2cc3c(c(C(C)N4CCOCC4)n2)C(=O)N([C@@H](C)C2CC2)C3)s1] | N-(5-(2-(1-cyclopropylethyl)-4-(1-morpholinoethyl)-3-oxo-2,3-dihydro-1H-pyrrolo[3,4-c]pyridin-6-yl)-4-methylthiazol-2-yl)acetamide |
| 56 | 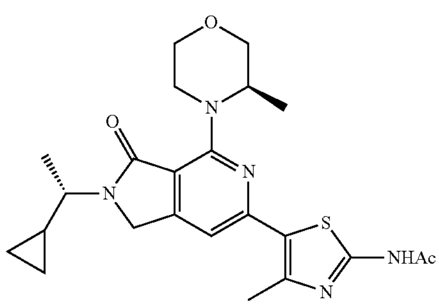 [SMILES: CC(=O)Nc1nc(C)c(-c2cc3c(c(N4CCOC[C@H]4C)n2)C(=O)N([C@@H](C)C2CC2)C3)s1] | N-(5-(2-(1-cyclopropylethyl)-4-(3-methylmorpholino)-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| | | |
| 57 | 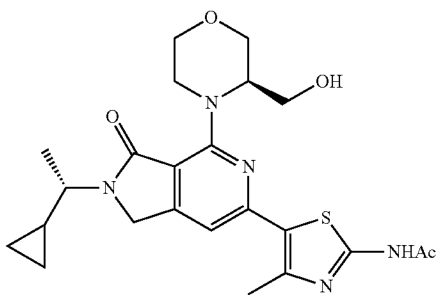 [SMILES: CC(=O)Nc1nc(C)c(-c2cc3c(c(N4CCOC[C@H]4CO)n2)C(=O)N([C@@H](C)C2CC2)C3)s1] | N-(5-(2-(1-cyclopropylethyl)-4-(3-(hydroxymethyl)morpholino)-3-oxo-2,3-dihydro-1H-pyrrolo[3,4-c]pyridin-6-yl)-4-methylthiazol-2-yl)acetamide |
| 58 | 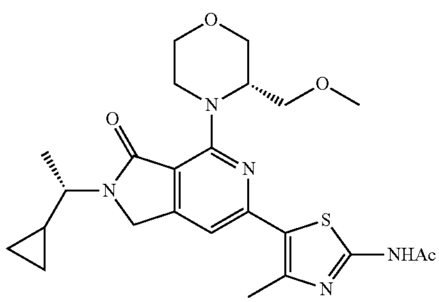 [SMILES: COC[C@H]1COCCN1c1nc(-c2sc(NC(C)=O)nc2C)cc2c1C(=O)N([C@@H](C)C1CC1)C2] | N-(5-(2-(1-cyclopropylethyl)-4-(3-(hydroxymethyl)morpholino)-3-oxo-2,3-dihydro-1H-pyrrolo[3,4-c]pyridin-6-yl)-4-methylthiazol-2-yl)acetamide |
| 59 | 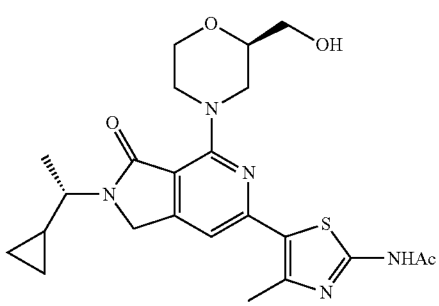 [SMILES: CC(=O)Nc1nc(C)c(-c2cc3c(c(N4CCO[C@@H](CO)C4)n2)C(=O)N([C@@H](C)C2CC2)C3)s1] | N-(5-(2-(1-cyclopropylethyl)-4-(2-(hydroxymethyl)morpholino)-3-oxo-2,3-dihydro-1H-pyrrolo[3,4-c]pyridin-6-yl)-4-methylthiazol-2-yl)acetamide |
| 60 | 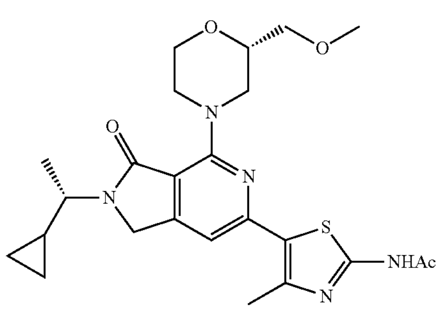 [SMILES: COC[C@@H]1CN(c2nc(-c3sc(NC(C)=O)nc3C)cc3c2C(=O)N([C@@H](C)C2CC2)C3)CCO1] | N-(5-(2-(1-cyclopropylethyl)-4-(2-(methoxymethyl)morpholino)-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| 61 | 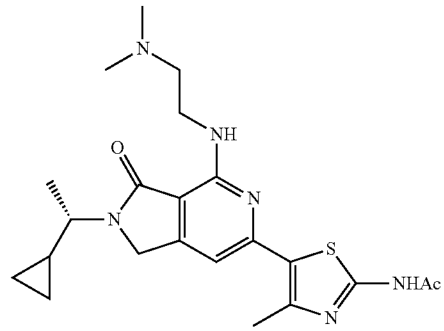 [SMILES: CC(=O)Nc1nc(C)c(-c2cc3c(c(NCCN(C)C)n2)C(=O)N([C@@H](C)C2CC2)C3)s1] | N-(5-(2-(1-cyclopropylethyl)-4-((2-(dimethylamino)ethyl)amino)-3-oxo-2,3-dihydro-1H-pyrrolo[3,4-c]pyridin-6-yl)-4-methylthiazol-2-yl)acetamide |
| 62 | 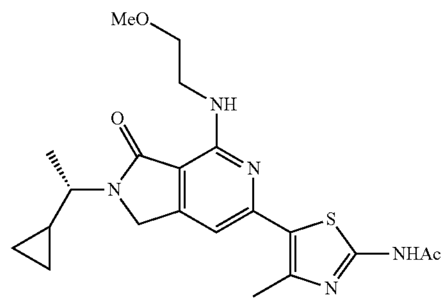 [SMILES: COCCNc1nc(-c2sc(NC(C)=O)nc2C)cc2c1C(=O)N([C@@H](C)C1CC1)C2] | N-(5-(2-(1-cyclopropylethyl)-4-((2-methoxyethyl)amino)-3-oxo-2,3-dihydro-1H-pyrrolo[3,4-c]pyridin-6-yl)-4-methylthiazol-2-yl)acetamide |
| 63 | 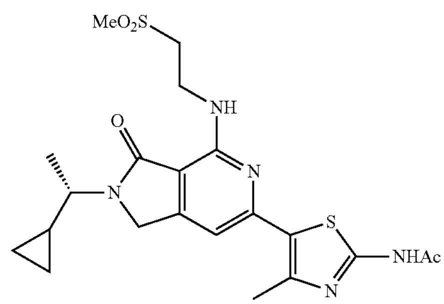 [SMILES: CC(=O)Nc1nc(C)c(-c2cc3c(c(NCCS(C)(=O)=O)n2)C(=O)N([C@@H](C)C2CC2)C3)s1] | N-(5-(2-(1-cyclopropylethyl)-4-((2-(methylsulfonyl)ethyl)amino)-3-oxo-2,3-dihydro-1H-pyrrolo[3,4-c]pyridin-6-yl)-4-methylthiazol-2-yl)acetamide |
| 64 | 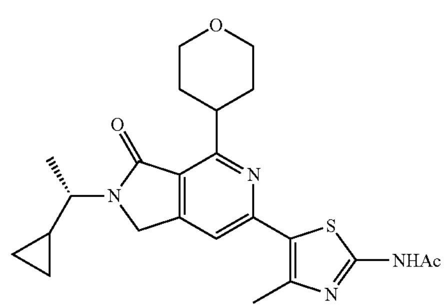 [SMILES: CC(=O)Nc1nc(C)c(-c2cc3c(c(C4CCOCC4)n2)C(=O)N([C@@H](C)C2CC2)C3)s1] | N-(5-(2-(1-cyclopropylethyl)-3-oxo-4-(tetrahydro-2H-pyran-4-yl)-2,3-dihydro-1H-pyrrolo[3,4-c]pyridin-6-yl)-4-methylthiazol-2-yl)acetamide |
| 65 | 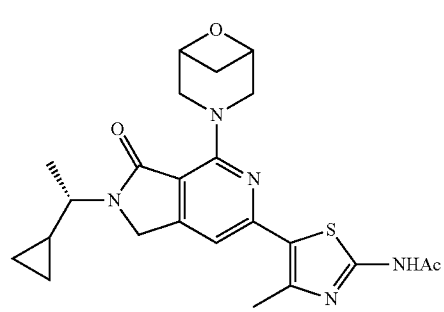 [SMILES: CC(=O)Nc1nc(C)c(-c2cc3c(c(N4CC5CC(C4)O5)n2)C(=O)N([C@@H](C)C2CC2)C3)s1] | N-(5-(4-(6-oxa-3-azabicyclo[3.1.1]heptan-3-yl)-2-(1-cyclopropylethyl)-3-oxo-2,3-dihydro-1H-pyrrolo[3,4-c]pyridin-6-yl)-4-methylthiazol-2-yl)acetamide |

TABLE 1-continued

Representative Compounds and their flat names.

| # | Structure | Flat Name |
|---|---|---|
| 66 | 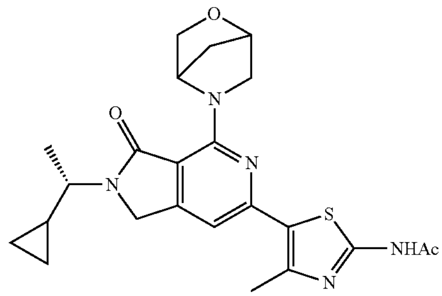 [SMILES: CC(=O)Nc1nc(C)c(-c2cc3c(c(N4CC5CC4CO5)n2)C(=O)N([C@@H](C)C2CC2)C3)s1] | N-(5-(4-(2-oxa-5-azabicyclo[2.2.1]heptan-5-yl)-2-(1-cyclopropylethyl)-3-oxo-2,3-dihydro-1H-pyrrolo[3,4-c]pyridin-6-yl)-4-methylthiazol-2-yl)acetamide |
| 67 | 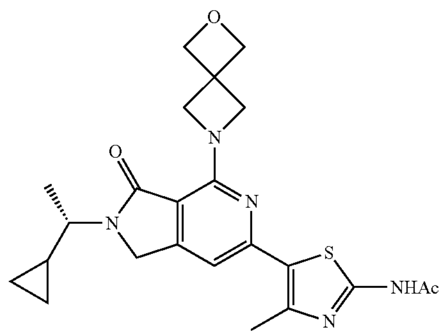 [SMILES: CC(=O)Nc1nc(C)c(-c2cc3c(c(N4CC5(COC5)C4)n2)C(=O)N([C@@H](C)C2CC2)C3)s1] | N-(5-(2-(1-cyclopropylethyl)-3-oxo-4-(2-oxa-6-azaspiro[3.3]heptan-6-yl)-2,3-dihydro-1H-pyrrolo[3,4-c]pyridin-6-yl)-4-methylthiazol-2-yl)acetamide |
| 68 | 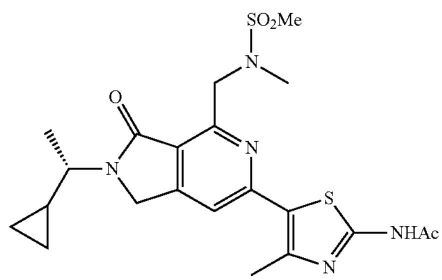 [SMILES: CC(=O)Nc1nc(C)c(-c2cc3c(c(CN(C)S(C)(=O)=O)n2)C(=O)N([C@@H](C)C2CC2)C3)s1] | N-(5-(2-(1-cyclopropylethyl)-4-((N-methylmethylsulfonamido)methyl)-3-oxo-2,3-dihydro-1H-pyrrolo[3,4-c]pyridin-6-yl)-4-methylthiazol-2-yl)acetamide |
| 69 | 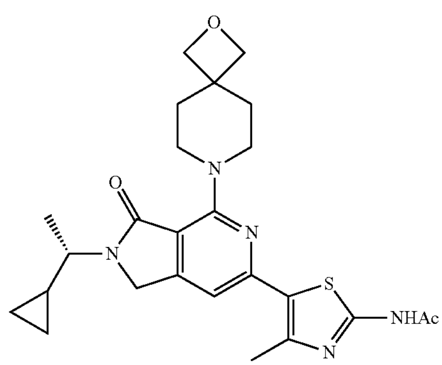 [SMILES: CC(=O)Nc1nc(C)c(-c2cc3c(c(N4CCC5(CC4)COC5)n2)C(=O)N([C@@H](C)C2CC2)C3)s1] | N-(5-(2-(1-cyclopropylethyl)-3-oxo-4-(2-oxa-7-azaspiro[3.5]nonan-7-yl)-2,3-dihydro-1H-pyrrolo[3,4-c]pyridin-6-yl)-4-methylthiazol-2-yl)acetamide |

Provided are also compounds of Formula (I) including (I-a), (I-b), (I-c), and (I-d), or pharmaceutically acceptable salts, prodrugs, or solvates thereof. In certain embodiments, provided herein are also crystalline and amorphous forms of the compounds of Formula (I) including (I-a), (I-b), (I-c), and (I-d), or pharmaceutically acceptable salts, stereoisomers, prodrugs, or solvents thereof.

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$).

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

"Pharmaceutically-acceptable salt" means a salt prepared by conventional means, and are well known by those skilled in the art. The "pharmacologically acceptable salts" include basic salts of inorganic and organic acids (Berge et al., J. Pharm. Sci. 1977, 66:1). "Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases which can be used to prepared salts include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. "Pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

A "solvate" is formed by treating a compound in a solvent. Solvates of salts of the compounds of Formula (I) including (I-a), (I-b), (I-c), and (I-d) are also provided. In the case of treating compounds with water, the solvate is hydrates. Hydrates of the compounds of Formula (I) including (I-a), (I-b), (I-c), and (I-d) are also provided.

A "prodrug" includes any compound that converts into a compound of Formula (I) including (I-a), (I-b), (I-c), and (I-d), when administered to a subject, e.g., upon metabolic processing of the prodrug.

Therapeutic Uses of the Compounds

The compounds of Formula (I) including (I-a), (I-b), (I-c), and (I-d), or pharmaceutically acceptable salt, stereoisomer, prodrug, or solvate thereof may be used for treating PI3K mediated diseases or disorders. In one embodiment, provided are methods for inhibiting PI3K gamma activity using a compound of Formula (I) including (I-a), (I-b), (I-c), and (I-d), or a pharmaceutically acceptable salt, stereoisomer, prodrug, or solvate thereof.

In addition to the therapeutic uses described herein, selected compounds of Formula (I) including (I-a), (I-b), (I-c), and (I-d), or a pharmaceutically acceptable salt, stereoisomer, prodrug, or solvate thereof, have improved physicochemical and pharmacokinetic properties, for an example, improved solubility in water and oral bioavailability.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of an individual. In some embodiments, "treatment" of a disorder does not include prevention of the disorder, and "prevention" is understood to refer to the prophylactic administration of a drug to substantially diminish the likelihood or severity of a disorder or biological manifestation thereof, or to delay the onset of such disorder or biological manifestation thereof.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount is an amount sufficient to delay development. In some embodiments, an effective amount is an amount sufficient to prevent or delay recurrence. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "subject" is a mammal, including humans. A subject includes, but is not limited to, human, bovine, horse, feline, canine, rodent, or primate. In some embodiments, the subject is human (including adults and children).

"Inhibition of PI3K gamma activity" or variants refer to a decrease in PI3K gamma activity as a direct or indirect response to the presence of a compound of Formula (I) including (I-a), (I-b), (I-c), and (I-d), or a pharmaceutically acceptable salt, stereoisomer, prodrug, or solvate thereof, relative to the activity of PI3K gamma in the absence of the compound of Formula (I) including (I-a), (I-b), (I-c), and (I-d), or a pharmaceutically acceptable salt, stereoisomer, prodrug, or solvate thereof.

The term "PI3K gamma selective inhibitor" generally refers to a compound that inhibits the activity of the PI3K gamma isoform more effectively than other isoforms of the PI3K family (e.g., PI3K alpha, beta, or delta).

The potencies of compounds as inhibitors of an enzyme activity (or other biological activity) can be established by determining the concentrations at which each compound inhibits the activity to a predefined extent and then comparing the results. "IC50" or "IC90" of an inhibitor can be determined by the concentration that inhibits 50% or 90% of the activity in a biochemical assay, which can be accomplished using conventional techniques known in the art, including the techniques describes in the Examples below.

PI3K gamma is expressed primarily in hematopoietic cells including leukocytes such as T-cells, dendritic cells, neutrophils, mast cells, B-cells, and macrophages. Due to its integral role in immune system function, PI3K gamma is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. By inhibiting aberrant proliferation of hematopoietic cells, PI3K gamma inhibitors can ameliorate the symptoms and secondary conditions that result from a primary effect such as excessive system or localized levels of leukocytes or lymphocytes.

In one aspect, the invention thus provides a method of treating a disorder mediated by inappropriate PI3-kinase activity comprising administering a safe and effective dose of a compound of Formula (I) including (I-a), (I-b), (I-c), and (I-d), or a pharmaceutically acceptable salt, stereoisomer, prodrug, or solvate thereof.

In one embodiment, PI3K mediated diseases or disorders are selected from the group consisting of respiratory diseases (including asthma, chronic obstructive pulmonary disease (COPD) and idiopathic pulmonary fibrosis (IPF)); allergic diseases (including allergic rhinitis and atopic dermatitis); autoimmune diseases (including SLE, rheumatoid arthritis and multiple sclerosis); inflammatory disorders (including inflammatory bowel disease); hematologic malignancies; solid tumors; neurodegenerative diseases; pancreatitis; kidney diseases; transplantation rejection; graft rejection; lung injuries In one embodiment, the compounds described herein may be used to treat cancers that are mediated by inappropriate PI3K gamma activity. In certain embodiments, the disease is a hematologic malignancy. In certain embodiments, the disease is lymphoma, such as Burkitt lymphoma, diffuse large B-cell lymphoma (DLBCL) and mantle cell lymphoma (MCL), follicular lymphoma, lymphoplasmacytic lymphoma, Waldenstrom macroglobulinemia, and marginal zone lymphoma. In one embodiment, the disorder is multiple myeloma, or leukemia, such as acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML).

In other embodiments, the disease is a solid tumor. In particular embodiments, the indication is to treat solid tumor with abnormal PI3K gamma expression, such as pancreatic ductal adenocarcinoma (PDAC) and hepatocellular carcinoma (HCC), gastrointestinal cancer, prostate cancer, ovarian cancer, medulloblastoma, and breast cancer. In some embodiment, the compounds alone or with combination of other anti-cancer therapies may be used to treat prostate cancer, bladder cancer, colorectal cancer, renal cancer, hepatocellular cancer, lung cancer, ovarian cancer, cervical cancer, head and neck cancer, melanoma, neuroendocrine cancers, brain tumors, bone cancer, or soft tissue sarcoma.

In some embodiments, PI3K mediated diseases or disorders are severe autoimmune disease as asthma, type I diabetes, rheumatoid arthritis, multiple sclerosis, chronic obstructive pulmonary disease (COPD), and lupus.

Combination Therapies

In one embodiment, a compound of Formula (I) including (I-a), (I-b), (I-c), and (I-d), or a pharmaceutically acceptable salt, stereoisomer, prodrug, or solvate may be used in combination with one or more additional therapeutic agents to treat cancers or inflammatory disorders. The one or more additional therapeutic agents may be a chemotherapeutic agent, a radiotherapy, a targeted therapy, an immunotherapeutic agent or any current best of care treatment, either as a small molecule or a biologic nature.

Targeted therapies include but not limit to an inhibitor to cyclin-dependent kinase (CDK) such as CDK1, CDK2, CDK4/6, CDK7, and CDK9, Janus kinase (JAK) such as JAK1, JAK2 and/or JAK3, spleen tyrosine kinase (SYK), Bruton's tyrosine kinase (BTK), mitogen-activated protein kinase (MEK) such as MEK 1 and MEK2, bromodomain containing protein inhibitor (BRD) such as BRD4, isocitrate dehydrogenase (IDH) such as IDHL histone deacetylase (HDAC), or any combination thereof.

Chemotherapeutic agents may be categorized by their mechanism of action into: alkylating agents, antimetabolites, anti-microtubule agents, topoisomerase inhibitors and cytotoxic agents. A compound of Formula (I) including (I-a), (I-b), (I-c), and (I-d), or a pharmaceutically acceptable salt, stereoisomer, prodrug, or solvate may be used in combination with chemotherapeutics to sensitize and improve the efficacy of certain chemotherapeutic agents to treat blood or solid tumors.

The immunotherapeutic agents include and are not limited to therapeutic antibodies, small molecules and vaccines suitable for treating patients; such as IDO1 and TDO2 inhibitors, A2A receptor inhibitors, arginase inhibitors, toll-like receptor agonists, chemokine regulators (including CCR and CXCR families), check point blockage antibodies such as antibodies that regulate PD-1, PD-L1, CTLA-4, OX40-OX40 ligand, LAGS, TIM3, or any combination thereof.

Radiotherapy is part of cancer treatment to control or kill malignant cells and commonly applied to the cancerous tumor because of its ability to control cell growth. A compound of Formula (I) including (I-a), (I-b), (I-c), and (I-d), or a pharmaceutically acceptable salt, stereoisomer, prodrug, or solvate may be used in combination with radiotherapy, to improve the efficacy of radiotherapy to treat blood or solid tumors, or with surgery, chemotherapy, immunotherapy and combination of the four.

In certain embodiments, a compound of Formula (I) including (I-a), (I-b), (I-c), and (I-d), or a pharmaceutically acceptable salt, stereoisomer, prodrug, or solvate may be used in combination with one or more additional therapeutic agents to treat patients who are substantially refractory to at least one chemotherapy treatment, or in relapse after treatment with chemotherapy.

Pharmaceutical Compositions

In another aspect, the present invention provides a pharmaceutical composition comprising a compound of Formula (I) including (I-a), (I-b), (I-c), and (I-d), or a pharmaceutically acceptable salt, stereoisomer, prodrug, or solvate salt thereof and a pharmaceutically acceptable carrier or excipient. The pharmaceutical composition can be formulated for particular routes of administration such as oral administration, parenteral administration, and topical administration, etc.

Compositions intended for oral use are prepared according to any method known in the art for the manufacture of pharmaceutical compositions and can be prepared in the form of tablets, pills, powders, suspensions, emulsions, solutions, syrups, and capsules. Oral composition may contain the active ingredient in admixture with nontoxic pharmaceutically acceptable excipients which are suitable for the manufacture of tablets. The tablets are uncoated or coated by known techniques to delay disintegration and absorption in the gastrointestinal tract and thereby provide a sustained action over a longer period. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or spray formulations, e.g., for delivery by aerosol or the like. Such topical delivery systems will in particular be appropriate for dermal application, e.g., for the treatment of skin cancer, e.g., for prophylactic use in sun creams, lotions, sprays and the like.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Modes of Administration and Dosing

The pharmaceutical compositions may be administered in either single or multiple doses. A compound of Formula (I) including (I-a), (I-b), (I-c), and (I-d), or a pharmaceutically acceptable salt, stereoisomer, prodrug, or solvate salt thereof can be formulated so as to provide the desired release schedule of the active ingredient based on the therapeutic treatment purpose.

The pharmaceutical composition is preferably made in the form of a dosage unit containing a particular amount of the active ingredient in the form of tablets, pills, powders, suspensions, emulsions, solutions, syrups, and capsules. For example, these may contain an amount of active ingredient from about 0.1 to 1000 mg, preferably from about 0.1 to 500 mg. A suitable daily dose for a human or other mammal may vary widely depending on the condition of the patient and other factors, but, once again, can be determined using routine methods. The daily dose can be administered in one to four doses per day. For therapeutic purposes, the active compounds of this invention are ordinarily combined with one or more adjuvants appropriate to the indicated route of administration drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g. from 1% to 2% by weight of the formulation, preferably not more than 5% w/w, and more preferably from 0.1% to 1% of the formulation.

In a particular embodiment, the method comprises administering to the subject an initial daily dose of about 0.1 to 500 mg of a compound of Formula (I) including (I-a), (I-b), (I-c), and (I-d) and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds

The compounds of Formula (I) including (I-a), (I-b), (I-c), and (I-d) may be prepared using the methods disclosed herein and routine modifications thereof, which will be apparent given the disclosure herein and methods are well known in the art. Conventional and well-known synthetic methods may be used in addition to the teachings herein. The synthesis of representative compounds described herein may be accomplished as described in the following examples. If available, reagents may be purchased commercially, e.g., from Sigma Aldrich or other chemical suppliers.

Enumerated Embodiments

1. A selective phosphoinositide 3-kinase gamma (PI3K) inhibitor compound having a structure of formula (A), or a pharmaceutically acceptable salt, or solvate thereof. In one embodiment, provided is a compound of formula (A), or a pharmaceutically acceptable salt, prodrug, or solvate wherein:

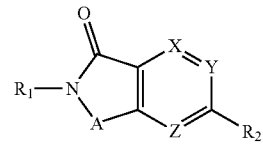

Formula (A)

A is selected from $CH_2$, CH(Me), O, and S;
X is selected from N, CH, and CR;
When Y=Z=CH, X is selected from N, CH and CR,
R is selected from:

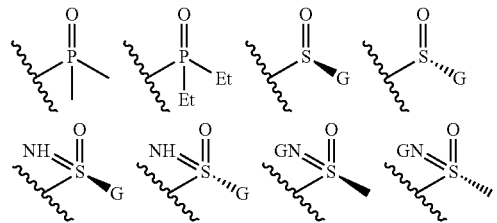

G is selected from $C_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

Y is CH or N
Z is CH or N
When either Z or Y is N and X=CH and CR, R is selected from the following groups:
NHSO$_2$G, SO$_2$G, SO$_2$NHG, OG, H, Me and

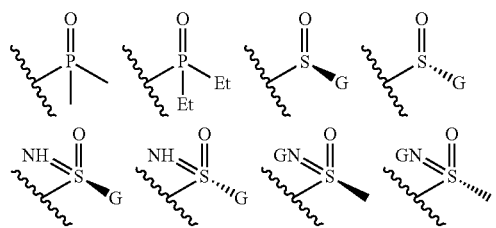

G is selected from C$_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

R1 is branched alkane, including substituted cyclopropanes, cyclobutanes and alkyl fluorides, selected from:

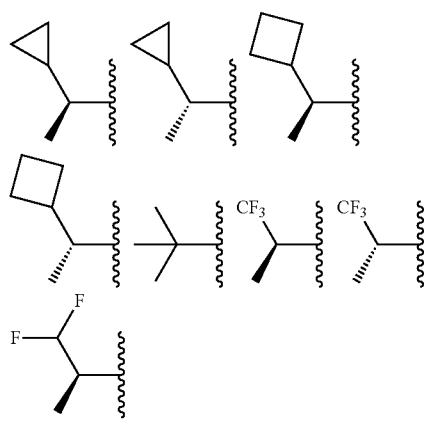

In one embodiment of formula (A), R$_2$ is selected from:

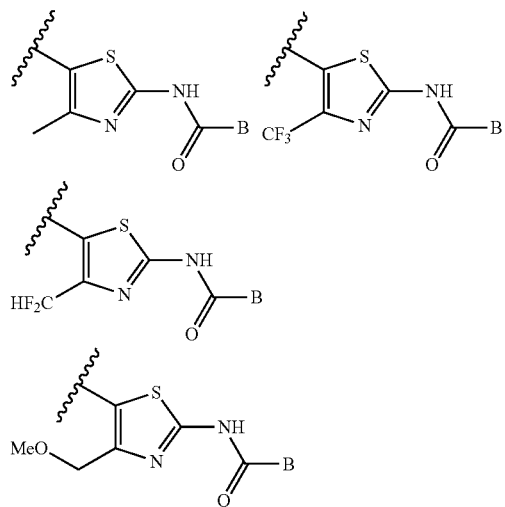

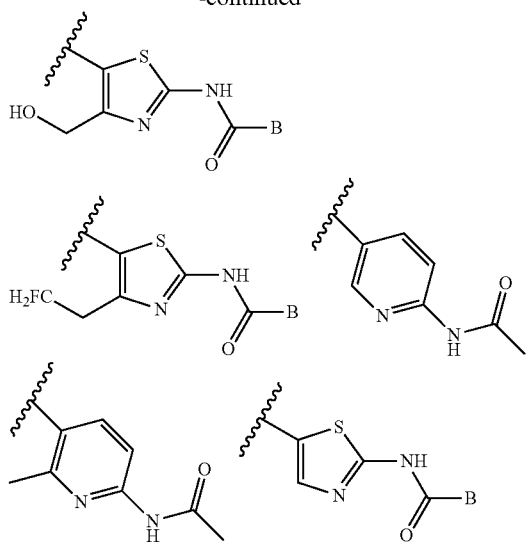

In one embodiment, B is selected from: Me, Et, isopropyl, cyclopropyl, monofluoromethyl and difluoromethyl.

2. The selective phosphoinositide 3-kinase gamma (PI3Kγ) inhibitor compound of embodiment 1, wherein A is independently selected for the group consisting of O, S, CH$_2$, and CH(Me), or a pharmaceutically acceptable salt, or solvate thereof.

3. The selective phosphoinositide 3-kinase gamma (PI3Kγ) inhibitor compound of embodiment 1, wherein X is N, each of Y and Z is CH, or a pharmaceutically acceptable salt, or solvate thereof.

4. The selective phosphoinositide 3-kinase gamma (PI3Kγ) inhibitor compound of embodiment 1, wherein X is CH, each of Y and Z is CH, or a pharmaceutically acceptable salt, or solvate thereof.

5. The selective phosphoinositide 3-kinase gamma (PI3Kγ) inhibitor compound of embodiment 1, wherein X is CR, each of Y and Z is CH, or a pharmaceutically acceptable salt, or solvate thereof, R is selected from:

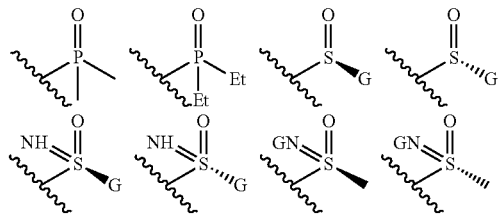

G is selected from C$_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

6. The selective phosphoinositide 3-kinase gamma (PI3Kγ) inhibitor compound of embodiment 1, wherein X is CR, Y is N and Z is CH, or a pharmaceutically acceptable salt, or solvate thereof, R is selected from NHSO$_2$G, SO$_2$G, SO$_2$NHG, OG, H, Me, and

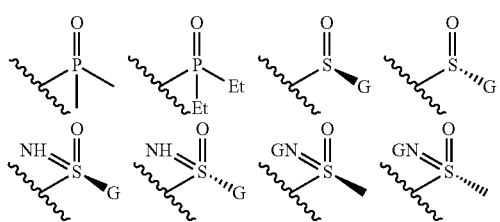

G is selected from C$_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

7. The selective phosphoinositide 3-kinase gamma (PI3Kγ) inhibitor compound of embodiment 1, wherein A is O or S, each of Y and Z is CH, or a pharmaceutically acceptable salt, or solvate thereof.

8. The selective phosphoinositide 3-kinase gamma (PI3Kγ) inhibitor compound of embodiment 1, wherein A is CH$_2$, each of Y and Z is CH, X is CR, R is

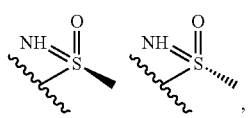

, or a pharmaceutically acceptable salt, or solvate thereof.

9. A method of selectively inhibiting a growth or a proliferation phosphoinositide 3-kinase gamma (PI3Kγ) comprising: contacting kinase cells with an effective amount of a phosphoinositide 3-kinase gamma (PI3Kγ) inhibitor compound having a structure of formula (A), or a pharmaceutically acceptable salt, or solvate thereof:

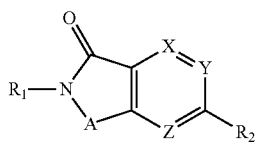

(A)

A is selected from CH$_2$, CH(Me), O, and S;
X is selected from N, CH, and CR;
When Y=Z=CH, X is selected from N, CH and CR, R is selected from:

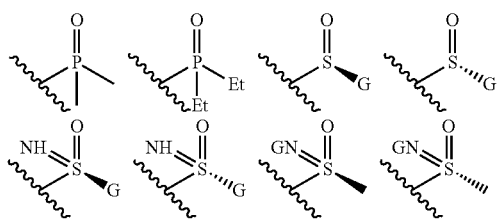

G is selected from C$_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

Y is CH or N
Z is CH or N
When either Z or Y is N and X=CH and CR, R is selected from the following groups:
NHSO$_2$G, SO$_2$G, SO$_2$NHG, OG, H, Me and

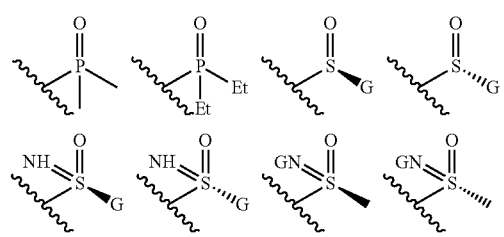

G is selected from C$_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

R1 is branched alkane, including substituted cyclopropanes, cyclobutanes and alkyl fluorides, selected from:

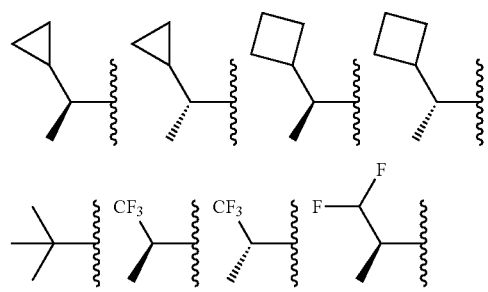

In some embodiments of formula (A), R2 is selected from:

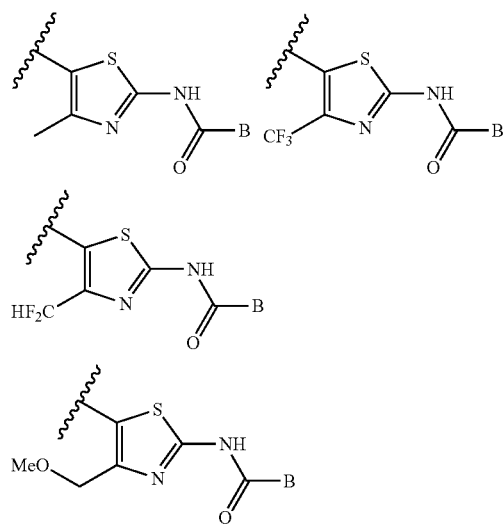

-continued

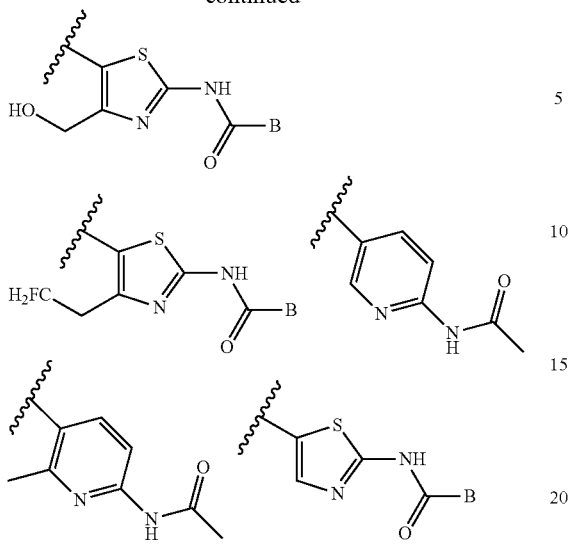

In some embodiments, B is selected from: Me, Et, isopropyl, cyclopropyl, monofluoromethyl and difluoromethyl.

10. The method of selectively inhibiting a growth or a proliferation phosphoinositide 3-kinase gamma (PI3Kγ) according to embodiment 9, wherein A is independently selected for the group consisting of CH₂, O and S, or a pharmaceutically acceptable salt, or solvate thereof.

11. The method of selectively inhibiting a growth or a proliferation phosphoinositide 3-kinase gamma (PI3Kγ) according to embodiment 9, wherein X is N, each of Y and Z is CH, or a pharmaceutically acceptable salt, or solvate thereof 12. The method of selectively inhibiting a growth or a proliferation phosphoinositide 3-kinase gamma (PI3Kγ) according to embodiment 9, wherein A is independently selected for the group consisting of O, S, CH₂, and CH(Me), or a pharmaceutically acceptable salt, or solvate thereof.

13. The method of selectively inhibiting a growth or a proliferation phosphoinositide 3-kinase gamma (PI3Kγ) according to embodiment 9, wherein X is N, each of Y and Z is CH, or a pharmaceutically acceptable salt, or solvate thereof 14. The method of selectively inhibiting a growth or a proliferation phosphoinositide 3-kinase gamma (PI3Kγ) according to embodiment 9, wherein X is CH, each of Y and Z is CH, or a pharmaceutically acceptable salt, or solvate thereof 15. The method of selectively inhibiting a growth or a proliferation phosphoinositide 3-kinase gamma (PI3Kγ) according to embodiment 9, wherein X is CR, each of Y and Z is CH, or a pharmaceutically acceptable salt, or solvate thereof, R is selected from:

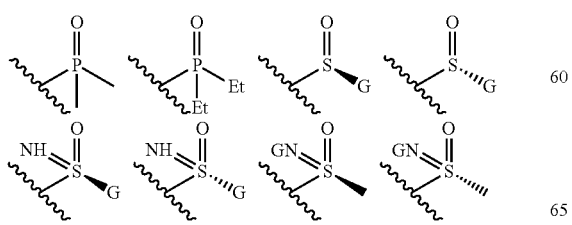

G is selected from $C_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

16. The method of selectively inhibiting a growth or a proliferation phosphoinositide 3-kinase gamma (PI3Kγ) according to embodiment 9, wherein X is CR, Y is N and Z is CH, or a pharmaceutically acceptable salt, or solvate thereof, R is selected from NHSO₂G, SO₂G, SO₂NHG, OG, H, Me, and

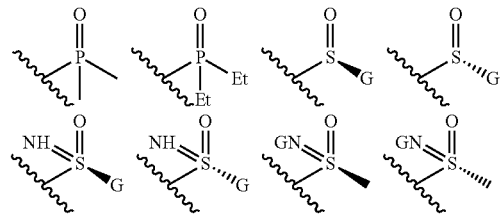

G is selected from $C_{1-4}$ alkyl, optionally substituted with OH and F, such as methyl, ethyl, isopropyl, cyclopropyl, trifluoroethyl, 2-hydroxyethyl, 2-methoxyethyl, 3-hydroxypropyl, 3-methoxypropyl.

17. The method of selectively inhibiting a growth or a proliferation phosphoinositide 3-kinase gamma (PI3Kγ) according to embodiment 9, wherein A is O or S, each of Y and Z is CH, or a pharmaceutically acceptable salt, or solvate thereof.

18. The method of selectively inhibiting a growth or a proliferation phosphoinositide 3-kinase gamma (PI3Kγ) according to embodiment 9, wherein A is CH₂, each of Y and Z is CH, X is CR, R is

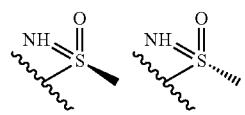

, or a pharmaceutically acceptable salt, or solvate thereof.

19. The method of selectively inhibiting a growth or a proliferation phosphoinositide 3-kinase gamma (PI3Kγ) according to embodiment 9, wherein the compound has optimized selectivity over PI3Kδ over a known PI3K gamma inhibitor.

20. A selective phosphoinositide 3-kinase gamma (PI3Kγ) inhibitor having a structure of formula (A), or a pharmaceutically acceptable salt, prodrug or solvate thereof: provided is a compound of formula (A), or a pharmaceutically acceptable salt, prodrug, or solvate wherein:

Formula (A)

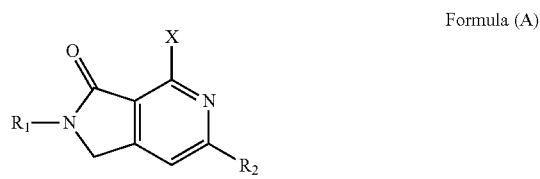

X=NHG, CH₂G, OG, SO₂G, SO₂NHG, NHC(O)G, NHSO₂G, C(O)NH₂, C(O)NHG, C(O)NG₁G₂, cyclic amines or amides with 0-2 of O, N, or S atom and substituted with group G, and functional group with examples shown below.

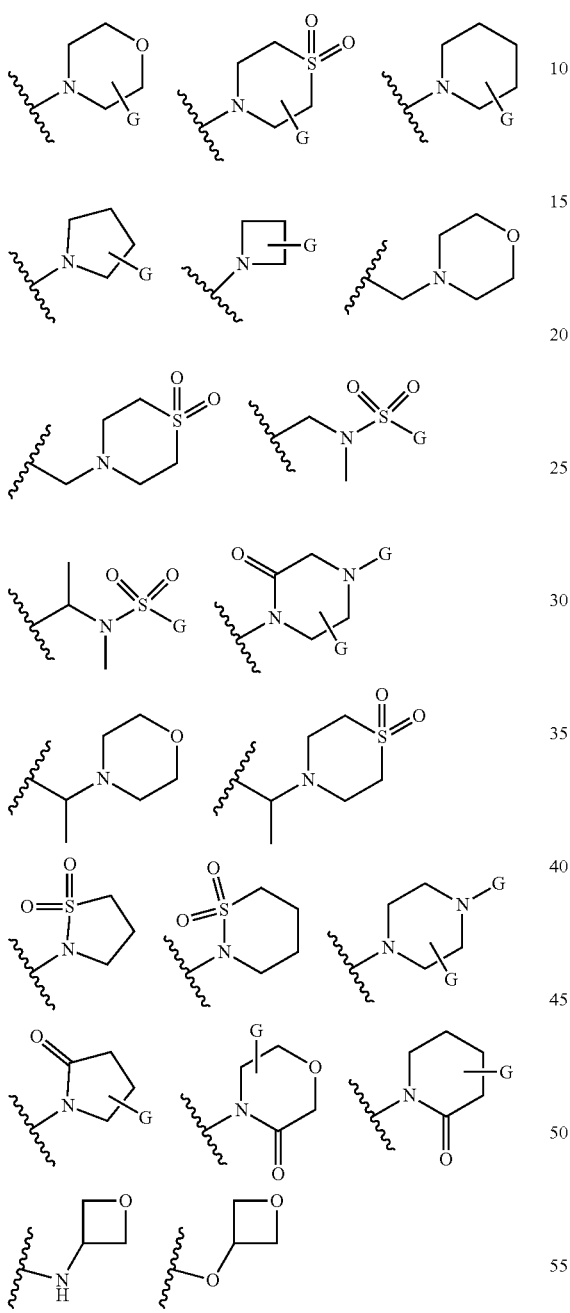

G is selected from H, D, OH, OMe, NH₂, SO₂Me, C$_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl R₁ is branched alkane, including substituted cyclopropanes, cyclobutanes and alkyl fluorides, selected from:

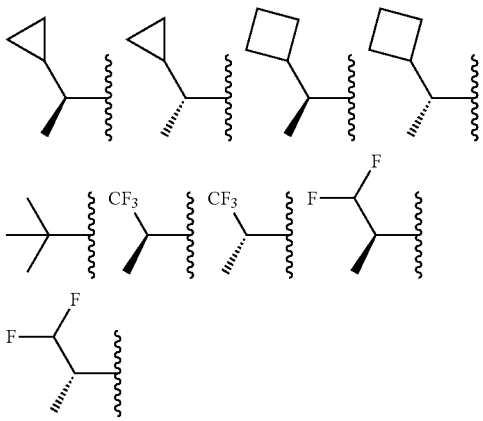

In formula (A), R₂ is selected from:

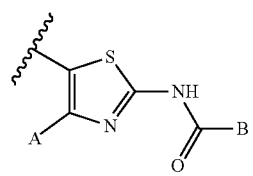

A is selected from H, Me, Cl and difluoromethyl, B is selected from Me, Et, isopropyl, cyclopropyl, and difluoromethyl.

21. The selective phosphoinositide 3-kinase gamma (PI3Kγ) inhibitor of embodiment 20 wherein R₁ is

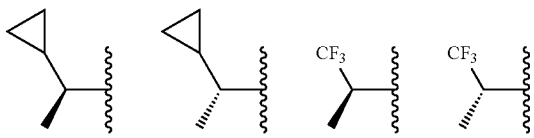

and R₂ is

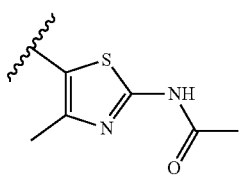 [SMILES: *c1sc(NC(C)=O)nc1C]

X=NHG, CH₂G, OG, SO₂G, SO₂NHG, NHSO₂G, NHC(O)G, C(O)NH₂, C(O)NHG, C(O)NG₁G₂, cyclic amines or amides with 0-2 of O, N, or S atom; G is selected from H, D, OH, OMe, NH₂, C$_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof 22. The selective phosphoinositide 3-kinase gamma (PI3Kγ) inhibitor of embodiment 20, wherein R₁ is

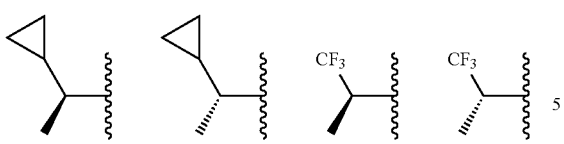

and R₂ is

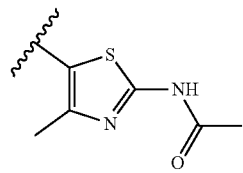 [SMILES: *c1sc(NC(C)=O)nc1C]

X=

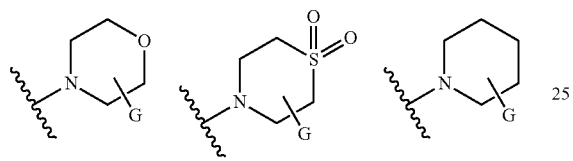

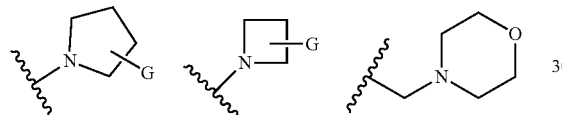

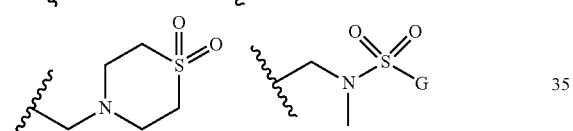

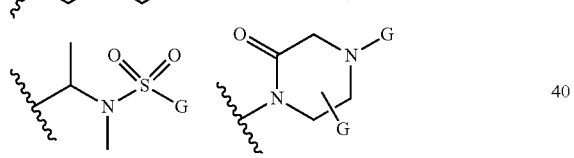

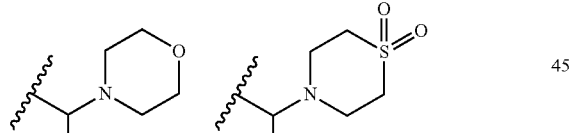

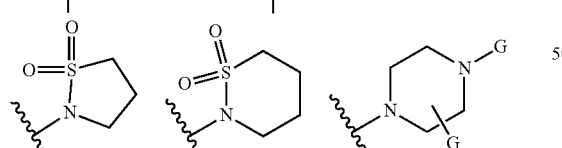

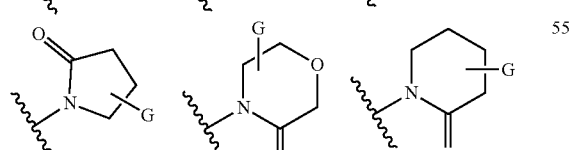

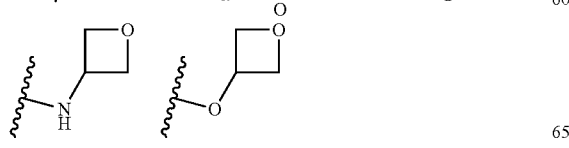

G is selected from H, D, OH, OMe, NH₂, SO₂Me, $C_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof 23. The selective phosphoinositide 3-kinase gamma (PI3Kγ) inhibitor of embodiment 20, wherein R₁ is

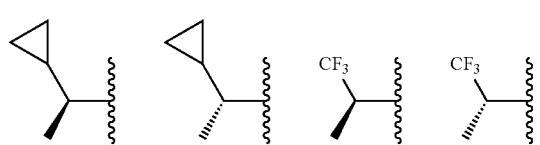

and R₂ is

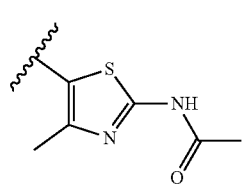 [SMILES: *c1sc(NC(C)=O)nc1C]

X=NHG, OG, OCD₃, NHSO₂G, C(O)NH₂, C(O)NHG, C(O)NG₁G₂; G is selected from $C_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof.

24. The selective phosphoinositide 3-kinase gamma (PI3Kγ) inhibitor of embodiment 20, wherein R₁ is

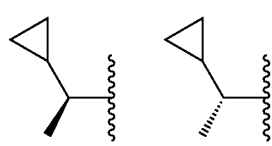

and R₂ is

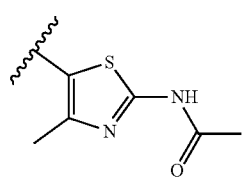 [SMILES: *c1sc(NC(C)=O)nc1C]

X=

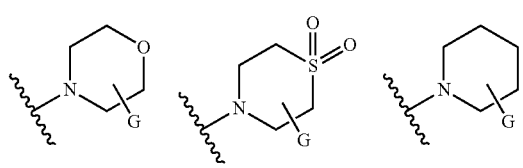

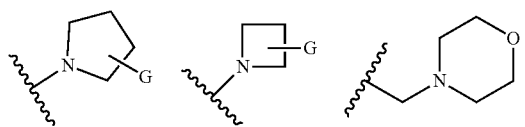
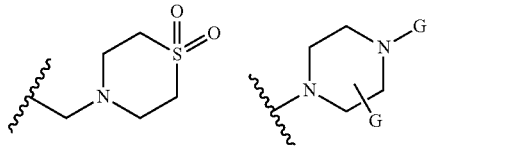
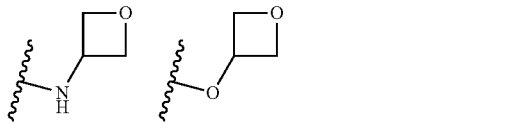

G is selected from H, D, OH, OMe, NH$_2$, SO$_2$Me, C$_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof 25. The selective phosphoinositide 3-kinase gamma (PI3Kγ) inhibitor of embodiment 20, wherein R is

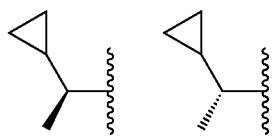

and R$_2$ is

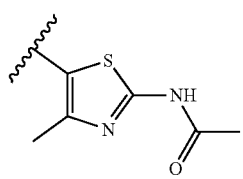 [SMILES: *c1sc(NC(C)=O)nc1C]

X=OMe, OCD$_3$, NHSO$_2$Me, NHSO$_2$Et, C(O)NH$_2$, C(O)NHMe, C(O)NMe$_2$, or a pharmaceutically acceptable salt, prodrug or solvate thereof 26. The selective phosphoinositide 3-kinase gamma (PI3Kγ) inhibitor compound of embodiment 20, wherein have the following structures, or a pharmaceutically acceptable salt, prodrug or solvate thereof

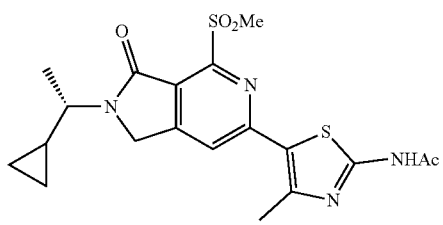
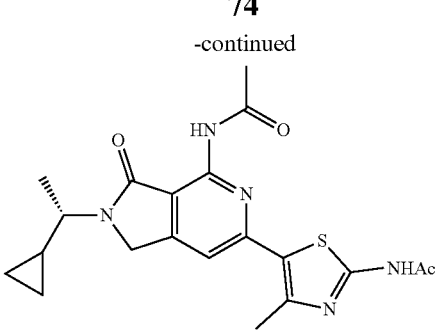
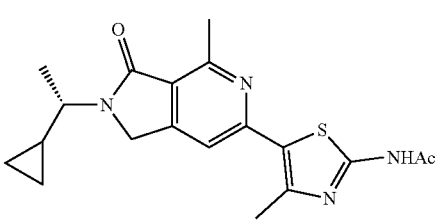
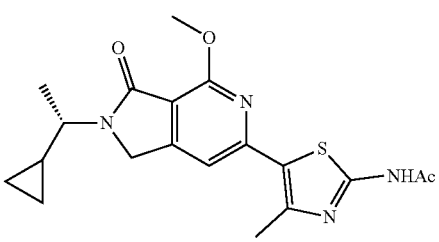
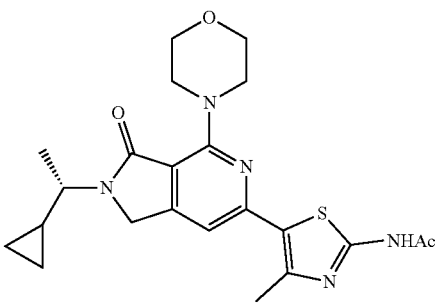
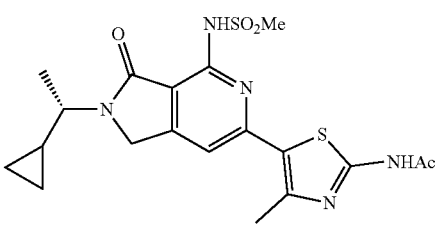
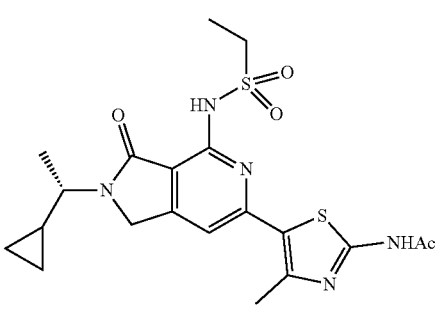

-continued
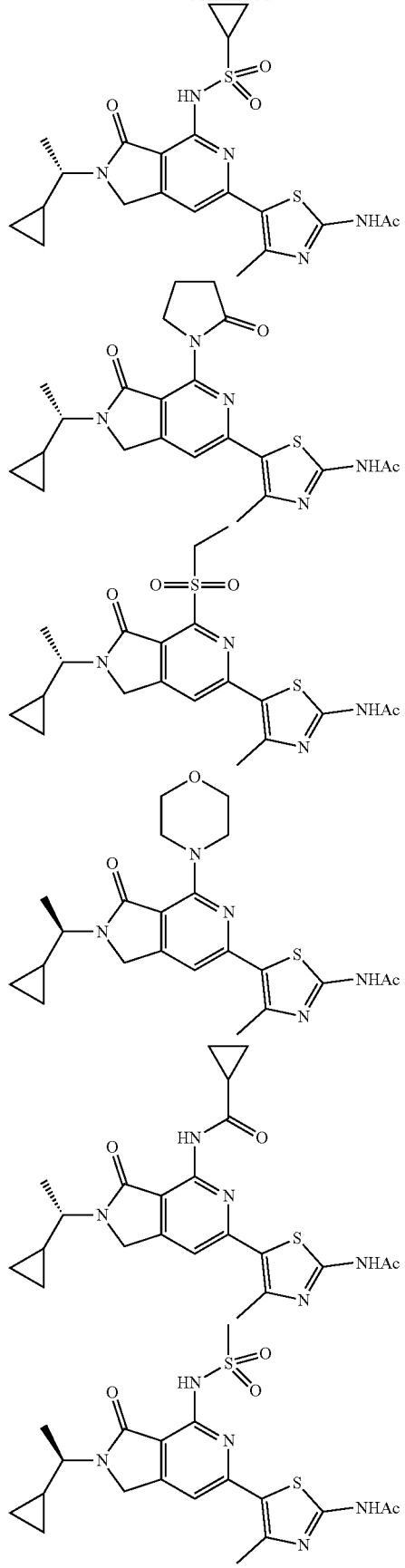
-continued
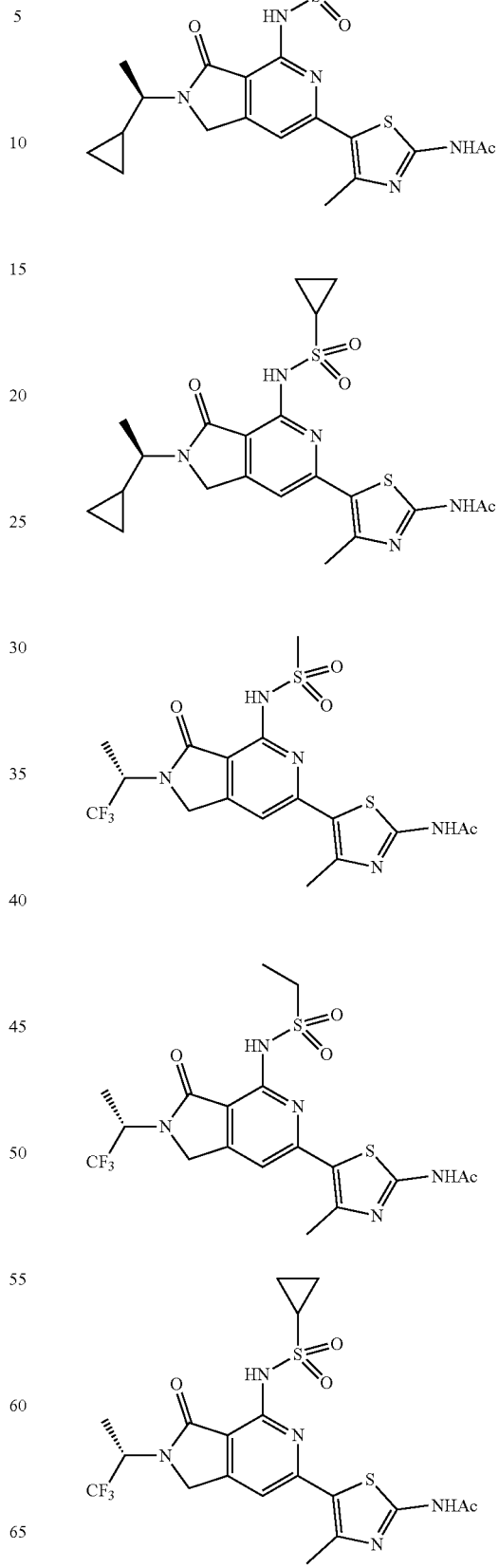

77
-continued
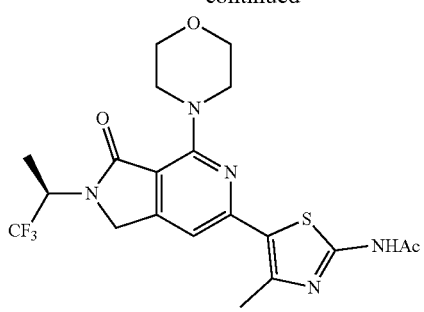
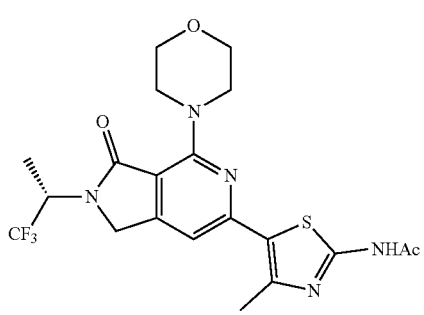
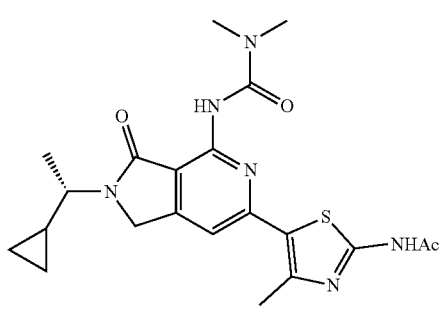
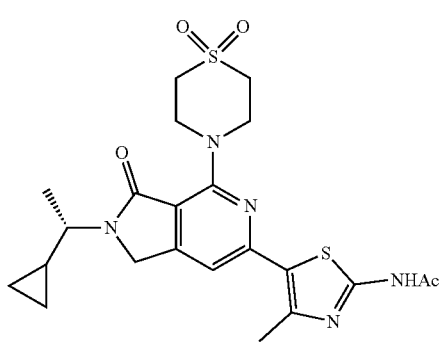
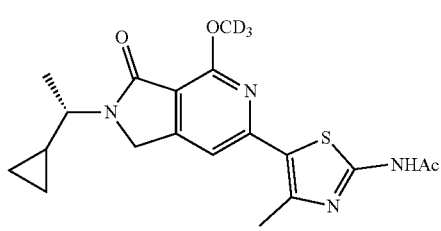
78
-continued
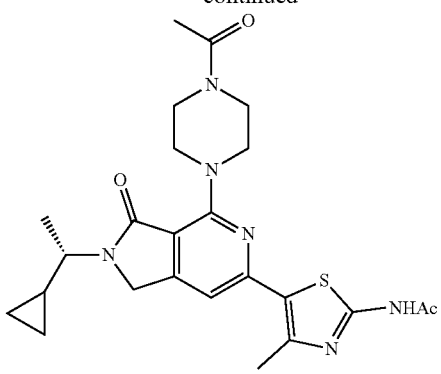
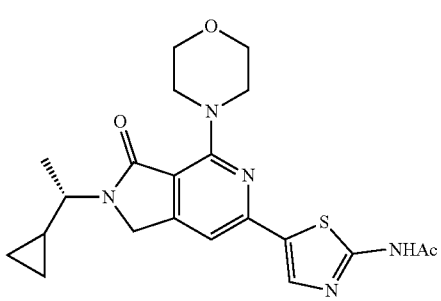
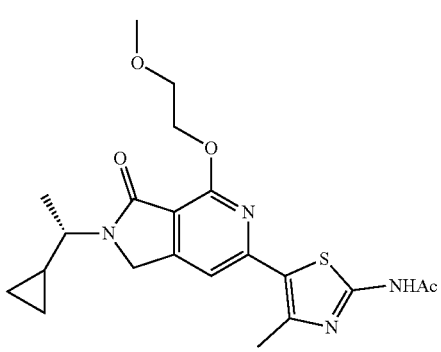
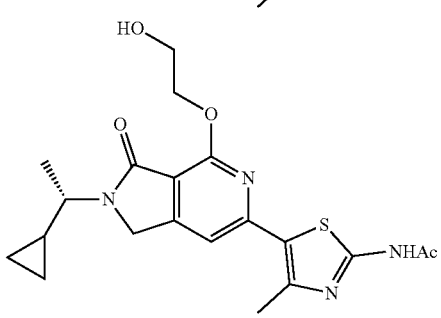
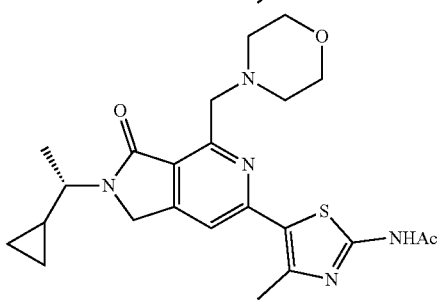

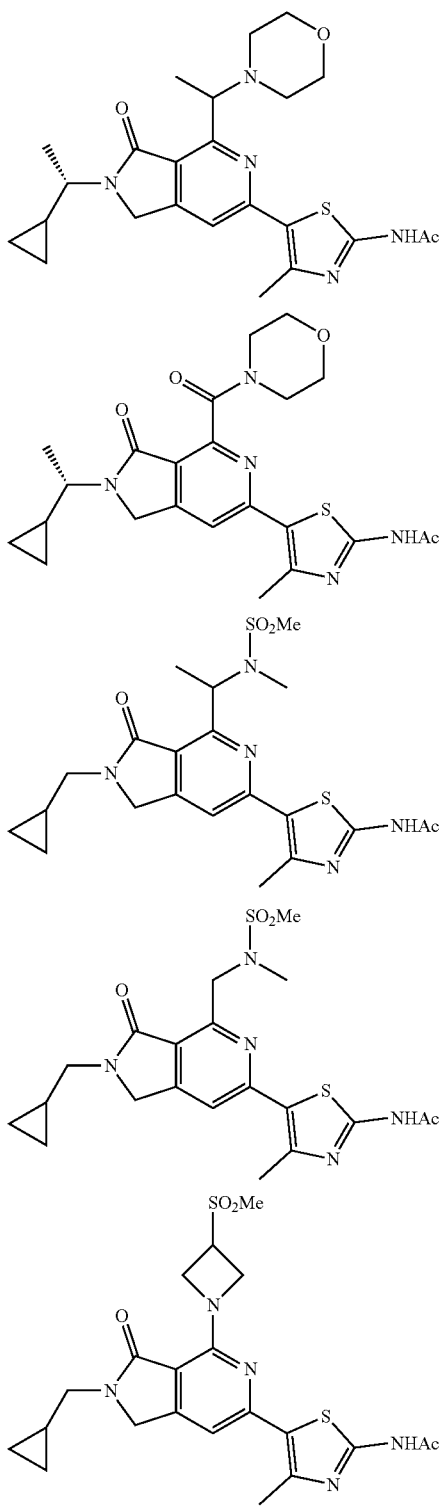

27. A method of selectively inhibiting a growth or a proliferation phosphoinositide 3-kinase gamma (PI3Kγ) comprising: contacting kinase cells with an effective amount of a phosphoinositide 3-kinase gamma (PI3Kγ) inhibitor compound having a structure of formula (A), or a pharmaceutically acceptable salt, prodrug or solvate thereof:

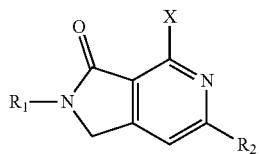

Formula (A)

X=NHG, CH$_2$G, OG, SO$_2$G, SO$_2$NHG, NHC(O)G, NHSO$_2$G, C(O)NH$_2$, C(O)NHG, C(O)NG$_1$G$_2$, cyclic amines or amides with 0-2 of O, N, or S atom and substituted with group G, and functional group with examples shown below.

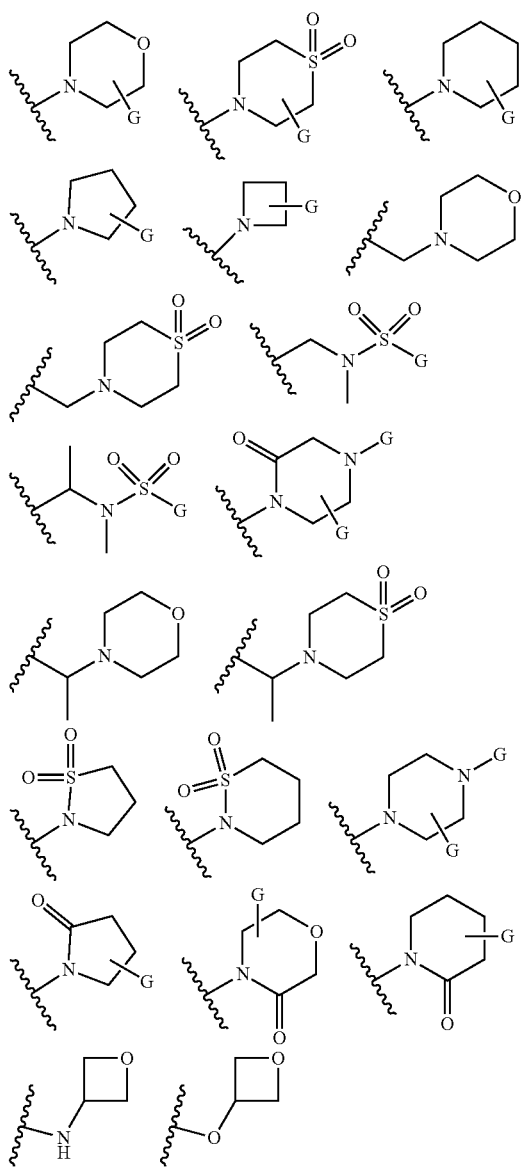

G is selected from H, D, OH, OMe, NH$_2$, SO$_2$Me, C$_{1-4}$ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl R₁ is branched alkane, including substituted cyclopropanes, cyclobutanes and alkyl fluorides, selected from:

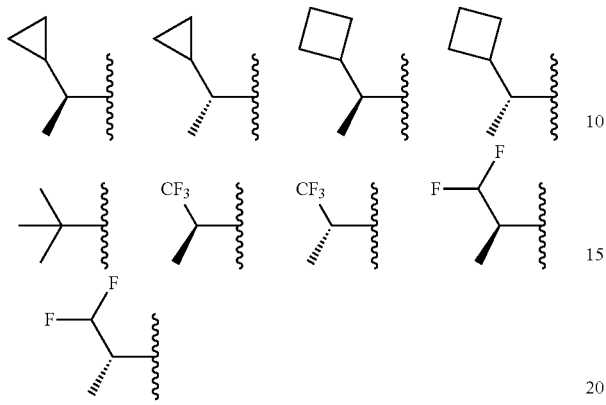

In one embodiment of formula (A), R₂ is selected from:

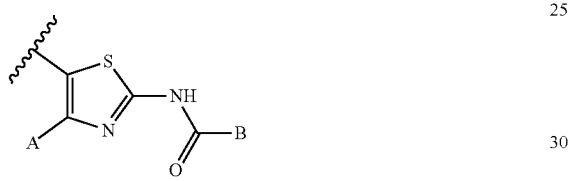

In one embodiment, A is selected from H, Me, Cl and difluoromethyl, B is selected from Me, Et, isopropyl, cyclopropyl, and difluoromethyl.

28. The method of selectively inhibiting a growth or a proliferation phosphoinositide 3-kinase gamma (PI3Kγ) according to embodiment 27, wherein R₁ is

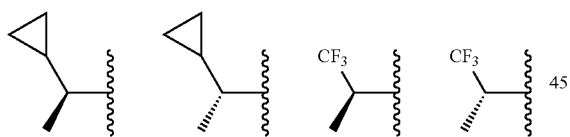

and R₂ is

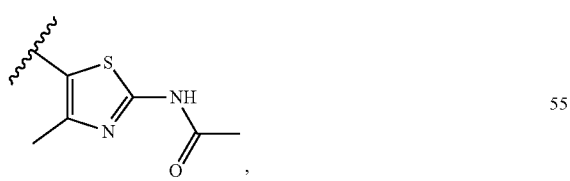

or a pharmaceutically acceptable salt, prodrug or solvate thereof

29. The method of selectively inhibiting a growth or a proliferation phosphoinositide 3-kinase gamma (PI3Kγ) according to embodiment 27, wherein, X=NHG, CH₂G, OG, SO₂G, SO₂NHG, NHC(O)G, NHSO₂G, C(O)NH₂, C(O)NHG, C(O)NG₁G₂, cyclic amines or amides with 0-2 of O, N, or S atom; G is selected from H, D, OH, OMe, NH₂, SO₂Me, C₁₋₄ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof.

30. The method of selectively inhibiting a growth or a proliferation phosphoinositide 3-kinase gamma (PI3Kγ) according to embodiment 27, wherein X is selected from the following groups:

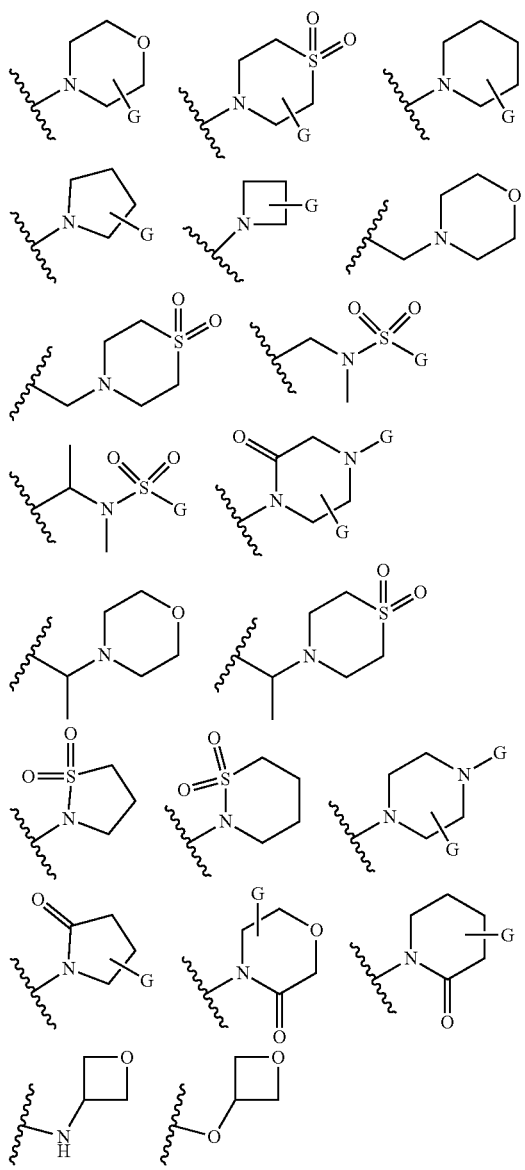

G is selected from H, D, OH, OMe, NH₂, SO₂Me, C₁₋₄ alkyl optionally substituted with H, OH, OMe, CN and F, such as methyl, ethyl, isopropyl, cyclopropyl, trifluoroethyl, 2-hydroxyethyl, 2-methoxyethyl, 3-hydroxypropyl, 3-methoxypropyl, or a pharmaceutically acceptable salt, prodrug or solvate thereof.

31. The method of selectively inhibiting a growth or a proliferation phosphoinositide 3-kinase gamma (PI3Kγ) according to embodiment 27, wherein X is,

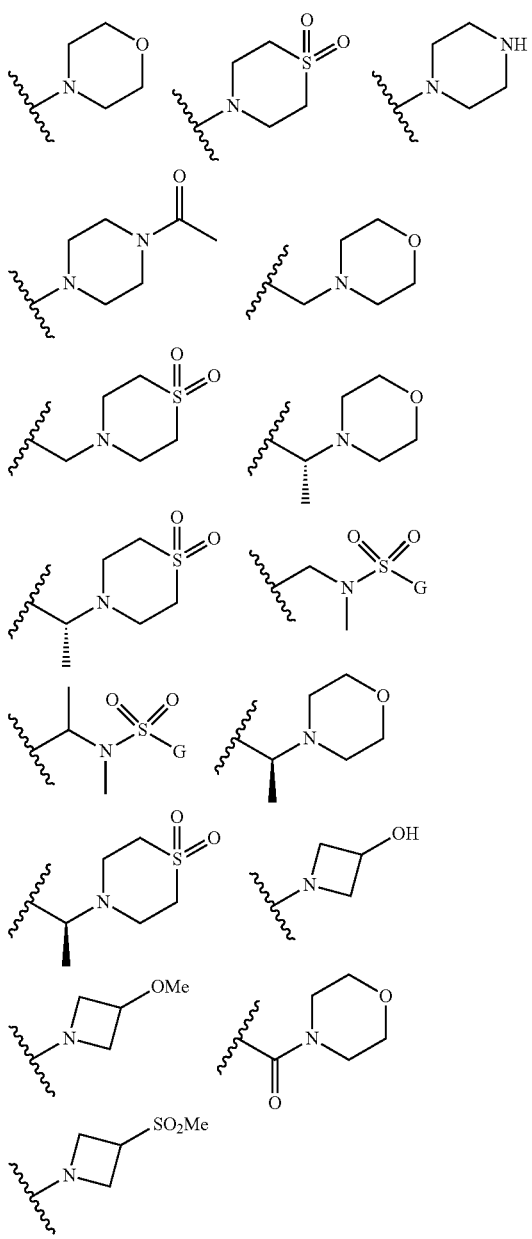

each of Y and Z is CH, or a pharmaceutically acceptable salt, or solvate thereof 32. The method of selectively inhibiting a growth or a proliferation phosphoinositide 3-kinase gamma (PI3Kγ) according to embodiment 27, wherein the compound has optimized PI3Kδ selectivity and solubility compared with a known PI3K gamma inhibitor.

Examples

Synthesis

Reagents and solvents used below can be obtained from commercial sources. 1H-NMR spectra were recorded on a Bruker 400 MHZ NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Mass spectrometry results are reported as the ratio of mass over charge, followed by the relative abundance of each ion (in parentheses Electrospray ionization (ES1) mass spectrometry analysis was conducted on an Shimadzu LC/MSD electrospray mass spectrometer.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), ethyl acetate (EA or EtOAc), dichloromethane (DCM), diethyl ether, methanol, pyridine, formic acid (FA) and the like. Unless specified to the contrary, the solvents used in the reactions of the present invention are inert organic solvents, and the reactions are carried out under an inert gas, preferably nitrogen and argon.

(S)-N-(5-(2-(1-cyclopropylethyl)-7-(dimethylphosphoryl)-1-oxoisoindolin-5-yl)-4-methylthiazol-2-yl)acetamide (1)

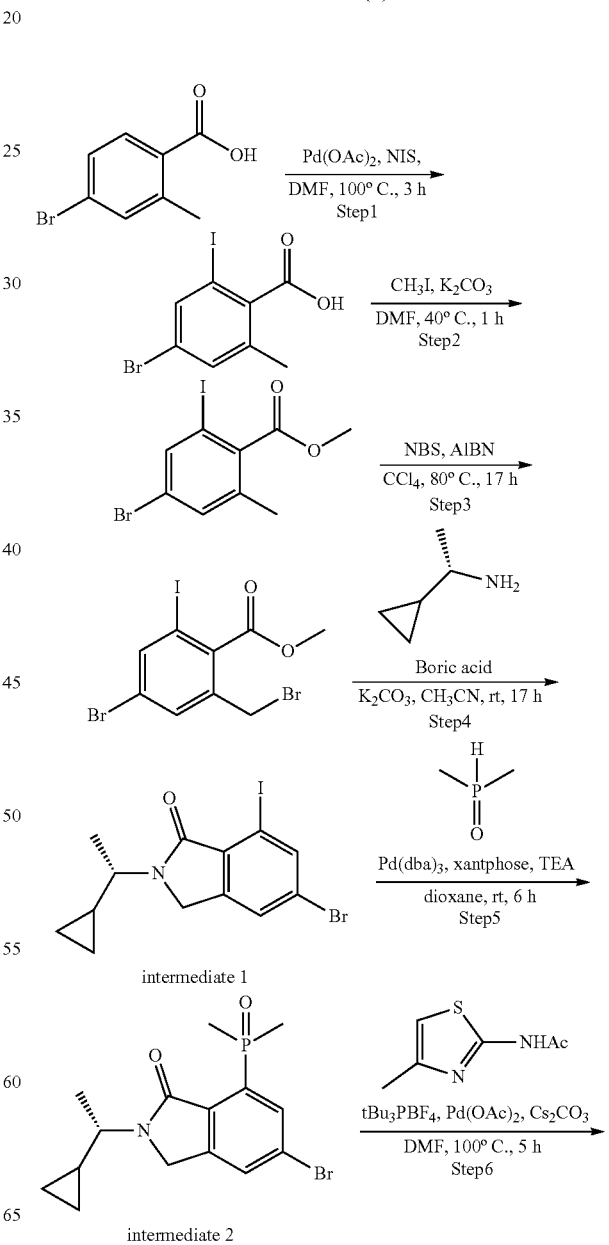

-continued

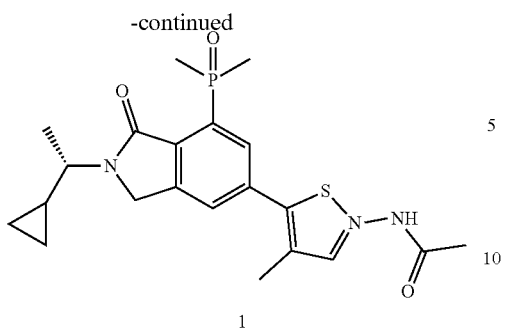

1

Step 1. A mixture of 4-bromo-2-methylbenzoic acid (1.0 g, 4.67 mmol), NIS (1.58 g, 7.01 mmol), Pd(OAc)$_2$ (209 mg, 0.93 mmol) in DMF (20 mL) was stirred at 100° C. for 3 h. The mixture was cooled to rt, diluted with EtOAc (150 mL), washed with H$_2$O (80 mL*4), brine (100 mL). The organic layer was dried, filtered, concentrated and purified by silica gel column eluting with ethyl acetate in petroleum ether (10%-25%) to afford 4-bromo-2-iodo-6-methylbenzoic acid as a light yellow solid (1.05 g, 66% yield). LC-MS (ESI) [M–H]$^-$ 339.1.

Step 2. To a solution of 4-bromo-2-iodo-6-methylbenzoic acid (1 g, 2.94 mmol) in DMF (15 mL) was added K$_2$CO$_3$ (1.22 g, 8.82 mmol) followed by CH$_3$I (835 mg, 5.88 mmol). The mixture was stirred at 40° C. for 1 h. The mixture was cooled to rt, diluted with EtOAc (150 mL), washed with H$_2$O (80 mL*4), brine (100 mL). The organic layer was dried, filtered, concentrated and purified by silica gel column eluting with ethyl acetate in petroleum ether (0% 5%) to afford methyl 4-bromo-2-iodo-6-methylbenzoate as a yellow oil (970 mg, 93% yield).

Step 3. To a solution of methyl 4-bromo-2-iodo-6-methylbenzoate (970 mg, 2.74 mmol) in CCl$_4$ (15 mL) was added NBS (1.17 g, 6.54 mmol), AIBN (180 mg, 1.1 mmol). The mixture was stirred at 80° C. for 17 h. The solvent was removed and the residue was purified by purified by silica gel column eluting with ethyl acetate in petroleum ether (0%-5%) to afford methyl 4-bromo-2-(bromomethyl)-6-iodobenzoate as a yellow oil. (920 mg, 82% yield).

Step 4. Preparation of (S)-5-bromo-2-(1-cyclopropylethyl)-7-iodoisoindolin-1-one (intermediate 1). To a solution of methyl 4-bromo-2-(bromomethyl)-6-iodobenzoate (920 mg, 2.12 mmol) in MeCN (15 mL) was added (S)-1-cyclopropylethan-1-amine (270 mg, 3.18 mmol), boric acid (129 mg, 2.12 mmol), K$_2$CO$_3$ (878 mg, 6.36 mmol). The mixture was stirred at rt for 17 h. Water (30 mL) and EtOAc (50 mL) were added. The reaction mixture was extracted with EtOAc (50 mL×2). The organic layer was dried, filtered, concentrated and purified by silica gel column eluting with ethyl acetate in petroleum ether (10%-80%) to afford (S)-5-bromo-2-(1-cyclopropylethyl)-7-iodoisoindolin-1-one as a yellow solid (470 mg, 55% yield). LC-MS (ESI) [M–H]$^+$ 408.0.

Step 5. Synthesis of (S)-5-bromo-2-(1-cyclopropylethyl)-7-(dimethylphosphoryl)-isoindolin-1-one (intermediate 2)

To a solution of (S)-5-bromo-2-(1-cyclopropylethyl)-7-iodoisoindolin-1-one (340 mg, 0.84 mmol) in 1,4-dioxane (12 mL) was added dimethylphosphine oxide (72 mg, 0.92 mmol), Pd$_2$(dba)$_3$ (77 mg, 0.084 mmol), xantphose (49 mg, 0.084 mmol), TEA (254 mg, 2.52 mmol) under N$_2$. The mixture was stirred at rt for 6 h. Water (50 mL) and EA (50 mL) were added. The reaction mixture was extracted with EA (50 mL×2). The organic layer was dried, filtered, concentrated and purified by silica gel column eluting with ethyl acetate in petroleum ether (50%-100%) to afford (S)-5-bromo-2-(1-cyclopropylethyl)-7-(dimethylphosphoryl) isoindolin-1-one as a yellow solid (160 mg, 54% yield). LC-MS (ESI) [M–H]$^+$ 356.1.

Step 6: (S)-N-(5-(2-(1-cyclopropylethyl)-7-(dimethylphosphoryl)-1-oxoisoindolin-5-yl)-4-methylthiazol-2-yl)acetamide (General Procedure A)

To a solution of (S)-5-bromo-2-(1-cyclopropylethyl)-7-(dimethylphosphoryl)-isoindolin-1-one (60 mg, 0.17 mmol) in DMF (3 mL) was added N-(4-methylthiazol-2-yl)acetamide (32 mg, 0.20 mmol), t-Bu$_3$PBF$_4$ (10 mg, 0.034 mmol), Cs$_2$CO$_3$ (110 mg, 0.34 mmol) and Pd(OAc)$_2$ (4 mg, 0.017 mmol) under N$_2$. The mixture was stirred at 100° C. for 5 h. Water (20 mL) and EA (20 mL) were added. The reaction mixture was extracted with EA (30 mL×3). The organic layer was dried, filtered, concentrated and purified by HPLC, condition: (SunFire C18 5 um 4.6×150 mm 25 C 1.000 mL/min 16 min; Mobile Phase B: 0.03% HCl in MeCN, Mobile Phase A: 0.03% HCl in H$_2$O; rt: 8.86 min; 254 nm: 99.59%, 214 nm: 96.54%). LC-MS (ESI) [M+H]$^+$ 432.1. $^1$H NMR (400 MHz, DMSO) δ 12.25 (s, 1H), 8.10 (dd, J=12.3, 1.5 Hz, 1H), 7.91 (s, 1H), 4.66 (s, 2H), 3.72-3.53 (m, 1H), 2.43 (s, 3H), 2.17 (s, 3H), 1.88 (d, J=14.4 Hz, 6H), 1.30 (d, J=6.8 Hz, 3H), 1.22-1.03 (m, 1H), 0.67-0.51 (m, 1H), 0.48-0.32 (m, 2H), 0.31-0.17 (m, 1H).

(S)-N-(5-(2-(1-cyclopropylethyl)-7-(dimethylphosphoryl)-1-oxoisoindolin-5-yl)-4-methylthiazol-2-yl) propionamide (2)

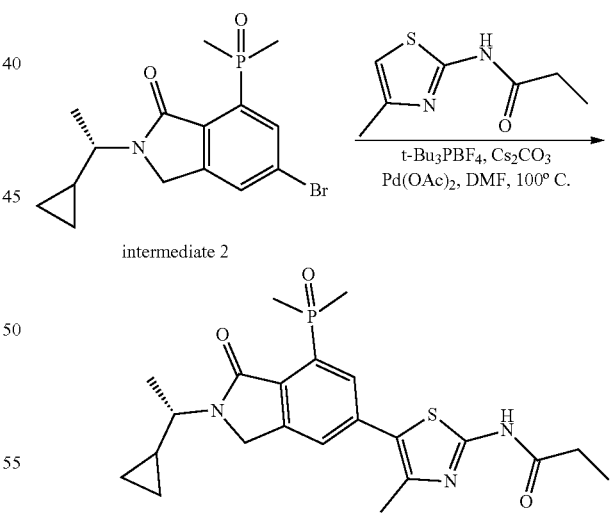

A mixture of (S)-5-bromo-2-(1-cyclopropylethyl)-7-(dimethylphosphoryl)isoindolin-1-one (174 mg, 0.49 mmol), N-(4-methylthiazol-2-yl)propanamide (100 mg, 0.588 mmol), t-Bu$_3$PBF$_4$ (29 mg, 0.1 mmol), cesium carbonate (325 mg, 1.0 mmol) and palladium (II) acetate (11 mg, 0.05 mmol) in dimethylformamide (2 mL) was stirred at 100° C. for 16 h under N$_2$. Cooled to rt, added EA (30 mL), washed with water (20 mL×2) and brine, dried over anhydrous Na$_2$SO$_4$ and concentrated. The residue was purified by Pre-HPLC to afford (S)-N-(5-(2-(1-cyclopropylethyl)-7-(dimethylphosphoryl)-1-oxoisoindolin-5-yl)-4-methylthiazol-2-yl)propionamide. (6.28 mg, 2.7%). LC-MS (ESI) [M+H]$^+$= 446.2. 1H NMR (400 MHz, MeOH) δ 8.20 (d, J=12.8 Hz, 1H, 7.90 (s, 1H), 4.80-4.60 (m, 2H), 3.65 (dd, J=9.3, 6.9 Hz), 2.51 (q, J=7.6 Hz, 3H), 2.45 (s, 3H), 2.03 (dd, J=14.5, 2.5 Hz, 6H), 1.49-1.34 (m, 4H), 1.25-1.11 (m, 4H), 0.76-0.61 (m, 1H), 0.55-0.23 (m, 3H).

(S)-N-(5-(2-(1-cyclopropylethyl)-7-(dimethylphosphoryl)-1-oxoisoindolin-5-yl)-4-methylthiazol-2-yl)cyclopropanecarboxamide (3)

Step 1. To a solution of 4-methylthiazol-2-amine (500 mg, 4.38 mmol) in pyridine (10 mL) was added cyclopropanecarbonyl chloride (547 mg, 5.26 mmol) at room temperature. Then the reaction mixture was stirred for 2 h at room temperature. The solvent was evaporated and the residue was diluted EA (30 mL), washed with aqueous HCl (3N, 10 mL) and brine (20 mL), dried over anhydrous Na$_2$SO$_4$, filtered and the filtrate was concentrated. The residue was purified by silica gel column eluting with ethyl acetate/petroleum (0-20%) to afford N-(4-methylthiazol-2-yl)cyclopropanecarboxamide as a white solid (800 mg, 100% yield). LC-MS (ESI) [M+H]$^+$ 183.2.

Step 2. (S)-N-(5-(2-(1-cyclopropylethyl)-7-(dimethylphosphoryl)-1-oxoisoindolin-5-yl)-4-methylthiazol-2-yl)cyclopropanecarboxamide was prepared according to the general procedure A as an off-white solid (2.65 mg, 4.1% yield). LC-MS (ESI) [M+H]$^+$ 458.2. $^1$H NMR (400 MHz, MeOD-d$_4$) δ 8.60-8.43 (m, 1H), 8.19 (d, J=12.8 Hz, 1H), 7.90 (s, 1H), 4.77-4.65 (m, 2H), 3.70-3.62 (m, 1H), 2.48 (s, 3H), 2.04 (dd, J=14.5, 2.4 Hz, 6H), 1.94-1.88 (m, 1H), 1.40 (d, J=6.8 Hz, 3H), 1.21-1.13 (m, 1H), 1.08-1.02 (m, 2H), 1.01-0.95 (m, 2H), 0.72-0.65 (m, 1H), 0.54-0.48 (m, 1H), 0.46-0.40 (m, 2H), 0.30-0.18 (m, 1H).

(S)-N-(5-(2-(1-cyclopropylethyl)-7-(dimethylphosphoryl)-1-oxoisoindolin-5-yl)-4-methylthiazol-2-yl)isobutyramide (4)

(S)-N-(5-(2-(1-cyclopropylethyl)-7-(dimethylphosphoryl)-1-oxoisoindolin-5-yl)-4-methylthiazol-2-yl)isobutyramide was prepared according to the general procedure A as a yellow solid (14.92 mg, 7.2%). LC-MS (ESI) [M+H]$^+$= 460.2, 1H NMR (400 MHz, DMSO) δ 8.10 (dd, J=12.4 Hz, 1H), 7.86 (s, 1H), 4.65 (s, 2H), 3.62 (dd, J=8.9, 6.8 Hz, 1H), 2.69 (dd, J=13.7, 6.8 Hz, 1H), 2.41 (s, 3H), 1.87 (d, J=14.1-6H), 1.29 (d, J=6.8 Hz, 3H), 1.13 (t, J=8.4 Hz, 7H), 0.64-0.50 (m, 1H), 0.48-0.31 (m, 2H), 0.30-0.18 (m, 1H).

(S)-N-(5-(2-(1-cyclopropylethyl)-7-(diethylphosphoryl)-1-oxoisoindolin-5-yl)-4-methylthiazol-2-yl)acetamide (5)

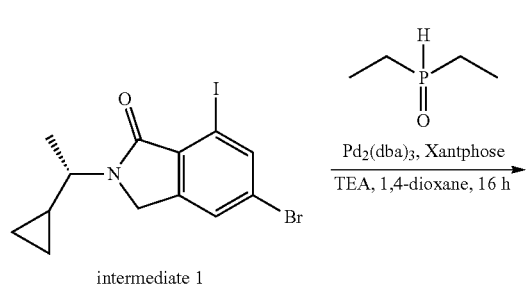

intermediate 1

Step 1. To a solution of (S)-5-bromo-2-(1-cyclopropylethyl)-7-iodoisoindolin-1-one (250 mg, 0.62 mmol) in 1,4-dioxane (5 mL) was added diethylphosphine oxide (71 mg, 0.68 mmol), Pd$_2$(dba)$_3$ (56 mg, 0.06 mmol), Xantphose (35 mg, 0.06 mmol), TEA (0.3 mL, 1.15 mmol) under N$_2$. The mixture was stirred at rt for 16 h. Water (30 mL) and EA (30 mL) were added. The reaction mixture was extracted with EA (30 mL×3). Then it was washed with brine, dried over anhydrous Na$_2$SO$_4$ and concentrated. The crude was purified by silica gel chromatography (PE:EA=1:0-1:1-0:1) the (DCM:MeOH=10:1) to give (S)-5-bromo-2-(1-cyclopropylethyl)-7-(diethylphosphoryl)isoindolin-1-one (100 mg, 42.1%) as a yellow oil. LC-MS (ESI) [M+H]$^+$ 384.1.

Step 2. A mixture of (S)-5-bromo-2-(1-cyclopropylethyl)-7-(diethylphosphoryl)isoindolin-1-one (60 mg, 0.16 mmol), N-(4-methylthiazol-2-yl)acetamide (36 mg, 0.23 mmol), t-Bu$_3$PBF$_4$ (10 mg, 0.03 mmol), cesium carbonate (102 mg, 0.31 mmol) and palladium (II) acetate (4 mg, 0.016 mmol) in dimethylformamide (2 mL) was stirred at 100° C. for 16 hs under N$_2$. Cooled to rt, added EA (30 mL), washed with water (20 mL×2) and brine, dried over anhydrous Na$_2$SO$_4$ and concentrated. The residue was purified by Pre-HPLC to afford (S)-N-(5-(2-(1-cyclopropylethyl)-7-(diethylphosphoryl)-1-oxoisoindolin-5-yl)-4-methylthiazol-2-yl)acetamide (20 mg, 28.3%) as a white solid. LC-MS (ESI) [M+H]$^+$= 460.1; 1H NMR (400 MHz, DMSO) δ: 12.22 (s, 1H), 8.11 Cm, 1H), 7.90 (s, 1H), 4.67 (s, 2H), 3.65 (m, 1H), 2.34 (s, 3H), 2.28 (m, 4H), 2.19 (s, 3H), 1.30 (d, 3H), 1.15 (m, 1H), 0.97 (m, 6H), 0.63 (m, 1H), 0.45 (m, 2H), 0.24 (m, 1H).

(S)-N-(5-(2-(1-cyclopropylethyl)-7-(dimethylphosphoryl)-1-oxoisoindolin-5-yl)pyridin-2-yl)acetamide (6)

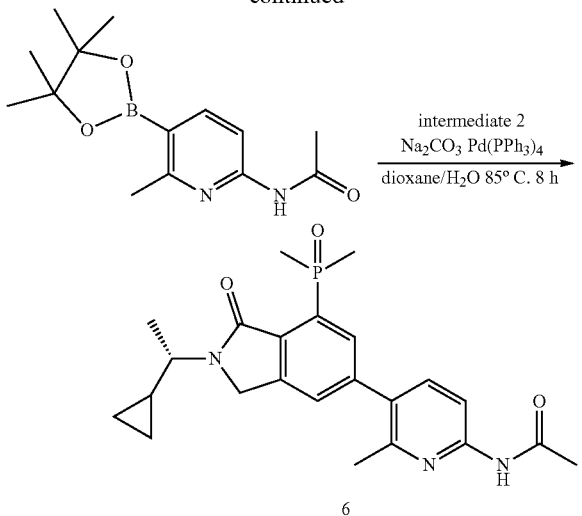

Step 1. To a solution of N-(5-bromo-6-methylpyridin-2-yl)acetamide (300.0 mg, 1.31 mol) in dioxane (3 mL) was added 4,4,4',4',5,5,5',5'-octamethyl-2,2'-bi(1,3,2-dioxaborolane) (399.07 mg, 1.57 mol), potassium acetate (192.75 mg, 1.96 mol) and Pd(dppf)Cl$_2$ (10 mg). The mixture was stirred at 120° C. for 3 h under the N$_2$. LCMS showed the reaction was completed. Water was added and extracted with EtOAc (3*10 mL). The organic layer was dried by NaSO$_4$ and filtration. The filtrate was concentrated to afford crude product. The crude product was purification by silica gel chromatography PE:EtOAc (5:1) to afford N-(5-(4,4,5,5-tetramethyl-1,3,2-dioxaborolan-2-yl)pyridin-2-yl)acetamide (300 mg, 82.96%) as a white solid.

Step 2. To a solution of N-(6-methyl-5-(4,4,5,5-tetramethyl-1,3,2-dioxaborolan-2-yl)pyridin-2-yl)acetamide (50.0 mg, 181.1 umol) in dioxane/H$_2$O (2:0.5 mL), was added (S)-5-bromo-2-(1-cyclopropylethyl)-7-(dimethylphosphoryl)isoindolin-1-one (77.39 mg, 0.22 mmol), Na$_2$CO$_3$ (38.38 mg, 0.36 mmol) and Pd(dppf)Cl$_2$ (5 mg). The mixture was stirred at 85° C. for 8 h under N$_2$. LCMS showed the reaction was completed. Water was added and exacted with EtOAc (3*10 mL). The organic layer was dried by Na$_2$SO$_4$ and filtration. The filtrate was concentrated to afford crude product. The crude product was purification by HPLC (AcOH in water, ACN) to afford (S)-N-(5-(2-(1-cyclopropylethyl)-7-(dimethylphosphoryl)-1-oxoisoindolin-5-yl)pyridin-2-yl)acetamide (19.08 mg 26%) as white solid. LC-MS (ESI) [M+H]$^+$ 426.3, 1H NMR (400 MHz, DMSO) δ 10.61 (s, 1H), 8.13 (s, 1H), 8.04 (d, J=8.4 Hz, 1H), 7.99 (d, J=12.1 Hz, 1H), 7.85 (s, 1H), 7.67 (d, J=8.5 Hz, 1H), 4.67 (s, 2H), 3.63 (s, 1H), 2.40 (s, 3H), 2.11 (s, 3H), 1.88 (d, J=14.3 Hz, 6H), 1.31 (d, J=6.8 Hz, 3H), 1.18-1.10 (m, 1H), 0.59 (s, 1H), 0.41 (dd, J=11.4, 5.4 Hz, 2H), 0.26 (d, J=5.4 Hz, 1H).

(S)-N-(5-(2-(1-cyclopropylethyl)-7-(dimethylphosphoryl)-1-oxoisoindolin-5-yl)pyridin-2-yl)acetamide (7)

(S)-N-(5-(2-(1-cyclopropylethyl)-7-(dimethylphosphoryl)-1-oxoisoindolin-5-yl)pyridin-2-yl)acetamide was prepared in the similar manner as the above analog (2.98 mg 4.75%) as white solid. LC-MS (ESI) [M+H]$^+$ 412.3 1H NMR (400 MHz, MeOD) δ 8.71 (s, 1H), 8.50 (s, 1H), 8.35 (d, J=12.8 Hz, 1H), 8.25 (d, J=8.5 Hz, 1H), 8.20-8.15 (m, 1H), 8.11 (s, 1H), 4.58 (s, 2H), 3.72-3.59 (m, 1H), 2.21 (s, 3H), 2.04 (dd, J=14.4, 2.1 Hz, 6H), 1.40 (d, J=6.8 Hz, 3H), 1.18 (d, J=5.8 Hz, 1H), 0.69 (d, J=4.5 Hz, 1H), 0.55-0.37 (m, 2H), 0.36-0.26 (m, 1H).

(S)-N-(5-(6-(1-cyclopropylethyl)-7-oxo-6,7-dihydro-5H-pyrrolo[3,4-b]pyridin-3-yl)-4-methylthiazol-2-yl)acetamide (8)

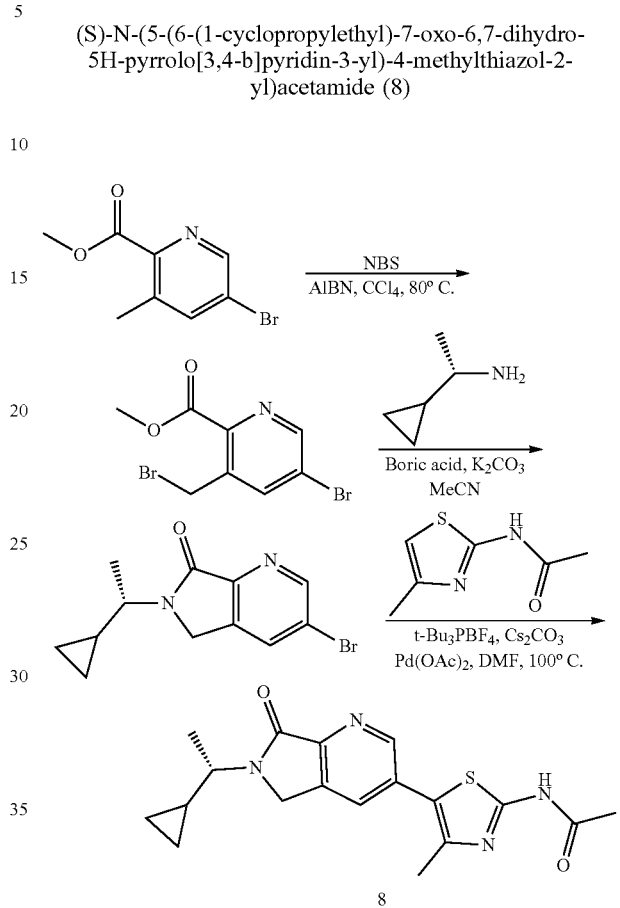

Step 1. A mixture of methyl 5-bromo-3-methylpicolinate (1.0 g, 4.35 mmol), N-bromosuccinimide (851 mg, 4.81 mmol), 2,2'-azobis(2-methylpropionitrile) (72 mg, 0.44 mmol) in carbon tetrachloride (20 mL) was stirred for 16 hr at 80° C. Removed solvent in vacuo, the residue was purified by silica gel chromatography (PE/EtOAc=1/1) to afford methyl 5-bromo-3-(bromomethyl)picolinate (800 mg, 59.7%) as white solid. LC-MS (ESI) [M+H]$^+$=307.9

Step 2. A mixture of methyl 5-bromo-3-(bromomethyl)picolinate (150 mg, 0.49 mmol), (S)-1-cyclopropylethan-1-amine hydrochloride (59 mg, 0.49 mmol), boric acid (30 mg, 0.49 mmol) and potassium carbonate (201 mg, 1.46 mmol) in acetonitrile (4 mL) was stirred at rt for 16 hr under the Na. Filtered, the filtrate was concentrated in vacuo. The residue was purified by silica gel chromatography (MeOH/DCM=1/10) to afford (S)-3-bromo-6-(1-cyclopropylethyl)-5,6-dihydro-7H-pyrrolo[3,4-b]pyridin-7-one (70 mg, 51.2% yield). LC-MS (ESI) [M+H]$^+$=281.0.

Step 3. A mixture of (S)-3-bromo-6-(1-cyclopropylethyl)-5,6-dihydro-7H-pyrrolo[3,4-b]pyridin-7-one (70 mg, 0.25 mmol), N-(4-methylthiazol-2-yl)acetamide (58 mg, 0.37 mmol), t-Bu$_3$PBF$_4$ (14 mg, 0.05 mmol), cesium carbonate (163 mg, 0.5 mmol) and palladium (II) acetate (6 mg, 0.025 mmol) in dimethylformamide (2 mL) was stirred at 100° C. for 16 hr under N$_2$. Cooled to rt, added EA (30 mL), washed with water (20 mL×2) and brine, dried over anhydrous Na$_2$SO$_4$ and concentrated. The residue was purified by Pre-HPLC to afford (S)-N-(5-(6-(1-cyclopropylethyl)-7-oxo-6,7-dihydro-5H-pyrrolo[3,4-b]pyridin-3-yl)-4-methylthiazol-2-yl)acetamide (11.21 mg, 12.6%) as a white solid. LC-MS (ESI) [M+H]⁺=357.2, 1H NMR (400 MHz, DMSO) δ H: 12.27 (s, 1H), 8.79 (5, 1H), 8.15 (s, 1H), 4.61 (s, 2H), 7.67 (q, 1H), 2.41 (s, 3H), 2.17 (s, 3H), 1.32 (d, 3H), 1.28 (m, 1H), 0.58 (m, 1H), 0.43 (m, 2H), 0.24 (m, 2H).

(S)-N-(5-(6-(1-cyclopropylethyl)-5-oxo-6,7-dihydro-5H-pyrrolo[3,4-b]pyridin-2-yl)-4-methylthiazol-2-yl)acetamide (9)

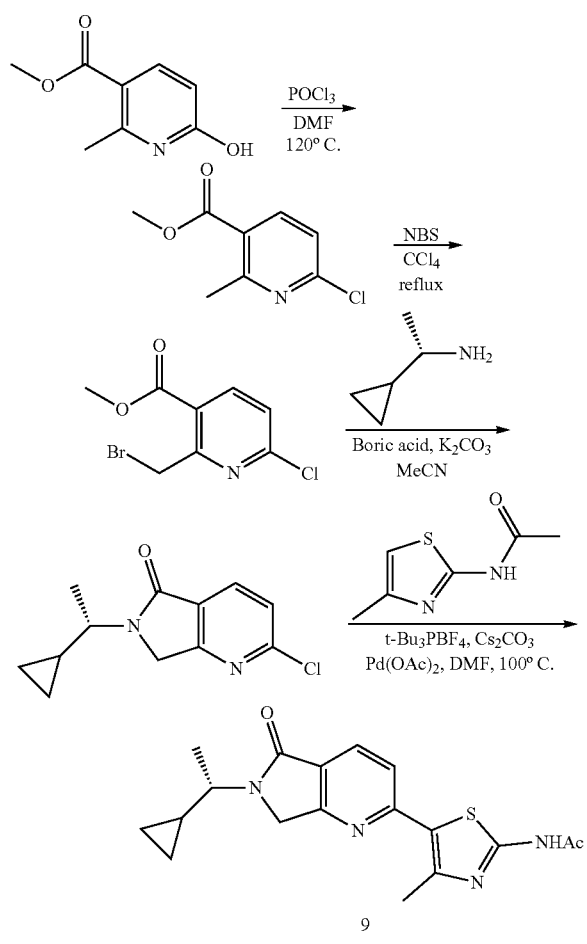

Step 1. A mixture of compound of methyl 6-hydroxy-2-methylnicotinate (500 mg, 2.99 mmol), POCl₃ (2 mL) was added in DMF (5 mL) stirred at 120° C. under N₂ for 2 h. After the reaction completed, the mixture was added Na₂CO₃ aqueous solution to adjust to pH=8. EA (30 mL) was added, washed with water (20 mL×2) and brine, dried over anhydrous Na₂SO₄ and concentrated. The residue was purified by column chromatography on silica gel to afford methyl 6-chloro-2-methylnicotinate as a white solid (450 mg, 81.3%).

Step 2. A mixture of compound of methyl 6-chloro-2-methylnicotinate (361 mg, 2 mmol), NBS (391 mg, 2.2 mmol) and AIBN (32.8 mg, 0.2 mmol) was added in CCl₄ (5 mL) then stirred under reflux for 4 h. After the reaction was completed, to the mixture was added EA (30 mL), washed with water (20 mL×2) and brine, dried over anhydrous Na₂SO₄ and concentrated. The residue was purified by column chromatography on silica gel to afford methyl 2-(bromomethyl)-6-chloronicotinate as a white solid (300 mg, 52.3%).

Step 3. A mixture of compound of methyl 2-(bromomethyl)-6-chloronicotinate (260 mg, 1.1 mmol), (S)-1-cyclopropylethan-1-amine hydrochloride (180 mg, 1.5 mmol), boric acid (61 mg 1.0 mmol), K₂CO₃ (560 mg, 4 mmol) was added in MeCN (10 mL) and stirred at rt overnight. After the reaction was completed, to the mixture was added EA (30 mL), washed with water (20 mL×2) and brine, dried over anhydrous Na₂SO₄ and concentrated. The residue was purified by column chromatography on silica gel to afford (S)-2-chloro-6-(1-cyclopropylethyl)-6,7-dihydro-5H-pyrrolo[3,4-b]pyridin-5-one as white solid (74 mg, 31.3%).

Step 4. A mixture of compound of (S)-2-chloro-6-(1-cyclopropylethyl)-6,7-dihydro-5H-pyrrolo[3,4-b]pyridin-5-one (74 mg, 0.315 mmol), N-(4-methylthiazol-2-yl)acetamide (60 mg, 0.378 mmol). t-Bu₃PBF₄ (18 mg, 0.063 mmol), cesium carbonate (204.7 mg, 0.63 mmol), and palladium (II) acetate (7 mg, 0.0315 mmol) was added in DMF (4 mL) stirred at 100° C. overnight. After the reaction was completed, to the mixture was added EA (30 mL), washed with water (20 mL×2) and brine, dried over anhydrous Na₂SO₄ and concentrated. The residue was purified by Pre-HPLC to afford (S)-N-(5-(6-(1-cyclopropylethyl)-5-oxo-6,7-dihydro-5H-pyrrolo[3,4-b]pyridin-2-yl)-4-methylthiazol-2-yl)acetamide as white solid (8.64 mg, 7.1%). 1H NMR (400 MHz, DMSO) δ H: 8.07-8.05 (d, J=8.0 Hz, 1H), 7.74-7.72 (d, J=8 Hz, 1H) 4.62 (s, 2H), 3.65-3.61 (m, 1H), 2.60 (s, 3H), 2.15 (s, 3H), 1.31-1.29 (d, J=8 Hz, 3H), 1.18-1.11 (m, 1H), 0.59-0.54 (m, 1H), 0.43-0.37 (m, 2H), 0.27-0.20 (m, 1H).

(S)-5-bromo-7-chloro-2-(1-cyclopropylethyl)isoindolin-1-one (intermediate 3) and (S)-N-(5-(7-chloro-2-(1-cyclopropylethyl)-1-oxoisoindolin-5-yl)-4-methylthiazol-2-yl)acetamide (Intermediate 4)

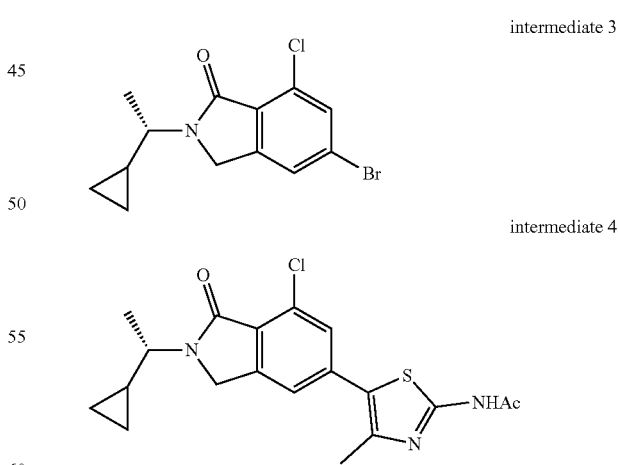

(S)-5-bromo-7-chloro-2-(1-cyclopropylethyl)isoindolin-1-one (intermediate 3) and (S)-N-(5-(7-chloro-2-(1-cyclopropylethyl)-1-oxoisoindolin-5-yl)-4-methylthiazol-2-yl) acetamide (intermediate 4) were prepared according to a known procedure (Pemberton, N., et al, Journal of Medicinal Chemistry 2018, 61, 5435-5441)

93

(S)-N-(5-(2-(1-cyclopropylethyl)-1-oxoisoindolin-5-yl)-4-methylthiazol-2-yl)acetamide (10)

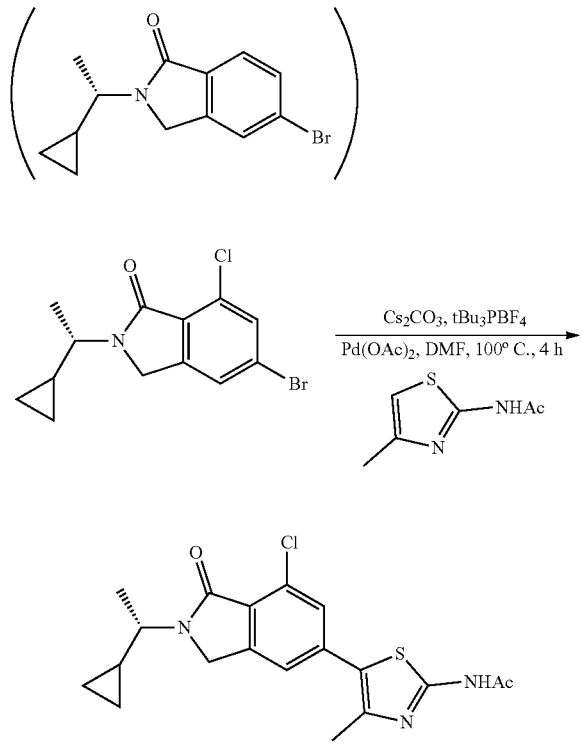

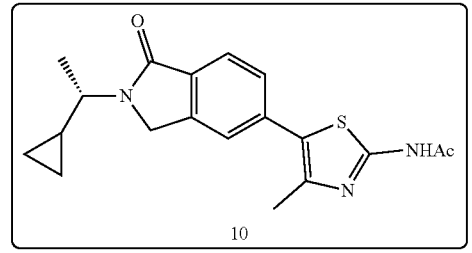

To a solution of (S)-5-bromo-7-chloro-2-(1-cyclopropylethyl)isoindolin-1-one containing 20% of (S)-5-bromo-2-(1-cyclopropylethyl)isoindolin-1-one (700 mg, 2.23 mmol) in DMF (10 mL) was added N-(4-methylthiazol-2-yl)acetamide (417 mg, 2.68 mmol), Cs$_2$CO$_3$ (1.4 g, 4.46 mmol), Pd(OAc)$_2$ (50 mg, 0.22 mmol), t-Bu$_3$PBF$_4$ (129 mg, 0.46 mmol) under N$_2$. The mixture was stirred at 100° C. for 3 h. Water (20 mL) and EtOAc (30 mL) were added. The reaction mixture was extracted with EtOAc (50 mL×3). Then it was washed with water (20 mL×4), dried over anhydrous Na$_2$SO$_4$ and concentrated to give the crude (700 mg). The crude (100 mg) was purified by pre-HPLC to give (S)-N-(5-(2-(1-cyclopropylethyl)-1-oxoisoindolin-5-yl)-4-methylthiazol-2-yl)acetamide (7.82 mg) as a white solid. LCMS (ESI)[M+H]$^+$ 356.2, 1 H NMR (400 MHz, DMSO) δ 12.18 (s, 1H), 7.75-7.65 (m, 2H), 7.56 (d, J=7.9 Hz, 1H), 4.59 (s, 2H), 3.63-3.53 (m, 1H), 2.41 (d, J=9.0 Hz, 3H), 2.15 (d, J=4.6 Hz, 3H), 1.29 (d, J=6.8 Hz, 3H), 1.17-1.08 (m, 1H), 0.62-0.53 (m, 1H), 0.44-0.34 (m, 2H), 0.27-0.18 (m, 1H).

94

(S)-2-(1-cyclopropylethyl)-7-(dimethylphosphoryl)-5-(4-methyl-2-(oxetan-3-ylamino)thiazol-5-yl)isoindolin-1-one (11)

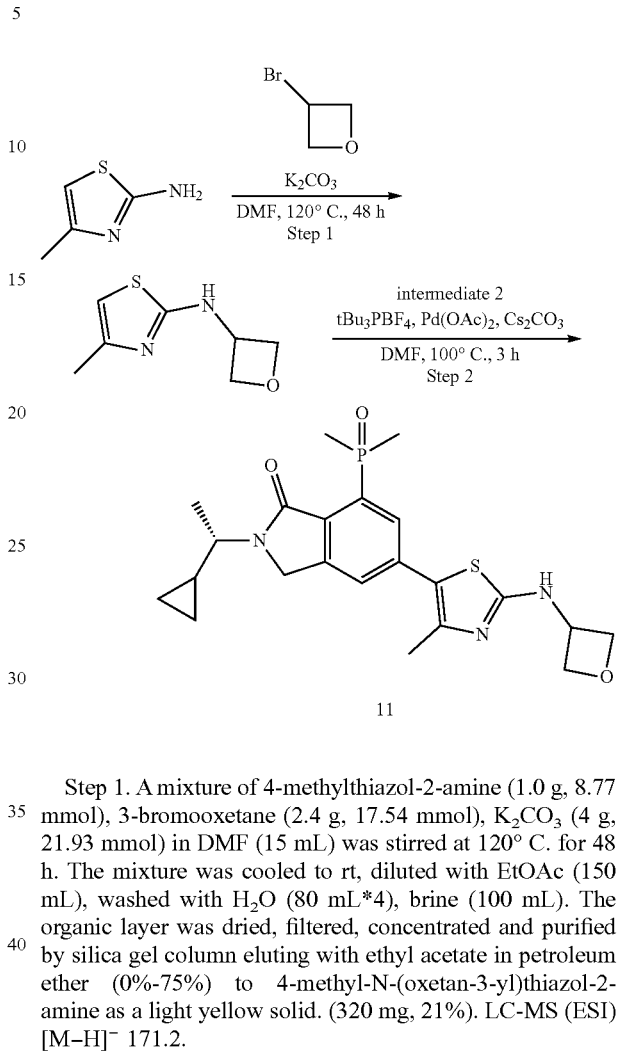

Step 1. A mixture of 4-methylthiazol-2-amine (1.0 g, 8.77 mmol), 3-bromooxetane (2.4 g, 17.54 mmol), K$_2$CO$_3$ (4 g, 21.93 mmol) in DMF (15 mL) was stirred at 120° C. for 48 h. The mixture was cooled to rt, diluted with EtOAc (150 mL), washed with H$_2$O (80 mL*4), brine (100 mL). The organic layer was dried, filtered, concentrated and purified by silica gel column eluting with ethyl acetate in petroleum ether (0%-75%) to 4-methyl-N-(oxetan-3-yl)thiazol-2-amine as a light yellow solid. (320 mg, 21%). LC-MS (ESI) [M−H]$^-$ 171.2.

Step 2. To a solution of (S)-5-bromo-2-(1-cyclopropylethyl)-7-(dimethylphosphoryl)isoindolin-1-one (60 mg, 0.17 mmol) in DMF (3 mL) was added 4-methyl-N-(oxetan-3-yl)thiazol-2-amine (57 mg, 0.34 mmol), t-Bu$_3$PBF$_4$ (10 mg, 0.034 mmol), Cs$_2$CO$_3$ (110 mg, 0.34 mmol) and Pd(OAc)$_2$ (3.8 mg, 0.017 mmol) under N$_2$. The mixture was stirred at 100° C. for 3 h. Water (30 mL) and EA (30 mL) were added. The reaction mixture was extracted with EA (30 mL×3). The organic layer was dried, filtered, concentrated and purified by Prep-HPLC to afford (S)-2-(1-cyclopropylethyl)-7-(dimethylphosphoryl)-5-(4-methyl-2-(oxetan-3-ylamino)thiazol-5-yl)isoindolin-1-one as a white solid (5.42 mg, 7% yield). HPLC condition: (SunFire C18 5 um 4.6× 150 mm 25 C 1.000 mL/min 16 min; Mobile Phase B: 0.03% HCl in MeCN, Mobile Phase A: 0.03% HCl in H$_2$O; rt: 8.86 min; 254 nm: 89.52%, 214 nm: 92.87%). LC-MS (ESI) [M+H]$^+$ 446.2 $^1$H NMR (400 MHz, MeOD) δ 8.11 (d, J=12.5 Hz, 1H), 7.95 (s, 1H), 4.81-4.66 (m, 2H), 4.14 (s, 1H), 3.98-3.75 (m, 4H), 3.73-3.60 (m, 1H), 2.43 (s, 3H), 2.05 (d, 6H), 1.40 (d, J=6.8 Hz, 3H), 1.23-1.11 (m, 1H), 0.76-0.65 (m, 1H), 0.55-0.39 (m, 2H), 0.37-0.28 (m, 1H), 0.36-0.30 (m, 1H).

Synthesis of (N-(5-(2-((S)-1-cyclopropylethyl)-7-(methylsulfinyl)-1-oxoisoindolin-5-yl)-4-methylthiazol-2-yl)acetamide (12)

Preparation of N-(5-(2-((S)-1-cyclopropylethyl)-7-(ethylsulfinyl)-1-oxoisoindolin-5-yl)-4-methylthiazol-2-yl)acetamide (13)

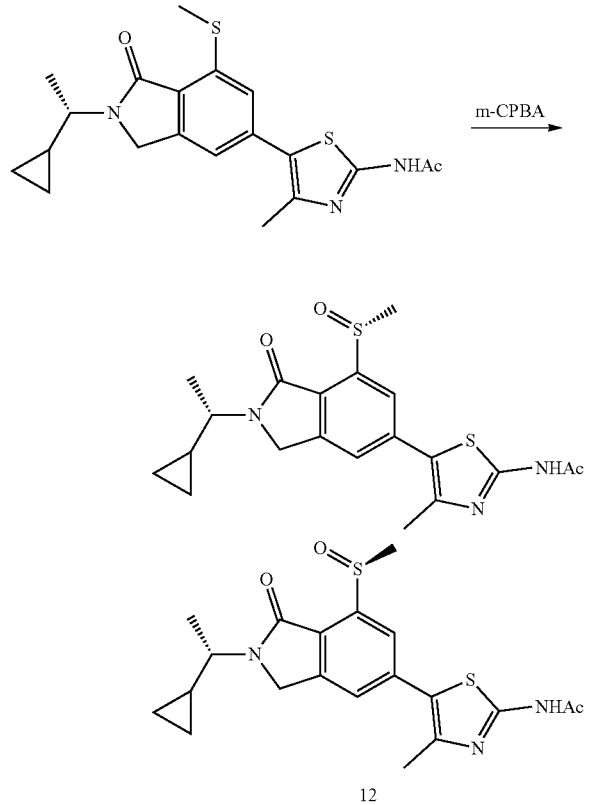

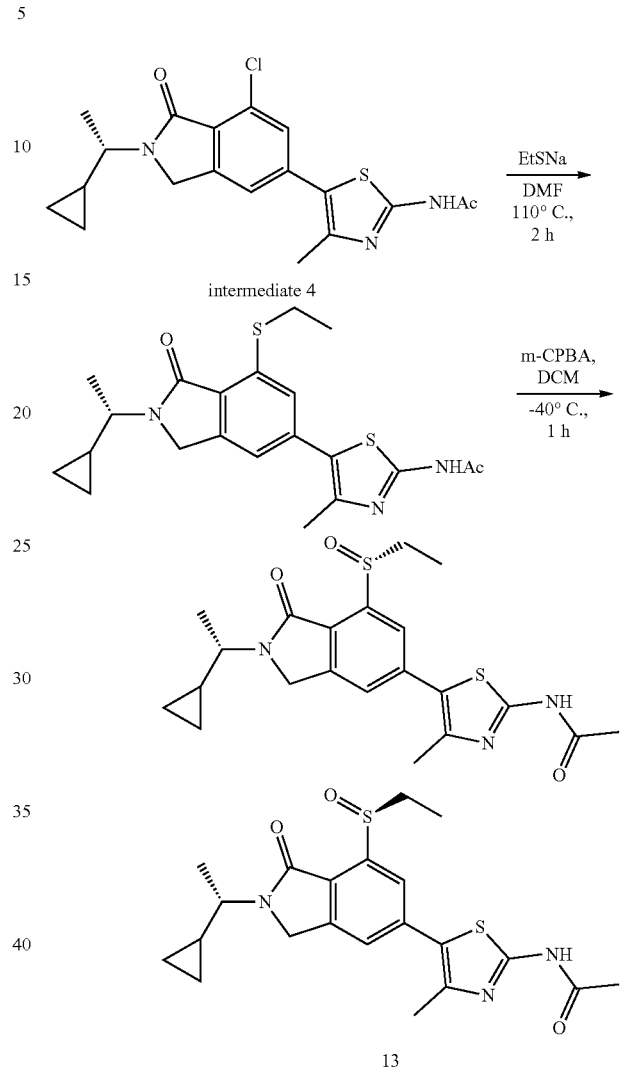

To a solution of (S)-N-(5-(2-(1-cyclopropylethyl)-7-(methylthio)-1-oxoisoindolin-5-yl)-4-methylthiazol-2-yl)acetamide (prepared according to a known procedure (Pemberton, N., et al, Journal of Medicinal Chemistry 2018, 61, 5435-5441) (230 mg, 057 mmol) in DCM (4 mL) was added mCPBA (99 mg, 0.57 mmol) at −40° C. The mixture was stirred at −40° C. for 1 h. Then aq.NaHCO$_3$ (5 mL) was added, and stirring was continued for about 30 min. Water (30 mL) and DCM (20 mL) were added. The reaction mixture was extracted with DCM (20 mL×3). Then it was washed with brine, dried over anhydrous Na$_2$SO$_4$ and concentrated to give the crude product (135 mg). The crude product (50 mg) was purified by pre-HPLC to give racemic mixture of N-(5-(2-((S)-1-cyclopropylethyl)-7-((R)-methylsulfinyl)-1-oxoisoindolin-5-yl)-4-methylthiazol-2-yl)acetamide and N-(5-(2-((S)-1-cyclopropylethyl)-7-((S)-methylsulfinyl)-1-oxoisoindolin-5-yl)-4-methylthiazol-2-yl)acetamide (12.54 mg, 24.12%) as a white solid. LC-MS (ESI) [M+H]$^+$ 418.2. 1 H NMR (400 MHz, DMSO) δ 12.23 (s, 1H), 7.89 (s, 1H), 7.85 (s, 1H), 4.71 (s, 2H), 3.55 (t, J=6.9 Hz, 1H), 2.90 (d, J=3.8 Hz, 3H), 2.44 (s, 3H), 2.17 (s, 3H), 1.31-1.26 (m, 3H), 1.13 (d, J=7.6 Hz, 1H), 0.61-0.54 (m, 1H), 0.45-0.35 (m, 2H), 0.25 (d, J=4.9 Hz, 1H).

Step 1. To a solution of intermediate 4 (100 mg, 0.250 mmol) in DMF (2.00 mL) was added EtSNa (43.0 mg, 0.510 mmol) under N$_2$. The mixture was stirred at 110° C. for 2 h. After being cooled to room temperature, the reaction was diluted with water (30 mL) and extracted with EA (20 mL×3). The combined organic layers was washed with brine (20 mL×3), dried over anhydrous Na$_2$SO$_4$, filtered and concentrated to give (S)-N-(5-(2-(1-cyclopropylethyl)-7-(ethylthio)-1-oxoisoindolin-5-yl)-4-methylthiazol-2-yl)acetamide (80.0 mg, 0.193 mmol, 75.0% yield) as an oil. LC-MS (ESI) [M+H]$^+$ 416.2.

Step 2. To a solution of (S)-N-(5-(2-(1-cyclopropylethyl)-7-(ethylthio)-1-oxoisoindolin-5-yl)-4-methylthiazol-2-yl)acetamide (80 mg, crude) in DCM (2 mL) was added m-CPBA (33 mg, 0.190 mmol) at −40° C. under Ar. The mixture was stirred at −40° C. for 1 h. aq.NaHCO$_3$ (5 mL) was added, and then the mixture was stirred for about 30 min, diluted with water (30 mL) and extracted with DCM (20 mL×3). The combined organic layers was dried over anhydrous Na$_2$SO$_4$, filtered, concentrated and purified by prep-HPLC to give a racemic mixture of N-(5-(2-((S)-1- cyclopropylethyl)-7-((R)-ethylsulfinyl)-1-oxoisoindolin-5-yl)-4-methylthiazol-2-yl)acetamide and N-(5-(2-((S)-1-cyclopropylethyl)-7-((S)-ethylsulfinyl)-1-oxoisoindolin-5-yl)-4-methylthiazol-2-yl)acetamide (18.1 mg, 0.0421 mmol, 22.5% yield) as a white solid. LC-MS (ESI) [M+H]$^+$ 432.1. $^1$H NMR (400 MHz, DMSO-$d_6$): δ 12.2 (s, 1H), 7.83-7.82 (m, 2H), 4.71 (s, 2H), 3.56-3.52 (m, 1H), 3.30-3.25 (m, 1H), 2.94-2.88 (m, 1H), 2.43 (s, 3H), 2.17 (s, 3H), 1.29 (t, J=6.6 Hz, 3H), 1.16-1.12 (m, 1H), 1.10-1.05 (m, 3H) 0.61-0.55 (m, 1H), 0.44-0.36 (m, 2H), 0.27-0.24 (m, 1H).

Preparation of N-(5-(2-((S)-1-cyclopropylethyl)-7-(isopropylsulfinyl)-1-oxoisoindolin-5-yl)-4-methylthiazol-2-yl)acetamide (14)

reaction mixture was diluted with water (30 mL) and extracted with EA (20 mL×3). The combined organic layers was washed with brine (20 mL×3) and dried over anhydrous Na$_2$SO$_4$, filtered and concentrated to give (S)-N-(5-(2-(1-cyclopropylethyl)-7-(isopropylthio)-1-oxoisoindolin-5-yl)-4-methylthiazol-2-yl)acetamide (40 mg, 0.0932 mmol, 36.3% yield). LC-MS (ESI) [M+H]$^+$ 430.1.

Step 2. Compound 14 was prepared according to a similar procedure as the preparation of 13 (14.1 mg, 0.0317 mmol, 28.9% yield) as a white solid. LC-MS (ESI) [M+H]$^+$ 446.1. $^1$H NMR (400 MHz, DMSO-$d_6$): δ 7.82 (s, 1H), 7.75 (s, 1H), 4.70 (d, J=2.4 Hz, 2H), 3.55-3.53 (m, 1H), 3.36-3.32 (m, 1H), 2.42 (s, 3H), 2.15 (s, 3H), 1.39 (d, J=6.8 Hz, 3H), 1.29 (t, J=8.0 Hz, 3H), 1.19-1.07 (m, 1H), 0.82 (t, J=7.6 Hz, 3H), 0.62-0.20 (m, 4H).

Synthesis of N-(5-(2-((S)-1-cyclopropylethyl)-7-(S-methylsulfonimidoyl)-1-oxoisoindolin-5-yl)-4-methylthiazol-2-yl)acetamide (15)

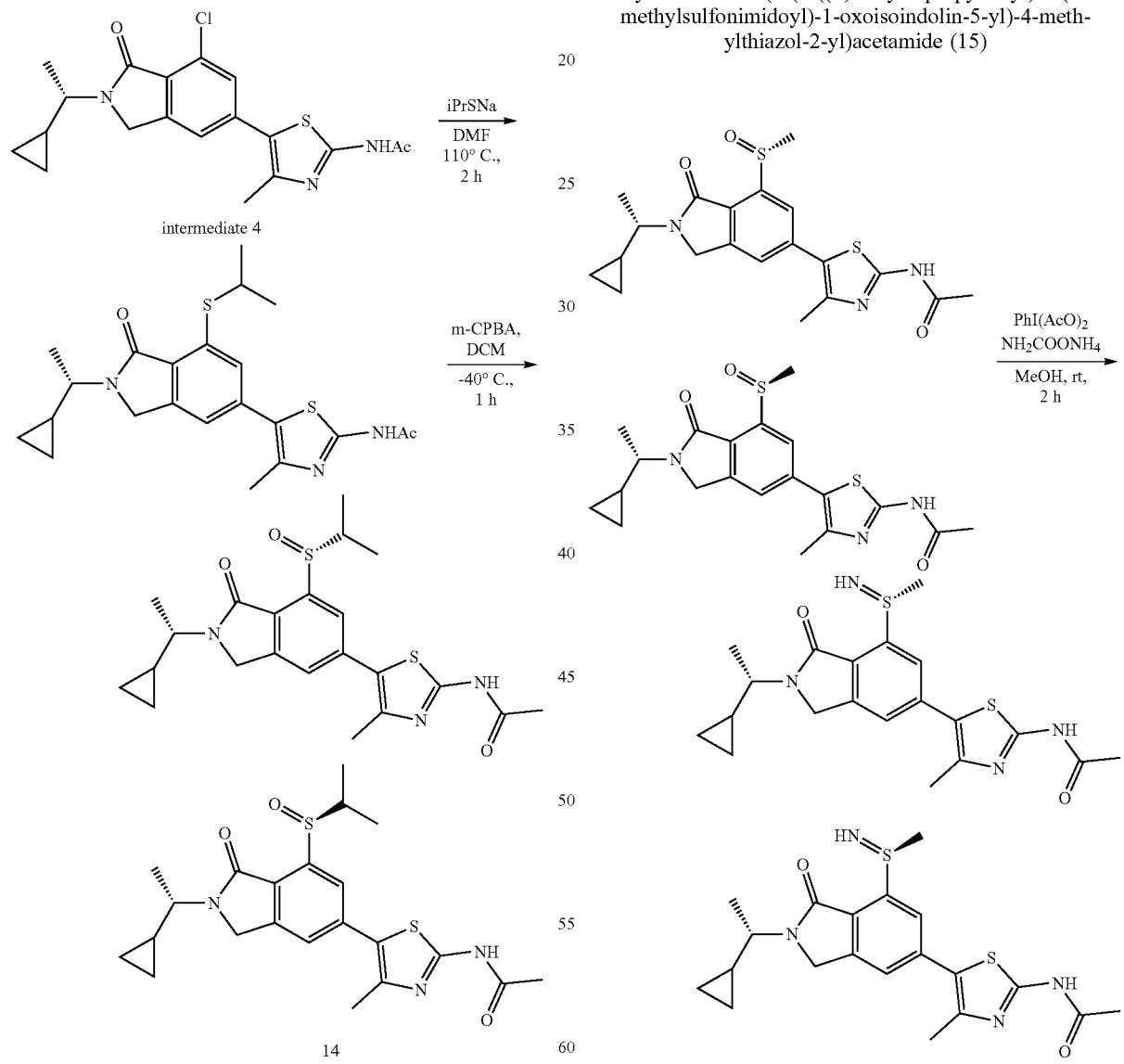

Step 1. To a solution of intermediate 4 (100 mg, 0.256 mmol) in DMF (2 mL) was added NaH (20.5 mg, 0.512 mmol, 60% w/w dispersion in mineral oil) and propane-2-thiol (39.0 mg, 0.512 mmol) at rt. The mixture was stirred at 110° C. for 2 h under N$_2$. After being cooled to rt, the To a solution of N-(5-(2-((S)-1-cyclopropylethyl)-7-(methylsulfinyl)-1-oxoisoindolin-5-yl)-4-methylthiazol-2-yl)acetamide (20 mg, 0.048 mmol) in MeOH (3 mL) was added NH$_2$COONH$_4$ (16 mg, 0.192 mmol), PhI(OAc)$_2$ (46 mg, 0.144 mmol). The mixture was stirred at 45° C. for 2 h. The mixture was purified by pre-HPLC to give a racemic mixture of N-(5-(2-((S)-1-cyclopropylethyl)-7-((R)-S-methylsulfinimidoyl)-1-oxoisoindolin-5-yl)-4-methylthiazol-2-yl)acetamide and N-(5-(2-((S)-1-cyclopropylethyl)-7-((S)-S-methylsulfinimidoyl)-1-oxoisoindolin-5-yl)-4-methylthiazol-2-yl)acetamide (3.22 mg, 15.54%) as a white solid. LC-MS (ESI) [M+H]$^+$ 433.2, 1 H NMR (400 MHz, DMSO) δ 12.26 (s, 1H), 8.01 (s, 1H), 7.94 (s, 1H), 4.69 (s, 2H), 4.60 (s, 1H), 3.67-3.58 (m, 1H), 3.46 (s, 3H), 2.44 (s, 3H), 2.17 (s, 3H), 1.31 (d, J=5.2 Hz, 3H), 1.20-1.12 (m, 1H), 0.64-0.55 (m, 1H), 0.47-0.37 (m, 2H), 0.31-0.23 (m, 1H).

N-(5-((R)-2-((S)-1-cyclopropylethyl)-7-(dimethylphosphoryl)-3-methyl-1-oxoisoindolin-5-yl)-4-methylthiazol-2-yl)acetamide and N-(5-((S)-2-((S)-1-cyclopropylethyl)-7-(dimethylphosphoryl)-3-methyl-1-oxoisoindolin-5-yl)-4-methylthiazol-2-yl)acetamide (16)

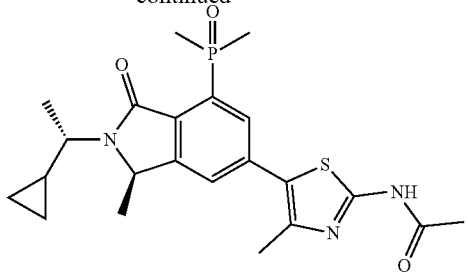

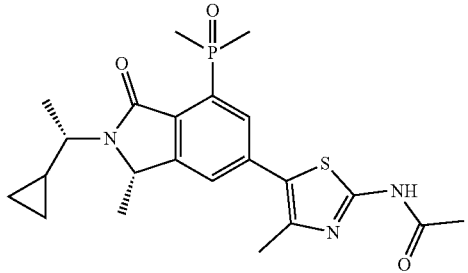

16

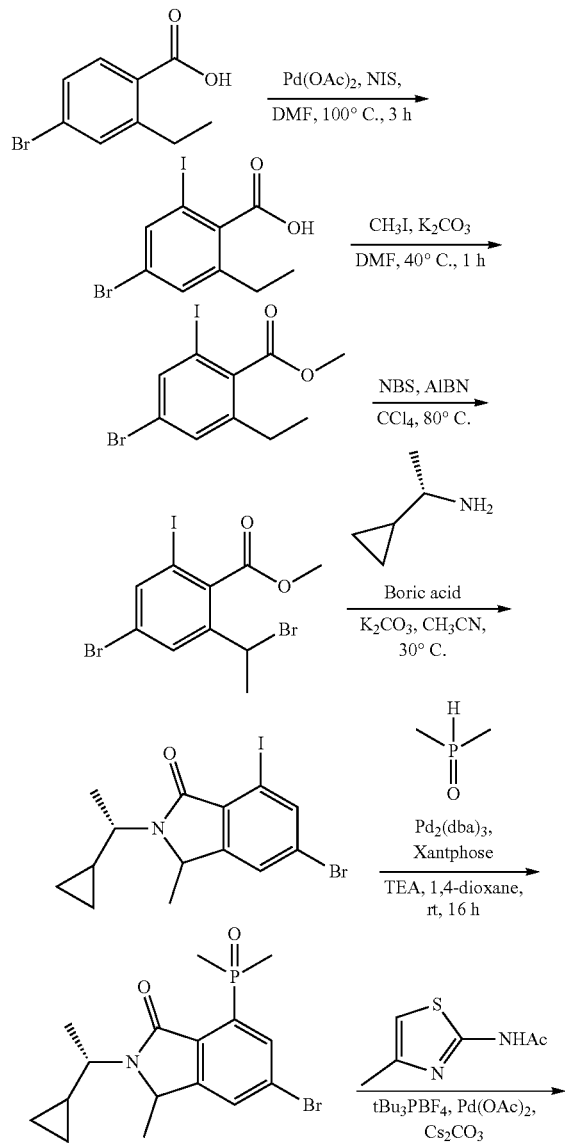

Step 1. To a solution of 4-bromo-2-ethylbenzoic acid (Prepared according to Buckley, D. et al, U.S. Pat. Appl. Publ., 20170119786) (2 g, 8.7 mmol) in DMF (20 mL) was added Pd(OAc)$_2$ (194 mg, 0.87 mmol), NIS (2.9 g, 13.1 mmol) under N$_2$. The mixture was stirred at 100° C. for 3 h. Water (30 mL) and EtOAc (30 mL) were added. The reaction mixture was extracted with EtOAc (30 mL×2). Then it was washed with water (20 mL×3), dried over anhydrous Na$_2$SO$_4$ and concentrated. The crude was purified by silica gel column (PE:EA, 1:0-5:1) to give 4-bromo-2-ethyl-6-iodobenzoic acid (3.2 g, crude).

Step 2. To a solution of 4-bromo-2-ethyl-6-iodobenzoic acid (3 g, 8.47 mmol) in DMF (50 mL) was added CH$_3$I (2.41 g, 16.96 mmol), K$_2$CO$_3$ (3.5 g, 25.4 mmol). The mixture was stirred at 40° C. for 2 h. Water (30 mL) and EtOAc (30 mL) were added. The reaction mixture was extracted with EtOAc (30 mL×2). Then it was washed with water (30 mL×5), dried over anhydrous Na$_2$SO$_4$ and concentrated. The crude was purified by silica gel column (PE:EA 100:0-100:15) to give methyl 4-bromo-2-ethyl-6-iodobenzoate (2.2 g, 71%) as a yellow oil. 1H NMR (400 MHz, DMSO) δ 7.95 (d, J=1.8 Hz, 1H), 7.60 (d, J=1.8 Hz, 1H), 3.87 (s, 3H), 2.49 (s, 2H), 1.11 (t, J=7.5 Hz, 3H).

Step 3. To a solution of methyl 4-bromo-2-ethyl-6-iodobenzoate (1 g, 2.82 mmol) in CCl$_4$ (10 mL) was added NBS (528 mg, 2.97 mmol), AIBN (93 mg, 0.56 mmol). The mixture was stirred at 80° C. for 3 h. After being concentrated, the crude was purified by silica gel column (PE:EA=20:1) to give methyl 4-bromo-2-(1-bromoethyl)-6-iodobenzoate (1.1 g, 90%) as a yellow solid. 1H NMR (400 MHz, DMSO) δ 8.12 (d, J=1.7 Hz, 1H), 7.98 (d, J=1.7 Hz, 1H), 5.19 (d, J=6.8 Hz, 1H), 3.91 (s, 3H), 1.95 (d, J=6.8 Hz, 3H).

Step 4. To a solution of methyl 4-bromo-2-(1-bromoethyl)-6-iodobenzoate (1 g, 2.25 mmol) in MeCN (30 mL) was added (S)-1-cyclopropylethan-1-amine (286 mg, 3.37 mmol), boric acid (137 mg, 2.25 mmol), K$_2$CO$_3$ (1.3 g, 8.99 mmol). The mixture was stirred at 85° C. for 17 h. Water (30 mL) and EtOAc (50 mL) were added. The reaction mixture was extracted with EtOAc (50 mL×2). Then it was washed with brine, dried over anhydrous Na$_2$SO$_4$ and concentrated. The crude was purified by silica gel column (PE:EA, 1:0-

20:1-10:1-5:1) to give 5-bromo-2-((S)-1-cyclopropylethyl)-7-iodo-3-methylisoindolin-1-one (650 mg, 69.31%) as a yellow oil. LC-MS (ESI) [M+H]+ 420.0.

Step 5. To a solution of 5-bromo-2-((S)-1-cyclopropylethyl)-7-iodo-3-methylisoindolin-1-one (650 mg, 1.56 mmol) in 1,4-dioxane (25 mL) was added dimethylphosphine oxide (133 mg, 1.71 mmol), Pd$_2$(dba)$_3$ (142 mg, 0.16 mmol), xantphose (90 mg, 0.16 mmol), TEA (0.64 mL, 4.67 mmol) under N$_2$. The mixture was stirred at rt for 17 h. Water (50 mL) and EA (50 mL) were added. The reaction mixture was extracted with EA (50 mL×2). Then it was washed with brine, dried over anhydrous Na$_2$SO$_4$ and concentrated. The crude was purified by silica gel column (PE:EA=1:0-10:1-0:1; DCM:MeOH=10:1) to give 5-bromo-2-((S)-1-cyclopropylethyl)-7-(dimethylphosphoryl)-3-methylisoindolin-1-one (300 mg, 52.37%) as a yellow oil. LC-MS (ESI) [M+H]+ 372.0.

Step 6. To a solution of 5-bromo-2-((S)-1-cyclopropylethyl)-7-(dimethylphosphoryl)-3-methylisoindolin-1-one (260 mg, 0.71 mmol) in DMF was added N-(4-methylthiazol-2-yl)acetamide (132 mg, 0.85 mmol), t-Bu$_3$PBF$_4$ (41 mg, 0.14 mmol), Cs$_2$CO$_3$ (460 mg, 1.41 mmol) and Pd(OAc)$_2$ (16 mg, 0.07 mmol) under N$_2$. The mixture was stirred at 100° C. for 2 h. Water (30 mL) and EA (30 mL) were added. The reaction mixture was extracted with EA (30 mL×3). Then it was washed with brine, dried over anhydrous Na$_2$SO$_4$ and concentrated. The crude was purified by pre-HPLC to give P1 (6.42 mg) and P2 (5.84 mg). LC-MS (ESI) [M+H]+ 446.3. P1: 1H NMR (400 MHz, DMSO) δ 8.10 (d, J=12.6 Hz, 1H), 7.92 (s, 1H), 4.94 (d, J=6.5 Hz, 1H), 2.43 (s, 3H), 2.17 (s, 3H), 1.92-1.80 (m, 6H), 1.59 (d, J=6.5 Hz, 3H), 1.38 (t, J=6.7 Hz, 4H), 0.62 (d, J=3.6 Hz, 1H), 0.49 (s, 1H), 0.37 (d, J=4.6 Hz, 1H), 0.13 (d, J=4.4 Hz, 1H); P2: 1H NMR (400 MHz, DMSO) δ 8.10 (dd, J=12.3, 1.3 Hz, 1H), 7.90 (s, 1H), 4.84 (d, J=6.6 Hz, 1H), 2.42 (s, 3H), 2.17 (s, 3H), 1.88 (t, J=13.9 Hz, 6H), 1.60 (d, J=6.6 Hz, 3H), 1.43 (d, J=7.0 Hz, 3H), 1.37-1.28 (m, 1H), 0.55 (dd, J=8.5, 5.0 Hz, 1H), 0.40 (dd, J=9.1, 5.0 Hz, 2H), 0.31 (dd, J=9.2, 4.5 Hz, 1H).

Preparation of N-(5-(2-(tert-butyl)-7-(methylsulfinyl)-1-oxoisoindolin-5-yl)-4-methylthiazol-2-yl)acetamide (17)

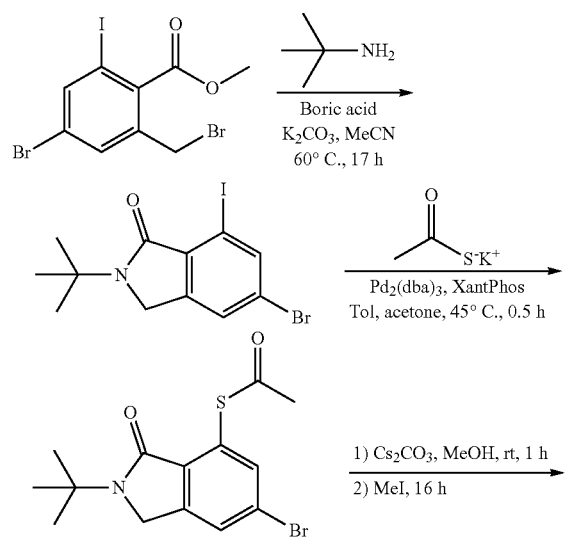

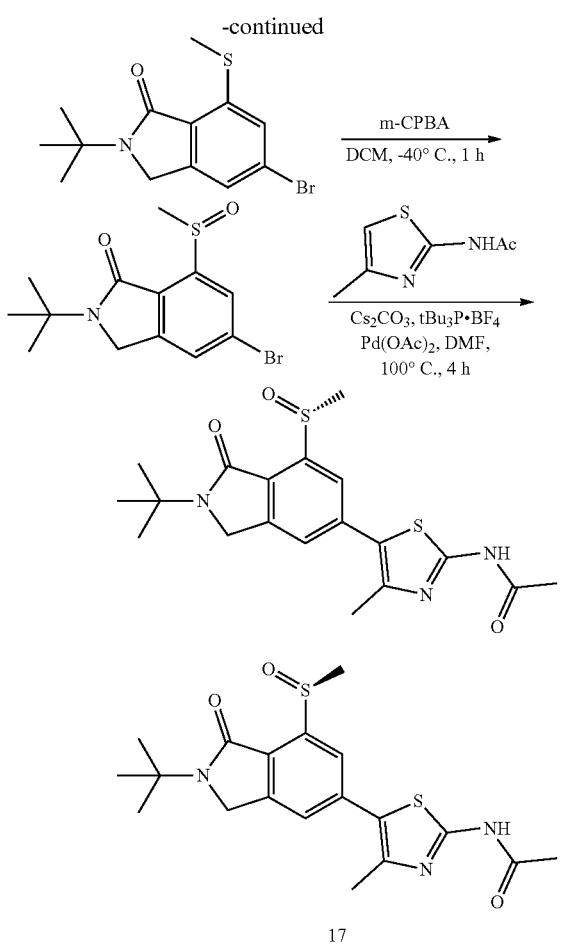

Step 1. 5-bromo-2-(tert-butyl)-7-iodoisoindolin-1-one was synthesized based on the similar procedure of preparation of intermediate 1 (100 mg, yield 10.9%) as colorless oil. LC-MS (ESI) [M+H]+ 393.9

Step 2. To a mixture of 5-bromo-2-(tert-butyl)-7-iodoisoindolin-1-one (90 mg, 0.219 mmol) in Tol/acetone (3 mL/1.5 mL) was added potassium ethanethioate (21 mg, 0.276 mmol), Pd$_2$(dba)$_3$ (19.8 mg, 0.0319 mmol) and XantPhos (25.2 mg, 0.0438 mmol) at room temperature. The mixture was stirred at 45° C. under argon atmosphere for 0.5 hours. The reaction mixture was cooled to room temperature and concentrated in vacuum to give the residue, which was purified by prep-TLC (PE:EA=3:1) to give S-(6-bromo-2-(tert-butyl)-3-oxoisoindolin-4-yl) ethanethioate (90 mg, crude) as a white solid. LC-MS (ESI) [M+H]+ 342.0

Step 3. To a solution of S-(6-bromo-2-(tert-butyl)-3-oxoisoindolin-4-yl) ethanethioate (60 mg, 0.175 mmol) in MeOH (4.00 mL) was added Cs$_2$CO$_3$ (85 mg, 0.262 mmol) at room temperature. The mixture was stirred at room temperature under argon atmosphere for 1 hour. MeI (124 mg, 0.877 mmol) was added and the mixture was stirred at room temperature under argon atmosphere for another 16 hours. The reaction mixture was concentrated in vacuum to give the residue, which was purified by prep-TLC (PE:EA=3:1, v/v) to give 5-bromo-2-(tert-butyl)-7-(methylthio)isoindolin-1-one (60 mg, over 100% yield) as a white solid. LC-MS (ESI) [M+H]+ 316.2

Step 4 and 5. Racemic mixture of (R)-N-(5-(2-(tert-butyl)-7-(methylsulfinyl)-1-oxoisoindolin-5-yl)-4-methylthiazol-2-yl)acetamide and (S)-N-(5-(2-(tert-butyl)-7-

(methylsulfinyl)-1-oxoisoindolin-5-yl)-4-methylthiazol-2-yl)acetamide was synthesized in a similar manner as the preparation of 13 (5 mg, 13.0% yield) as a white solid. LC-MS (ESI) [M+H]+ 406.0. ¹H NMR (400 MHz, MeOD-d₄): δ 8.00 (s, 1H), 7.77 (s, 1H), 4.76 (s, 2H), 2.98 (s, 3H), 2.45 (s, 3H), 2.23 (s, 3H), 1.56 (s, 9H).

N-(4-(difluoromethyl)-5-iodothiazol-2-yl)acetamide (intermediate 5)

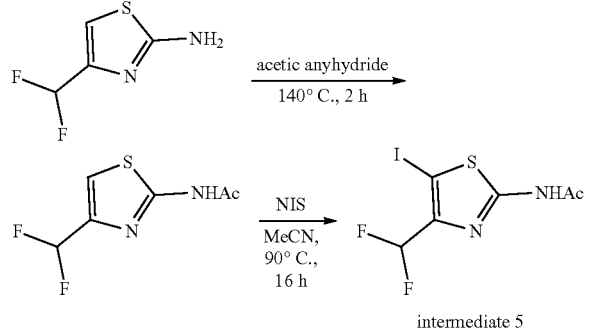

Step 1. A solution of 4-(difluoromethyl)thiazol-2-amine hydrochloride (Prepared according to Guo, L. et al, PCT Int. Appl., 2014037480) (700 mg, crude) in acetic anhydride (12.0 mL) was stirred at 140° C. for 2 hours. The reaction mixture was cooled to rt and concentrated in vacuum to give the residue, which was purified by chromatography on silica gel (PE:EA=10:1 to 3:1) to give the title compound N-(4-(difluoromethyl)thiazol-2-yl)acetamide (350 mg, 39.0% yield over 2 steps) as a white solid. LC-MS (ESI) [M+H]+= 193.1

Step 2. A solution of N-(4-(difluoromethyl)thiazol-2-yl)acetamide (120 mg, 0.624 mmol) and NIS (168 mg, 0.748 mmol) in MeCN (5.00 mL) was stirred at 90° C. for 16 hours under Ar. The reaction mixture was cooled to rt and concentrated in vacuum to give the residue, which was purified by chromatography on silica gel (PE:EA=10:1 to 3:1) to give intermediate 5 N-(4-(difluoromethyl)-5-iodothiazol-2-yl)acetamide (130 mg, 65.5% yield) as a yellow solid. LC-MS (ESI) [M+H]+ 318.9

Preparation of N-(5-(2-((S)-1-cyclopropylethyl)-7-(methylsulfinyl)-1-oxoisoindolin-5-yl)-4-(difluoromethyl)thiazol-2-yl)acetamide (18)

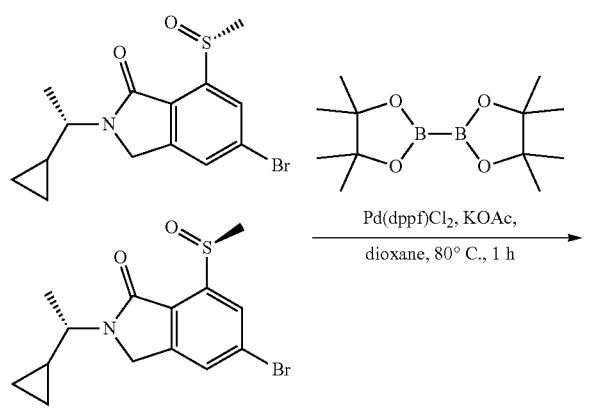

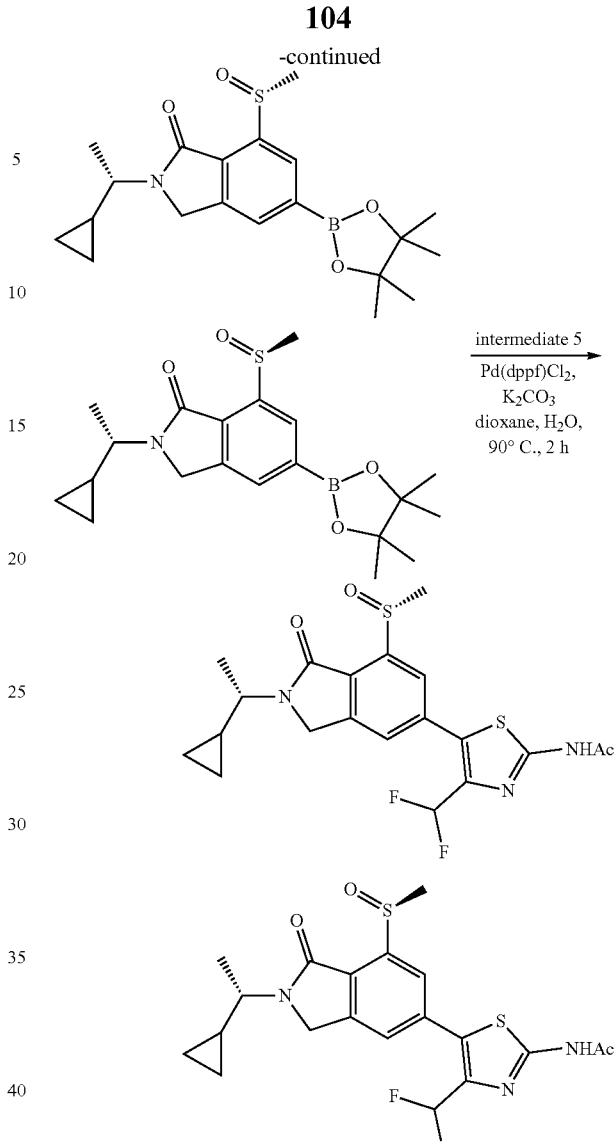

Step 1. A mixture of 5-bromo-2-((S)-1-cyclopropylethyl)-7-(methylsulfinyl)isoindolin-1-one (260 mg, 0.760 mmol), 4,4,4',4',5,5,5',5'-octamethyl-2,2'-bi(1,3,2-dioxaborolane) (386 mg, 1.519 mmol), Pd(dppf)Cl₂ (56 mg, 0.076 mmol) and KOAc (224 mg, 2.280 mmol) in dioxane (2.00 mL) was stirred at 80° C. under argon atmosphere for 1 hours. The reaction mixture was cooled to rt and concentrated in vacuum to give the residue, which was purified by chromatography on silica gel (PE:EA=10:1 to 3:1) to give the title compound 2-((S)-1-cyclopropylethyl)-7-(methylsulfinyl)-5-(4,4,5,5-tetramethyl-1,3,2-dioxaborolan-2-yl)isoindolin-1-one (160 mg, yield 54.1%) as a white solid. LC-MS (ESI) [M+H]+ 390.1

Step 2. A mixture of 2-((S)-1-cyclopropylethyl)-7-(methylsulfinyl)-5-(4,4,5,5-tetramethyl-1,3,2-dioxaborolan-2-yl)isoindolin-1-one (50 mg, 0.128 mmol), intermediate 5 (45 mg, 0.141 mmol), Pd(dppf)Cl₂ (10 mg, 0.0130 mmol) and K₂CO₃ (53 mg, 0.385 mmol) in dioxane/H₂O (2.00 mL/0.4 mL) was stirred at 90° C. under argon atmosphere for 2 hours. The reaction mixture was cooled to rt and concentrated in vacuum to give the residue, which was purified by prep-HPLC (base, NH$_3$H$_2$O) to give a racemic mixture of N-(5-(2-((S)-1-cyclopropylethyl)-7-((R)-methylsulfinyl)-1-oxoisoindolin-5-yl)-4-(difluoromethyl)thiazol-2-yl)acetamide and N-(5-(2-((S)-1-cyclopropylethyl)-7-((S)-methylsulfinyl)-1-oxoisoindolin-5-yl)-4-(difluoromethyl)-thiazol-2-yl)acetamide (5 mg, yield 8.60%) as a white solid. LC-MS (ESI) [M+H]$^+$ 454.1. $^1$H NMR (400 MHz, CDCl$_3$) δ: 9.80 (s, 1H), 8.10 (s, 1H), 7.57 (s, 1H), 6.50 (t, J=54.0 Hz, 1H), 4.65-4.49 (m, 2H), 3.65-3.61 (m, 3H), 2.97 (s, 3H), 1.32-1.29 (m, 3H), 0.96-0.81 (m, 1H), 0.80-0.79 (m, 1H), 0.43-0.33 (m, 3H).

General Procedure B:

To a solution of intermediate 8 (0.128 mmol) in 1,4-dioxane (2.00 mL) was added amide or other nucleophilic reagents (0.512 mmol), Cs$_2$CO$_3$ (125 mg, 0.384 mmol), X-phos G3 (8.80 mg, 0.0128 mmol) and Pd(OAc)$_2$ (8.32 mg, 0.0256 mmol) at room temperature. The mixture was heated to 110° C. for 1 hour-8 hours under Ar. The reaction mixture was cooled to room temperature. The mixture was concentrated under reduced pressure. The residue was purified by prep-HPLC to give the desired product.

General Procedure C:

A mixture of halides (0.375 mmol), thiazole (0.375 mmol), Pd(OAc)$_2$ (17 mg, 0.0750 mmol), t-Bu$_3$P.BF$_4$ (22 mg, 0.0750 mmol) and Cs$_2$CO$_3$ (366 mg, 1.13 mmol) in DMA (2 mL) was stirred at 100° C.-135° C. for 1 h-4 h under Ar. The mixture was cooled to rt and diluted with water (10 mL), extracted with ethyl acetate (10 mL×3). The combined organic layers were washed with brine, dried over Na$_2$SO$_4$, filtered and concentrated under reduced pressure. The residue was purified by prep-HPLC to give the title product.

Preparation of (S)-4,6-dichloro-2-(1-cyclopropylethyl)-1H-pyrrolo[3,4-c]pyridin-3(2H)-one (Intermediate 6)

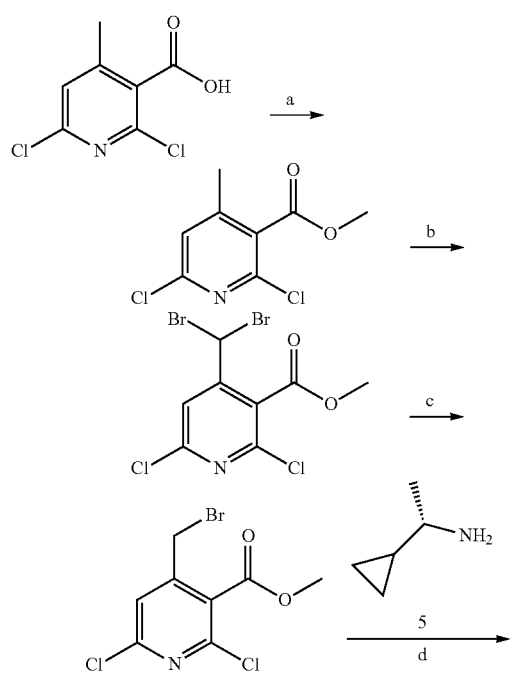

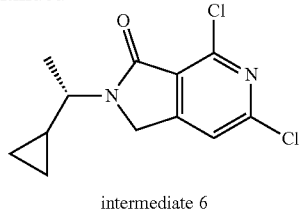

intermediate 6

Step a. To a solution of 2,6-dichloro-4-methylnicotinic acid (50.0 g, 244 mmol) in DMF (350 mL) was added K$_2$CO$_3$ (101 g, 731 mmol) and CH$_3$I (104 g, 731 mmol) at rt. The mixture was stirred at 40° C. for 2 h. After being cooled to rt, the mixture was diluted with water (530 mL) and extracted with EtOAc (250 mL×3). The combined organic layers was washed with brine (250 mL×4), dried over anhydrous Na$_2$SO$_4$ and concentrated. The residue was purified by silica gel chromatography (PE:EA=1:0-20:1, v/v) to give 2,6-dichloro-4-methylnicotinate (50.2 g, 93.93% yield, contained DMF) as a white solid. $^1$H NMR (400 MHz, CDCl$_3$): δ 7.14 (s, 1H), 3.95 (s, 3H), 2.32 (s, 3H).

Step b. To a solution of methyl 2,6-dichloro-4-methylnicotinate (50.0 g, 228 mmol) in CCl$_4$ (450 mL) was added NBS (163 g, 913 mmol), BPO (55.3 g, 159 mmol) at rt. The mixture was stirred at 90° C. and with concomitant irradiation from a tungsten lamp for 48 hours. After being cooled to rt, the mixture was concentrated under reduced pressure. The residue was purified by silica gel column chromatography (PE:EA=1:0-20:1, v/v) to give methyl 2,6-dichloro-4-(dibromomethyl)nicotinate (85.2 g, 99.25% yield, contained benzoic acid) as a yellow oil. $^1$H NMR (400 MHz, CDCl$_3$): δ 7.87 (s, 1H), 6.69 (s, 1H), 4.03 (s, 3H).

Step c. To a solution of 2,6-dichloro-4-(dibromomethyl)nicotinate (85.2 g, 226 mmol) in 260 mL of CH$_3$CN, DIPEA (58.5 g, 453 mmol) was added at 0° C. Then a solution of diethyl phosphite (31.3 g, 227 mmol) in 200 mL of CH$_3$CN was added drop wise carefully at 0° C. The mixture was stirred at 0° C. for another hour. The mixture was diluted with cold aq. NaHCO$_3$ (200 mL) and extracted with EA (200 mL×4). The combined organic layers was washed with brine (200 mL) and dried over Na$_2$SO$_4$, filtered and concentrated under reduced pressure. The residue was purified by silica gel column chromatography (PE:EA=1:0-20:1, v/v) to give methyl 4-(bromomethyl)-2,6-dichloronicotinate (60.2 g, 88.9% yield) as a yellow oil. $^1$H NMR (400 MHz, CDCl$_3$): δ 7.37 (s, 1H), 4.40 (s, 2H), 4.01 (s, 3H).

Step d. To a solution of methyl 4-(bromomethyl)-2,6-dichloronicotinate (60.2 g, 201 mmol) in MeCN (350 mL) was added (S)-1-cyclopropylethan-1-amine (29.4 g, 242 mmol), boric acid (14.9 g, 242 mmol) and K$_2$CO$_3$ (83.4 g, 604 mmol) at rt. The mixture was stirred at 60° C. for 2 h. After being cooled to rt, the mixture was diluted with water (450 mL) and EA (350 mL). The reaction mixture was extracted with EA (250 mL×3). The combined organic layers was washed with brine (200 mL), dried over anhydrous Na$_2$SO$_4$, filtered and concentrated. The residue was purified by silica gel column chromatography (PE:EA=1:0-20:1, v/v) to give (5)-4,6-dichloro-2-(1-cyclopropylethyl)-1H-pyrrolo[3,4-c]pyridin-3(2H)-one (intermediate 6) (30.2 g, 55.6% yield) as a white solid. LC-MS (ESI) [M+H]$^+$ 271.1. $^1$H NMR (400 MHz, DMSO-d$_6$): δ 7.89 (s, 1H), 4.62 (s, 2H), 3.57-3.53 (m, 1H), 1.27 (d, J=6.8 Hz, 3H), 1.12-1.09 (m, 1H), 0.59-0.54 (m, 1H), 0.43-0.21 (m, 3H).

Preparation of tert-butyl (4-methyl-5-(tributylstannyl)thiazol-2-yl)carbamate (Intermediate 7)

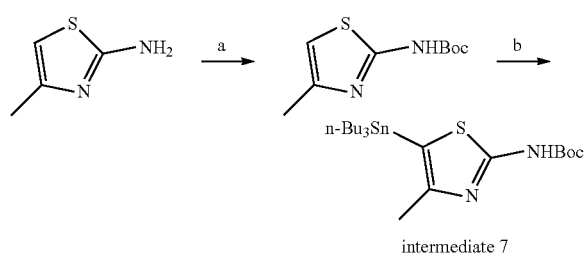

intermediate 7

Step a. To a solution of 4-methylthiazol-2-amine (40.0 g, 347 mmol) in THF/H₂O (800 mL/800 mL) was added NaHCO₃ (175 g, 2.09 mol) and Boc₂O (454 g, 2.09 mol) at rt. The mixture was stirred at 50° C. for 16 hours. The reaction mixture was cooled to rt. The mixture was concentrated in vacuum to remove the THF. The mixture was diluted with n-hexane, the solid was filtered and dried to give tert-butyl (4-methylthiazol-2-yl)carbamate (42.0 g, yield 56.6%) as a white solid. LC-MS (ESI): [M+H]⁺ 215.1

Step b. To a solution of tert-butyl (4-methylthiazol-2-yl)carbamate (42.0 g, 196 mmol) in THF (300 mL) was added LDA (304 mL, 608 mmol, 2.0 M) dropwise at −78° C. under argon atmosphere. The mixture was stirred at −78° C. for 1 hour under Ar. To the mixture was added a solution of n-Bu₃SnCl (63.8 g, 196 mmol) in THF (120 mL). And then the mixture was stirred at −78° C. for 12 h. The reaction mixture was quenched with ice water (200 mL) and extracted with EA (200 mL×3). The combined organic phase was concentrated in vacuum to give the residue, which was purified by chromatography on silica gel (PE:EA=200:1 to 10:1) to give intermediate 7 tert-butyl (4-methyl-5-(tributylstannyl)thiazol-2-yl)carbamate (32.0 g, yield 32.4%) as a colorless oil. ¹H NMR (400 MHz, DMSO-d₆): δ: 11.27 (s, 1H), 2.22 (s, 3H), 1.55-1.41 (m, 15H), 1.33-1.26 (m, 6H), 1.19-1.10 (m, 5H), 0.99-0.78 (m, 10H).

Preparation of (S)-N-(5-(4-chloro-2-(1-cyclopropylethyl)-3-oxo-2,3-dihydro-M-pyrrolo[3,4-c]pyridin-6-yl)-4-methylthiazol-2-yl)acetamide (intermediate 8)

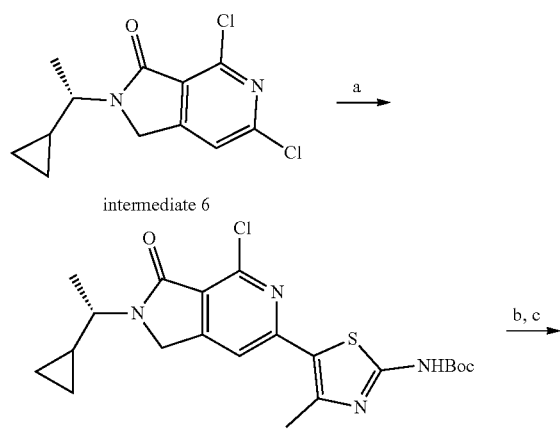

intermediate 8

Step a. To a solution of (S)-4,6-dichloro-2-(1-cyclopropylethyl)-1,2-dihydro-3H-pyrrolo[3,4-c]pyridin-3-one (intermediate 6) (500 mg, 1.80 mmol) in dioxane (10 mL) was added tert-butyl (4-methyl-5-(tributylstannyl)thiazol-2-yl)carbamate (intermediate 7) (1.81 g, 3.60 mmol), Pd(PPh₃)₄ (415 mg, 0.360 mmol) at rt. The mixture was stirred at 160° C. for 1 h under argon atmosphere in microwave reactor. The reaction mixture was cooled to rt, diluted with ice water (50 mL) and extracted with EA (50 mL×3). The combined organic phase was washed with brine and dried over Na₂SO₄, filtered and concentrated. The residue was purified by chromatography on silica gel (DCM:MeOH=200:1 to 20:1, v/v) to give the title compound tert-butyl (S)-(5-(4-chloro-2-(1-cyclopropylethyl)-3-oxo-2,3-dihydro-1H-pyrrolo[3,4-c]pyridin-6-yl)-4-methylthiazol-2-yl)carbamate (566 mg, 35.0% yield) as a white solid. ¹H NMR (400 MHz, DMSO-d₆): δ: 11.67 (s, 1H), 7.86 (s, 1H), 4.63 (s, 2H), 3.61-3.55 (m, 1H), 2.57 (s, 3H), 1.47 (s, 9H), 1.31-1.23 (m, 3H), 1.14-1.09 (m, 1H), 0.59-0.57 (m, 1H), 0.42-0.37 (m, 2H), 0.33-0.26 (m, 1H).

Step b. To a solution of tert-butyl (S)-(5-(4-chloro-2-(1-cyclopropylethyl)-3-oxo-2,3-dihydro-1H-pyrrolo[3,4-c]pyridin-6-yl)-4-methylthiazol-2-yl)carbamate (566 mg, 1.26 mmol) in DCM (2 mL) was added TFA (1.5 mL) at rt. The mixture was stirred at rt for 1 h. The mixture was quenched with aq. NaHCO₃ (20 mL) and extracted with DCM/MeOH (20 mL/1 mL×3). The combined organic phase was washed with brine and dried over Na₂SO₄, filtered and concentrated. The residue was purified by chromatography on silica gel (DCM:MeOH=200:1 to 20:1) to give the title compound (S)-6-(2-amino-4-methylthiazol-5-yl)-4-chloro-2-(1-cyclopropylethyl)-1,2-dihydro-3H-pyrrolo[3,4-c]pyridin-3-one (300 mg, 68.3% yield) as a yellow solid. LC-MS (ESI): [M+H]⁺ 349.1

Step c. To a solution of (S)-6-(2-amino-4-methylthiazol-5-yl)-4-chloro-2-(1-cyclopropylethyl)-1,2-dihydro-3H-pyrrolo[3,4-c]pyridin-3-one (300 mg, 0.86 mmol) in DCM (10 mL) was added TEA (261 mg, 2.58 mmol) and acetyl chloride (134 mg, 1.72 mmol) at 0° C. The mixture was stirred at rt for 1 h under Ar. The reaction mixture was diluted with ice water (50 mL) and extracted with EA (50 mL×3). The combined organic phase was washed with brine and dried over Na₂SO₄, filtered and concentrated. The residue was purified by chromatography on silica gel (DCM:MeOH=200:1 to 20:1, v/v) to give the title compound (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (intermediate 8) (56 mg, yield 16.7%) as a yellow solid. LC-MS (ESI): [M+H]⁺ 391.0. ¹H NMR (400 MHz, DMSO-d₆): δ: 12.30 (s, 1H) 7.90 (s, 1H), 4.64 (s, 2H), 3.59-3.55 (m, 1H), 2.61 (s, 3H), 2.17 (s, 3H), 1.27 (d, J=6.8 Hz, 3H), 1.15-1.10 (m, 1H), 0.59-0.57 (m, 1H), 0.43-0.41 (m, 2H), 0.33-0.25 (m, 1H).

Preparation of (S)-N-(5-(2-(1-cyclopropylethyl)-4-(methylsulfonyl)-3-oxo-2,3-dihydro-1H-pyrrolo[3,4-c]pyridin-6-yl)-4-methylthiazol-2-yl)acetamide (19)

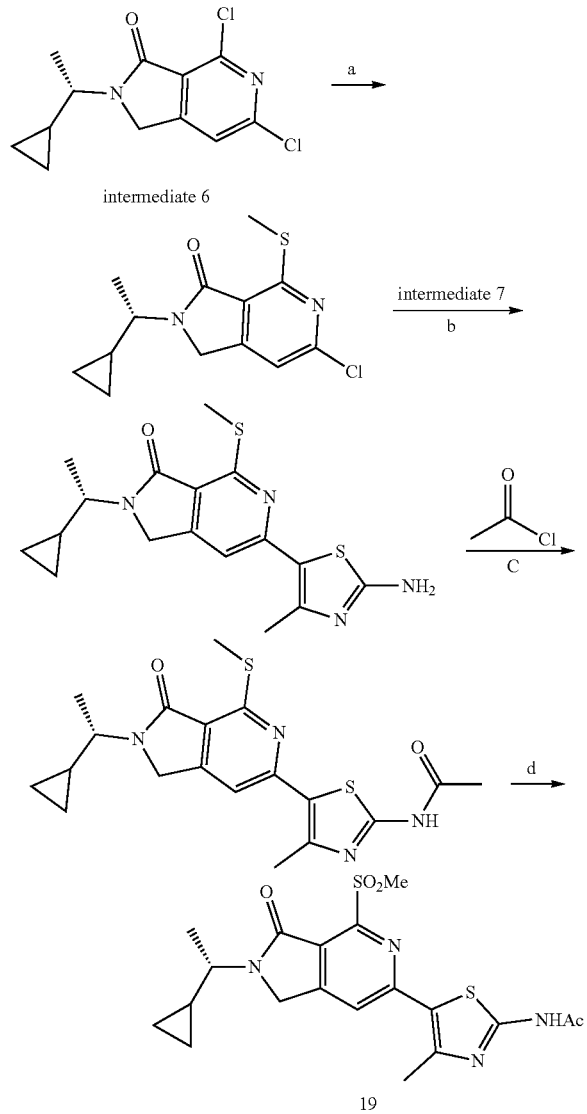

Step a. To a solution of (S)-4,6-dichloro-2-(1-cyclopropylethyl)-1H-pyrrolo[3,4-c]pyridin-3(2H)-one (intermediate 6) (1.00 g, 3.69 mmol) in DMF (10.0 mL) was added sodium methanethiolate (271 mg, 3.87 mmol) at room temperature. The mixture was stirred at room temperature for 16 h. The mixture was diluted with water (100 mL) and extracted with ethyl acetate (50.0 mL×3). The combined organic layer was washed with brine (50 mL), dried over $Na_2SO_4$, filtered and concentrated under reduced pressure. The residue was purified by silica gel column chromatography (PE/EA=5/1, v/v) to give (S)-6-chloro-2-(1-cyclopropylethyl)-4-(methylthio)-1H-pyrrolo[3,4-c]pyridin-3(2H)-one (300 mg, 28.8% yield) as a yellow solid. LC-MS (ESI) [M+H]+ 283.0

Step b. (S)-6-(2-amino-4-methylthiazol-5-yl)-2-(1-cyclopropylethyl)-4-(methylthio)-1,2-dihydro-3H-pyrrolo[3,4-c]pyridin-3-one was prepared according to general procedure C (200 mg, 40.1%) as a brown solid. Boc group was removed under this reaction condition. LC-MS (ESI) [M+H]+ 361.1

Step c. To a solution of (S)-6-(2-amino-4-methylthiazol-5-yl)-2-(1-cyclopropylethyl)-4-(methylthio)-1H-pyrrolo[3,4-c]pyridin-3(2H)-one (200 mg, 76.3% purity, 0.424 mmol) in dichloromethane (10.0 mL) was added triethylamine (128 mg, 1.27 mmol) and acetyl chloride (66 mg, 0.848 mmol) at 0° C. under Ar. The mixture was stirred at room temperature for 1 hour. The mixture was diluted with water (30.0 mL) and extracted with ethyl acetate (20.0 mL×3). The combined organic layer was washed with brine (30.0 mL), dried over $Na_2SO_4$, filtered and concentrated under reduced pressure. The residue was purified by silica gel column chromatography (dichloromethane/methanol=10/1, v/v) to give (S)-N-(5-(2-(1-cyclopropylethyl)-4-(methylthio)-3-oxo-2,3-dihydro-1H-pyrrolo[3,4-c]pyridin-6-yl)-4-methylthiazol-2-yl)acetamide (60 mg, 35.1% yield) as a slight yellow solid. LC-MS (ESI) [M+H]+ 403.2. $^1$H NMR (400 MHz, MeOD-$d_4$): δ 7.51 (s, 1H), 4.69-4.57 (m, 2H), 3.62-3.57 (m, 1H), 2.63 (d, J=8.4 Hz, 6H), 2.23 (s, 3H), 1.37 (d, J=6.8 Hz, 3H), 1.14-1.11 (m, 1H), 0.68-0.64 (m, 1H), 0.51-0.48 (m, 1H), 0.42-0.38 (m, 1H), 0.35-0.30 (m, 1H).

Step d. To a solution of (S)-N-(5-(2-(1-cyclopropylethyl)-4-(methylthio)-3-oxo-2,3-dihydro-1H-pyrrolo[3,4-c]pyridin-6-yl)-4-methylthiazol-2-yl)acetamide (60 mg, 0.149 mmol) in dichloromethane (5.00 mL) was added 3-chlorobenzoperoxoic acid (76 mg, 0.440 mmol) at 0° C. The mixture was stirred at 0° C. for 4 hours. The mixture was diluted with sodium sulfite solution (20.0 mL) and extracted with ethyl acetate (20.0 mL×3). The combined organic layer was washed with brine, dried over $Na_2SO_4$, filtered and concentrated under reduced pressure. The residue was purified by prep-HPLC to give (S)-N-(5-(2-(1-cyclopropylethyl)-4-(methylsulfonyl)-3-oxo-2,3-dihydro-1H-pyrrolo[3,4-c]pyridin-6-yl)-4-methylthiazol-2-yl)acetamide (19) (37.91 mg, 58.5% yield) as a white solid. LC-MS (ESI) [M+H]+ 435.1. $^1$H NMR (400 MHz, MeOD-$d_4$): δ 8.08 (s, 1H), 4.86-4.73 (m, 2H), 3.70-3.65 (m, 1H), 3.52 (s, 3H), 2.71 (s, 3H), 2.24 (s, 3H), 1.39 (d, J=7.2 Hz, 3H), 1.16-1.15 (m, 1H), 0.69-0.67 (m, 1H), 0.52-0.34 (m, 3H).

Preparation of (S)-N-(5-(2-(1-cyclopropylethyl)-4-(methylsulfonamido)-3-oxo-2,3-dihydro-1H-pyrrolo[3,4-c]pyridin-6-yl)-4-methylthiazol-2-yl)acetamide (20)

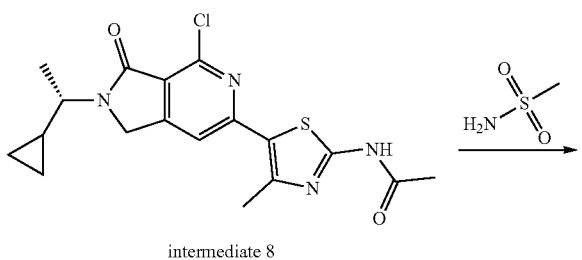

intermediate 8

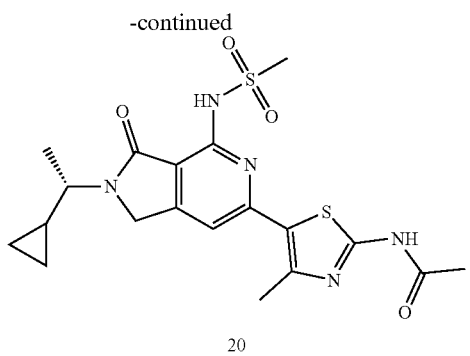

20

Prepared 20 according to the general procedure B (110° C. for 1 hours) (4.47 mg, 7.78% yield) as a light yellow solid. LC-MS (ESI) [M+H]+ 450.1. $^1$H NMR (400 MHz, MeOD-d$_4$): δ 7.36 (s, 1H), 4.68-4.60 (m, 2H), 3.58-3.50 (m, 1H), 3.46 (s, 3H), 3.31 (m, 3H), 2.22 (s, 3H), 1.36 (d, J=6.8 Hz, 3H), 1.05-0.96 (m, 1H), 0.64-0.58 (m, 1H), 0.43-0.26 (m, 3H).

Preparation of (S)-N-(5-(2-(1-cyclopropylethyl)-4-(ethylsulfonyl)-3-oxo-2,3-dihydro-1H-pyrrolo[3,4-c]pyridin-6-yl)-4-methylthiazol-2-yl)acetamide (21)

Prepared 21 according to the similar procedure as that of 19 (1.86 mg, 6.70% yield) as a light yellow solid. LC-MS (ESI) [M+H]+ 449.3. $^1$H NMR (400 MHz, MeOD-d$_4$): δ 8.08 (s, 1H), 4.86-4.75 (m, 2H), 3.82-3.76 (m, 2H), 3.70-3.59 (m, 1H), 2.70 (s, 3H), 2.24 (s, 3H), 1.44-1.38 (m, 6H), 1.20-1.13 (m, 1H), 0.71-0.66 (m, 1H), 0.54-0.44 (m, 2H), 0.42-0.32 (m, 1H).

Preparation of (S)-N-(5-(2-(1-cyclopropylethyl)-4-methoxy-3-oxo-2,3-dihydro-1H-pyrrolo[3,4-c]pyridin-6-yl)-4-methylthiazol-2-yl)acetamide (22)

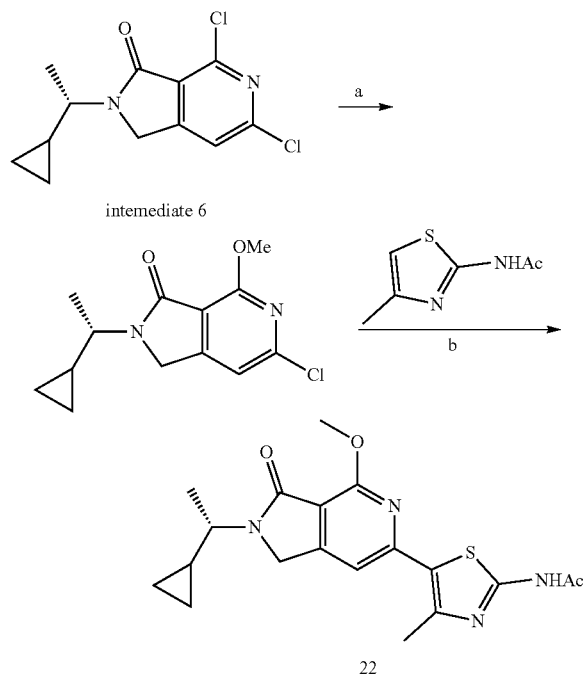

Step a. To a solution of (S)-4,6-dichloro-2-(1-cyclopropylethyl)-1,2-dihydro-3H-pyrrolo[3,4-c]pyridin-3-one (intermediate 6) (300 mg, 1.11 mmol) in MeOH (5 mL) was added MeONa (120 mg, 2.22 mmol) slowly at rt. The mixture was stirred at rt overnight. The mixture was quenched with aq. NH$_4$Cl (10 mL) and extracted with ethyl acetate (10 mL×3). The combined organic layers were washed with brine, dried over Na$_2$SO$_4$, filtered and concentrated under reduced pressure. The residue was purified by column chromatography eluted with petroleum ether:ethyl acetate (100:1~9:1) to give (S)-6-chloro-2-(1-cyclopropylethyl)-4-methoxy-1,2-dihydro-3H-pyrrolo[3,4-c]pyridin-3-one (130 mg, 43.9% yield) as a white solid. LC-MS (ESI) [M+H]+ 267.1.

Step b. Prepared 22 according to General procedure C (135° C., 1 h) (5.00 mg FA salt, 3.33% yield) as a white solid. LC-MS (ESI) [M+H]+ 387.0. $^1$H NMR (400 MHz, CDCl$_3$): δ 8.19 (s, 0.29H, FA), 7.21 (s, 1H), 4.56-4.40 (m, 2H), 4.14 (s, 3H), 3.76-3.72 (m, 1H), 2.68 (s, 3H), 2.31 (s, 3H), 1.33 (d, J=6.8 Hz, 3H), 1.00-0.98 (m, 1H), 0.63-0.62 (m, 1H), 0.44-0.37 (m, 3H).

Preparation of (R)-4,6-dichloro-2-(1-cyclopropylethyl)-1H-pyrrolo[3,4-c]pyridin-3(2H)-one (Intermediate 9)

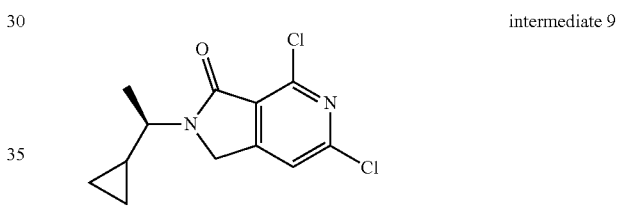

intermediate 9

Prepared 9 according to a similar procedure as preparation of intermediate 6 (60° C., 2 hours) (2.50 g, 9.26 mmol, 69.1% yield) as a white solid. LC-MS (ESI) [M+H]+ 270.9. $^1$H NMR (400 MHz, DMSO-d$_6$): δ 7.88 (s, 1H), 4.62 (s, 2H), 3.55-3.52 (m, 1H), 1.27 (d, J=6.8 Hz, 3H), 1.15-1.02 (m, 1H), 0.64-0.51 (m, 1H), 0.47-0.33 (m, 2H), 0.30-0.16 (m, 1H).

Preparation of 4,6-dichloro-2-(1,1,1-trifluoropropan-2-yl)-1H-pyrrolo[3,4-c]pyridin-3(2H)-one (Intermediate 10)

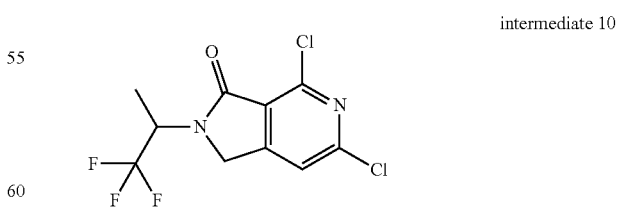

intermediate 10

Prepared intermediate 10 according to a similar procedure as the preparation of intermediate 6 (1.16 g, 3.89 mmol, 14.5% yield) as a white solid. LC-MS (ESI) [M+H]+ 298.9. $^1$H NMR (400 MHz, DMSO-d$_6$): δ 7.90 (s, 1H), 5.03-5.01 (m, 1H), 4.73-4.48 (m, 2H), 1.47 (d, J=7.2 Hz, 3H).

Preparation of (S)-N-(5-(2-(1-cyclopropylethyl)-4-(ethylsulfonamido)-3-oxo-2,3-dihydro-1H-pyrrolo[3,4-c]pyridin-6-yl)-4-methylthiazol-2-yl)acetamide (23)

Prepared 23 according to General procedure B (110° C. for 6 hours) (10.39 mg, 21.9% yield) as a slightly yellow solid. LC-MS (ESI) [M+H]$^+$ 464.3. $^1$H NMR (400 MHz, CDCl$_3$): δ 9.04 (s, 1H), 7.32 (s, 1H), 4.61-4.45 (m, 2H), 3.76-3.65 (m, 3H), 2.70 (s, 3H), 2.34 (s, 3H), 1.31 (t, J=7.2 Hz, 3H), 1.36 (d, J=6.8 Hz, 3H), 1.02-0.99 (m, 1H), 0.69-0.66 (m, 1H), 0.54-0.26 (m, 3H).

Preparation of (S)-N-(5-(4-(cyclopropanesulfonamido)-2-(1-cyclopropylethyl)-3-oxo-2,3-dihydro-1H-pyrrolo[3,4-c]pyridin-6-yl)-4-methylthiazol-2-yl)acetamide (24)

Prepared 24 according to General procedure B (110° C. for 8 hours) (5.90 mg, 12.1% yield) as a slight yellow solid. LC-MS (ESI) [M+H]$^+$ 476.3. $^1$H NMR (400 MHz, CDCl$_3$): δ 9.20 (s, 1H), 7.32 (s, 1H), 4.61-4.45 (m, 2H), 3.76-3.65 (m, 1H), 3.29-3.26 (m, 1H), 2.72 (s, 3H), 2.55 (s, 3H), 1.49-1.44 (m, 2H), 1.36 (d, J=6.8 Hz, 3H), 1.14-1.09 (m, 2H), 1.05-0.96 (m, 1H), 0.71-0.64 (m, 1H), 0.54-0.33 (m, 3H).

Preparation of (S)-N-(5-(2-(1-cyclopropylethyl)-3-oxo-4-(2-oxopyrrolidin-1-yl)-2,3-dihydro-M-pyrrolo[3,4-c]pyridin-6-yl)-4-methylthiazol-2-yl)acetamide (25)

Prepared 25 according to General procedure B (110° C. for 6 hours) (5.73 mg, 12.8% yield) as a white solid. LC-MS (ESI) [M+H]$^+$ 440.4. $^1$H NMR (400 MHz, MeOD-d$_4$): δ 7.76 (s, 1H), 4.75-4.61 (m, 2H), 4.10-4.07 (m, 2H), 3.69-3.55 (m, 1H), 2.65 (s, 3H), 2.62 (d, J=8.2 Hz, 2H), 2.34-2.25 (m, 2H), 2.15 (s, 1H), 1.37 (d, J=6.8 Hz, 3H), 1.18-1.10 (m, 1H), 0.72-0.61 (m, 1H), 0.53-0.27 (m, 3H).

Preparation of (S)-N-(6-(2-acetamido-4-methylthiazol-5-yl)-2-(1-cyclopropylethyl)-3-oxo-2,3-dihydro-M-pyrrolo[3,4-c]pyridin-4-yl)cyclopropanecarboxamide (26)

Prepared 26 according to General procedure B (110° C. for 2 hours) (2.11 mg, 4.69% yield) as a yellow solid. LC-MS (ESI) [M+H]$^+$ 440.3. $^1$H NMR (400 MHz, CDCl$_3$): δ 9.98 (s, 1H), 7.26 (s, 1H), 4.59-4.43 (m, 2H), 3.71-3.67 (m, 1H), 2.76 (s, 3H), 2.67 (m, 3H), 1.37 (d, J=6.8 Hz, 3H), 1.22-1.18 (m, 2H), 1.03-0.96 (m, 4H), 0.71-0.67 (m, 1H), 0.53-0.33 (m, 3H).

Preparation of (S)-N-(5-(2-(1-cyclopropylethyl)-4-methyl-3-oxo-2,3-dihydro-M-pyrrolo[3,4-c]pyridin-6-yl)-4-methylthiazol-2-yl)acetamide (27)

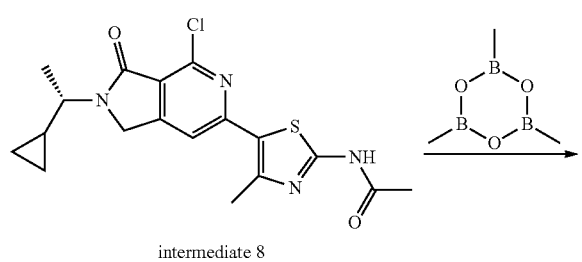

intermediate 8

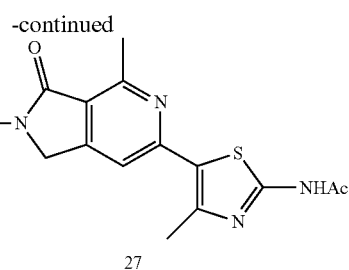

27

To a solution of (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (40.0 mg, 0.102 mmol) in dioxane (4.00 mL) was added 2,4,6-trimethyl-1,3,5,2,4,6-trioxatriborinane (154 mg, 1.22 mmol), Pd(PPh$_3$)$_4$ (12.0 mg, 0.0102 mmol) and K$_2$CO$_3$ (56.0 mg, 0.409 mmol) at rt. The mixture was stirred at 90° C. under argon atmosphere for 2 hours. The reaction mixture was cooled to rt. The mixture was filtered and the filtrate was concentrated in vacuum to give the residue, which was purified by prep-HPLC (base, NH$_3$H$_2$O) to give the title compound (S)-N-(5-(2-(1-cyclopropylethyl)-4-methyl-3-oxo-2,3-dihydro-1H-pyrrolo[3,4-c]pyridin-6-yl)-4-methylthiazol-2-yl)acetamide (27) (1.50 mg, yield 3.97%) as a white solid. LC-MS (ESI) [M+H]$^+$= 371.0. $^1$H NMR (400 MHz, MeOD-d$_4$): δ 7.68 (s, 1H), 4.66-4.61 (m, 1H), 3.66-3.62 (m, 1H), 2.82 (s, 3H), 2.61 (s, 3H), 2.23 (s, 3H), 1.37 (d, J=7.8, 3H), 1.15-1.13 (m, 1H), 0.67-0.66 (m, 1H), 0.49-0.42 (m, 2H), 0.41-0.37 (m, 1H).

Preparation of (S)-N-(5-(2-(1-cyclopropylethyl)-4-(3,3-dimethylureido)-3-oxo-2,3-dihydro-1H-pyrrolo[3,4-c]pyridin-6-yl)-4-methylthiazol-2-yl)acetamide (28)

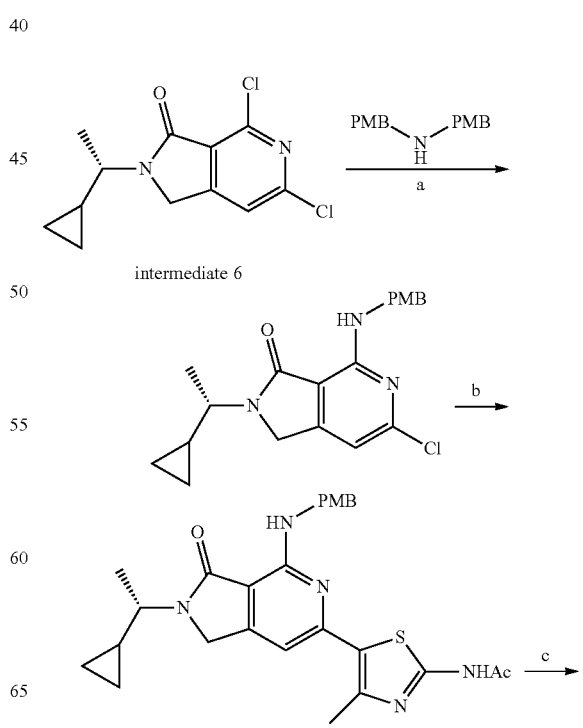

intermediate 6

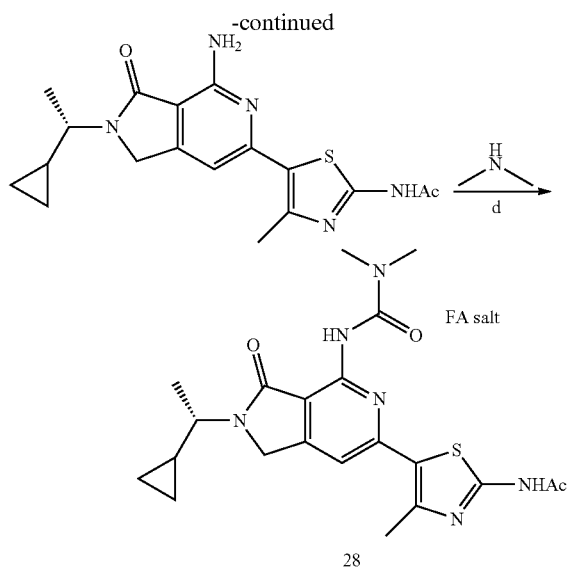

Step a. A solution of (S)-4,6-dichloro-2-(1-cyclopropylethyl)-1,2-dihydro-3H-pyrrolo[3,4-c]pyridin-3-one (intermediate 6) (2.00 g, 7.38 mmol), bis(2,4-dimethoxybenzyl)amine (7.00 g, 22.1 mmol) and Et₃N (1.50 g, 14.8 mmol) in dioxane (20 mL) was heated at 160° C. for 5 h in a sealed tube. The mixture was quenched with aq. NH₄Cl (60 mL) and extracted with ethyl acetate (60 mL×3). The combined organic layers were washed with brine, dried over Na₂SO₄, filtered and concentrated under reduced pressure. The residue was purified by column chromatography eluted with petroleum ether:ethyl acetate (100:1-8:1) to give (S)-6-chloro-2-(1-cyclopropylethyl)-4-(2,4-dimethoxybenzylamino)-1H-pyrrolo[3,4-c]pyridin-3(2H)-one (2.00 g, 67.4% yield) as a green solid (one of DMB was removed under reaction condition). ¹H NMR (400 MHz, CDCl₃): δ 7.30-7.26 (m, 1H), 7.23-7.20 (m, 1H), 6.55 (s, 1H), 6.46-6.40 (m, 2H), 4.64 (d, J=5.6 Hz, 2H), 4.37-4.22 (m, 2H), 3.86 (s, 3H), 3.80 (s, 3H), 3.61-3.57 (m, 1H), 1.28 (d, J=6.8 Hz, 3H), 0.95-0.93 (m, 1H), 0.63-0.59 (m, 1H), 0.45-0.35 (m, 3H).

Step b. Prepared (S)-N-(5-(2-(1-cyclopropylethyl)-4-(2,4-dimethoxybenzylamino)-3-oxo-2,3-dihydro-1H-pyrrolo[3,4-c]pyridin-6-yl)-4-methylthiazol-2-yl) according to General procedure C (135° C., 1 h) (1.20 g, 23.0% yield) as a yellow solid. LC-MS (ESI) [M+H]⁺ 522.1.

Step c. To a suspension of (S)-N-(5-(2-(1-cyclopropylethyl)-4-(2,4-dimethoxybenzylamino)-3-oxo-2,3-dihydro-1H-pyrrolo[3,4-c]pyridin-6-yl)-4-methylthiazol-2-yl)acetamide (1.00 g, 1.92 mmol) in DCM (6 mL) was added TFA (6 mL) at rt. The reaction mixture was stirred at rt overnight. The reaction mixture was concentrated. The residue was diluted with aq. NaHCO₃ (40 mL), extracted with ethyl acetate (30 mL×3). The combined organic layers were washed with brine, dried over Na₂SO₄, filtered and concentrated under reduced pressure to give (S)-N-(5-(4-amino-2-(1-cyclopropylethyl)-3-oxo-2,3-dihydro-1H-pyrrolo[3,4-c]pyridin-6-yl)-4-methylthiazol-2-yl)acetamide (600 mg, 84.1% yield) as a yellow solid. LC-MS (ESI) [M+H]⁺ 372.3.

Step d. To a suspension of (S)-N-(5-(4-amino-2-(1-cyclopropylethyl)-3-oxo-2,3-dihydro-1H-pyrrolo[3,4-c]pyridin-6-yl)-4-methylthiazol-2-yl)acetamide (150 mg, 0.404 mmol) in DCM (3 mL) was added triphosgene (48 mg, 0.161 mmol) slowly at 0° C., followed by the addition of Et₃N (82 mg, 0.808 mmol) at 0° C. The resulting mixture was stirred at rt for 6 h. After that, to the above mixture was added dimethylamine (0.6 mL, 1.21 mmol, 2.0 M in THF) slowly at 0° C. The reaction mixture was stirred at rt overnight. The mixture was quenched with aq. NH₄Cl (10 mL) and extracted with dichloromethane (10 mL×3). The combined organic layers were washed with brine, dried over Na₂SO₄, filtered and concentrated under reduced pressure. The residue was purified by prep-HPLC to give (S)-N-(5-(2-(1-cyclopropylethyl)-4-(3,3-dimethylureido)-3-oxo-2,3-dihydro-1H-pyrrolo[3,4-c]pyridin-6-yl)-4-methylthiazol-2-yl)acetamide (28) (7.48 mg FA salt, 4.20% yield) as a white solid. LC-MS (ESI) [M+H]⁺ 443.2. ¹H NMR (400 MHz, DMSO-d₆): δ 12.18 (br s, 1H), 9.10 (s, 1H), 8.45 (s, 0.61H, FA), 7.41 (s, 1H), 4.61 (s, 2H), 3.54-3.50 (m, 1H), 2.98 (s, 6H), 2.64 (s, 3H), 2.15 (s, 3H), 1.28 (d, J=6.8 Hz, 3H), 1.13-1.11 (m, 1H), 0.59-0.58 (m, 1H), 0.43-0.30 (m, 3H).

(S)-6-(2-acetamido-4-methylthiazol-5-yl)-2-(1-cyclopropylethyl)-N,N-dimethyl-3-oxo-2,3-dihydro-1H-pyrrolo[3,4-c]pyridine-4-carboxamide (29), (S)-6-(2-acetamido-4-methylthiazol-5-yl)-2-(1-cyclopropylethyl)-3-oxo-2,3-dihydro-1H-pyrrolo[3,4-c]pyridine-4-carboxylic acid (30) and (S)-6-(2-acetamido-4-methylthiazol-5-yl)-2-(1-cyclopropylethyl)-3-oxo-2,3-dihydro-1H-pyrrolo[3,4-c]pyridine-4-carboxamide (31)

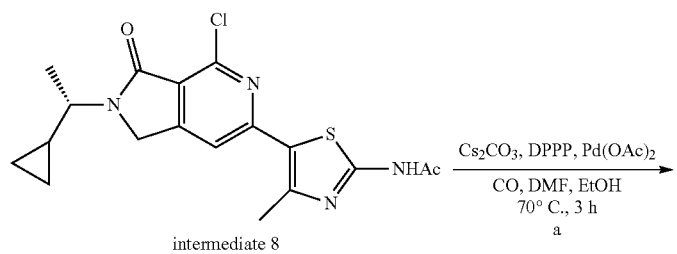

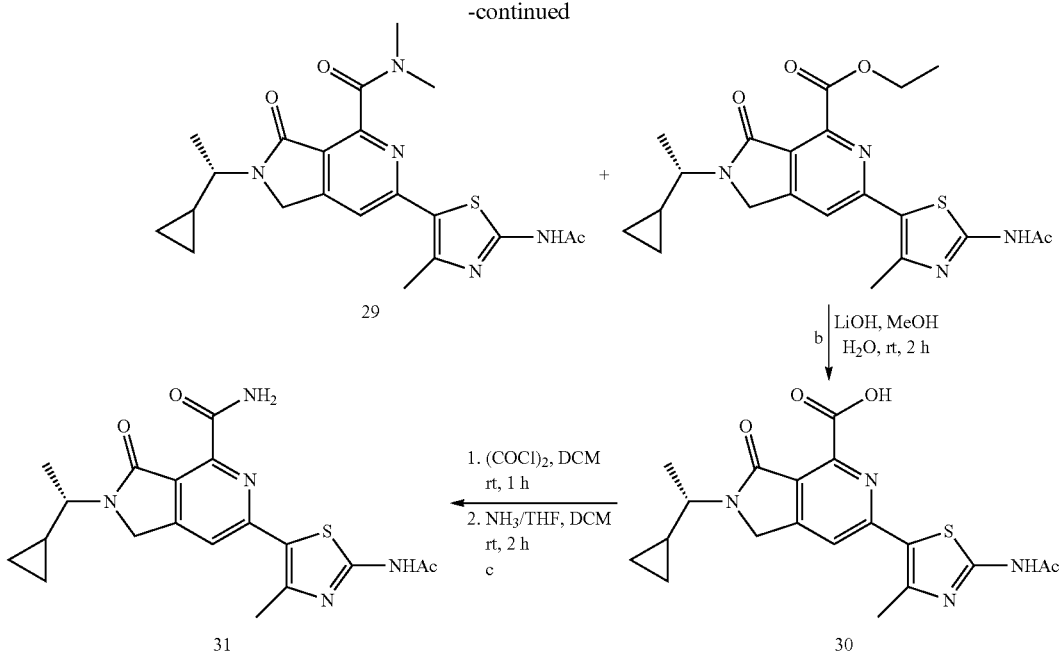

Step a. To a solution of (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (400 mg, 1.02 mmol) in DMF (5.00 mL) was added ethanol (5.00 mL), $Cs_2CO_3$ (834 mg, 2.56 mmol), DPPP (42 mg, 0.102 mmol) and $Pd(OAc)_2$ (23 mg, 0.103 mmol) at room temperature. The mixture was purged with a balloon of CO three times. The mixture was stirred at 70° C. for 3 hours under CO (1 atm). The mixture was cooled to rt and diluted with water (100 mL), extracted with ethyl acetate (50.0 mL×3). The combined organic layer was washed with brine, dried over $Na_2SO_4$, filtered and concentrated under reduced pressure. The residue was purified by silica gel column chromatography (DCM/MeOH=20/1) to give (S)-ethyl 6-(2-acetamido-4-methylthiazol-5-yl)-2-(1-cyclopropylethyl)-3-oxo-2,3-dihydro-1H-pyrrolo[3,4-c]pyridine-4-carboxylate (100 mg, 22.7% yield) as a yellow solid, LC-MS (ESI) $[M+H]^+$ 429.0, and amide byproduct 29 (30 mg), which was purified with prep-HPLC to give (S)-6-(2-acetamido-4-methylthiazol-5-yl)-2-(1-cyclopropylethyl)-N,N-dimethyl-3-oxo-2,3-dihydro-1H-pyrrolo[3,4-c]pyridine-4-carboxamide (29) (17.20 mg, 3.92% yield) as a white solid. LC-MS (ESI) $[M+H]^+$ 427.9. $^1$H NMR (400 MHz, DMSO-$d_6$): δ 12.22 (br s, 1H), 7.93 (s, 1H), 4.68 (s, 2H), 3.56-3.52 (m, 1H), 3.03 (s, 3H), 2.74 (s, 3H), 2.60 (s, 3H), 2.17 (s, 3H), 1.28 (d, J=6.8 Hz, 3H), 1.16-1.09 (m, 1H), 0.60-0.55 (m, 1H), 0.43-0.33 (m, 2H), 0.27-0.21 (m, 1H).

Step b. To a solution of (S)-ethyl 6-(2-acetamido-4-methylthiazol-5-yl)-2-(1-cyclopropylethyl)-3-oxo-2,3-dihydro-1H-pyrrolo[3,4-c]pyridine-4-carboxylate (100 mg, 0.233 mmol) in methanol (6 mL) was added water (2 mL) and lithium hydroxide monohydrate (49 mg, 1.17 mmol) at room temperature. The mixture was stirred at room temperature for 2 hours. The mixture was diluted with water (20.0 mL) and extracted with ethyl acetate (20.0 mL). The aqueous phase was adjusted pH to 2 with 1N hydrochloric acid aqueous solution and extracted with ethyl acetate (20.0 mL×3). The combined organic layers was washed with brine, dried over $Na_2SO_4$, filtered and concentrated under reduced pressure to give (S)-6-(2-acetamido-4-methylthiazol-5-yl)-2-(1-cyclopropylethyl)-3-oxo-2,3-dihydro-1H-pyrrolo[3,4-c]pyridine-4-carboxylic acid (30) (80 mg, 86.0% yield) as a white solid. LC-MS (ESI) $[M+H]^+$ 401.0

Step c. To a solution of (S)-6-(2-acetamido-4-methylthiazol-5-yl)-2-(1-cyclopropylethyl)-3-oxo-2,3-dihydro-1H-pyrrolo[3,4-c]pyridine-4-carboxylic acid (30) (40 mg, 0.100 mmol) in dichloromethane (5.00 mL) was added oxalyl dichloride (127 mg, 1.00 mmol) at 0° C. The mixture was stirred at room temperature for 1 hour. The mixture was concentrated under reduced pressure. The residue was dissolved in dichloromethane (5.00 mL) and cooled to 0° C. A solution of $NH_3$/THF (0.100 mL, 0.200 mmol) in dichloromethane (1.00 mL) was added at 0° C. The mixture was stirred at room temperature for 2 hours. The mixture was diluted with water (30.0 mL) and extracted with DCM (20.0 mL×3). The combined organic layers was washed with brine, dried over $Na_2SO_4$, filtered and concentrated under reduced pressure. The residue was purified by silica gel column chromatography (DCM/MeOH=20/1, v/v) to give (5)-6-(2-acetamido-4-methylthiazol-5-yl)-2-(1-cyclopropylethyl)-3-oxo-2,3-dihydro-1H-pyrrolo[3,4-c]pyridine-4-carboxamide (31) (10.40 mg, 26.1% yield) as a slight yellow solid. LC-MS (ESI) $[M+H]^+$ 400.1. $^1$H NMR (400 MHz, DMSO-$d_6$): δ 12.23 (s, 1H), 8.85 (s, 1H), 7.95 (s, 1H), 7.74 (s, 1H), 4.69 (s, 2H), 3.60-3.56 (m, 1H), 2.63 (s, 3H), 2.17 (s, 3H), 1.29 (d, J=6.8 Hz, 3H), 1.16-1.12 (m, 1H), 0.60-0.58 (m, 1H), 0.45-0.38 (m, 2H), 0.26-0.21 (m, 1H).

(S)-6-(2-acetamido-4-methylthiazol-5-yl)-2-(1-cyclopropylethyl)-N-methyl-3-oxo-2,3-dihydro-1H-pyrrolo[3,4-c]pyridine-4-carboxamide (32)

In a similar manner as the preparation of 31 (methylamine tetrahydrofuran solution was used), the title product (32) was synthesized (13.50 mg, 32.7% yield) as a pale yellow solid. LC-MS (ESI) $[M+H]^+$414.1 $^1$H NMR (400 MHz, $CDCl_3$): δ 10.95 (br s, 1H), 7.65 (s, 1H), 4.70-4.53 (s, 2H), 3.77-3.75 (m, 1H), 3.10 (d, J=4.4 Hz, 3H), 2.81 (s, 3H), 2.34 (s, 3H), 1.40 (d, J=6.8 Hz, 3H), 1.07-1.04 (m, 1H), 0.73-0.70 (m, 1H), 0.54-0.37 (m, 3H).

Preparation of (S)-N-(5-(2-(1-cyclopropylethyl)-4-(morpholine-4-carbonyl)-3-oxo-2,3-dihydro-M-pyrrolo[3,4-c]pyridin-6-yl)-4-methylthiazol-2-yl)acetamide (33)

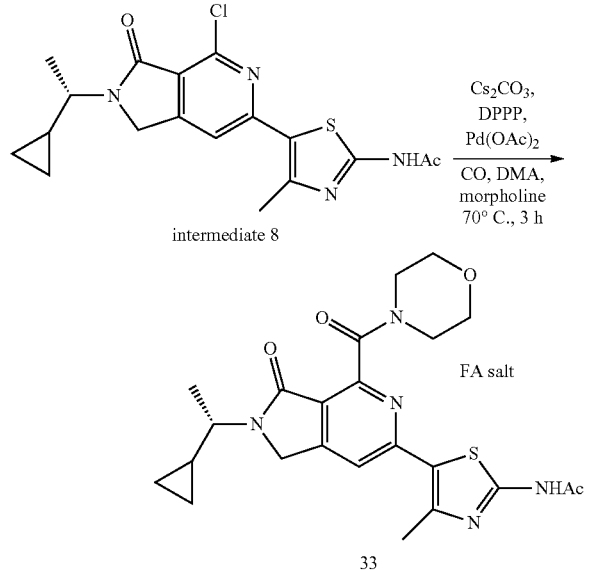

A mixture of (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (100 mg, 0.256 mmol), morpholine (224 mg, 2.56 mmol), Pd(OAc)$_2$ (6 mg, 0.0256 mmol), DPPP (11 mg, 0.0256 mmol) and Cs$_2$CO$_3$ (210 mg, 0.643 mmol) in DMA (2 mL) under a balloon of CO was stirred at 70° C. for 3 h. The mixture was cooled to rt, quenched with water (5 mL) and extracted with EtOAc (8 mL×3). The organic layer was dried over anhydrous Na$_2$SO$_4$, filtered and concentrated. The crude was purified by prep-HPLC to give (S)-N-(5-(2-(1-cyclopropylethyl)-4-(morpholine-4-carbonyl)-3-oxo-2,3-dihydro-1H-pyrrolo[3,4-c]pyridin-6-yl)-4-methylthiazol-2-yl)acetamide (1.9 mg FA salt, 2% yield) as a white solid. LC-MS (ESI) [M+H]$^+$ 470.1. $^1$H NMR (400 MHz, DMSO-d$_6$): δ 12.25 (s, 1H), 8.36 (s, 0.92H, FA salt), 7.94 (s, 1H), 4.69 (s, 2H), 3.69 (s, 4H), 3.58-3.49 (m, 1H), 3.14 (s, 4H), 2.60 (s, 3H), 2.17 (s, 3H), 1.28 (d, J=6.8 Hz, 3H), 1.19-1.05 (m, 1H), 0.60-0.52 (m, 1H), 0.45-0.18 (m, 3H).

Preparation of (S)-N-(5-(2-(1-cyclopropylethyl)-4-morpholino-3-oxo-2,3-dihydro-M-pyrrolo[3,4-c]pyridin-6-yl)-4-methylthiazol-2-yl)acetamide (34)

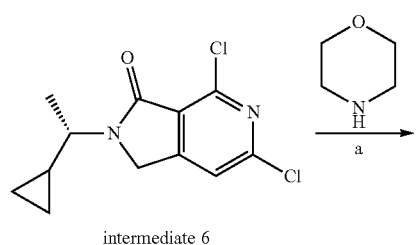

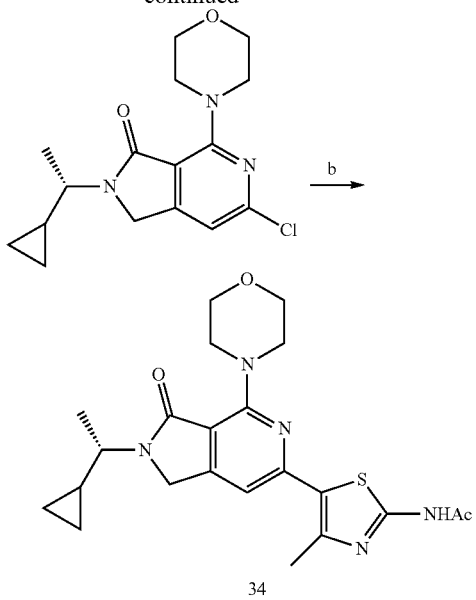

Step a. Prepared (S)-6-chloro-2-(1-cyclopropylethyl)-4-morpholino-1,2-dihydro-3H-pyrrolo[3,4-c]pyridin-3-one according to the preparation of 28 (160° C. for 1 hours) (200 mg, 56.0% yield) as a green solid. LC-MS (ESI) [M+H]$^+$ 322.3.

Step b. Prepared 34 according to general procedure C (135° C., 1 h) (14.94 mg, 7.26% yield) as a white solid. LC-MS (ESI) [M+H]$^+$ 442.0. $^1$H NMR (400 MHz, CDCl$_3$): δ 7.07 (s, 1H), 4.53-4.37 (m, 2H), 3.90 (t, J=4.0 Hz, 4H), 3.81 (t, J=4.0 Hz, 4H), 3.71-3.67 (m, 1H), 2.67 (s, 3H), 2.31 (s, 3H), 1.32 (d, J=6.8 Hz, 3H), 1.00-0.98 (m, 1H), 0.66-0.64 (m, 1H), 0.47-0.35 (m, 3H).

Preparation of (R)-N-(5-(2-(1-cyclopropylethyl)-4-morpholino-3-oxo-2,3-dihydro-1H-pyrrolo[3,4-c] pyridin-6-yl)-4-methylthiazol-2-yl)acetamide (35)

Prepared 35 according to general procedure C from intermediate 9 (135° C., 1 h) (20.2 mg, 12.3% yield) as a white solid. LC-MS (ESI) [M+H]$^+$ 442.1. $^1$H NMR (400 MHz, DMSO-d$_6$): δ 12.10 (s, 1H), 7.26 (s, 1H), 4.53 (s, 2H), 3.77-3.66 (m, 8H), 3.58-3.48 (m, 1H), 2.59 (s, 3H), 2.15 (s, 3H), 1.23 (t, J=8.0 Hz, 3H), 1.15-1.02 (m, 1H), 0.63-0.50 (m, 1H), 0.38-0.33 (m, 2H), 0.22-0.20 (m, 1H).

Preparation of (R)-N-(4-methyl-5-(4-morpholino-3-oxo-2-(1,1,1-trifluoropropan-2-yl)-2,3-dihydro-1H-pyrrolo[3,4-c]pyridin-6-yl)thiazol-2-yl)acetamide (36) & (S)-N-(4-methyl-5-(4-morpholino-3-oxo-2-(1,1,1-trifluoropropan-2-yl)-2,3-dihydro-1H-pyrrolo[3,4-c]pyridin-6-yl)thiazol-2-yl)acetamide (37)

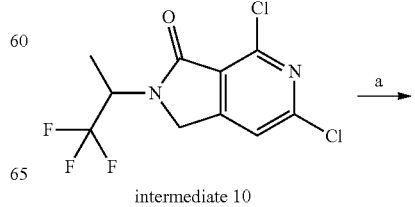

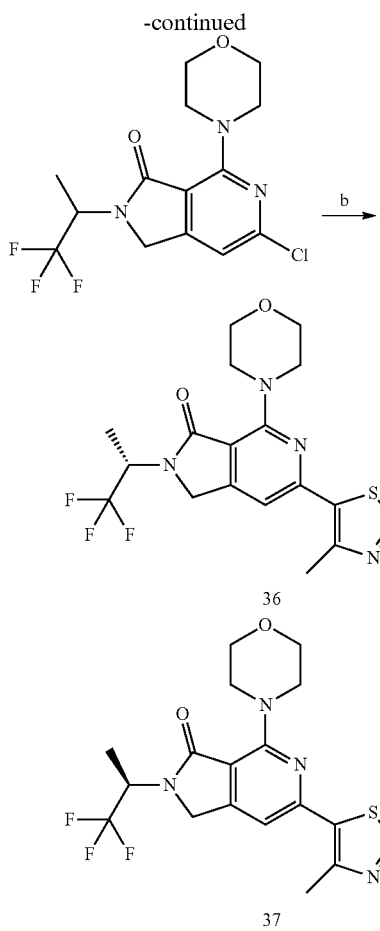

Step a. Prepared 6-chloro-4-morpholino-2-(1,1,1-trifluoropropan-2-yl)-1,2-dihydro-3H-pyrrolo[3,4-c]pyridin-3-one according to the preparation of 28 (160° C. for 1 hours) (230 mg, 0.660 mmol, 43.1% yield) as a light yellow solid. LC-MS (ESI) [M+H]+ 349.9. ¹H NMR (400 MHz, DMSO-d₆): δ 7.08 (s, 1H), 4.99-4.97 (m, 1H), 4.61-4.34 (m, 2H), 3.78-3.67 (m, 8H), 1.43 (d, J=7.2 Hz, 3H).

Step b. Prepared racemic mixture of 36 and 37 according to general procedure C (135° C., 1 h) (60.6 mg, 19.6% yield, racemic) as a white solid. The racemic solid was separated with SFC [Separation condition: Instrument: Waters-SFC80; Column: OZ (2.5*25 cm, 10 um); Mobile phase A: Supercritical CO₂, Mobile phase B: MeOH (0.1% NH₃); A:B=70/30; at 70 ml/min; Detector wavelength: 214 nm; column temperature: 25 centigrade; back pressure: 100 bar] to give First Enantiomer (11.80 mg, 0.0252 mmol, 3.81% yield, first eluent) as a white solid and Second Enantiomer (10.14 mg, 0.0216 mmol, 3.28% yield, second eluent) as a light yellow solid. First Enantiomer: LC-MS (ESI) [M+H]+ 470.0. ¹H NMR (400 MHz, DMSO-d₆): δ 12.2 (s, 1H), 7.28 (s, 1H), 5.00-4.95 (m, 1H), 4.65-4.39 (m, 2H), 3.74-3.67 (m, 8H), 2.59 (s, 3H), 2.15 (s, 3H), 1.45 (d, J=7.2 Hz, 3H); Second Enantiomer: LC-MS (ESI) [M+H]+ 470.0. ¹H NMR (400 MHz, DMSO-d₆): δ 12.2 (s, 1H), 7.28 (s, 1H), 5.00-4.95 (m, 1H), 4.65-4.39 (m, 2H), 3.74-3.67 (m, 8H), 2.59 (s, 3H), 2.15 (s, 3H), 1.45 (d, J=7.2 Hz, 3H)

A mixture of stereoisomers (including, for example, a pair of enantiomers or a mixture of diastereomers) may be separated by any suitable method, including, but not limited to, chiral HPLC. In some embodiments, when a mixture of stereoisomers is separated by HPLC, it is to be appreciated that the resultant individual stereoisomers or mixtures can be assigned sequential labels (e.g., a first enantiomer, and a second enantiomer), the order of which implies the order in which the isomers eluted from the HPLC column. The absolute stereochemistry for a first enantiomer and a second enantiomer may be obtained by known methods.

Preparation of (S)-N-(5-(2-(1-cyclopropylethyl)-4-(1,1-dioxidothiomorpholino)-3-oxo-2,3-dihydro-M-pyrrolo[3,4-c]pyridin-6-yl)-4-methylthiazol-2-yl) acetamide (38)

Step a. Prepared 38 according to the preparation of 34 (21.2 mg, 10.61%) as a yellow solid. LC-MS (ESI) [M+H]+ 490.1. ¹H NMR (400 MHz, CDCl₃): δ 7.16 (s, 1H), 4.51-4.44 (m, 2H), 4.38-4.35 (m, 4H), 3.73-3.62 (m, 1H), 3.24 (t, J=4.8 Hz, 4H), 2.63 (s, 3H), 2.28 (s, 3H), 1.33 (d, J=6.8 Hz, 4H), 1.03-0.93 (m, 1H), 0.69-0.58 (m, 1H), 0.51-0.27 (m, 3H).

(S)-N-(5-(2-(1-cyclopropylethyl)-3-oxo-4-(piperazin-1-yl)-2,3-dihydro-1H-pyrrolo[3,4-c]pyridin-6-yl)-4-methylthiazol-2-yl)acetamide (39)

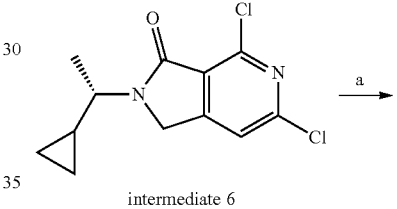

intermediate 6

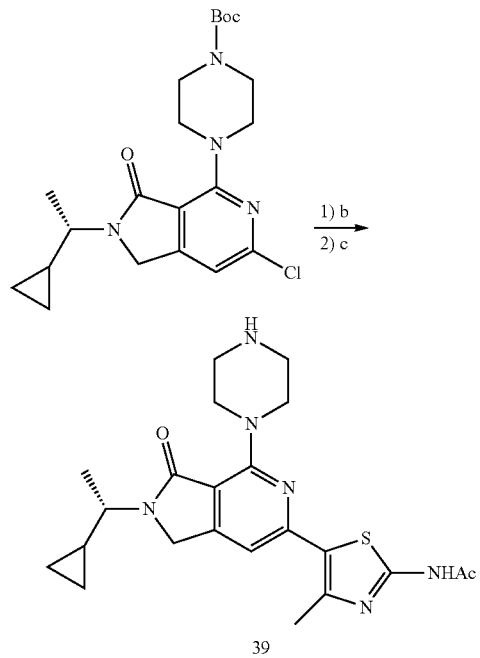

Step a. A solution of (S)-4,6-dichloro-2-(1-cyclopropylethyl)-1,2-dihydro-3H-pyrrolo[3,4-c]pyridin-3-one (intermediate 6) (300 mg, 1.11 mmol) and tert-butyl piperazine-1-carboxylate (2.06 g, 11.1 mmol) in dioxane (10.0 mL) was stirred at 160° C. for 1 h in sealed tube. The mixture was cooled to rt and concentrated under reduced pressure to give the residue, which was purified by silica gel column chromatography (PE:EA=50:1-1:1, v/v) to give tert-butyl (S)-4-(6-chloro-2-(1-cyclopropylethyl)-3-oxo-2,3-dihydro-1H-pyrrolo[3,4-c]pyridin-4-yl)piperazine-1-carboxylate (370 mg, 79.19% yield) as a green solid. LC-MS (ESI) [M+H]+ 421.0.

Step b. According to the general procedure B (135° C., 1 h), tert-butyl (S)-4-(6-(2-acetamido-4-methylthiazol-5-yl)-2-(1-cyclopropylethyl)-3-oxo-2,3-dihydro-1H-pyrrolo[3,4-c]pyridin-4-yl)piperazine-1-carboxylate was synthesized (300 mg, 80.5% yield) as a yellow gum. LC-MS (ESI) [M+H]+ 541.0.

Step c. To a suspension of tert-butyl (S)-4-(6-(2-acetamido-4-methylthiazol-5-yl)-2-(1-cyclopropylethyl)-3-oxo-2,3-dihydro-1H-pyrrolo[3,4-c]pyridin-4-yl)piperazine-1-carboxylate (43) (300 mg, 0.556 mmol) in DCM (3 mL) was added TFA (1 mL) at rt. The reaction mixture was stirred at rt overnight and then concentrated under reduced pressure. The residue was diluted with aq. NaHCO3 (10 mL) and extracted with ethyl acetate (10 mL×3). The combined organic layers was washed with brine, dried over Na2SO4, filtered and concentrated. The residue was purified by prep-TLC (DCM:MeOH=10:1, v/v) to give (S)-N-(5-(2-(1-cyclopropylethyl)-3-oxo-4-(piperazin-1-yl)-2,3-dihydro-1H-pyrrolo[3,4-c]pyridin-6-yl)-4-methylthiazol-2-yl)acetamide (70 mg, 23.4% yield). 10 mg of this material was re-purified by Prep-HPLC to give (S)-N-(5-(2-(1-cyclopropylethyl)-3-oxo-4-(piperazin-1-yl)-2,3-dihydro-1H-pyrrolo[3,4-c]pyridin-6-yl)-4-methylthiazol-2-yl)acetamide (39) (4.81 mg, free base) as a yellow solid. LC-MS (ESI) [M+H]+ 441.0. 1H NMR (400 MHz, DMSO-d6): δ 7.22 (s, 1H), 4.51 (s, 2H), 3.61 (br s, 4H), 3.55-3.53 (m, 1H), 2.86 (br s, 4H), 2.58 (s, 3H), 2.15 (s, 3H), 1.24 (d, J=6.8 Hz, 3H), 1.08-1.06 (m, 1H), 0.56-0.55 (m, 1H), 0.39-0.21 (m, 3H).

(S)-N-(5-(4-(4-acetylpiperazin-1-yl)-2-(1-cyclopropylethyl)-3-oxo-2,3-dihydro-1H-pyrrolo[3,4-c]pyridin-6-yl)-4-methylthiazol-2-yl)acetamide (40)

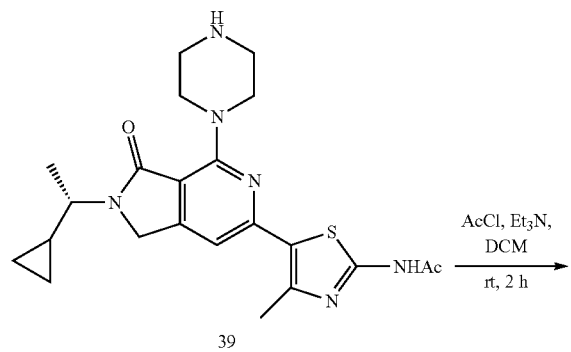

To a suspension of (S)-N-(5-(2-(1-cyclopropylethyl)-3-oxo-4-(piperazin-1-yl)-2,3-dihydro-1H-pyrrolo[3,4-c]pyridin-6-yl)-4-methylthiazol-2-yl)acetamide (39) (20 mg, 0.0455 mmol) and Et3N (12 mg, 0.114 mmol) in DCM (1 mL) was added acetyl chloride (5 mg, 0.0591 mmol) slowly at 0° C. The reaction mixture was stirred at rt for 2 h. The mixture was quenched with methanol (3 mL) and concentrated under reduced pressure. The residue was purified by prep-HPLC to give (S)-N-(5-(4-(4-acetylpiperazin-1-yl)-2-(1-cyclopropylethyl)-3-oxo-2,3-dihydro-1H-pyrrolo[3,4-c]pyridin-6-yl)-4-methylthiazol-2-yl)acetamide (40) (12.69 mg, 57.8% yield) as a yellow solid. LC-MS (ESI) [M+H]+ 483.2. 1H NMR (400 MHz, DMSO-d6): δ 12.11 (s, 1H), 7.27 (s, 1H), 4.53 (s, 2H), 3.69-3.53 (m, 9H), 2.59 (s, 3H), 2.15 (s, 3H), 2.05 (s, 3H), 1.25 (d, J=6.8 Hz, 3H), 1.09-1.07 (m, 1H), 0.58-0.56 (m, 1H), 0.41-0.22 (m, 3H).

(S)-N-(5-(2-(1-cyclopropylethyl)-4-morpholino-3-oxo-2,3-dihydro-1H-pyrrolo[3,4-c]pyridin-6-yl)thiazol-2-yl)acetamide (41)

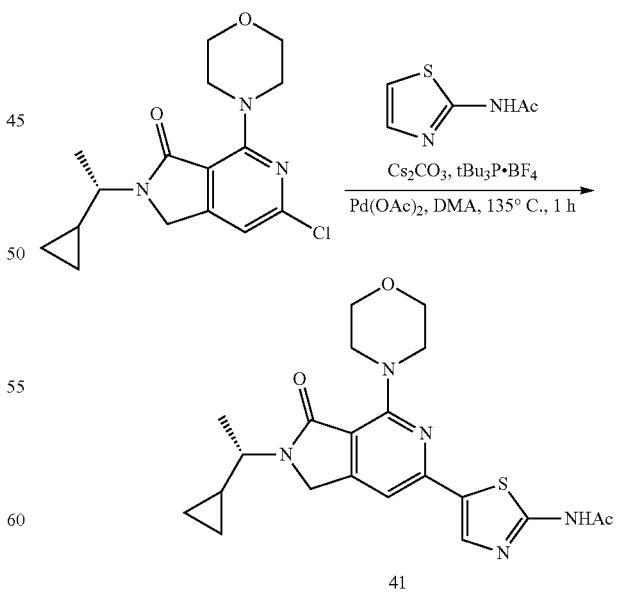

The title product (41) was synthesized from (S)-6-chloro-2-(1-cyclopropylethyl)-4-morpholino-1,2-dihydro-3H-pyrrolo[3,4-c]pyridin-3-one according to the general procedure C (135° C., 1 h) (23.81 mg, 17.9% yield) as a white solid. LC-MS (ESI) [M+H]+ 428.2. 1H NMR (400 MHz, DMSO-d6): δ 8.18 (s, 1H), 7.49 (s, 1H), 4.51 (s, 2H), 3.75-3.68 (m, 8H), 3.52-3.50 (m, 1H), 2.16 (s, 3H), 1.24 (d, J=6.8 Hz, 3H), 1.09-1.07 (m, 1H), 0.56-0.54 (m, 1H), 0.38-0.21 (m, 3H).

(S)-N-(5-(2-(1-cyclopropylethyl)-4-(2-methoxyethoxy)-3-oxo-2,3-dihydro-1H-pyrrolo[3,4-c]pyridin-6-yl)-4-methylthiazol-2-yl)acetamide (42)

According to the general procedure B (110° C., 2 h, 2-methoxyethan-1-ol was utilized), the title product (42) was synthesized (6.00 mg, 11.1% yield, 0.1 FA salt) as a white solid. LC-MS (ESI) [M+H]+ 431.0. 1H NMR (400 MHz, CDCl3): δ 8.21 (s, 0.1H, FA salt), 7.19 (s, 1H), 4.69-4.66 (m, 2H), 4.54-4.38 (m, 2H), 3.88 (t, J=4.8 Hz, 2H), 3.87-3.70 (m, 1H), 3.49 (s, 3H), 2.66 (s, 3H), 2.29 (s, 3H), 1.32 (d, J=7.2 Hz, 3H), 0.99-0.97 (m, 1H), 0.63-0.62 (m, 1H), 0.46-0.38 (m, 3H).

(S)-N-(5-(2-(1-cyclopropylethyl)-4-(methoxy-d3)-3-oxo-2,3-dihydro-1H-pyrrolo[3,4-c]pyridin-6-yl)-4-methylthiazol-2-yl)acetamide (43)

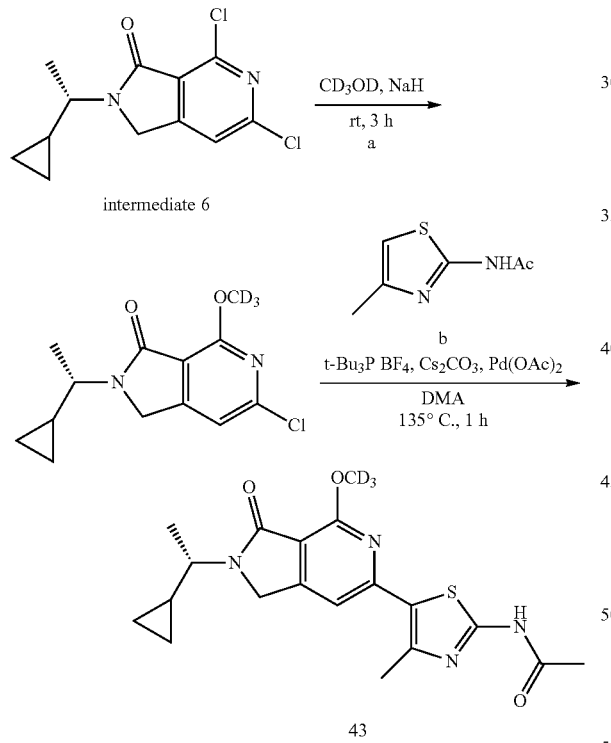

Step a. To methanol-d4 (0.600 mL) was added sodium hydride (80 mg, 2.00 mmol, 60% w/w dispersion in mineral oil) at 0° C. The mixture was stirred at room temperature for 0.5 hour, and then added to a solution of (S)-4,6-dichloro-2-(1-cyclopropylethyl)-1H-pyrrolo[3,4-c]pyridin-3(2H)-one (6) (271 mg, 1.00 mmol) in methanol-d4 (1.40 mL) at 0° C. The resulted mixture was stirred at room temperature for 3 hours. The mixture was diluted with water (10.0 mL) and extracted with ethyl acetate (10.0 mL×3). The combined organic layers was washed with brine, dried over Na2SO4, filtered and concentrated under reduced pressure. The residue was purified by silica gel column chromatography (PE/EA=2/1) to give (S)-6-chloro-2-(1-cyclopropylethyl)-4-(methoxy-d3)-1,2-dihydro-3H-pyrrolo[3,4-c]pyridin-3-one (170 mg, 63.0% yield) as a white solid. LC-MS (ESI) [M+H]+ 270.0. 1H NMR (400 MHz, CDCl3): δ 7.04 (s, 1H), 4.50-4.35 (m, 2H), 3.75-3.67 (m, 1H), 1.31 (d, J=6.8 Hz, 3H), 1.01-0.92 (m, 1H), 0.66-0.60 (m, 1H), 0.46-0.33 (m, 3H).

Step b. According to general procedure C (135° C., 1 h), the title product (43) was synthesized (50.07 mg, 23.1% yield) as a white solid. LC-MS (ESI) [M+H]+390.1. 1H NMR (400 MHz, CDCl3): δ 7.21 (s, 1H), 4.55-4.40 (m, 2H), 3.79-3.71 (m, 1H), 2.69 (s, 3H), 2.30 (s, 3H), 1.33 (d, J=6.8 Hz, 3H), 1.02-0.94 (m, 1H), 0.65-0.60 (m, 1H), 0.46-0.32 (m, 3H).

(S)-N-(5-(4-acetamido-2-(1-cyclopropylethyl)-3-oxo-2,3-dihydro-M-pyrrolo[3,4-c]pyridin-6-yl)-4-methylthiazol-2-yl)acetamide (44)

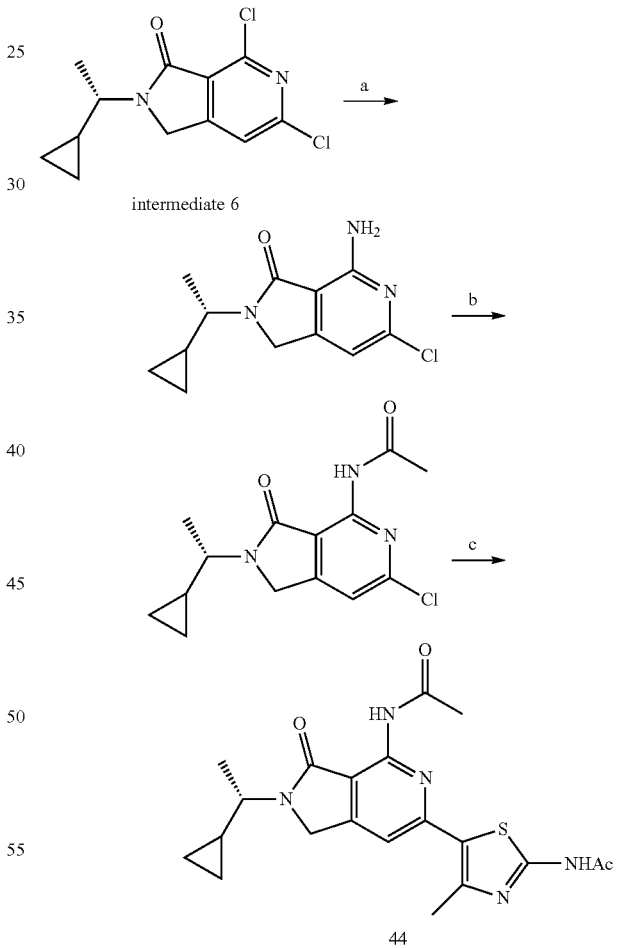

Step a. A solution of (S)-4,6-dichloro-2-(1-cyclopropylethyl)-1H-pyrrolo[3,4-c]pyridin-3(2H)-one (intermediate 6) (500 mg, 1.11 mmol) and NH3.H2O (3 mL) in THF (10 mL) was heated in a sealed tube at 160° C. for 1 h. After being cooled to rt, the mixture was quenched with aq. NH4Cl (20 mL) and extracted with ethyl acetate (50 mL×3). The combined organic layers was washed with brine, dried over Na₂SO₄, filtered and concentrated under reduced pressure. The residue was purified by silica gel column chromatography eluted with petroleum ether:ethyl acetate (100:1~5:1, v/v) to give (S)-4-amino-6-chloro-2-(1-cyclopropylethyl)-1H-pyrrolo[3,4-c]pyridin-3(2H)-one (356 mg, 1.42 mmol, 76.6% yield) as a pink solid. LC-MS (ESI) [M+H]⁺ 252.1.

Step b. A solution of (S)-4-amino-6-chloro-2-(1-cyclopropylethyl)-1H-pyrrolo[3,4-c]pyridin-3(2H)-one (130 mg, 0.516 mmol) in Ac₂O (1.50 mL) was heated at 130° C. for 3 h. The mixture was cooled to rt and quenched with aq. NaHCO₃ (10 mL) and extracted with ethyl acetate (10 mL×3). The combined organic layers were washed with brine, dried over Na₂SO₄, filtered and concentrated under reduced pressure. The residue was purified by prep-TLC (petroleum ether:ethyl acetate=2:1, v/v) to give (S)-N-(6-chloro-2-(1-cyclopropylethyl)-3-oxo-2,3-dihydro-1H-pyrrolo[3,4-c]pyridin-4-yl)acetamide (70 mg, 46.2% yield) as a yellow solid. LC-MS (ESI) [M+H]⁺ 294.1.

Step c. Prepared 44 according to general procedure C (135° C., 1 h) (4.31 mg FA salt, 5.10% yield) as a white solid. LC-MS (ESI) [M+H]⁺ 414.4. ¹H NMR (400 MHz, CDCl₃): δ 9.82 (s, 1H), 8.16 (s, 0.24H, FA), 7.29 (s, 1H), 4.56-4.50 (m, 2H), 3.72-3.68 (m, 1H), 2.74 (s, 3H), 2.56 (s, 3H), 2.31 (s, 3H), 1.36 (d, J=6.8 Hz, 3H), 1.02-1.01 (m, 1H), 0.69-0.66 (m, 1H), 0.50-0.38 (m, 3H).

N-(6-(2-acetamido-4-methylthiazol-5-yl)-2-((S)-1-cyclopropylethyl)-3-oxo-2,3-dihydro-1H-pyrrolo[3,4-c]pyridin-4-yl)-2-cyanocyclopropane-1-carboxamide (45)

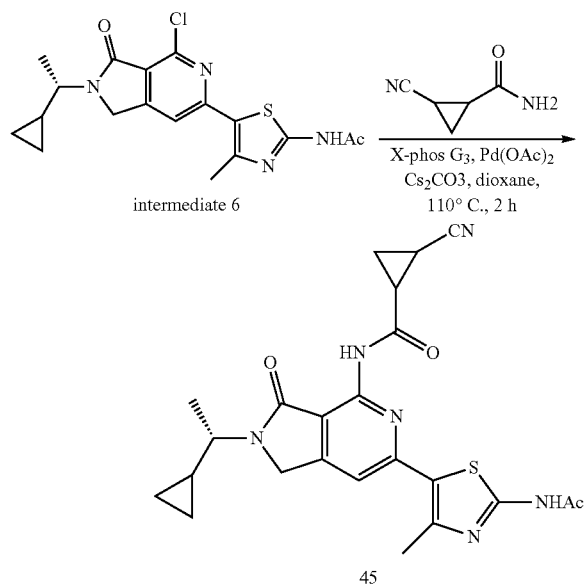

According to the general procedure B (110° C., 2 h), the title product (45) was synthesized (10.9 mg, 0.0235 mmol, 26.2% yield) as a white solid. LC-MS (ESI) [M+H]⁺ 465.1. ¹H NMR (400 MHz, DMSO-d₆): δ 12.2 (br s, 1H), 10.4 (br s, 1H), 7.67 (s, 1H), 4.65 (s, 2H), 3.56-3.44 (m, 1H), 2.62 (s, 3H), 2.23-2.18 (m, 1H), 2.16 (s, 3H), 1.64-1.61 (m, 1H), 1.50-1.44 (m, 1H), 1.28 (d, J=6.8 Hz, 3H), 1.24-1.21 (m, 1H), 1.17-1.06 (m, 1H), 0.62-0.53 (m, 1H), 0.47-0.34 (m, 2H), 0.26-0.19 (m, 1H).

Compounds 46-49 were prepared according to a similar procedure as the preparation of compound 34.

(S)-N-(5-(2-(1-cyclopropylethyl)-4-(4-hydroxypiperidin-1-yl)-3-oxo-2,3-dihydro-1H-pyrrolo[3,4-c]pyridin-6-yl)-4-methylthiazol-2-yl)acetamide (46) LC-MS (ESI) [M+H]⁺= 456.1. ¹H NMR (400 MHz, CD₃OD-d₄): δ 7.20 (s, 1H), 4.56-4.54 (m, 2H), 4.27-4.23 (m, 2H), 3.86-3.77 (m, 1H), 3.61-3.51 (m, 1H), 3.27-3.20 (m, 2H), 2.62 (s, 3H), 2.22 (s, 3H), 1.98-1.96 (m, 2H), 1.67-1.65 (m, 2H), 1.35-1.33 (m, 3H), 1.11-1.10 (m, 1H), 0.66-0.65 (m, 1H), 0.49-0.28 (m, 3H).

N-(5-(2-((S)-1-cyclopropylethyl)-4-(3-hydroxypyrrolidin-1-yl)-3-oxo-2,3-dihydro-1H-pyrrolo[3,4-c]pyridin-6-yl)-4-methylthiazol-2-yl)acetamide (47) LC-MS (ESI) [M+H]⁺=442.1. ¹H NMR (400 MHz, CD₃OD-d₄): δ 8.50 (s, 0.5H, FA), 7.06 (s, 1H), 4.59-4.46 (m, 3H), 4.02-4.01 (m, 2H), 3.85-3.84 (m, 1H), 3.74-3.69 (m, 1H), 3.68-3.60 (m, 1H), 2.62 (s, 3H), 2.22 (s, 3H), 2.08-1.96 (m, 2H), 1.37-1.31 (m, 3H), 1.11-1.10 (m, 1H), 0.66-0.65 (m, 1H), 0.47-0.28 (m, 3H).

(S)-N-(5-(2-(1-cyclopropylethyl)-4-(3-hydroxyazetidin-1-yl)-3-oxo-2,3-dihydro-1H-pyrrolo[3,4-c]pyridin-6-yl)-4-methylthiazol-2-yl)acetamide (48) LC-MS (ESI) [M+H]⁺= 428.1. ¹H NMR (400 MHz, CD₃OD-d₄): δ 7.08 (s, 1H), 4.66-4.53 (m, 5H), 4.10-4.05 (m, 2H), 3.57-3.47 (m, 1H), 2.62 (s, 3H), 2.22 (s, 3H), 1.42-1.30 (m, 3H), 1.11-1.10 (m, 1H), 0.66-0.65 (m, 1H), 0.47-0.28 (m, 3H).

(S)-N-(5-(2-(1-cyclopropylethyl)-4-(3-(methylsulfonyl)azetidin-1-yl)-3-oxo-2,3-dihydro-1H-pyrrolo[3,4-c]pyridin-6-yl)-4-methylthiazol-2-yl)acetamide (49)

LC-MS (ESI) [M+H]⁺ 4901 ¹H NMR (400 MHz, DMSO-d₆): δ 12.1 (br s, 1H), 7.18 (s, 1H), 4.54-4.50 (m, 4H), 4.42-4.41 (m, 3H), 3.53-3.48 (m, 1H), 3.05 (s, 3H), 2.59 (s, 3H), 2.15 (s, 3H), 1.24 (d, J=6.8 Hz, 3H), 1.14-1.03 (m, 1H), 0.61-0.51 (m, 1H), 0.44-0.30 (m, 2H), 0.26-0.17 (m, 1H).

Compounds 50-52 were prepared according to a similar procedure as the preparation of compound 42.

(S)-N-(5-(2-(1-cyclopropylethyl)-4-(2-hydroxyethoxy)-3-oxo-2,3-dihydro-1H-pyrrolo[3,4-c]pyridin-6-yl)-4-methylthiazol-2-yl)acetamide (50) LC-MS (ESI) [M+H]⁺ 450.1. ¹H NMR (400 MHz, MeOD-d₄): δ 7.36 (s, 1H), 4.68-4.60 (m, 2H), 3.58-3.50 (m, 1H), 3.46 (s, 3H), 3.31 (m, 3H), 2.22 (s, 3H), 1.36 (d, J=6.8 Hz, 3H), 1.05-0.96 (m, 1H), 0.64-0.58 (m, 1H), 0.43-0.26 (m, 3H).

N-(5-(2-((S)-1-cyclopropylethyl)-3-oxo-4-((tetrahydrofuran-3-yl)oxy)-2,3-dihydro-1H-pyrrolo[3,4-c]pyridin-6-yl)-4-methylthiazol-2-yl)acetamide (51) LC-MS (ESI) [M+H]⁺ 443.1. ¹H NMR (400 MHz, DMSO-d₆): δ 7.46 (s, 1H), 5.65-5.54 (m, 1H), 4.56 (s, 2H), 4.08-3.99 (m, 1H), 3.93-3.73 (m, 3H), 3.54-3.43 (m, 1H), 2.60 (s, 3H), 2.39-2.34 (m, 1H), 2.16 (s, 3H), 2.13-1.99 (m, 1H), 1.25 (d, J=6.8 Hz, 3H), 1.08-0.99 (m, 1H), 0.62-0.50 (m, 1H), 0.45-0.31 (m, 2H), 0.28-0.21 (m, 1H).

(S)-N-(5-(2-(1-cyclopropylethyl)-4-(oxetan-3-yloxy)-3-oxo-2,3-dihydro-1H-pyrrolo[3,4-c]pyridin-6-yl)-4-methylthiazol-2-yl)acetamide (52) LC-MS (ESI) [M+H]⁺ 429.0. ¹H NMR (400 MHz, DMSO-d₆): δ 12.2 (br s, 1H), 7.50 (s, 1H), 5.71-5.64 (m, 1H), 4.95 (t, J=6.8 Hz, 2H), 4.68-4.61 (m, 2H), 4.58 (s, 2H), 3.57-3.47 (m, 1H), 2.58 (s, 3H), 2.16 (s, 3H), 1.26 (d, J=6.8 Hz, 3H), 1.15-1.10 (m, 1H), 0.60-0.50 (m, 1H), 0.44-0.32 (m, 2H), 0.27-0.18 (m, 1H).

(S)-N-(4-chloro-5-(2-(1-cyclopropylethyl)-4-morpholino-3-oxo-2,3-dihydro-1H-pyrrolo[3,4-c]pyridin-6-yl)thiazol-2-yl)acetamide (53)

Compound 53 was prepared according to general procedure C from N-(4-chlorothiazol-2-yl)acetamide as a yellow solid. LC-MS (ESI) [M+H]$^+$ 462.0. $^1$H NMR (400 MHz, CDCl$_3$): δ 9.05 (s, 1H), 7.74 (s, 1H), 4.55-4.39 (m, 2H), 3.98-3.68 (m, 8H), 3.67-3.60 (m, 1H), 2.31 (s, 3H), 1.24 (d, J=6.8 Hz, 3H), 0.98-0.96 (m, 1H), 0.70-0.60 (m, 1H), 0.49-0.25 (m, 3H).

Preparation of (S)-N-(5-(2-(1-cyclopropylethyl)-4-(morpholinomethyl)-3-oxo-2,3-dihydro-1H-pyrrolo[3,4-c]pyridin-6-yl)-4-methylthiazol-2-yl)acetamide (54)

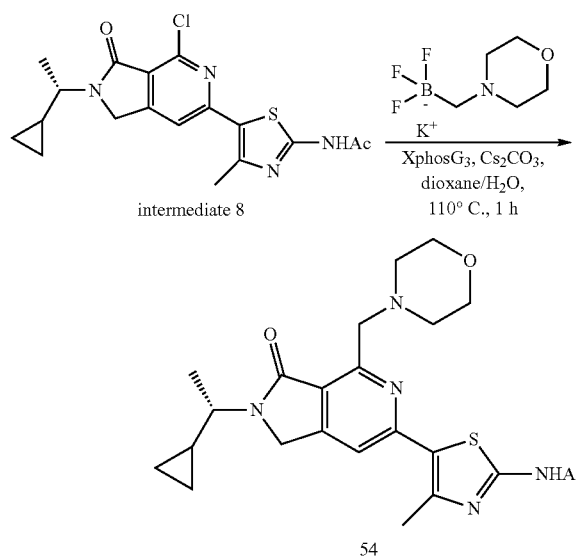

A mixture of (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (100 mg, 0.256 mmol), potassium trifluoro(morpholinomethyl)borate (159 mg, 0.767 mmol), Xphos-G3 (22 mg, 0.0256 mmol) and Cs$_2$CO$_3$ (167 mg, 0.512 mmol) in dioxane (6 mL) under Ar was stirred at 110° C. for 1 h. The mixture was quenched with water (5 mL) and extracted with EtOAc (8 mL×3). The organic layer was dried over anhydrous Na$_2$SO$_4$, filtered and concentrated. The crude was purified by prep-HPLC to give (S)-N-(5-(2-(1-cyclopropylethyl)-4-(morpholinomethyl)-3-oxo-2,3-dihydro-1H-pyrrolo[3,4-c]pyridin-6-yl)-4-methylthiazol-2-yl)acetamide (45 mg, 38.1% yield) as a yellow solid. LC-MS (ESI) [M+H]$^+$ 456.2. $^1$H NMR (400 MHz, CDCl$_3$): δ 9.74 (s, 1H), 7.53 (s, 1H), 4.58-4.42 (m, 2H), 4.32-4.21 (m, 2H), 3.77-3.72 (m, 5H), 2.83 (s, 4H), 2.66 (s, 3H), 2.28 (s, 3H), 1.25 (d, J=6.8 Hz, 3H), 1.03-0.98 (m, 1H), 0.69-0.65 (m, 1H), 0.50-0.28 (m, 3H).

Preparation of N-(5-(2-((S)-1-cyclopropylethyl)-4-(1-morpholinoethyl)-3-oxo-2,3-dihydro-1H-pyrrolo[3,4-c]pyridin-6-yl)-4-methylthiazol-2-yl)acetamide (55)

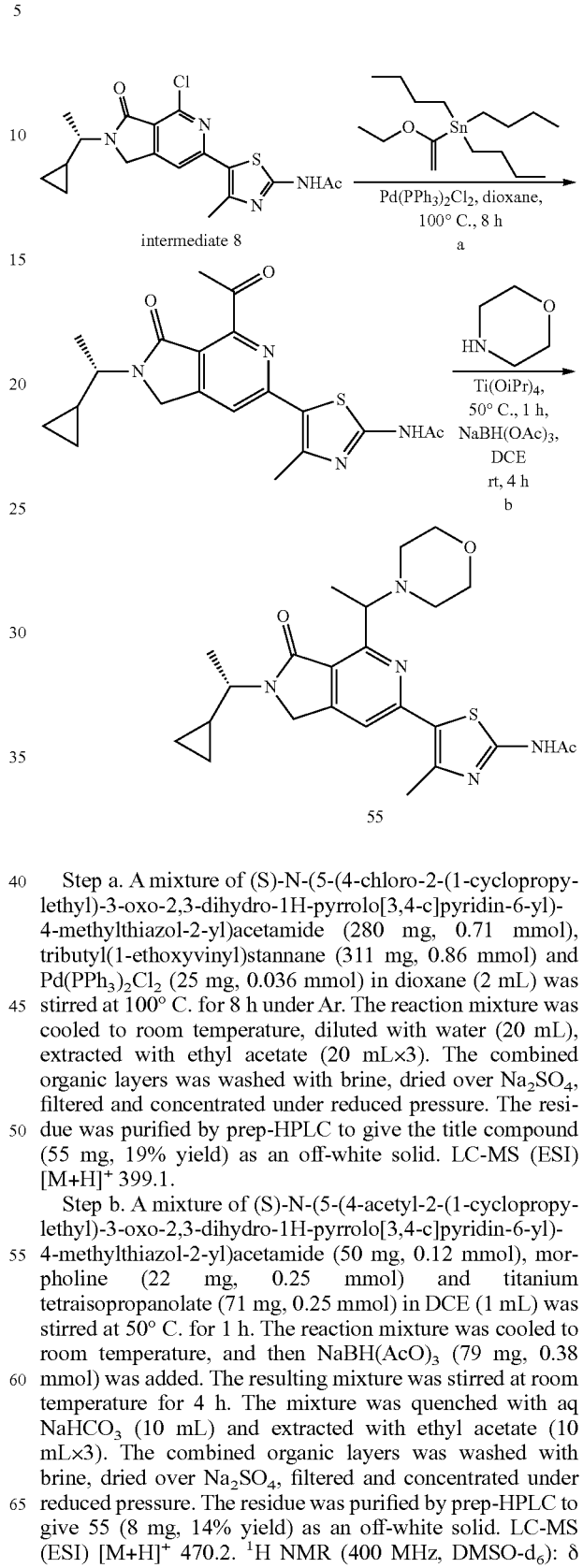

Step a. A mixture of (S)-N-(5-(4-chloro-2-(1-cyclopropylethyl)-3-oxo-2,3-dihydro-1H-pyrrolo[3,4-c]pyridin-6-yl)-4-methylthiazol-2-yl)acetamide (280 mg, 0.71 mmol), tributyl(1-ethoxyvinyl)stannane (311 mg, 0.86 mmol) and Pd(PPh$_3$)$_2$Cl$_2$ (25 mg, 0.036 mmol) in dioxane (2 mL) was stirred at 100° C. for 8 h under Ar. The reaction mixture was cooled to room temperature, diluted with water (20 mL), extracted with ethyl acetate (20 mL×3). The combined organic layers was washed with brine, dried over Na$_2$SO$_4$, filtered and concentrated under reduced pressure. The residue was purified by prep-HPLC to give the title compound (55 mg, 19% yield) as an off-white solid. LC-MS (ESI) [M+H]$^+$ 399.1.

Step b. A mixture of (S)-N-(5-(4-acetyl-2-(1-cyclopropylethyl)-3-oxo-2,3-dihydro-1H-pyrrolo[3,4-c]pyridin-6-yl)-4-methylthiazol-2-yl)acetamide (50 mg, 0.12 mmol), morpholine (22 mg, 0.25 mmol) and titanium tetraisopropanolate (71 mg, 0.25 mmol) in DCE (1 mL) was stirred at 50° C. for 1 h. The reaction mixture was cooled to room temperature, and then NaBH(AcO)$_3$ (79 mg, 0.38 mmol) was added. The resulting mixture was stirred at room temperature for 4 h. The mixture was quenched with aq NaHCO$_3$ (10 mL) and extracted with ethyl acetate (10 mL×3). The combined organic layers was washed with brine, dried over Na$_2$SO$_4$, filtered and concentrated under reduced pressure. The residue was purified by prep-HPLC to give 55 (8 mg, 14% yield) as an off-white solid. LC-MS (ESI) [M+H]$^+$ 470.2. $^1$H NMR (400 MHz, DMSO-d$_6$): δ

12.18 (br s, 1H), 8.32 (br s, 1H), 7.76 (s, 1H), 5.18-5.08 (m, 1H), 4.50-4.59 (m, 2H), 3.62-3.53 (m, 5H), 2.66-2.60 (m, 7H), 2.13 (s, 3H), 1.38-1.37 (m, 3H), 1.28-1.26 (m, 3H), 1.11-1.08 (m, 1H), 0.52-0.50 (m, 1H), 0.38-0.36 (m, 3H), 0.23-0.21 (m, 1H).

Biological Examples

Activity testing was conducted in the Examples below using methods described herein and those well known in the art.

Characterization of Compounds

This example compares the biological activity for compounds of Formula (I) including (I-a), (I-b), (I-c), and (I-d).

Enzymatic activity of different PI3K isoforms was measured to compare the inhibitory potency and selectivity of the compounds provided herein against PI3K isoforms, particularly selectivity against PI3K gamma over delta. Solubility was also measured to access drug-ability of the tested compounds in the aspect of physicochemical properties.

Each of these biological experiments are described below.

Enzymatic activity of PI3K isoforms: Enzymatic activity of the class I PI3K isoforms in the presence of the compounds of Table 1 was measured using ADP-Glo luminescent assay against PI3Kα, PI3Kβ, PI3Kδ and PI3Kγ with ATP concentration at 25 µM. IPI-549 was used as the reference compound. The compounds would be tested from 1 or 10 µM, 3-fold dilution for 10 doses, in duplicate.

Compound preparation: Dilute a compound to 100× of the final desired highest inhibitor concentration in reaction by 100% DMSO. Transfer 100 µl of this compound dilution to a well in a 96-well plate and serially dilute it with DMSO for a total of 10 concentrations.

Kinase reaction: Prepare a solution of PI3K in 1× kinase buffer at 2-fold the final concentration of each reagent in the assay. Control wells contain 1× kinase buffer without enzyme. Prepare substrate solution of PIP2 substrate and ATP in 1× kinase reaction buffer at 2-fold of the final concentration. Add concentration substrate solution to each well to the final concentration. Cover the assay plate, shake to mix, and incubate at room temperature for 1 hour. Add 5 µl of ADP-Glo reagent to each well to stop the reaction. Mix briefly with a quick spin, shake slowly on the shaker for 120 min. Add 10 ul Kinase Detection Reagent to each well, shake 1 min, equilibrate for 30 min before reading on a luminescence plate reader.

Data Analysis: Convert RLU values to percent inhibition values as Percent inhibition=(max−sample RLU)/(max−min)*100. "min"—no enzyme control; "max"—DMSO control. Fit the data in XLFit excel add-in version 5.4.0.8 to obtain IC50 values. Y=Bottom+(Top−Bottom)/(1+(IC50/X)^HillSlope). Compounds of the present disclosure, as exemplified in Examples, showed the $IC_{50}$ values in table 2 and 3.

Kinetic solubility test: The stock solutions of test compounds and control compound progesterone were prepared in DMSO at the concentrations of 10 mM. 15 µL of stock solution (10 mM) was placed in order into their proper 96-well rack. 485 µL of PBS pH7.4 was added into each vial of the cap-less Solubility Sample plate. The assay was performed in singlet. Add one stir stick to each vial and seal using a molded PTFE/Silicone plug. Then the solubility sample plate was shaken at 25° C. at 1100 rpm for 2 hours. After completion of the 2 hours, the samples from the Solubility Sample plate were transferred into the filter plate. all the samples were filtered using the Vacuum Manifold. Aliquot of 5 µL was taken from the filtrate followed by addition of 495 µL of a mixture of H₂O and acetonitrile containing internal standard (1:1). A certain proportion of ultrapure water was used to dilute the diluent according to the peak shape. The dilution factor was changed according to the solubility values and the LC-MS signal response.

Preparation of 3 µM standards (STD): From the 10 mM DMSO STD plate, 6 µL was transferred into the remaining empty plate, and then 194 µL of DMSO was added to that plate to have a STD concentration of 300 µM. From the 300 µM DMSO STD plate, 5 µL was transferred into the remaining empty plate, and then 495 µL of a mixture of H₂O and acetonitrile containing internal standard (1:1) was added to that plate to have a final STD concentration of 3 µM. A certain proportion of ultrapure water was used to dilute the diluent according to the peak shape. The concentrations of the standard samples were changed according to the LC-MS signal response.

Procedure for sample analysis: The plate was placed into the well plate autosampler. The samples were evaluated by LC-MS/MS analysis.

Data analysis: All calculations were carried out using Microsoft Excel.

The filtrate was analyzed and quantified against a standard of known concentration using LC coupled with mass spectral peak identification and quantitation. Solubility values of the test compound and control compound were calculated as follows:

$$[Sample] = \frac{\text{Area ratio}_{sample} \times INIJ\ VOL_{STO} \times DF_{sample} \times [STD]}{\text{Area ratio } STD \times INJ\ VOL\ sample},$$

Any value of the compounds that was not within the specified limits was rejected and the experiment was repeated. The solubility value is shown in table 2.

The claimed compounds demonstrate remarkable selectivity of PI3K gamma over delta, beta and alpha isoforms. In some embodiments, compounds have dramatically improved physicochemical properties such as solubility and pharmacokinetic properties. For an example, several compounds showed >1000 fold selectivity of PI3K gamma over delta; in another example, compound 20 showed >200 fold improvement over a known literature compound AZ-17 in kinetic solubility test at physiologic pH.

TABLE 2

Inhibitory activities ($IC_{50}$) of compounds 1-55 against PI3K gamma and delta isoform and solubility in PBS.

| # | PI3K gamma (nM) | PI3K delta (nM) | Solubility in PBS at pH 7.4 (µM) |
|---|---|---|---|
| IPI-549† | 1.4 | 65 | 6.4 |
| AZ-17** | 0.63* | 251* | <1* |
| 1 | 1.4 | >1000 | — |
| 2 | 3.7 | >1000 | — |
| 3 | 7.7 | — | — |
| 4 | 4.5 | — | — |
| 5 | 5.9 | — | — |
| 6 | — | — | — |
| 7 | — | — | — |
| 8 | 34 | 361 | — |
| 9 | 22 | — | — |
| 10 | 2.5 | 359 | — |
| 11 | — | — | — |
| 12 | 1.7 | 2080 | 211 |
| 13 | 3.1 | — | — |
| 14 | 4.2 | — | — |

TABLE 2-continued

Inhibitory activities (IC$_{50}$) of compounds 1-55 against PI3K gamma and delta isoform and solubility in PBS

| # | PI3K gamma (nM) | PI3K delta (nM) | Solubility in PBS at pH 7.4 (μM) |
|---|---|---|---|
| 15 | 1.9 | 784 | 245 |
| 16 | — | — | — |
| 17 | 4.5 | — | — |
| 18 | 16 | — | — |
| 19 | 1.6 | >1000 | — |
| 20 | 1.3 | 1168 | 240 |
| 21 | — | — | — |
| 22 | 1.7 | >1000 | 3.5 |
| 23 | 1.0 | 1209 | 202 |
| 24 | 1.5 | 794 | 83 |
| 25 | 3.8 | — | — |
| 26 | 1.4 | >1000 | — |
| 27 | 29 | | |
| 28 | 1.5 | — | |
| 29 | 2.5 | — | — |
| 30 | 56 | | |
| 31 | 2.3 | — | — |
| 32 | 2.2 | — | — |
| 33 | 6.5 | — | — |
| 34 | 1.5 | >1000 | 9.6 |
| 35 | 1.0 | 1326 | 23 |
| 36 | 2.4 | 1254 | 32 |
| 37 | 9.0 | — | — |
| 38 | 1.9 | 1552 | 2.3 |
| 39 | 3.7 | — | — |
| 40 | 2.0 | — | 25 |
| 41 | 2.3 | — | 3.5 |
| 42 | 1.8 | — | 2.6 |
| 43 | 2.6 | — | — |
| 44 | 0.87 | >1000 | 1.2 |
| 45 | 0.80 | — | — |
| 46 | 0.70 | — | 6.1 |
| 47 | 0.61 | — | — |
| 48 | 0.84 | — | — |
| 49 | 1.0 | — | — |
| 50 | 1.0 | — | — |
| 51 | 0.65 | — | — |
| 52 | 1.1 | — | — |
| 53 | 1.8 | — | — |
| 54 | 4.6 | — | — |
| 55 | 1.7 | — | — |

†IPI-549 is a PI3Kγ selective inhibitor in phase II clinical trial (Evans, C. et al, ACS Med. Chem. Lett. 2016, 7, 862-867).
**Compound AZ-17 is a known compound for comparison purpose (*reported data: Pemberton, N, et al, Journal of Medicinal Chemistry 2018, 61, 5435-5441)

TABLE 3

Inhibitory activities (IC$_{50}$) of representative compounds 20, 23, 34, 35 and 38 against PI3K alpha and beta isoforms.

| # | PI3K alpha (nM) | PI3K beta (nM) | PI3K gamma (nM) |
|---|---|---|---|
| 20 | 3887 | >10000 | 1.3 |
| 23 | 3333 | >10000 | 1.0 |
| 34 | 3333 | >10000 | 1.5 |
| 35 | 4144 | >10000 | 1.0 |
| 38 | 8421 | >10000 | 1.9 |

Cellular Activity Test

This study aims to determine the inhibitory effect of compounds on PI3K gamma and PI3K delta in corresponding cell based assays. PI3K gamma activity was reflected by phosphorylation of AKT in C5a stimulated RAW264.7 cells, and PI3K delta activity was reflected by phosphorylation of AKT in anti-IgM stimulated Raji cells. Phosphorylation of AKT in cells was determined using AlphaLISA technology from PerkinElmer.

Raji cell assay: Prepare Passage 11 Raji cell and add 6 μL of 60K cells per well in 384-well plate. Centrifuge at 500 RPM for 30 s and incubate for 2 hours at 37° C., 5% CO$_2$. Add 30 nL compound by Echo and incubate for 30 min at 37° C. Add 2 μL of IgM (4×, 12 μg/mL) per well, centrifuge at 500 RPM for 30 s and incubate for 10 min at 37° C. Add 2 μL of 5× lysis buffer by Multidrop. Shake 10 min on a plate shaker. Add 5 μL acceptor mix provided in the kit. Centrifuge at 1000 RPM for 1 min. Add 5 μL donor mix provided in the kit. Centrifuge at 1000 RPM for 1 min. Then incubate for 2 hours at 25° C., keep the plate in dark. Read AlphaLISA signal on Envision.

Raw264.7 cell assay: Prepare Passage 15 Raw264.7 cell and add 6 μL of 30K cells per well in 384-well plate by multidrop. Centrifuge at 500 RPM for 30 s and incubate for 2 hours at 37° C., 5% CO$_2$. Add 30 nL compound by echo and incubate for 30 min at 37° C., 5% CO$_2$. Add 2 μL of C5α (4×, 320 ng/mL) per well by multidrop, centrifuge at 500 RPM for 30 s and incubate for 5 min at 37° C., 5% CO$_2$. Add 2 μL of 5× lysis buffer by multidrop, incubate for 10 min on a plate shaker. Add 5 μL acceptor mix provided in the kit, centrifuge at 1000 RPM for 1 min. Add 5 μL donor mix provided in the kit, centrifuge at 1000 RPM for 1 min and incubate in dark for 2 hours at 25° C. Read AlphaLISA signal on Envision.

Data analysis: Fit the cpd IC50 from non-linear regression equation.

$$Y = \text{Bottom} + (\text{Top} - \text{Bottom})/(1 + 10^{((\text{Log } IC50 - X) * \text{Hill Slope})})$$

X: Log of cpd concentration
Y: Inhibition

TABLE 4

Cellular Activity for compounds 1-55 (nM)

| # | PI3K gamma Raw264.7 cell (nM) | PI3K delta Raji cell (nM) |
|---|---|---|
| IPI-549 | 2.1 | 133 |
| AZ-17* | 4.0 | 1190 |
| 1 | 315 | >1000 |
| 4 | 1853 | — |
| 5 | 307 | |
| 8 | 115 | — |
| 10 | 290 | — |
| 12 | 30 | — |
| 13 | 22 | — |
| 14 | 27 | — |
| 15 | 130 | — |
| 17 | 118 | — |
| 19 | 28 | — |
| 20 | 4.3 | 2163 |
| 22 | 2.5 | 2282 |
| 23 | 2.0 | 1509 |
| 24 | 2.2 | 1423 |
| 25 | 446 | — |
| 27 | 29 | — |
| 28 | 65 | — |
| 29 | 3243 | — |
| 32 | 208 | — |
| 34 | 1.6 | 1964 |
| 35 | 3.2 | — |
| 36 | 3.3 | — |
| 38 | 9.3 | — |
| 39 | 271 | — |
| 40 | 6.3 | — |
| 44 | 5.1 | — |
| 46 | 3.8 | — |
| 48 | 14 | — |
| 49 | 38 | — |
| 50 | 20 | — |
| 52 | 12 | — |
| 54 | 17 | — |
| 55 | 18 | — |

TABLE 4-continued

Cellular Activity for compounds 1-55 (nM)

| # | PI3K gamma Raw264.7 cell (nM) | PI3K delta Raji cell (nM) |
|---|---|---|

Compound AZ-17

Compound 20

Pharmacokinetics Studies:

Pharmacokinetics in Dogs

Dosing solutions were prepared at 1 mg/mL in 5% DMSO/40% PEG400/55% water. A dosing solution was administered to male beagle dogs (Approximately 9-14 kg, 3 dogs each group) via intravenous (IV) bolus at 1 mg/kg and by oral gavage (PO) at 5 mg/kg. The dosing volume was 1 mL/kg for IV administration and 5 mL/kg for oral gavage. Blood samples (~0.3 mL each time point) were collected into tubes containing potassium ethylenediaminetetraacetic acid ($K_2EDTA$) as the anticoagulant at 0.033, 0.083, 0.25, 0.5, 1, 2, 4, 8 and 24 hours post dose for IV administration and 0.083, 0.25, 0.5, 1, 2, 4, 8 and 24 hours post dose for PO administration. The blood samples were then centrifuged for 5 minutes in a centrifuge refrigerated at 4° C. The resultant plasma samples were analyzed using LC/MS/MS to determine concentrations of a test compound. Non-compartmental model with WinNonlin (Phoenix™, version 6.1) software was used to calculate pharmacokinetic (PK) parameters. The PK results are listed in Table 5. The pharmacokinetic profiles of the compounds provided herein including oral bioavailability (F), half-life time (T v2) and volume of distribution at steady state (Vss) are much improved over AZ-17. In particular, the oral bioavailability of compound 20 in dog was 107%, in comparison, the oral bioavailability of AZ-17 in dog was reported to be 1.6% (Pemberton, N, et al, Journal of Medicinal Chemistry 2018, 61, 5435-5441).

TABLE 5

PK parameters for Compound 20, Compound 34 and AZ-17 in dogs#

| | Cl (mL/min/kg) | $T_{1/2}$ (h) | $Vss_{obs}$ (L/kg) | F (%) |
|---|---|---|---|---|
| Compound 34* | 4.5 | 9.1 | 2.7 | >68 |
| Compound 20* | 6.1 | 7.2 | 2.1 | 108 |
| AZ-17** | 6.2 | 1.3 | 0.7 | 1.6 |

*IV bolus at 1 mg/kg and PO at 5 mg/kg in beagle dogs
**Reported by Pemberton, N, et al, Journal of Medicinal Chemistry 2018, 61, 5435-5441

Pharmacokinetics in Mice

A dosing solution of Compound 34 was prepared at 2 mg/mL in 5% DMSO/40% PEG400/55% water. The dosing solution was administered to male CD-1 mice via oral gavage (PO) at 20 mg/kg. Blood and brain tissue samples were collected at 0.5, 2 and 8 hours post-dose. The blood samples were then centrifuged for 5 minutes in a centrifuge refrigerated at 4° C. The brain samples after blood removal were homogenized in water. The plasma and brain homogenate samples were then analyzed using LC/MS/MS to determine concentrations of Compound 34. The results are listed in Table 6. Compound 34 showed good exposure in the brain tissues of mice, demonstrating good penetration of blood-brain.

TABLE 6

Concentrations of Compound 34 in brain tissues and plasma following oral gavage Administration of Compound 34 in Male CD1 Mouse at 20 mg/kg

| Time (h) | Plasma (ng/mL) | Brain (ng/g) | Ratio (Brain/Plasma) |
|---|---|---|---|
| 0.5 | 2803 | 2494 | 0.890 |
| 2 | 1205 | 473 | 0.392 |
| 8 | 1367 | 454 | 0.332 |

Anti-Tumor Efficacy of the Compounds Described Herein in Syngeneic Mouse Tumor Models A dosing solution of Compound 34 was prepared at 2 mg/mL in 5% DMSO/40% PEG400/55% water. BALB/c mice were inoculated subcutaneously at the fourth mammary pad with 4T1 cells for tumor development. On the next day after tumor cell inoculation, the mice were assigned into 2 groups using stratified randomization with 10 mice in each group based upon their body weight and inoculation order. The treatments of the mice via oral gavage with either the vehicle or Compound 34 at 100 mg/kg were started from the day of randomization. The tumor sizes were measured three times per week during the treatment. Tumor volume was calculated by the formula: length×width$^2$/2. As shown in FIG. 1, treatment of Compound 34 significantly suppressed tumor growth.

Efficacy Study of Compound 34 on MOG35-55 Induced EAE in C57BL/6 Mice

Objective: Experimental autoimmune encephalomyelitis (EAE) is the most common animal model of human Multiple Sclerosis for evaluating the efficacy of treatment strategies. The objective of this study was to evaluate the efficacy of compound 34 on myelin oligodendrocyte glycoprotein (MOG) induced EAE mouse model.

Experiment Procedure: Animal model: Mix 10 mL of Complete Freund's adjuvant (CFA) with 50 mg of *Mycobacterium tuberculosis* H37Ra into 6 mg/mL of final concentration. Synthetic peptide MOG35-55 was dissolved in saline to 4 mg/ml of final concentration. Emulsify MOG35-55 solution in equal volume of the mixed CFA on ice for 1 hour, using a high-speed homogenizer (30000 rpm, IKA Equipment Shanghai Co., Ltd).

Forty female C57BL/6 mice at age 6-8 weeks were randomly allocated into 4 groups as below.

TABLE 7

| | Group | n | Dosage (mg/kg) | Route |
|---|---|---|---|---|
| 1. | Vehicle | 10 | N/A | PO, QD |
| 2. | Reference FTY-720 | 10 | 1 | PO, QD |
| 3. | Compound 34 −20 MPK | 10 | 20 | PO, BID |
| 4. | Compound 34 −80 MPK | 10 | 80 | PO, BID |

Inject 0.1 mL of MOG35-55 emulsion subcutaneously on the shaved back of the mice at three sites: one along the midline of the back between the shoulders, and one on each side of the midline on the lower back. *Bordetella pertussis* toxin (PTX) (400 ng in 200 μL of PBS) was injected intra-peritoneally on day 0 and 48 hours after immunization.

Treatment: Mice in group 3 and 4 were received Compound 34 following the dosing regimen specified. Mice in group 2 were received positive compound FTY-720 as the reference. Mice in group 1 were the vehicle control. The dosing started from disease onset day 10 and continued for 14 days.

Assessment: Body weight was measured before immunization. From day 8, body weight was measured daily till the end of the study. EAE clinical score was recorded before immunization. From day 8, score was recorded daily still the end of the study. Scoring system for clinical assessment of EAE:

| Score | Clinical signs |
|---|---|
| 0 | Normal mouse; no overt signs of disease |
| 1 | Limp tail[a] or hind limb weakness[b] but not both |
| 2 | Limp tail[a] and hind limb weakness[b] |
| 3 | Partial hind limb paralysis[c] |
| 4 | Complete hind limb paralysis[d] |
| 5 | Moribund state; death by EAE: sacrifice for humane reasons |

[a]Limp tail: complete flaccidity of the tail, and absence of curling at the tip of the tail when mouse is picked up.
[b]Hind limb weakness: observed as a waddling gait, the objective sign being that, in walking, mouse's hind limbs fall through the wire cage tops.
[c]Partial hind limb paralysis: mouse can no longer use hind limbs to maintain rump posture or walk but can still move one or both limbs to some extent.
[d]Complete hind limb paralysis: total loss of movement in hind limbs; mouse drags itself only on its forelimbs.
Data analysis: Clinical score at baseline, day 8 and during treatment was analyzed with GraphPad Prism software.

Result

Figure 2:
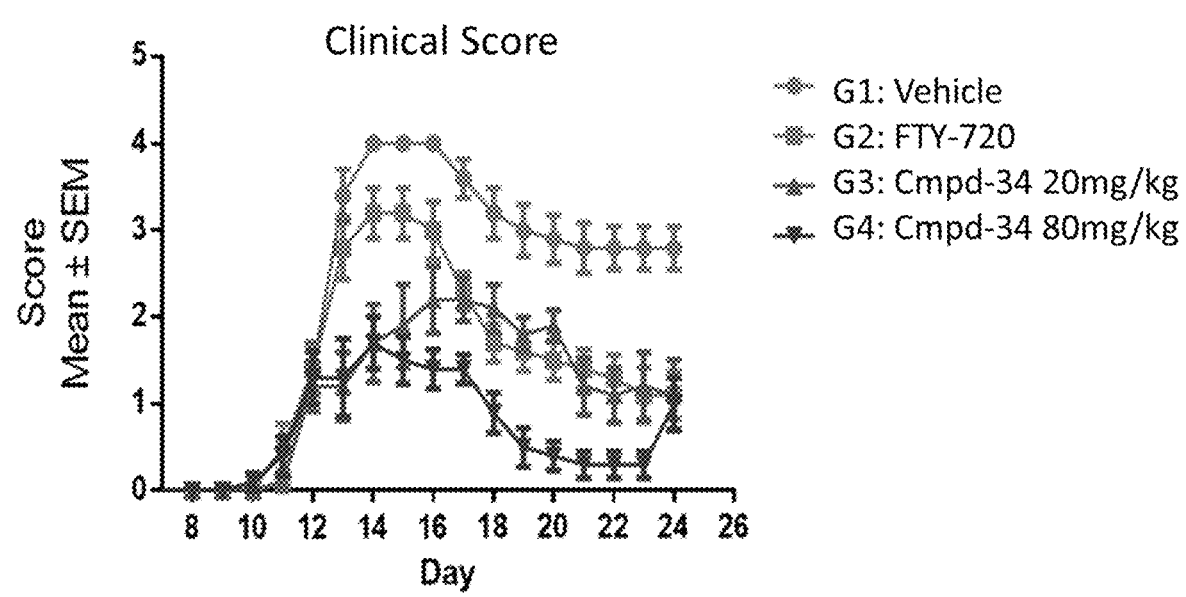
FIG. 2 shows that treatment with an exemplary compound (compound 34) at 20 mg/kg and 80 mg/kg BID significantly ameliorated the clinical disability symptom of EAE induced mice.

As shown in FIG. 2, compound 34 treatment at 20 mg/kg and 80 mg/kg BID significantly ameliorated the clinical disability symptom of EAE induced mice with efficacy comparable to 1 mg/kg of fingolimod (FTY-720).

What is claimed is:

1. A compound of Formula (I):

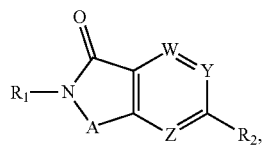

(I)

or a pharmaceutically acceptable salt, stereoisomer, prodrug, or solvate thereof, wherein:
A is $CH_2$, $CH(C_{1-6}alkyl)$, O, or S;
Y is CH or N;
Z is CH or N;
W is N, CH, or CX; wherein X is selected from the group consisting of

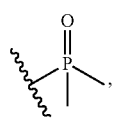 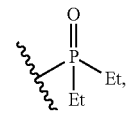 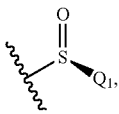

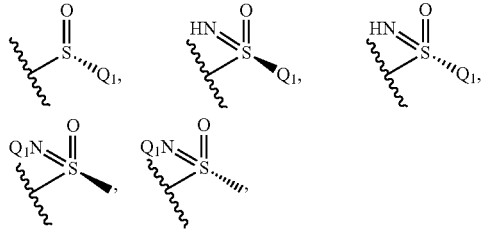

NHG, $CHG_2$, COOH, OG, $SO_2G$, $SO_2NHG$, $NGSO_2G$, $C_{1-6}alkyl$-$NGSO_2G$, NHC(O)G, $NHC(O)NG_2$, C(O)NHG, $C(O)NG_2$, $C_{3-10}cycloalkyl$, and 3-10 membered heterocyclyl, wherein each 3-10 membered heterocyclyl independently contains 1 or 2 heteroatoms, wherein the 1 or 2 heteroatoms are selected from the group consisting of O, N, and S, and wherein each $C_{3-10}cycloalkyl$ or 3-10 membered heterocyclyl is independently optionally substituted with one or more G, wherein:
$Q_1$ is $C_{1-6}alkyl$, wherein the $C_{1-6}alkyl$ is optionally substituted with one or more OH or halo, and
each G is independently selected from the group consisting of H, D, OH, $C_{1-6}alkoxy$, oxo, $NH_2$, $SO_2(C_{1-6}alkyl)$, $C(O)$-$C_{1-6}alkyl$, $C_{3-10}cycloalkyl$, 3-10 membered heterocyclyl, and $C_{1-6}alkyl$, wherein the $C_{3-10}cycloalkyl$ or $C_{1-6}alkyl$ is independently optionally substituted with one or more D, OH, $C_{1-6}$ alkoxy, CN, $N(C_{1-6}alkyl)_2$, $SO_2(C_{1-6}alkyl)$, or halo, or
two G groups, together with the atoms to which they are attached, form a $C_{3-10}cycloalkyl$ or 3-10 membered heterocyclyl,
$R_1$ is $C_{1-6}alkyl$, $C_{3-10}cycloalkyl$, or $C_{1-6}alkyl$-$C_{3-10}cycloalkyl$, wherein the $C_{1-6}alkyl$, $C_{3-10}$ cycloalkyl, or $C_{1-6}alkyl$-$C_{3-10}cycloalkyl$ is independently optionally substituted with one or more halo;
$R_2$ is selected from the group consisting of

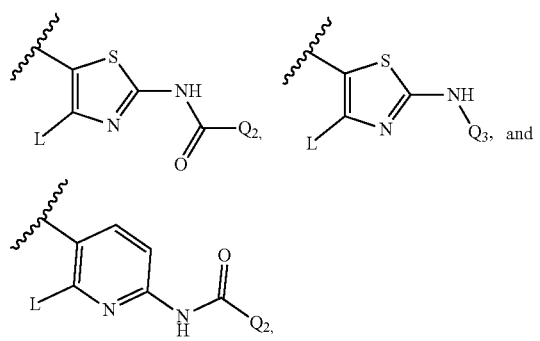

wherein:
L is H, halo, or $C_{1-6}alkyl$, wherein the $C_{1-6}alkyl$ is optionally substituted with one or more halo, $C_{1-6}alkoxy$, or OH, and
each $Q_2$ and $Q_3$ is independently $C_{1-6}alkyl$, $C_{3-10}cycloalkyl$, or 3-10 membered heterocyclyl, wherein the $C_{1-6}alkyl$, $C_{3-10}cycloalkyl$, or 3-10 membered heterocyclyl is independently optionally substituted with one or more halo; and
wherein at least one of Y, Z and W is N.

2. The compound of claim 1, wherein is N.

3. The compound of claim 1, wherein the compound has the structure of Formula (I-b):

(I-b)

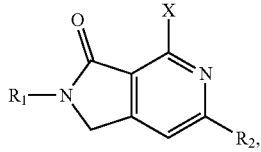

or a pharmaceutically acceptable salt, stereoisomer, solvate, or prodrug thereof.

4. The compound of claim 1, or a pharmaceutically acceptable salt, stereoisomer, prodrug, or solvate thereof, wherein $R_2$ is

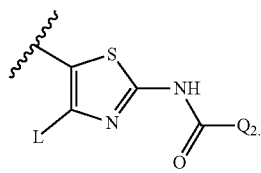

5. The compound of claim 1, or a pharmaceutically acceptable salt, stereoisomer, prodrug, or solvate thereof, wherein $R_2$ is selected from the group consisting of

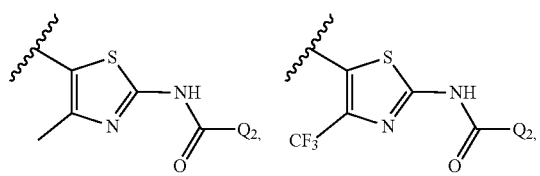

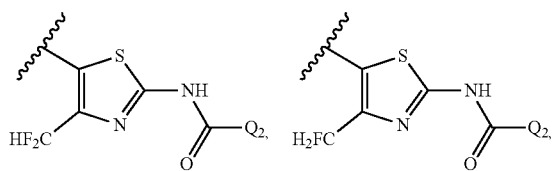

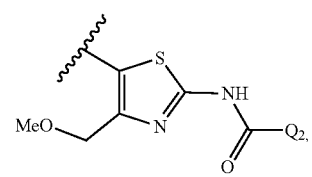

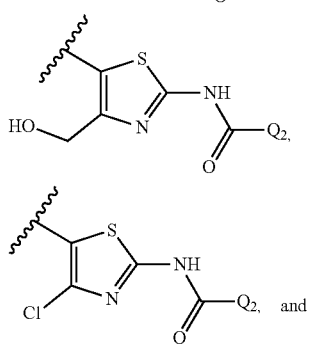

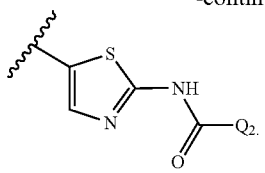

6. The compound of claim 1, or a pharmaceutically acceptable salt, stereoisomer, prodrug, or solvate thereof, wherein $Q_2$ is methyl, ethyl, isopropyl, cyclopropyl, or difluoromethyl.

7. The compound of claim 1, wherein the compound has the structure of Formula (I-c):

(I-c)

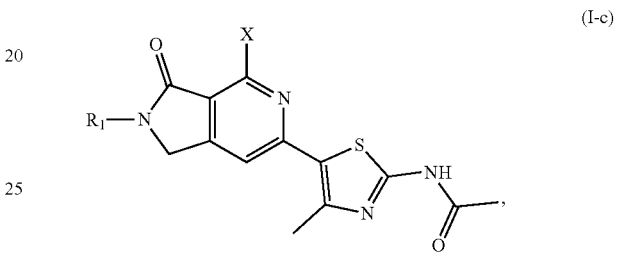

or a pharmaceutically acceptable salt, stereoisomer, prodrug, or solvate thereof.

8. The compound of claim 1, or a pharmaceutically acceptable salt, stereoisomer, prodrug, or solvate thereof, wherein $R_1$ is selected from the group consisting of

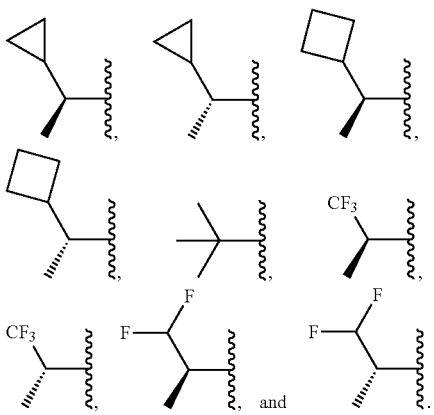

9. The compound of claim 1, or a pharmaceutically acceptable salt, stereoisomer, prodrug, or solvate thereof, wherein $R_1$ is selected from the group consisting of

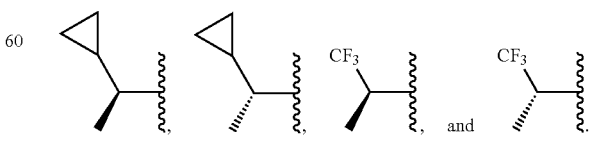

10. The compound of claim 1, wherein the compound has the structure of Formula (I-d):

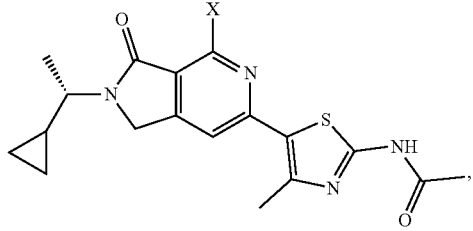

(I-d)

or a pharmaceutically acceptable salt, stereoisomer, prodrug, or solvate thereof.

11. The compound of claim 1, or a pharmaceutically acceptable salt, stereoisomer, prodrug, or solvate thereof, wherein X is selected from the group consisting of

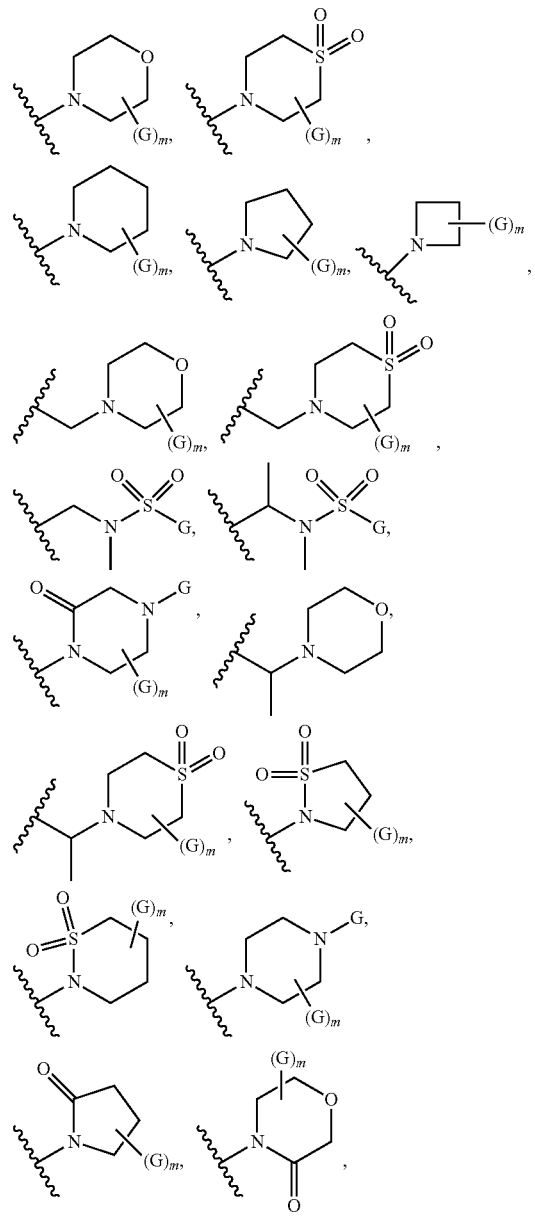

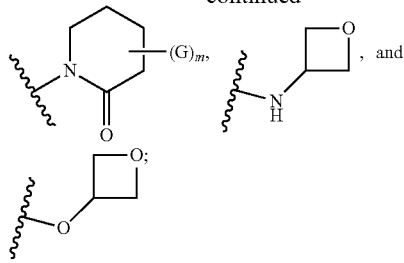

-continued and m is an integer selected from the group consisting of 0, 1, 2, 3, 4, and 5.

12. The compound of claim 11, or a pharmaceutically acceptable salt thereof, wherein m is 0 or 1.

13. The compound of claim 1, or a pharmaceutically acceptable salt, stereoisomer, prodrug, or solvate thereof, wherein X is selected from the group consisting of

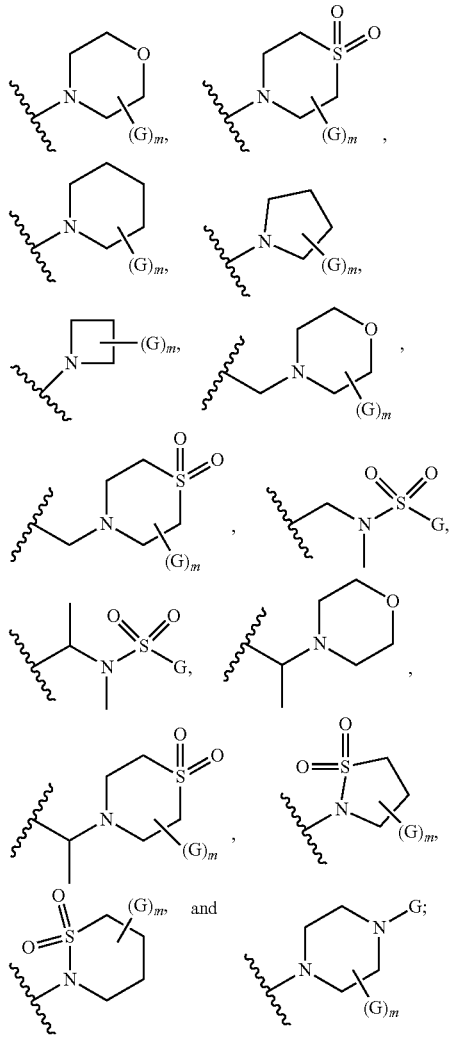

and m is an integer selected from the group consisting of 0, 1, 2, 3, 4, and 5.

14. The compound of claim 13, or a pharmaceutically acceptable salt thereof, wherein m is 0 or 1.

15. The compound of claim 1, or a pharmaceutically acceptable salt, stereoisomer, prodrug, or solvate thereof, wherein X is selected from the group consisting of NHG, OG, NHSO$_2$G, and C(O)NG$_2$.

16. The compound of claim 1, or a pharmaceutically acceptable salt, stereoisomer, prodrug, or solvate thereof, wherein X is selected from the group consisting of OMe, OCD$_3$, NHSO$_2$Me, NHSO$_2$Et, C(O)NH$_2$, C(O)NHMe, and C(O)NMe$_2$.

17. The compound of claim 1, or a pharmaceutically acceptable salt, stereoisomer, prodrug, or solvate thereof, wherein the compound is selected from the group consisting of:

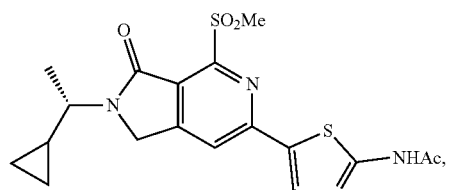

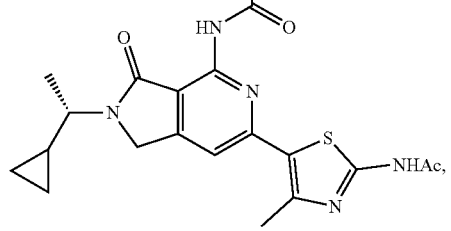

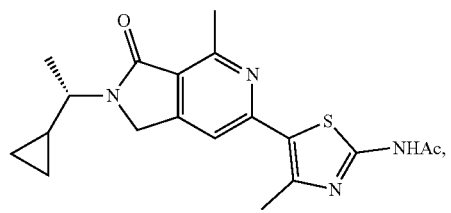

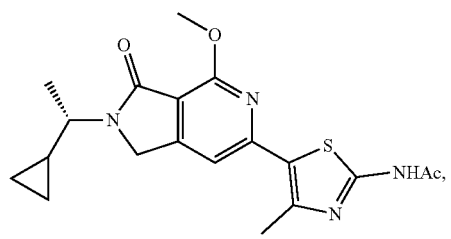

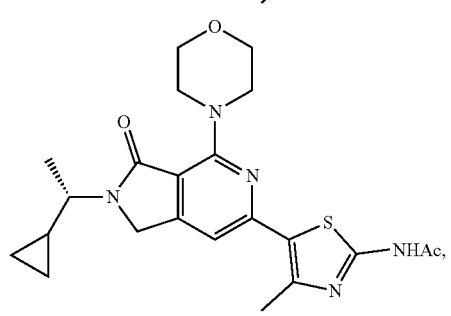

-continued

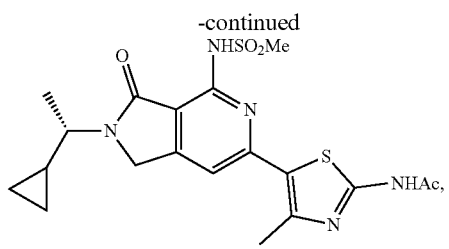

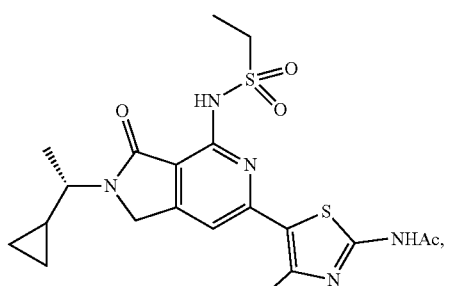

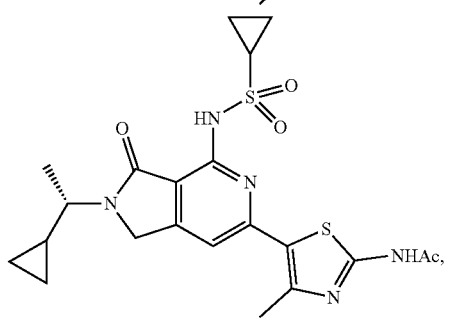

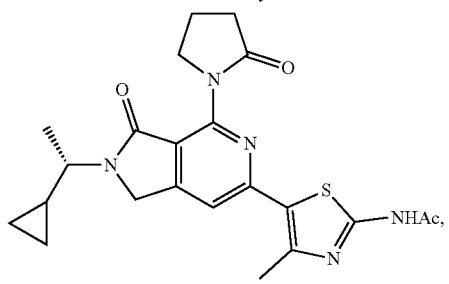

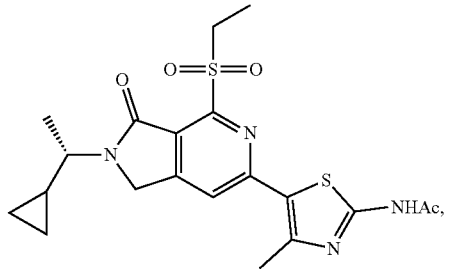

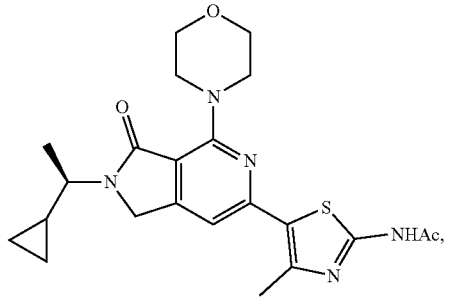

-continued
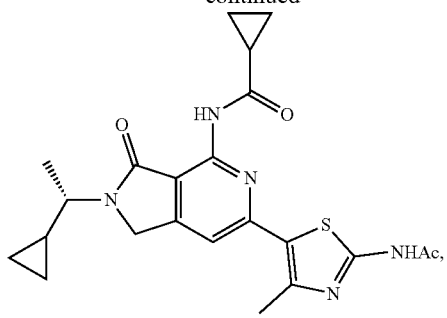
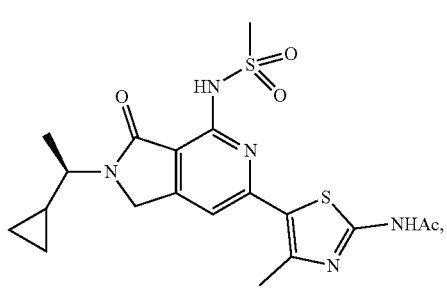
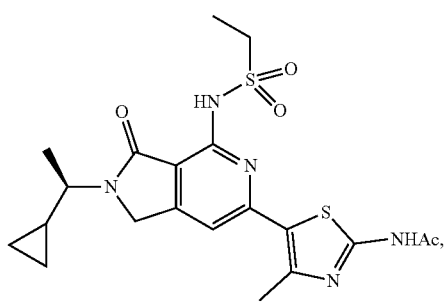
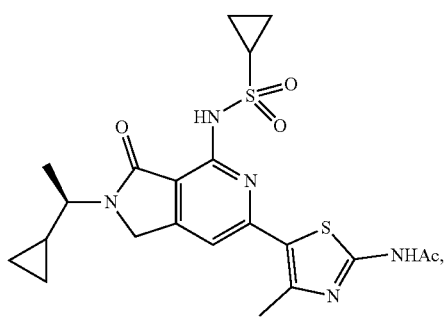
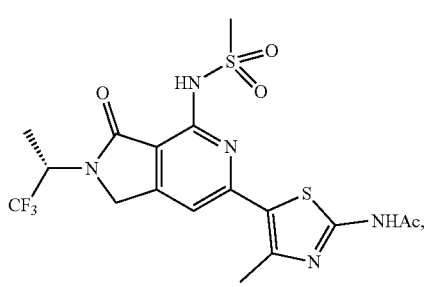
-continued
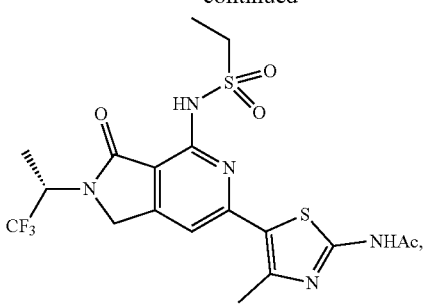
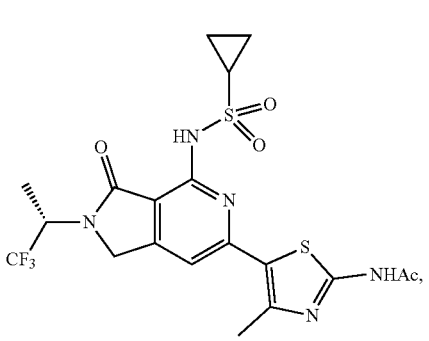
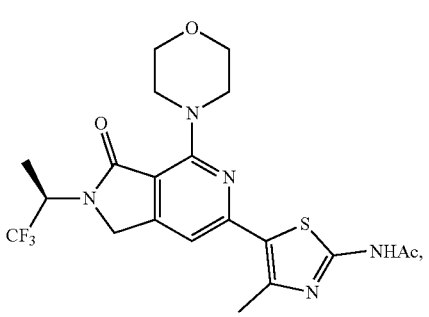
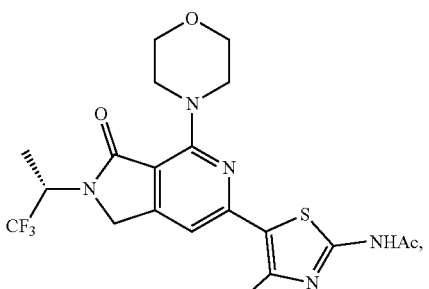
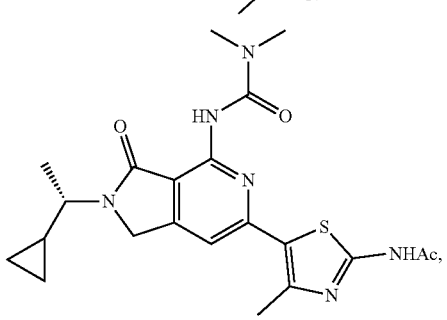

147
-continued
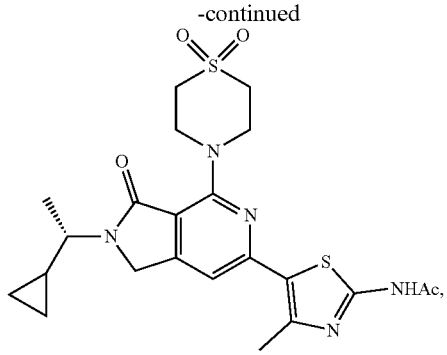
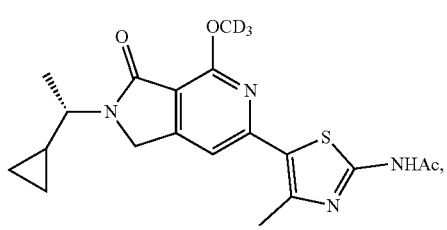
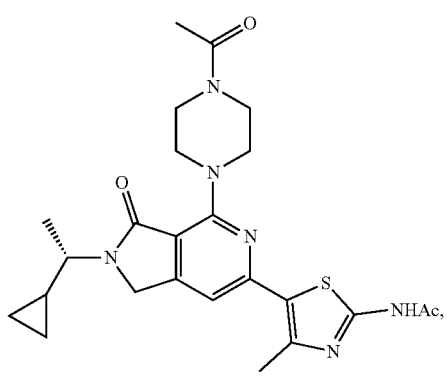
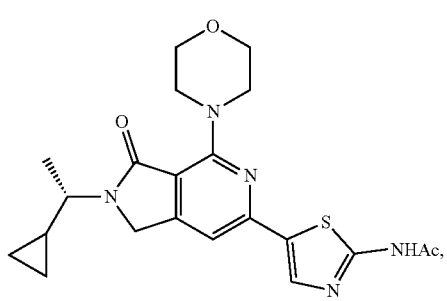
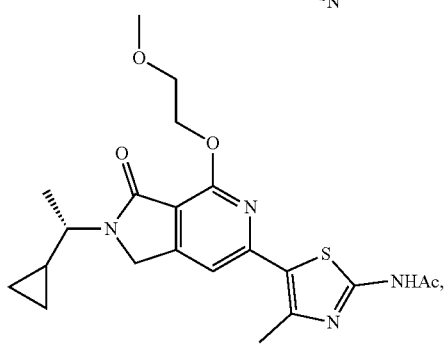
148
-continued
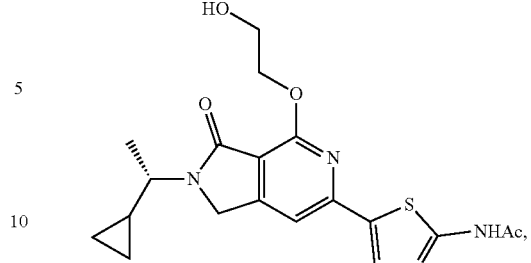
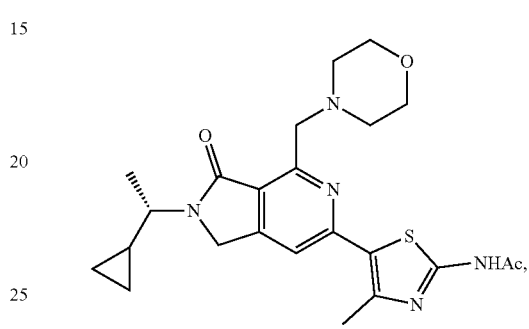
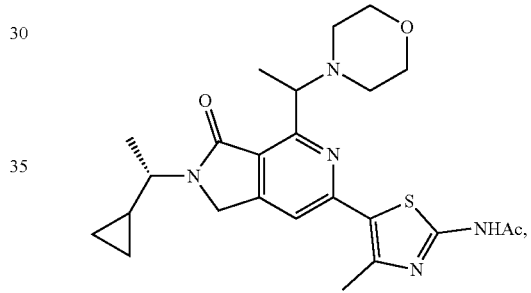
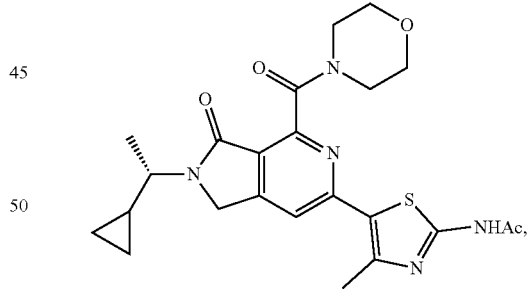
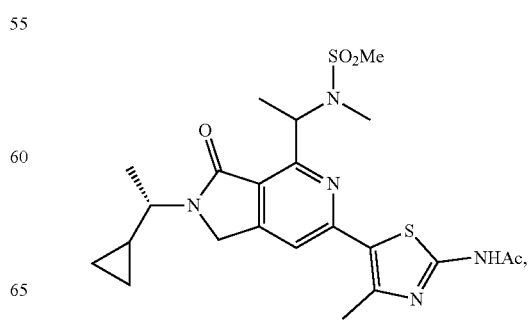

149
-continued
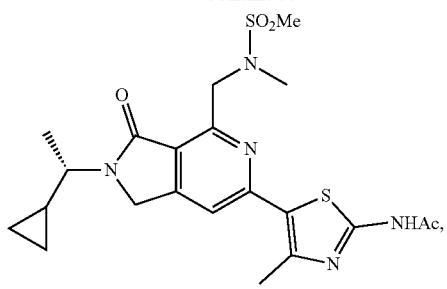
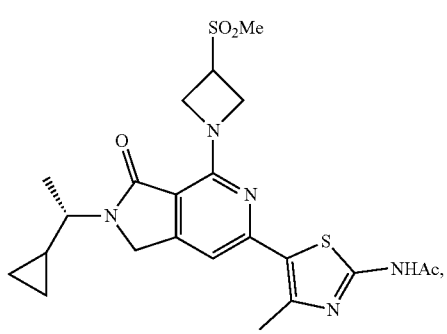
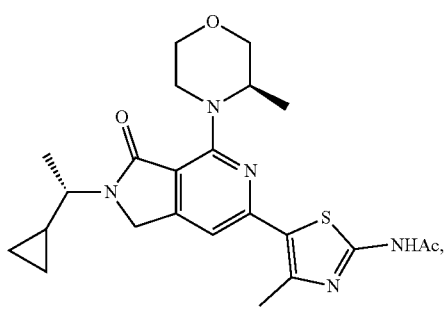
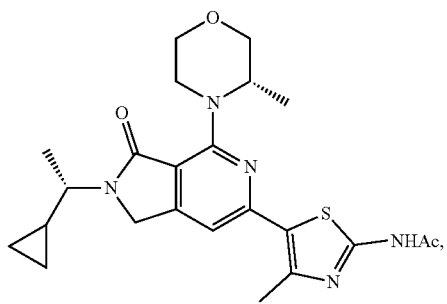
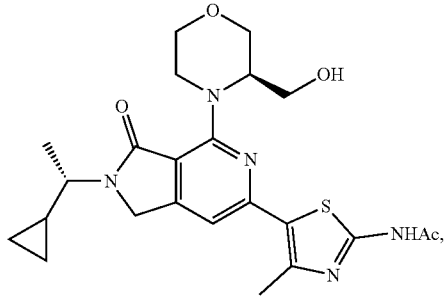
150
-continued
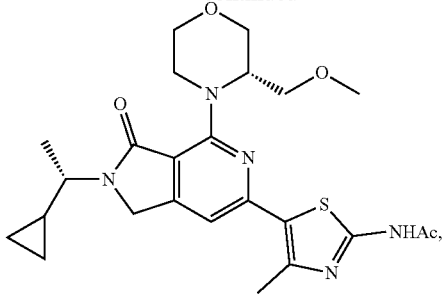
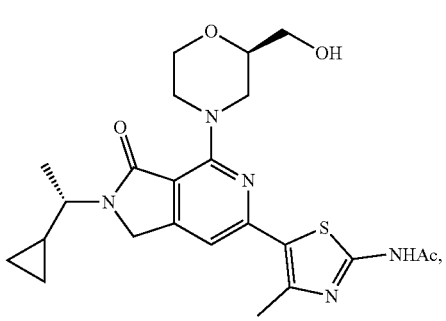
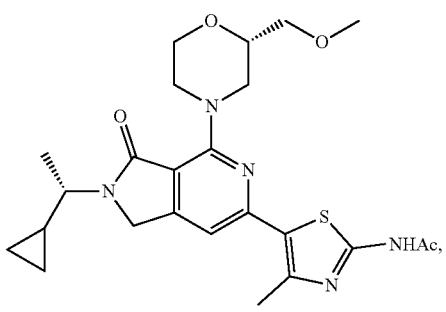
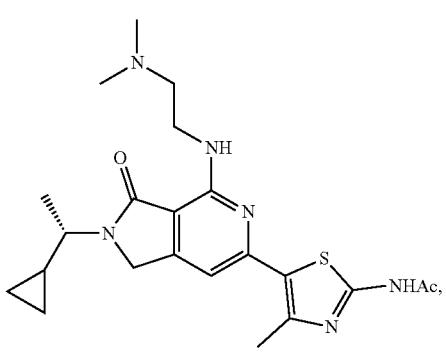
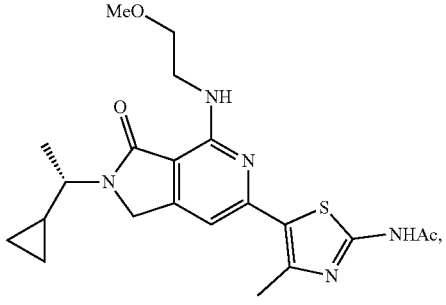

151
-continued

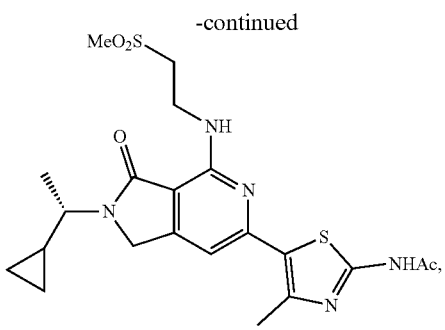

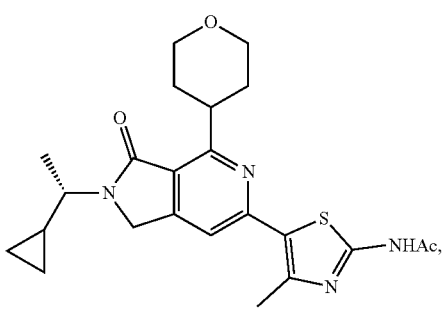

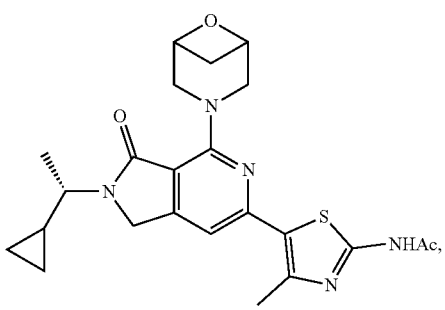

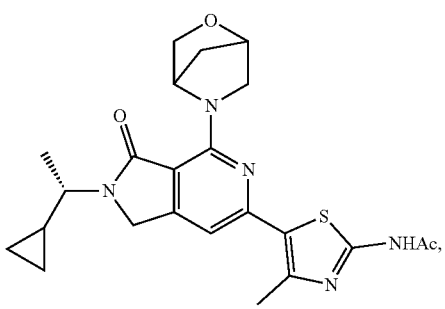

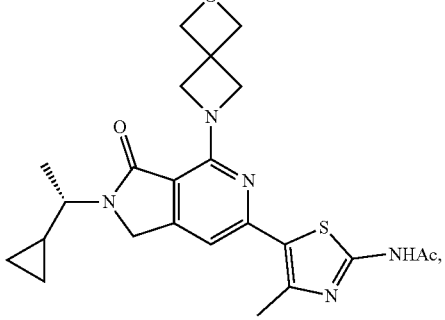

152
-continued

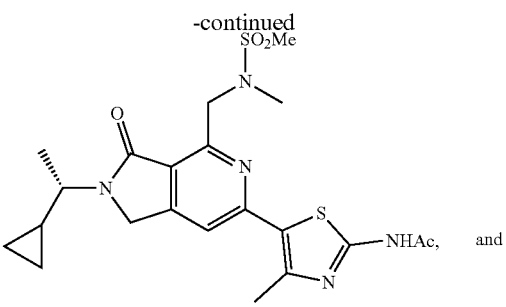
and

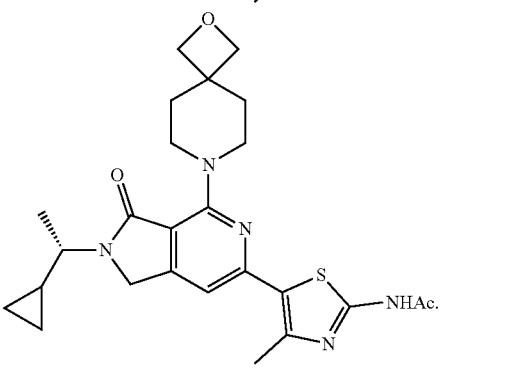

18. The compound of claim 1, wherein Z is N, A is CH$_2$, Y is CH, and W is CH, or a pharmaceutically acceptable salt, stereoisomer, prodrug, or solvate thereof.

19. The compound of claim 1, wherein the compound has the structure of Formula (I-a):

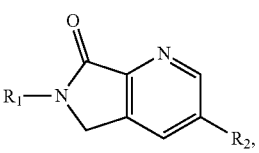

(I-a)

or a pharmaceutically acceptable salt, stereoisomer, solvate, or prodrug thereof.

20. The compound of claim 1, or a pharmaceutically acceptable salt, stereoisomer, solvate, or prodrug thereof, wherein the compound is selected from the group consisting of:

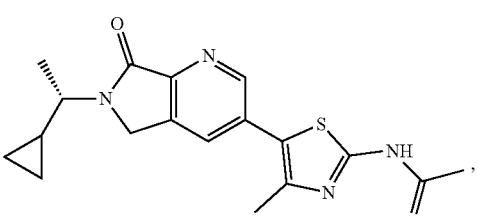

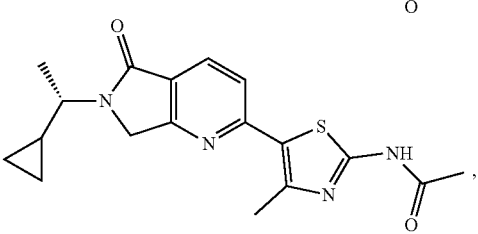

-continued
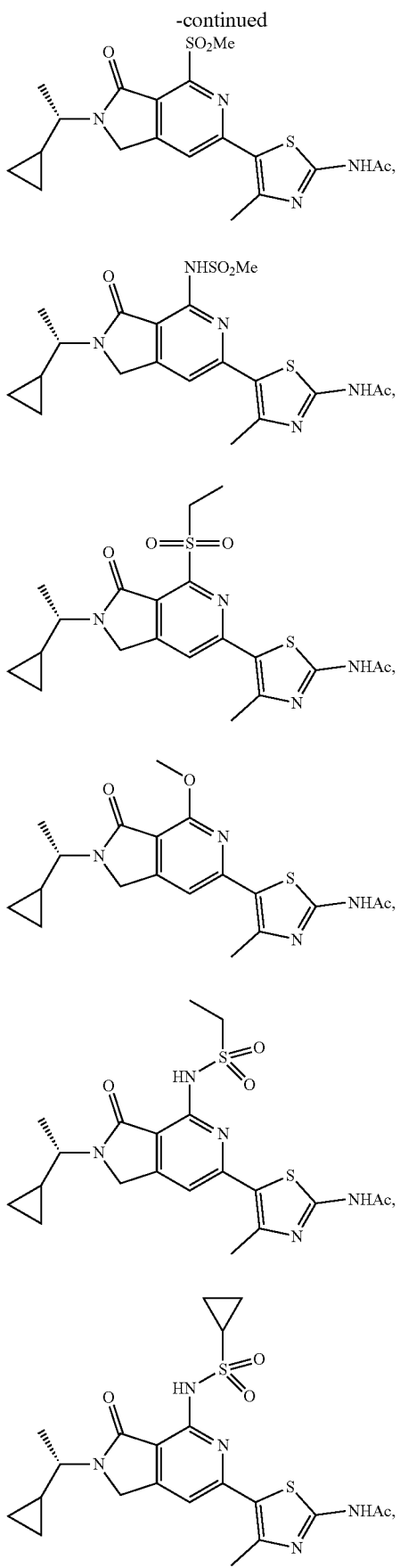
-continued
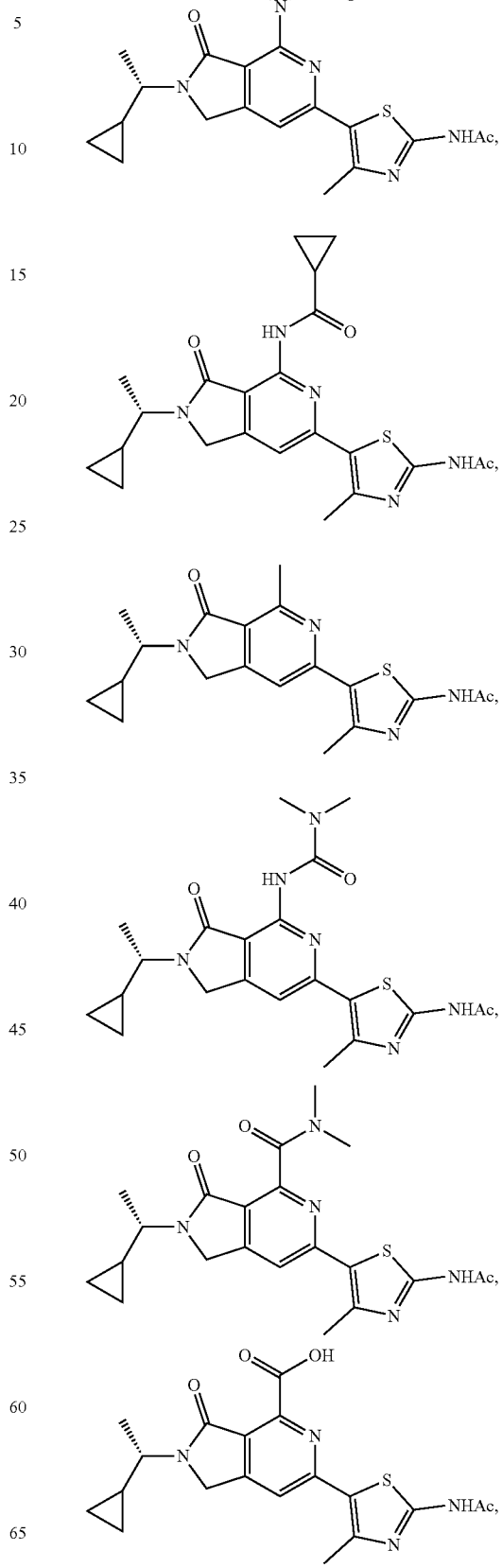

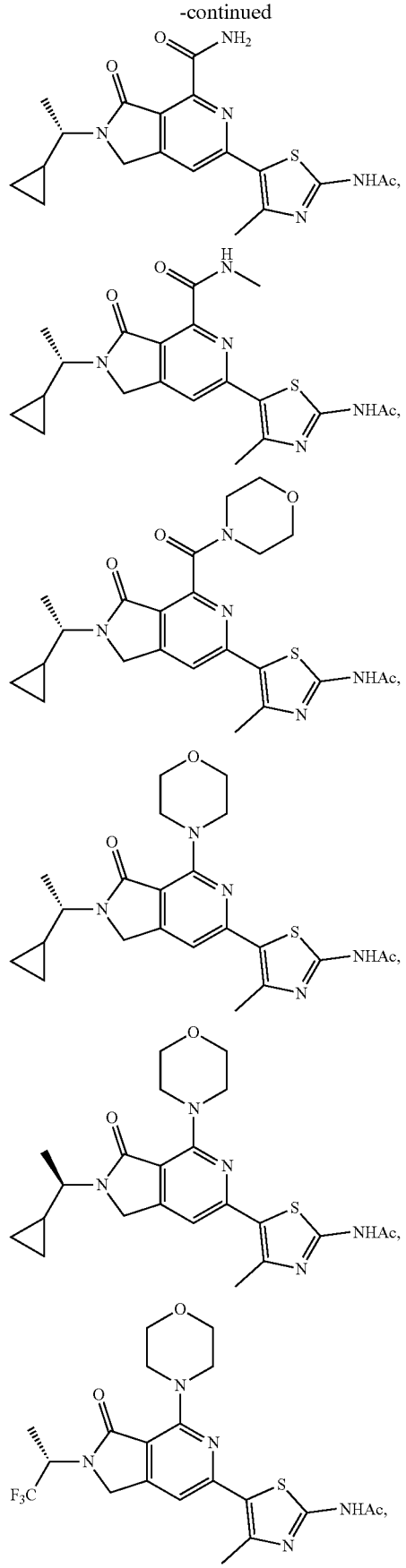
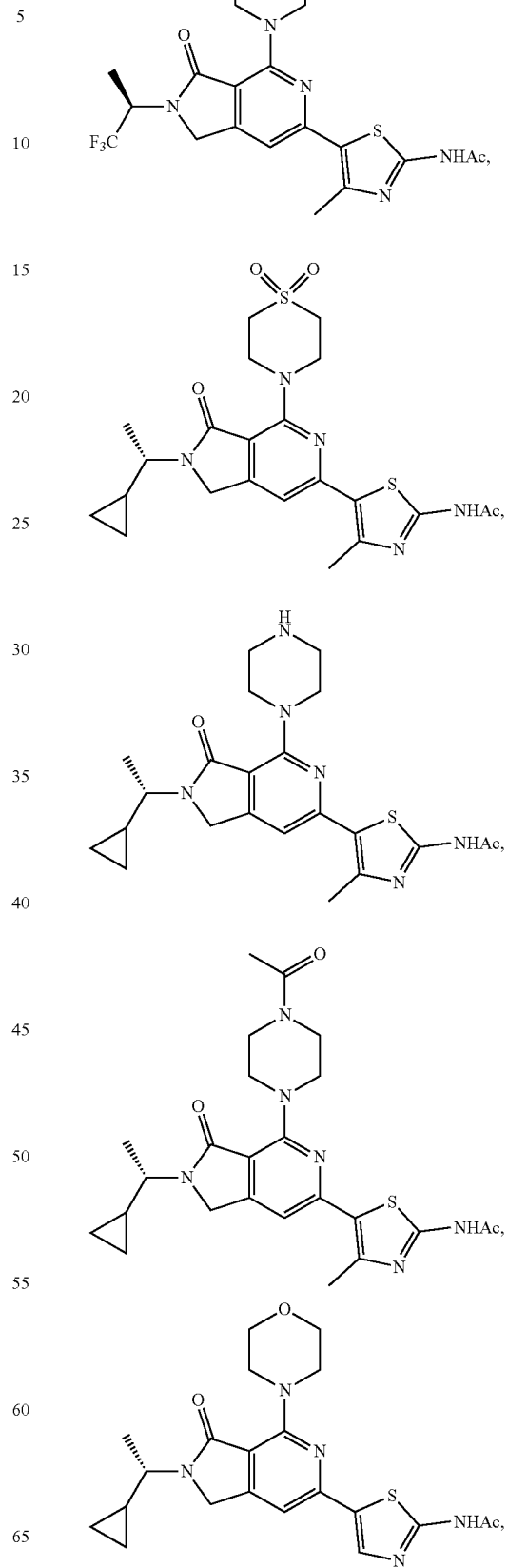

157
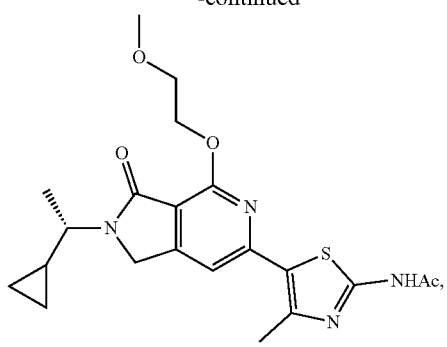
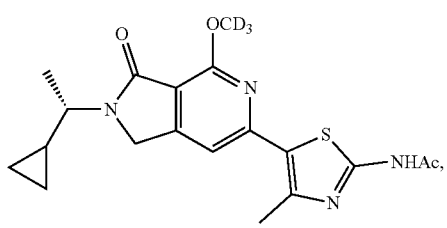
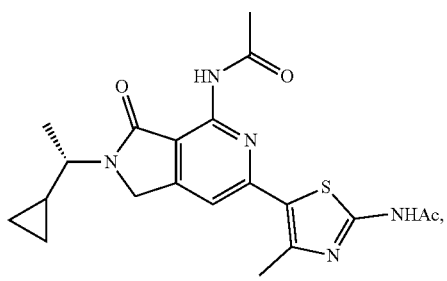
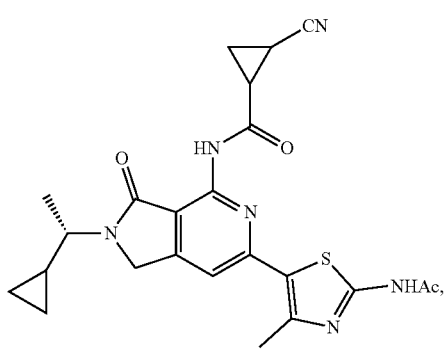
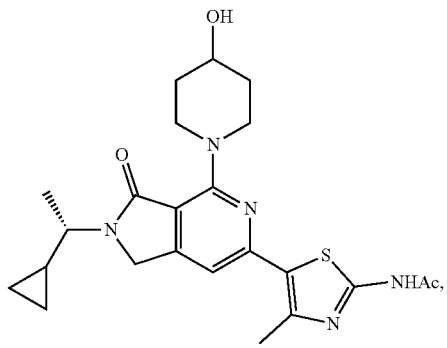
158
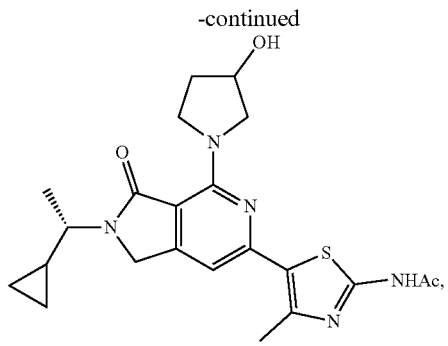
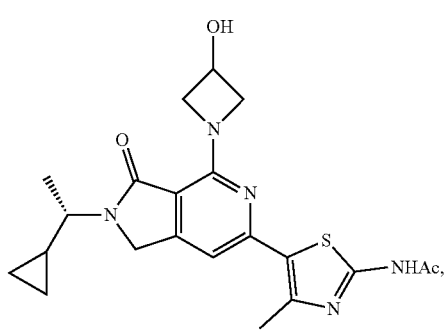
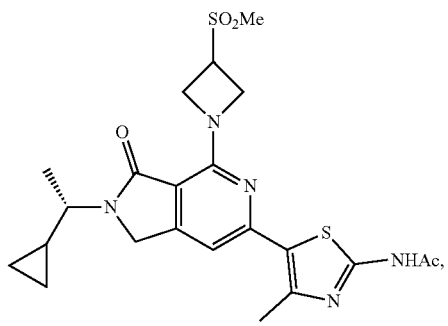
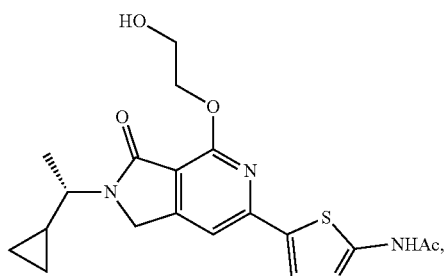
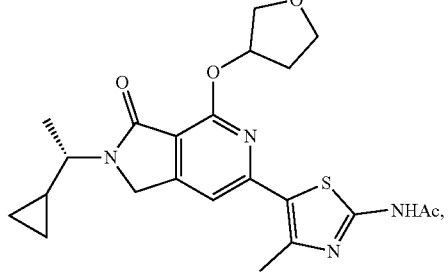

| 159 -continued | 160 -continued |
|---|---|
| 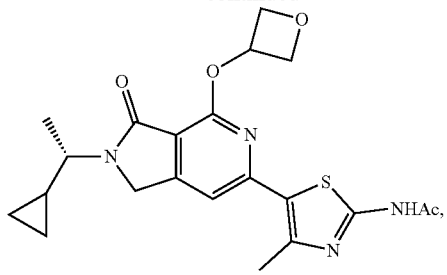 | 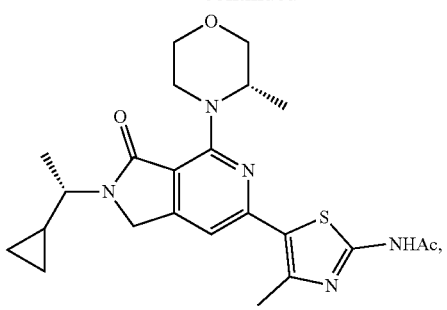 |
| 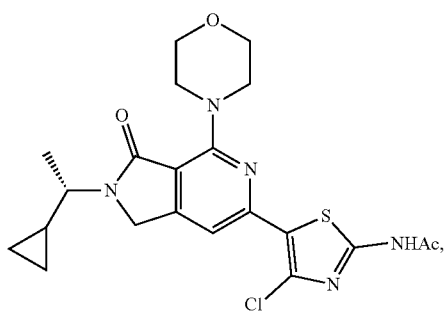 | 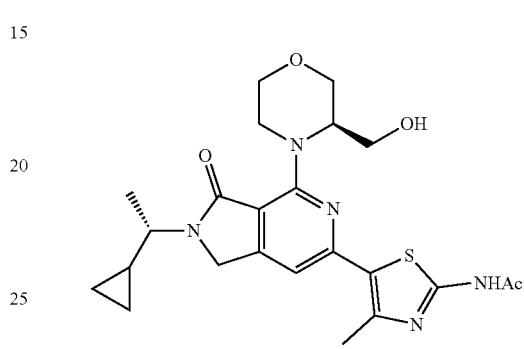 |
| 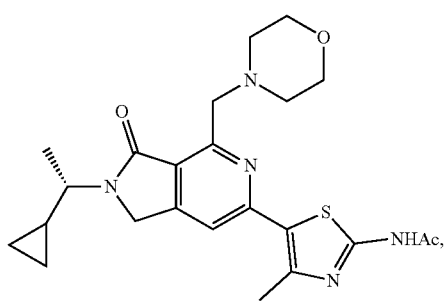 | 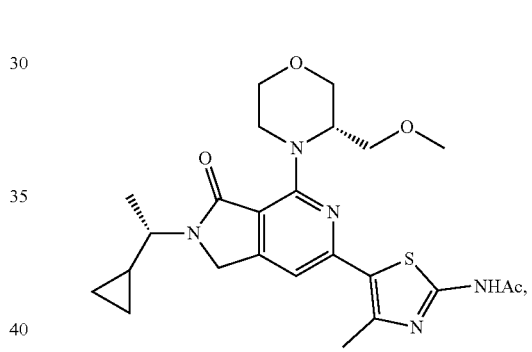 |
| 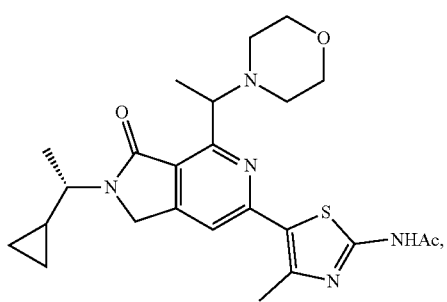 | 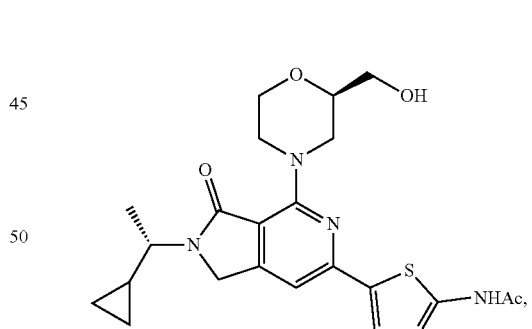 |
| 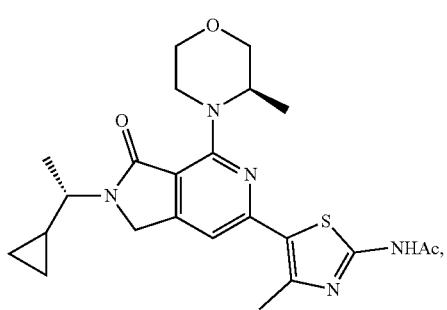 | 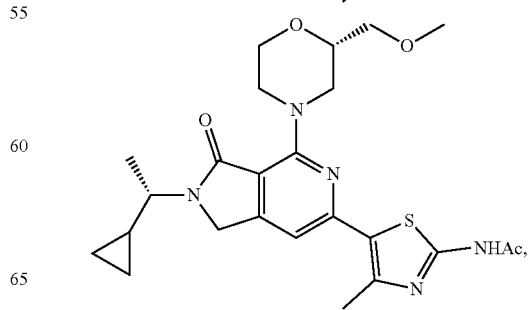 |

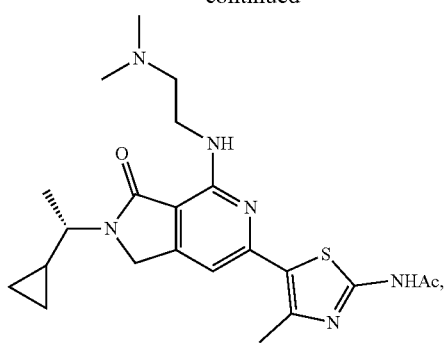

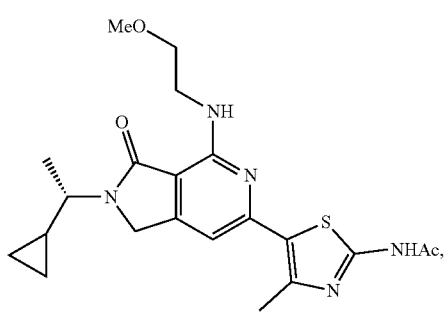

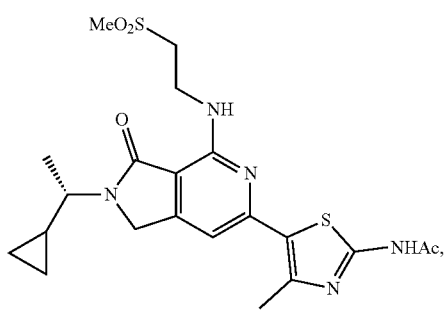

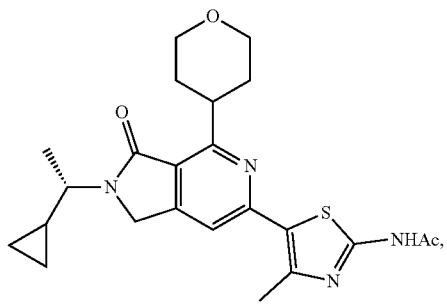

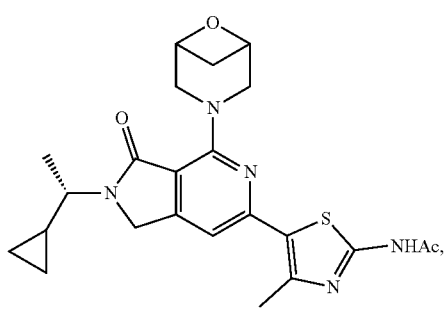

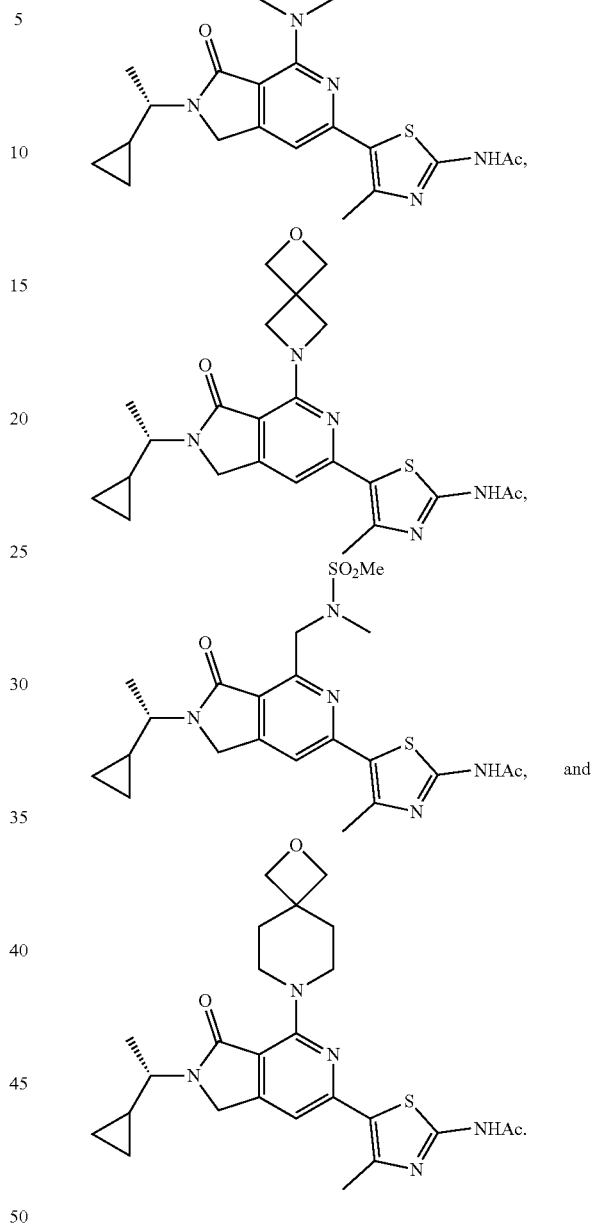

21. A pharmaceutical composition comprising a compound of claim 1, or a pharmaceutically acceptable salt, stereoisomer, solvate, or prodrug thereof, and a pharmaceutically acceptable carrier.

22. A method of selectively inhibiting phosphoinositide 3-kinase gamma (PI3Kγ) comprising contacting the PI₃Kγ with a compound of claim 1, or a pharmaceutically acceptable salt, stereoisomer, solvate, or prodrug thereof.

23. A method of treating a disorder of uncontrolled cellular proliferation related to one or more PI3K isoforms comprising administering to a subject in need thereof a therapeutically effective amount of a compound of claim 1, or a pharmaceutically acceptable salt, stereoisomer, solvate, or prodrug thereof.

24. The method of claim 23, wherein the one or more PI3K isoforms comprise PI3K gamma (PI3Kγ).

25. A method of treating an autoimmune disease, comprising administering to a subject in need thereof a therapeutically effective amount of a compound of claim 1, or a pharmaceutically acceptable salt, stereoisomer, solvate, or prodrug thereof.

26. A method of treating a cancer, comprising administering to a subject in need thereof a therapeutically effective amount of a compound of claim 1, or a pharmaceutically acceptable salt, stereoisomer, solvate, or prodrug thereof.

* * * * *